US00RE46955E

(19) United States
(12) Reissued Patent
Ferro et al.

(10) Patent Number: US RE46,955 E
(45) Date of Reissued Patent: Jul. 17, 2018

(54) SULFATED OLIGOSACCHARIDE DERIVATIVES

(71) Applicant: Progen PG500 Series Pty Ltd, Melbourne (AU)

(72) Inventors: Vito Ferro, Mt. Ommaney (AU); Tomislav Karoli, Kenmore (AU); Ligong Liu, Eight Mile Plains (AU); Paul Newton Handley, Goodna (AU); Kenneth David Johnstone, Gordon Park (AU); Norbert Wimmer, Moorooka (AU); Edward Timothy Hammond, Inala (AU)

(73) Assignee: Progen PG500 Series Pty Ltd, Melbourne (AU)

(21) Appl. No.: 15/261,470

(22) Filed: Sep. 9, 2016

Related U.S. Patent Documents

Reissue of:
(64) Patent No.: 8,828,952
Issued: Sep. 9, 2014
Appl. No.: 12/738,552
PCT Filed: Oct. 16, 2008
PCT No.: PCT/AU2008/001535
§ 371 (c)(1),
(2) Date: Apr. 7, 2011
PCT Pub. No.: WO2009/049370
PCT Pub. Date: Apr. 23, 2009

(30) Foreign Application Priority Data

Oct. 16, 2007 (AU) ..... 2007905680

(51) Int. Cl.

| | |
|---|---|
| ***A61K 31/70*** | (2006.01) |
| ***C07H 15/00*** | (2006.01) |
| ***C07H 17/02*** | (2006.01) |
| ***C07J 43/00*** | (2006.01) |
| ***C07H 5/02*** | (2006.01) |
| ***C07H 5/04*** | (2006.01) |
| ***C07H 5/06*** | (2006.01) |
| ***C07H 11/00*** | (2006.01) |
| ***C07H 15/04*** | (2006.01) |
| ***C07H 15/207*** | (2006.01) |
| ***C07H 15/24*** | (2006.01) |
| ***C07H 15/26*** | (2006.01) |
| ***C07J 17/00*** | (2006.01) |
| ***C07J 41/00*** | (2006.01) |
| ***C07J 31/00*** | (2006.01) |
| ***C07H 3/04*** | (2006.01) |
| ***C07H 3/06*** | (2006.01) |

(52) U.S. Cl.
CPC ..... *C07J 43/003* (2013.01); *C07H 3/04* (2013.01); *C07H 3/06* (2013.01); *C07H 5/02* (2013.01); *C07H 5/04* (2013.01); *C07H 5/06* (2013.01); *C07H 11/00* (2013.01); *C07H 15/04* (2013.01); *C07H 15/207* (2013.01); *C07H 15/24* (2013.01); *C07H 15/26* (2013.01); *C07H 17/02* (2013.01); *C07J 17/005* (2013.01); *C07J 31/006* (2013.01); *C07J 41/0088* (2013.01); *C07J 41/0094* (2013.01)

(58) Field of Classification Search
CPC ..... C07J 43/003
USPC ..... 514/25
See application file for complete search history.

(56) References Cited

U.S. PATENT DOCUMENTS

| | | | | |
|---|---|---|---|---|
| 5,498,602 | A | 3/1996 | Shoji | |
| 5,563,151 | A | 10/1996 | Bowles | |
| 5,591,835 | A | 1/1997 | Abbas et al. | |
| 5,663,151 | A | 9/1997 | Martel et al. | |
| 5,728,685 | A | 3/1998 | Abbas et al. | |
| 5,739,115 | A | 4/1998 | Fugedi et al. | |
| 5,783,568 | A | 7/1998 | Schlessinger | |
| 6,143,730 | A | 11/2000 | Parish et al. | |
| 6,291,434 | B1 | 9/2001 | Dollings | |
| 6,534,481 | B1 | 3/2003 | Driguez et al. | |
| 7,741,311 | B2 | 6/2010 | Mousa et al. | |
| 7,875,592 | B2 * | 1/2011 | Ferro et al. | C07H 3/04 514/25 |
| 8,173,606 | B2 * | 5/2012 | Ferro et al. | 514/25 |
| 2007/0270354 | A1 | 11/2007 | Petitou et al. | |
| 2015/0065440 | A1 | 3/2015 | Ferro et al. | |

FOREIGN PATENT DOCUMENTS

| | | | |
|---|---|---|---|
| CA | 2105345 | A1 | 3/1994 |
| CN | 1347919 | A | 5/2002 |
| CN | 1450075 | A | 10/2003 |
| EP | 0771815 | A1 | 5/1997 |
| EP | 1908768 | A1 | 4/2008 |
| FR | 2912409 | A1 | 8/2008 |

(Continued)

OTHER PUBLICATIONS

Supplementary European Search Report and Opinion issued in corresponding European Patent Application No. 08839676.7 dated Apr. 4, 2013 and published on May 1, 2013.

Chung and Scanu, Isolation, Molecular Properties, and Kinetic Characterization of Lipoprotein Lipase from Rat Heart, The Journal of Biological Chemistry, 252, 4202-4209, (1977).

Parish et al. (1998) Treatment of Central Nervous System Inflammation with Inhibitors of Basement Membrane Degradation, Immunology and Cell Biology, 76, 104-113.

(Continued)

*Primary Examiner* — Timothy J. Kugel

(74) *Attorney, Agent, or Firm* — McDermott Will & Emery LLP; Richard G. A. Bone

(57) ABSTRACT

The invention relates to novel compounds that have utility as inhibitors of heparan sulfate-binding proteins; compositions comprising the compounds, and use of the compounds and compositions thereof for the antiangiogenic, antimetastatic, anti-inflammatory, antimicrobial, anticoagulant and/or antithrombotic treatment of a mammalian subject.

22 Claims, 92 Drawing Sheets

(56) References Cited

FOREIGN PATENT DOCUMENTS

| | | | |
|---|---|---|---|
| JP | HEI 07-082292 | A | 3/1995 |
| WO | 94/22885 | A1 | 10/1994 |
| WO | 1994/022885 | A1 | 10/1994 |
| WO | 95/18144 | A1 | 7/1995 |
| WO | 1995/018144 | A1 | 7/1995 |
| WO | 95/32717 | A1 | 12/1995 |
| WO | 95/34313 | A1 | 12/1995 |
| WO | 1995/32717 | A1 | 12/1995 |
| WO | 1995/034313 | A1 | 12/1995 |
| WO | 2005/085264 | A1 | 9/2005 |
| WO | 2006/021653 | A2 | 3/2006 |
| WO | 2006/0120576 | A2 | 11/2006 |
| WO | WO2006/120576 | A2 | 11/2006 |

OTHER PUBLICATIONS

Feldman et al. (2000) The Fusion Glycoprotein of Human Respiratory Syncytial Virus Facilitates Virus Attachment and Infectivity via an Interaction with Cellular Heparan Sulfate, Journal of Virology, 6442-6447.

Dredge, et al., "Heparan Sulfate Mimetics—Potent Angiogenesis Inhibitors for Cancer Therapy," Progen Pharmaceuticals, AACR Molecular Cancer Therapeutics Meeting, Oct. 2008.

Boyango, et al., "Heparanase Cooperates with Ras to Drive Breast and Skin Tumorigenesis," Cancer Research, 74, (16), Jun. 26, 2014, pp. 1-11.

Brennan, et al., "Heparan sulfate mimetic PG545-mediated antilymphoma effects require TLR9-dependent NK cell activation," The Journal of Clinical Investigation, 2015, pp. 1-13.

Brennan, et al., "Heparan sulfate mimetic PG545-mediated antilymphoma effects require TLR9-dependent NK cell activation, Supplemental Data," The Journal of Clinical Investigation, 2015, Figures 1-6.

Dredge, et al., "PG545, a dual heparanase and angiogenesis inhibitor, induces potent anti-tumour and anti-metastatic efficacy in preclinical models," British Journal of Cancer, 2011, pp. 1-8.

Dredge, et al., "Table S1—Pharmacokinetic analysis of mean tumor [3H]-PG545 concentrations in mice," British Journal of Cancer, 2011.

Dredge, et al., "Supplementary Methods," British Journal of Cancer, 2011, pp. 1-4.

Dredge, et al., "The PG500 series: novel heparan sulfate mimetics as potent angiogenesis and heparanase inhibitors for cancer therapy," Invest New Drugs, 2009, (28), pp. 276-283.

Dredge, et al., "Table S1: The lethal concentration of PG500 series compounds that kill 50% (LC50) of HUVECs in a 48-hour cytotoxicity assay," Invest New Drugs, 2009.

Dredge, et al., "Fig S1: The effect of PI-88 on experimental lung metastases in the B16 melanoma model," Invest New Drugs, 2009.

Hammond, et al., "PG545, a Heparan Sulfate Mimetic, Reduces Heparanase Expression in Vivo, Blocks Spontaneous Metastases and Enhances Overall Survival in the 4T1 Breast Carcinoma Model," PLoS One, 2012, vol. 7, Issue 12, e52175.

Hua et al., "Synthesis and biological activities of octyl 2,3,4-tri-O-sulfo-α-L-fucopyranosyl-(1→3)-2,4-di-O-sulfo-α-L-fucopyranosyl-(1→3)-2,4-di-O-sulfo-α-L-fucopyranosyl-(1→3)-2,4-di-O-sulfo-β-L-fucopyranoside," Carbohydrate Research, 2014, 339, pp. 867-872.

Jung, et al., "The heparan sulfate mimetic PG545 interferes with Wnt/β-catenin signaling and significantly suppresses pancreatic tumorigenesis alone and in combination with gemcitabine," Oncotarget, 2014, pp. 1-13.

Kurana, et al., "Hypoxia Negatively Regulates Heparan Sulfatase 2 Expression in Renal Cancer Cell Lines," Molecular Carcinogenesis, 2011, pp. 1-11.

Mondal, et al., "HSulf-1 deficiency dictates a metabolic reprogramming of glycolysis and TCA cycle in ovarian cancer," Oncotarget, 2015, pp. 1-15.

Ekblad, Maria; "Anti-herpes simplex virus activities of sulfomannan oligosaccharide PI-88 and disulfated cyclitols"; Institute of Biomedicine, Dept. of Infectious Medicine, Göteborg University; Jun. 20, 2007; 43 pages; http://hdl.handle.net/2077/4600; Abstract.

Levidiotis, V., et al., "A Synthetic Heparanase Inhibitor Reduces Proteinuria in Passive Heymann Nephritis", Journal American Society of Nephrology, vol. 15, 2004 , pp. 2882-2892.

Ferro, V., et al., "The development of inhibitors of heparanase, a key enzyme involved in tumour metastasis, angiogenesis and inflammation", Mini-Reviews in Medical Chemistry, Aug. 2004, vol. 4, No. 6, pp. 693-702.

Karoli, T., et al., "Synthesis, Biological Activity, and Preliminary Pharmacokinetic Evaluation of Analogues of a Phosphosulfomannan Angiogenesis Inhibitor (PI-88)", Journal of Medicinal Chemistry, 2005, vol. 48 No. 26, pp. 5229-8236.

Ferro, V., et al., "Large-scale preparation of the oligosaccharide phosphate fraction of Pichia holstii NRRL Y-2448 phosphomannan for use in the manufacture of IP-88", Carbohydrate Research, May 18, 2001, vol. 332, No. 2 pp. 183-189.

Ahmed, S., et al., "Bisquaternary ammonium salts derived from 3α, 12-α-Diamino-5β-cholane and 3α,12α-Diamino-24-nor-5β-cholane", Australian Journal of Chemistry, 1971, vol. 24, No. 3, pp. 521-547.

Ferro, V., et al. "Synthesis of 2'- and 2"-O-acylated maltotriosides as potential fluorescence-quenched substrates for α-amylase", Journal of the Chemical Society, Perkin Transactions 1, 1994, pp. 2169-2176.

Gunay, N. S., et al., "Heparinoids: Structure, Biological Activities and Therapeutic Applications", Planta Medica, vol. 65, 1999, pp. 301-306.

Min, et al., "Capsaicin Inhibits in Vitro and in Vivo Angiogenesis", Cancer Research, 2004, vol. 64, pp. 644-651.

International Search Report in PCT/AU2008/01535, dated Dec. 12, 2008.

Chen, et al., "An Efficient and Practical Synthesis of α-(1→3)-Linked Mannohexaose and Mannooctaose", Journal of Carbohydrate Chemistry, vol. 21, No. 5, 2002, pp. 341-353.

Jung, et al., "The heparan sulfate mimetic PG545 interferes with Wnt/I3-catenin signaling and significantly suppresses pancreatic tumorigenesis alone and in combination with gemcitabine, Supplemental Material," Oncotarget, 2014, pp. 1-12.

Khurana, et al., "Hypoxia Negatively Regulates Heparan Sulfatase 2 Expression in Renal Cancer Cell Lines," Molecular Carcinogenesis, 2011, pp. 1-11.

Kundu, et al., "Heparanase promotes glioma progression and inversely correlates with patient survival," Progen Pharmaceuticals manuscript, 2016, pp. 1-34.

Ostapoff, et al., "PG545, an Angiogenesis and Heparanase Inhibitor, Reduces Primary Tumor Growth and Metastasis in Experimental Pancreatic Cancer," Molecular Cancer Therapeutics, 2013, 12, (7), pp. 1191-1202.

Shteingauz, et al., "Heparanase Enhances Tumor Growth and Chemoresistance by Promoting Autophagy," Cancer Research, 2015, 75, (18), pp. 1-12.

Weissman, et al., "Heparanase-neutralizing antibodies attenuate lymphoma tumor growth and metastasis," PNAS Early Edition, 2016, pp. 1-6.

Winterhoff, et al., "PG545 enhances anti-cancer activity of chemotherapy in ovarian models and increases surrogate biomarkers such as VEGF in preclinical and clinical plasma samples," European Journal of Cancer, 2015, pp. 1-14.

Non-final office action dated Feb. 1, 2016 in U.S. Appl. No. 14/479,101.

(56) References Cited

OTHER PUBLICATIONS

Final office action dated Jul. 28, 2016 in U.S. Appl. No. 14/479,101.
Holland, et al., "Herpes simplex virus type 1 glycoprotein C-negative mutants exhibit multiple phenotypes, including secretion of truncated glycoproteins", Journal of Virology, Nov. 1984, vol. 52, No. 2, pp. 566-574.
CAS Registry No. 758666-32-9, Entry Date, Oct. 8, 2004.
CAS Registry No. 156706-87-5, Entry Date, Jul. 29, 1994.
Pazur, J. H., "Maltotriose", Digestion of Amylose with Salivary Amylase, Methods Carbohydr. Chem., vol. 1, 1962, p. 337.
Hallak, L.K. et al., "Iduronic Acid-Containing Glycosaminoglycans on Target Cells are Required for Efficient Respiratory Syncytial Virus Infection", Virology, vol. 271, No. 2, 2000, pp. 264-275, (DOI: 10.1006/viro.2000.0293).
Karger, A. et al., "Glycoproteins gIII and gp50 Play Dominant Roles in the Biphasic Attachment of Pseudorabies Virus", Virology, vol. 194, No. 2, 1993, pp. 654-664, (DOI: 10.1006/viro.1993.1305.).
Parish, et al., "Identification of Sulfated Oligosaccharide-based Inhibitors of Tumor Growth and Metastasis Using Novel in Vitro Assays for Angiogenesis and Heparanase Activity", Cancer Research 1999, Published Jul. 1, 1999, vol. 59. pp. 3433-3441.
Iversen, et al., "Inhibitors of angiogenesis selectively reduce the malignant cell load in rodent models of human myeloid leukemias", Leukemia, 2002, vol. 16, No. 3, pp. 376-381.
Baskaran, et al., "Glycosaminoglycan-Mimetic Biomaterials. 3. Glycopolymers Prepared from Alkene-Derivatized Mono- and Disaccharide-Based Glycomoncimers", Bioconjugate Chemistry, 2002, vol. 13, No. 6, pp. 1309-1313.
Joyce, et al., "A functional heparan sulfate mimetic implicates both heparanase and heparan sulfate in tumor angiogenesis and invasion in a mouse model of multistage cancer", Oncogene, Apr. 4, 2005, vol. 24, pp. 4037-4051.
Basche, et al., "A Phase I Biological and Pharmacologic Study of the Heparanase Inhibitor PI-88 in Patients with Advanced Solid Tumors", Clin Cancer Res., Sep. 15, 2006,vol. 12, pp. 5471-5480.
Ferro, et al., "PI-88 and Novel Heparan Sulfate Mimetics Inhibit Angiogenesis", Seminar Thrombosis and Hemostatis, 2007; vol. 33, No. 5, pp. 557-568.
Ferro, et al., "Determination of the composition of the oligosaccharide phosphate fraction of *Pichia* (Hansenula) *holstii* NRRL Y-2448 phosphomannan by capillary electrophoresis and HPLC", Carbohydrate Research, vol. 337, No. 2, Feb. 5, 2002, pp. 139-146.
Yu, et al., "Preparation and anticoagulant activity of the phosphosulfomannan PI-88", European Journal of Medical Chemistry, Oct. 2002, vol. 37 No. 10, pp. 783-791.
Cochran, et al., "Probing the Interactions of Phosphosulfomannans with Angiogenic Growth Factors by Surface Plasmon Resonance", Journal of Medicinal Chemistry, Oct. 9, 2003. vol. 46, No. 21, pp. 4601-4608.
Vlodavsky, et al., "Molecular properties and involvement of heparanase in cancer metastasis and angiogenesis", Journal of Clinical Investigation, Aug. 1, 2001, vol. 108, No. 3 , pp. 341-347.
Parish, C.R., et al., "Heparanase: a key enzyme involved in cell invasion", Biochim Biophys Acta. Mar. 21, 2001 vol. 1471, No. 3, pp. M99-M108.
Demir, M., et al., "Anticoagulant and Antiprotease Profiles of a Novel Natural Heparinomimetic Mannopentaose Phosphate Sulfate (PI-88)", Clin Appl Thromb Hemost Apr. 2001. vol. 7, pp. 131-140.
Wall, D., et al., "Characterisation of the Anticoagulant Properties of a Range of Structurally Diverse Sulfated Oligosaccharides", Thrombosis Research, vol. 103, No. 4, Aug. 15, 2001, pp. 325-335.
Hembrough, Todd A., et al., "Tissue Factor Pathway Inhibitor Inhibits Endothelial Cell Proliferation via Association with the Very Low Density Lipoprotein Receptor", J. Biol. Chem., Jan. 17, 2001, vol. 276, pp. 12241-12248.
Amirkhosravi, A., et al., "Tissue factor pathway inhibitor reduces experimental lung metastasis of B16 melanoma", Thromb Haemost., Jun. 2002, vol. 87, No. 6, pp. 930-936.
Francis, D.J., et al., "Blockade of Vascular Smooth Muscle Cell Proliferation and Intimal Thickening After Balloon Injury by the Sulfated Oligosaccharide PI-88: Phosphomannopentaose Sulfate Directly Binds FGF-2, Blocks Cellular Signaling, and Inhibits Proliferation", Circulation Research., Apr. 10, 2003, vol. 92, pp. e70-e77.
Nyberg, K., et al., "The low molecular weight heparan sulfate-mimetic, PI-88, inhibits cell-to-cell spread of herpes simplex virus", Antiviral Research, vol. 63, No. 1, Jul. 2004, pp. 15-24.
Lee, E., et al., "Antiviral effect of the heparan sulfate mimetic, PI-88, against dengue and encephalitic flaviviruses", Antiviral Research, vol. 69, No. 1, Jan. 2006, pp. 31-38.
Adams, Y., et al., "Inhibition of *Plasmodium falciparum* Growth In Vitro and Adhesion to Chondroitin-4-Sulfate by the Heparan Sulfate Mimetic PI-88 and Other Sulfated Oligosaccharides", Antimicrobial Agents and Chemotherapy, Aug. 2006, vol. 50, No. 8, pp. 2850-2852.
Foxall, C., et al., "Sulfated malto-oligosaccharides bind to basic FGF, inhibit endothelial cell proliferation, and disrupt endothelial cell tube formation", Journal of Cellular Physiology, vol. 168, No. 3, Sep. 1996, pp. 657-667.
Katsuraya, K., et al., "Synthesis of sulfated oligosaccharide glycosides having high anti-HIV activity and the relationship between activity and chemical structure", Carbohydr Res. Feb. 28, 1999, vol. 315, No. 3-4, pp. 234-242.
Wessel, H. P., "Heparinoid Mimetics", Topics in Current Chemistry 1997, vol. 187, pp. 215-239.
Farndale, R. W., et al. "Improved quantitation and discrimination of sulphated glycosaminoglycans by use of dimethylmethylene blue", Biochimica et Biophysica Acta (BBA)—General Subjects, Sep. 4, 1986 vol. 883, No. 2, pp. 173-177.
Aucagne, V., et al., "Catalytic "Click" Rotaxanes: A Substoichiometric Metal-Template Pathway to Mechanically Interlocked Architectures", Journal of the American Chemical Society, 2006, vol. 128, No. 7, pp. 2186-2187.
Dubber, M., et al., "Synthesis of Carbohydrate-Centered Oligosaccharide Mimetics Equipped with a Functionalized Tether", The Journal of Organic Chemistry, 2000, vol. 65, No. 17, pp. 5275-5281.
Fairweather, J. K., et al. "The synthesis of phosphorylated disaccharide components of the extracellular phosphomannan of *Pichia* (Hansenula) *holstii* NRRL Y-2448", Bioorganic & Medicinal Chemistry, Dec. 1, 2004, vol. 12, No. 23, pp. 6063-6075.
Narumi, A., et al., "End-Functionalization of Polystyrenes by Malto-oligosaccharides Generating Aggregation-Tunable Polymeric Reverse Micelle", Journal of Polymer Science Part A: Polymer Chemistry, 2006, vol. 44, pp. 4864-4879.
Bisio, A., et al., "High-performance liquid chromatographic/mass spectrometric studies on the susceptibility of heparin species to cleavage by heparanase", Seminars in Thrombosis and Hemostasis, Jul. 2007 vol. 33 No. 5, pp. 488-495.
Malinda, K. M., et al., "Identification of laminin α1 and β1 chain peptides active for endothelial cell adhesion, tube formation, and aortic sprouting", Faseb Journal, Jan. 1, 1999 vol. 13, pp. 53-62.
Nicosia, R.F., et al. "Growth of microvessels in serum-free matrix culture of rat aorta. A quantitative assay of angiogenesis in vitro", Lab. Invest., 1990, vol. 63, pp. 115-122.
Dredge, et al., "Novel thalidomide analogues display anti-angiogenic activity independently of immunomodulatory effects", British Journal of Cancer, 2002, vol. 87, pp. 1166-1172.
Ng, et al., "Antitumor Effects of Thalidomide Analogs in Human Prostate Cancer Xenografts Implanted in Immunodeficient Mice", Clinical Cancer Research, 2004, vol. 10, pp. 4192-4197.
Rapp, et al., "Absence of Leukosis Virus Markers in Hamster Cells Transformed by Herpes Simplex Virus Type 2", Journal of Virology, Jun. 1972, vol. 9, No. 6, pp. 1059-1063.
Lewis, et al., "A syncytial virus associated with epidemic disease of the lower respiratory tract in infants and young children", The Medical Journal of Australia, 1961, vol. 2, pp. 932-933.
Hallak, et al., "Glycosaminoglycan Sulfation Requirements for Respiratory Syncytial Virus Infection", Journal of Virology, Nov. 2000, vol. 74, No. 22, pp. 10508-10513.
Gupta, et al., "Stabilization of respiratory syncytial virus (RSV) against thermal inactivation and freeze-thaw cycles for development and control of RSV vaccines and immune globulin", Vaccine, 1996, vol. 14, pp. 1417-1420.

(56) References Cited

OTHER PUBLICATIONS

Karger, et al., "Cell surface proteoglycans are not essential for infection by pseudorabies virus", Journal of Virology, Jun. 1995, vol. 69, No. 6, pp. 3482-3489.

Trybala, et al., "Herpes Simplex Virus Types 1 and 2 Differ in Their Interaction with Heparan Sulfate", Journal of Virology, Oct. 2000, vol. 74, No. 19, pp. 9106-9114.

Guan, et al., "A Glycopolymer Chaperone for Fibroblast Growth Factor-2", Bioconjugate Chemistry, 2004, vol. 15, No. 1, pp. 145-151.

Mousa, et al., "Synthetic oligosaccharide stimulates and stabilizes angiogenesis: structure-function relationships and potential mechanisms", Journal of Cardiovascular Pharmacology, Aug. 2006, vol. 48, No. 2, pp. 6-13.

Gunalp, "Growth and Cytopathic Effect of Rubella Virus in a Line of Green Monkey Kidney Cells", Proceedings of the Society for Experimental Biology and Medicine, 1965, vol. 118, pp. 85-90.

Vlodavsky, et al., "Heparanase: Structure, Biological Functions, and Inhibition by Heparin-Derived Mimetics of Heparan Sulfate", Current Pharmaceutical Design, 2007, vol. 13, No. 20, pp. 2057-2073.

Yeh, et al., "Structural Basis for Activation of Fibroblast Growth Factor Signaling by Sucrose Octasulfate", Molecular and Cellular Biology, 2002, vol. 22, No. 20, pp. 7184-7192.

* cited by examiner

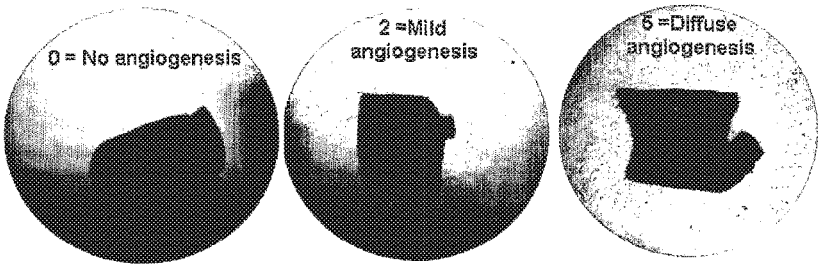
Figure 1: Examples of the extent of angiogenic sprouting in the rat aortic angiogenesis assay.
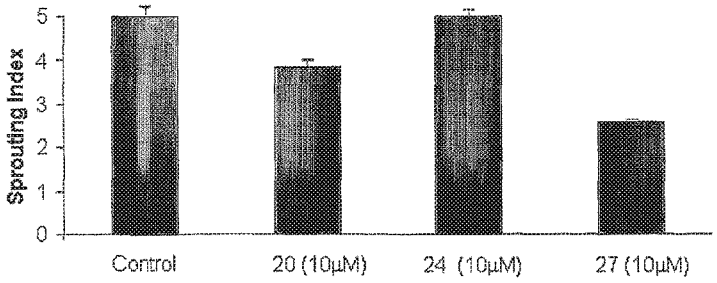
Figure 2: Extent of angiogenesis in aortic cultures.

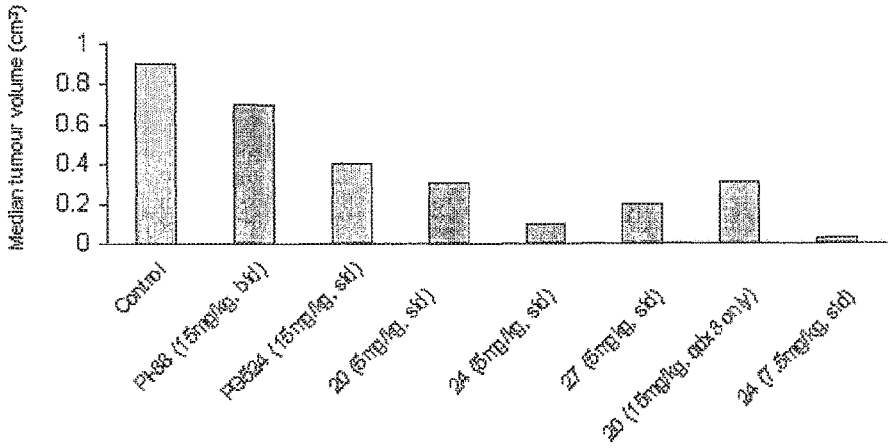
Figure 3: Median tumour volumes of untreated controls, PI-88, analogue PG524 and selected test compounds.

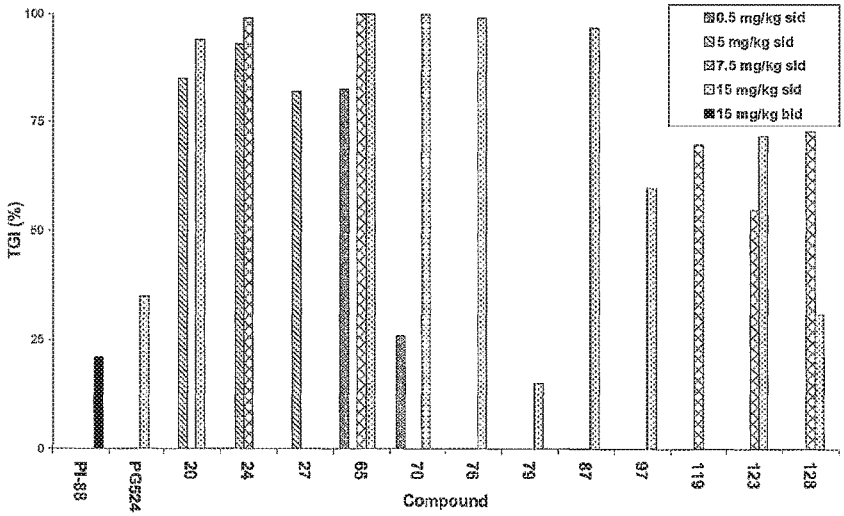
Figure 4: Percent tumour growth inhibition (%TGI) data from tumour bearing mice treated with PI-88, analogue PG524 and selected test compounds.
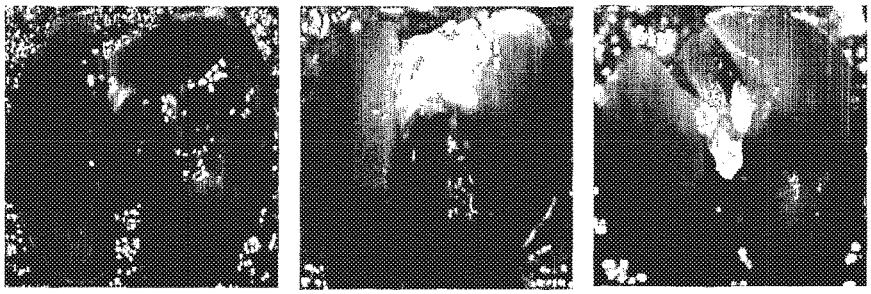
Control (PBS) | PI-88 30mg/kg | 65 10mg/kg
Figure 5: Examples of test compounds blocking the formation of lung colonies (dark spots) of B16F1 melanoma cells in mice.

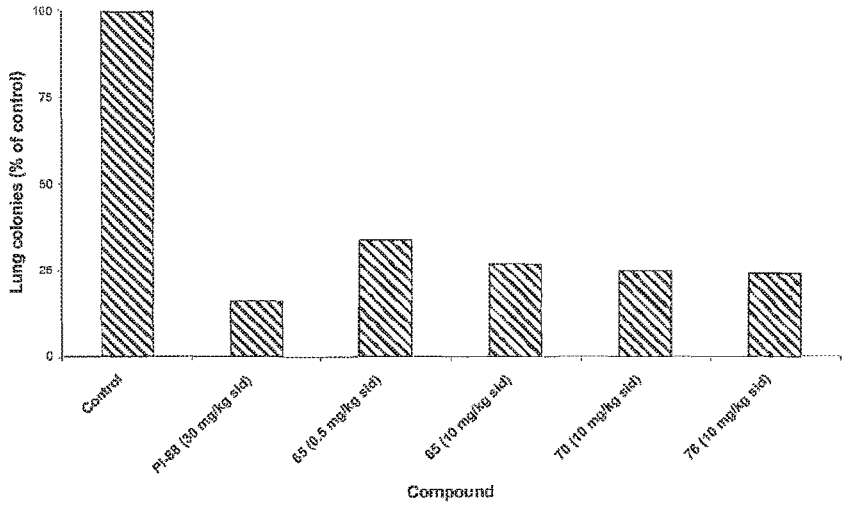
Figure 6: Metastatic nodule in mice treated with PI-88 and the selected compounds.
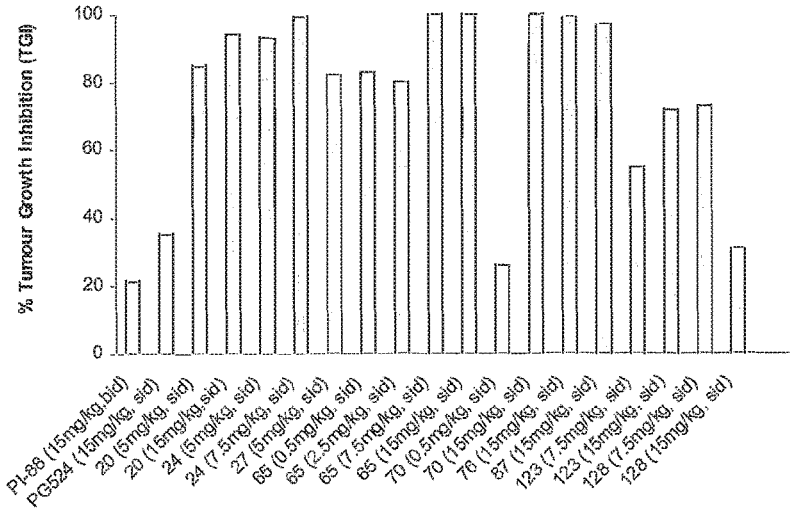
Figure 7: Percent tumour growth inhibition (%TGI) data from the colorectal cancer HT29 xenograft model.

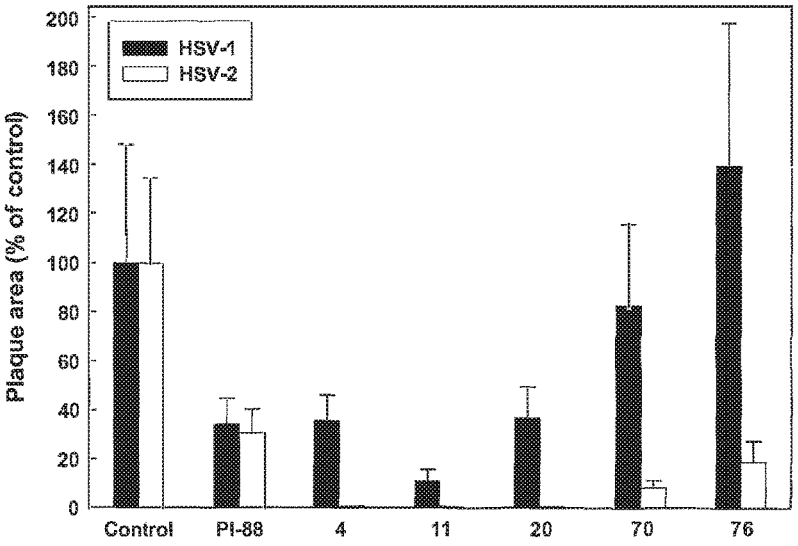
Figure 8: Effect of test compounds on the cell-to-cell transmission of HSV.

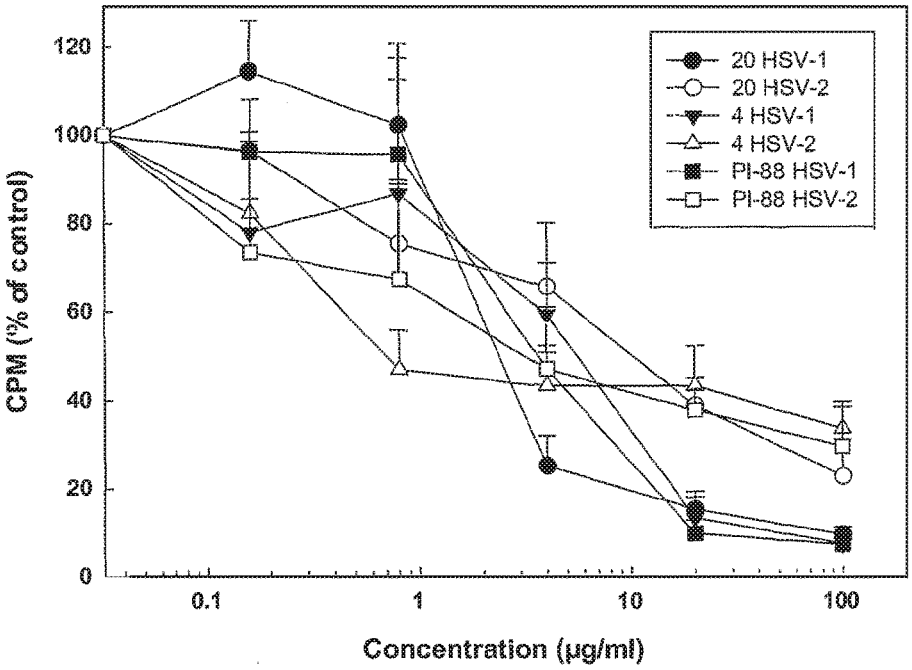
Figure 9: Effect of test compounds on the binding of HSV virions to the cells.

9

14

82

106

Figure 37C;
133
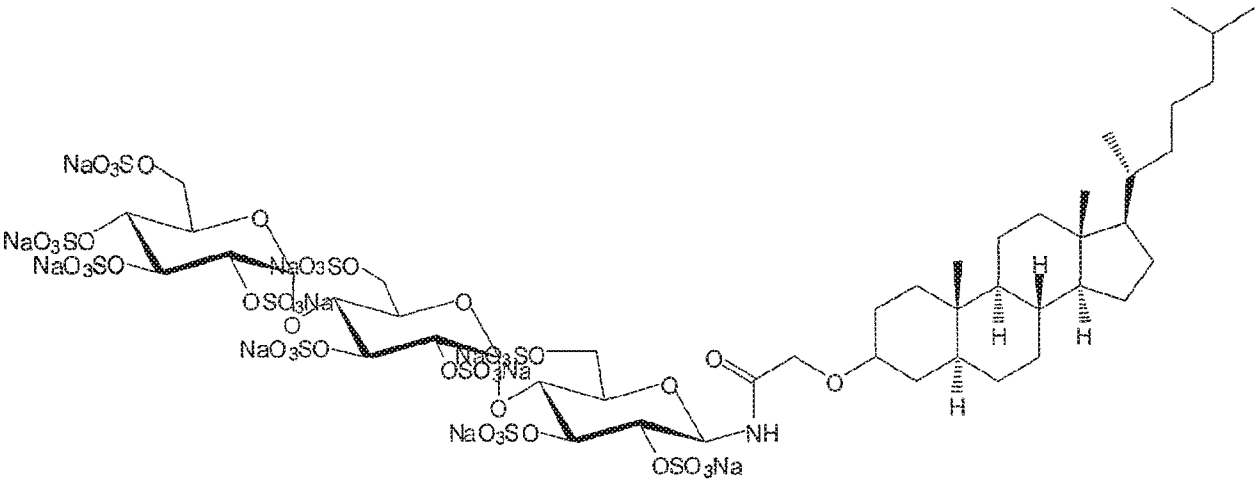
134

142

143

SULFATED OLIGOSACCHARIDE DERIVATIVES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The invention described herein relates to compounds having activity as inhibitors of heparan sulfate-binding proteins, including the enzyme heparanase. In particular, the invention is directed to sulfated oligosaccharide derivatives, although the scope of the invention is not necessarily limited thereto. Specifically, the invention relates to polysulfated oligosaccharides modified with specific, highly lipophilic groups. The invention also relates to methods for the preparation of the compounds, compositions comprising the compounds, and use of the compounds and compositions thereof for the antiangiogenic, antimetastatic, antiinflammatory, antimicrobial, anticoagulant and/or antithrombotic treatment of a mammalian subject. The compounds additionally have utility in the prevention of the foregoing disorders when administered to a mammalian subject.

BACKGROUND ART

The sulfated oligosaccharide agent known as PI-88[1,2] is a promising inhibitor of tumour growth and metastasis[3,4,1] and has undergone clinical trials in cancer patients[5,6]. PI-88 is a mixture of highly sulfated, monophosphorylated mannose oligosaccharides ranging in size from di- to hexasaccharide[7,8]. PI-88 exerts antiangiogenic effects by inhibiting the interactions of angiogenic growth factors (principally FGF-1, FGF-2 and VEGF) and their receptors with heparan sulfate[9,1]. In addition, PI-88 is a potent inhibitor of the enzyme heparanase, a glycosidase that cleaves the heparan sulfate side chains of proteoglycans that are a major constituent of the extracellular matrix (ECM) and basement membranes surrounding tumour cells[1,2]. Heparanase has been strongly implicated in angiogenesis: it is able to liberate active heparan sulfate-bound angiogenic growth factors from the ECM and is involved in the degradation of the ECM and subsequent tissue remodeling associated with the sprouting of new blood vessels[10]. The degradation of the ECM by heparanase is also crucial in the spread of tumour cells (metastasis) by allowing them to pass into the blood stream and lodge in remote sites where they can form secondary tumours[11,10].

In addition to its antiangiogenic effects, PI-88 inhibits the blood coagulation cascade by (i) inhibiting proteases in the intrinsic pathway, (ii) stimulating the release of tissue factor pathway inhibitor (TFPI), and (iii) activating the heparin cofactor II-mediated inhibition of thrombin. However, PI-88 does not interact with AT III and thus shows no anti-Xa or AT III-mediated anti-IIa activityl[2,13]. In vivo studies in monkeys have shown that low doses of PI-88 stimulate release of all heparan sulfate bound TFPI from the vascular cell wall[12]. Apart from its effect on coagulation, TFPI is also an antiangiogenic agent[14] and an inhibitor of metastasis[15]. PI-88 has also been shown to block vascular smooth muscle cell proliferation and intimal thickening[16], to inhibit herpes simplex virus (HSV) infection of cells and the cell-to-cell spread of HSV-1 and HSV-2[17], to inhibit infectivity and improve survival in murine models of dengue and encephalitic flaviviruses,[18] to inhibit proteinuria in passive Heymann nephritis[19] and to display in vitro antimalarial activity against Plasmodium falciparum[20].

Various other polysulfated oligo- and polysaccharides and their derivatives are well known to exhibit similar types of biological activities to PI-88[21-26]. These biological activities are attributed to the inhibition of various heparan sulfate (HS)-binding proteins. Recently, some sulfated oligosaccharide derivatives were disclosed with improved pharmacokinetic and/or ADME (absorption, distribution, metabolism, excretion) profiles[27,28]. The compounds comprised a single carbon skeleton and thus also provide synthesis and characterization advantages over mixtures such as PI-88.

The object of the present invention is the creation of HS-mimetics with even greater potency, improved pharmacokinetic properties and a reduced side effect profile.

SUMMARY OF THE INVENTION

According to a first embodiment of the invention, there is provided a compound of the general formula:

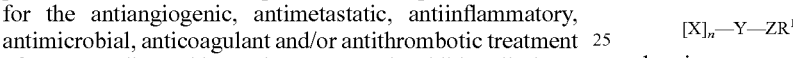

$$[X]_n—Y—ZR^1R^2 \quad \text{I}$$

wherein:

X and Y are each a monosaccharide unit wherein each hydroxyl group not involved in a glycosidic linkage is substituted independently by a group $SO_3M$ or H, where M is any pharmaceutically acceptable cation;

X and Y are any D- or L-hexose or pentose;

Y is in a cyclic or ring opened form;

Z is O, N, S or C or their higher oxidation states, or a bond, and is linked to the anomeric carbon when Y is a reducing monosaccharide;

$R^1$ is a linker selected from the group including alkyl, alkenyl, alkynyl, aryl, heteroalkyl, heteroaryl, acyl, aroyl, alkylamido, alkylthioamido, triazolyl, or is a bond;

$R^2$ is a lipophilic moiety selected from the group including cholesteryl, cholestanyl, cholate, deoxycholate, straight chain alkyl, branched alkyl, substituted alkyl, straight chain acyl, branched acyl, substituted acyl;

n is an integer from 0-6;

the level of sulfation of each compound is between 70 and 100% of the total hydroxyl groups, wherein When $R^1$ is a bond, then $R^2$ is not glycyrrhetinic acid or derivatives thereof;

When $R^1$ is a bond, and n=0 or 1, and Z is S, then $R^2$ is not C8 or C18 straight chain alkyl group;

When n is 3-6, and $R^1$ is a bond, and X and Y are $\alpha(1\rightarrow4)$-linked glucose, then $R^2$ is not a C12 to C18 straight chain alkyl group;

When n is 3-5, and $R^1$ is a bond, and X and Y are $\beta(1\rightarrow3)$-linked glucose, then $R^2$ is not a C4 to C12 straight chain alkyl group or cholesteryl group; and When X and Y are ribose, and $R^1$ is a bond, then $R^2$ is not a C18 group.

According to a second embodiment of the invention, there is provided a pharmaceutical or veterinary composition for the prevention or treatment in a mammalian subject of a disorder resulting from angiogenesis, metastasis, inflammation, coagulation/thrombosis, raised blood triglyceride levels, microbial infection and/or cardiovascular disease, which composition comprises at least one compound according to the first embodiment together with a pharmaceutically or veterinarially acceptable carrier or diluent for at least one said compound.

A third embodiment of the invention comprises the use of a compound according to Formula II in the manufacture of a medicament for the prevention or treatment in a mammalian subject of a disorder resulting from angiogenesis, metastasis, inflammation, coagulation/thrombosis, raised blood triglyceride levels, microbial infection and/or cardiovascular disease:

$$[X]_n—Y—ZR^1R^2 \quad \text{II}$$

wherein:

X and Y are each a monosaccharide unit wherein each hydroxyl group not involved in a glycosidic linkage is substituted independently by a group $SO_3M$ or H, where M is any pharmaceutically acceptable cation;

X and Y are any D- or L-hexose or pentose;

Y is in a cyclic or ring opened form;

Z is O, N, S or C or their higher oxidation states, or a bond, and is linked to the anomeric carbon when Y is a reducing monosaccharide;

$R^1$ is a linker selected from the group including alkyl, alkenyl, alkynyl, aryl, heteroalkyl, heteroaryl, acyl, aroyl, alkylamido, alkylthioamido, triazolyl, or is a bond;

$R^2$ is a lipophilic moiety selected from the group including cholesteryl, cholestanyl, cholate, deoxycholate, straight chain alkyl, branched alkyl, substituted alkyl, straight chain acyl, branched acyl, substituted acyl;

n is an integer from 0-6; and the level of sulfation of each compound is between 70 and 100% of the total hydroxyl groups.

According to a fourth embodiment of the invention there is provided a method for the prevention or treatment in a mammalian subject of a disorder resulting from angiogenesis, metastasis, inflammation, coagulation/thrombosis, raised blood triglyceride levels, microbial infection and/or cardiovascular disease, which method comprises administering to the subject an effective amount of at least one compound according to Formula II, or a composition comprising said at least one compound.

In order that the invention may be more readily understood and put into practice, one or more preferred embodiments thereof will now be described, by way of example only, with reference to the accompanying figures.

BRIEF DESCRIPTION OF THE DRAWINGS

FIG. 1 shows examples of the extent of angiogenic sprouting in the rat aortic angiogenesis assay used to demonstrate the antiangiogenic activity of the compounds.

FIG. 2 shows the data for aortic cultures treated with media (for untreated control group) or test compounds every 48 days from day 0 for 7 days. On day 7, VEGF (10 mg/mL) was added to cultures every 2-3 days for a further 7 days and the extent of angiogenesis was then scored, thus demonstrating that the compounds exert their inhibitory effects via an antiangiogenic mechanism as opposed to the induction of a toxic effect on the tissue. All three compounds potently inhibited angiogenesis (see Table 4).

FIG. 3 shows median tumour volumes of untreated control mice and of mice treated with selected test compounds in the B16 mouse melanoma model. Despite dose levels being reduced for the compounds of the invention, or limited duration of exposure, anti-tumour activity was still increased in comparison to PI-88 or non-lipophilic analogues. Bid=bis in die (twice daily), sid=semel in die (once daily), qd=quaque die (each day).

FIG. 4 shows the percentage of tumour growth inhibition (% TGI) data from tumour bearing mice treated with selected test compounds in the B16 mouse melanoma model. Despite dose levels being reduced for the compounds of the invention, % TGI values were still improved in comparison to PI-88 or non-lipophilic analogues. bid=his in die (twice daily), sid=semel in die (once daily).

FIG. 5 shows examples of the test compounds blocking the formation of lung colonies of B16F1 melanoma cells in mice. Compounds and doses administered are described below each image.

FIG. 6 shows the number of lung metastatic nodules as a percentage compared to the saline control with selected test compounds in the B16 lung metastases model. Mice treated with PI-88 and the selected compounds displayed fewer lung metastatic nodules when compared to saline control. Despite dose levels being reduced in most instances for the compounds of the invention, inhibition of metastases was still similar to that observed with higher dosages of PI-88. bid=his in die (twice daily), sid=semel in die (once daily).

FIG. 7 shows the percentage of tumour growth inhibition (% TGI) data from tumour bearing mice treated with selected test compounds in the colorectal cancer HT29 xenograft model. Despite dose levels being reduced for the compounds of the invention, % TGI values were still improved in comparison to PI-88 or non-lipophilic analogues. bid=bis in die (twice daily), sid=semel in die (once daily).

FIG. 8 shows the effect of test compounds on the cell-to-cell transmission of HSV. The cells were infected with ~200 PFU of either HSV-1 or HSV-2, and then overlaid with EMEM supplemented with 1% methylcellulose and 10 μg/ml of test compound. The results are expressed as a percentage of the average area of viral plaques developed in drug-treated cells relative to mock-treated controls. Images of twenty viral plaques were captured and subjected to area determinations using the IM500 software.

FIG. 9 shows the effect of test compounds on the binding of HSV virions to cells. Test compounds at specific concentrations were incubated at 4° C. with methyl-[$^3$H]thymidine labeled HSV-1 or HSV-2 during a 2 h period of virus adsorption to GMK AH1 cells. The results are expressed as a percentage of attached viral cpm found with compound-treated virions relative to mock-treated controls. In experiments with compound 4, the mean number of attached cpm of mock-treated virus that attached to cells at 4° C. was 4263 for HSV-1 and 1742 for HSV-2. Values shown are means of four determinations from two separate experiments.

DETAILED DESCRIPTION OF PREFERRED EMBODIMENTS

Figure 10A:
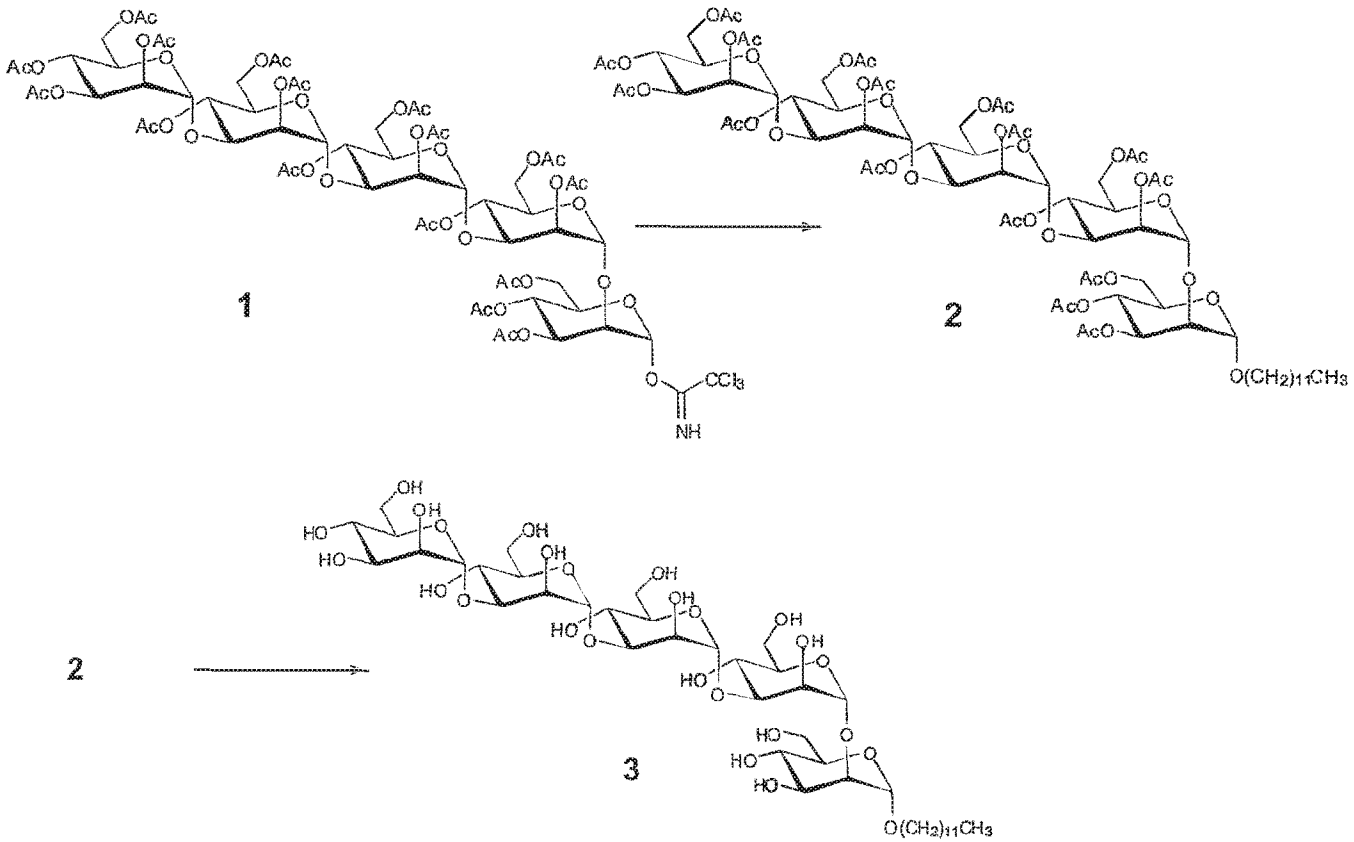
FIGS. 10 to 40 show reaction schemes and chemical structures of the invention.
Figure 10B:
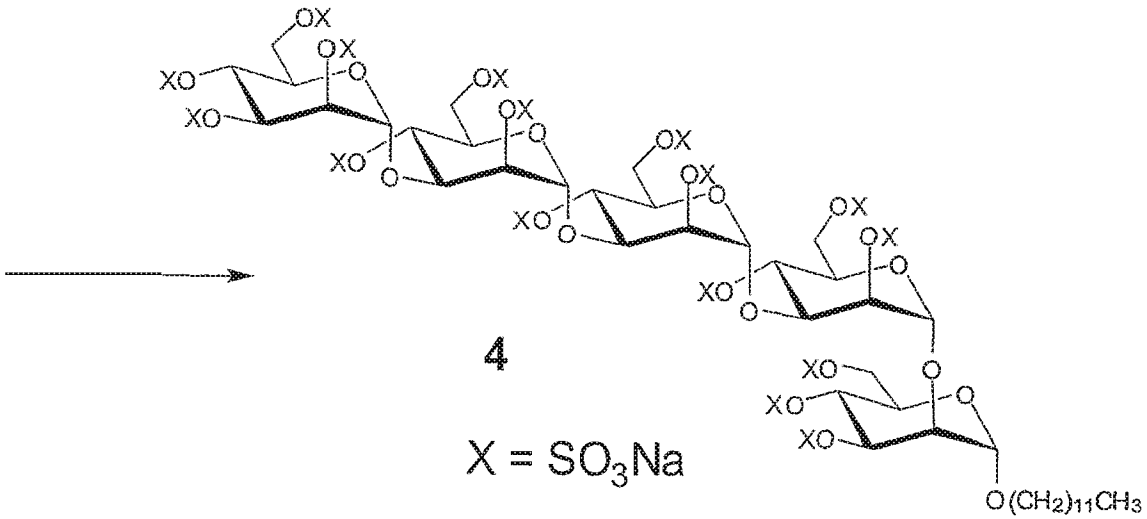
Figure 11A:
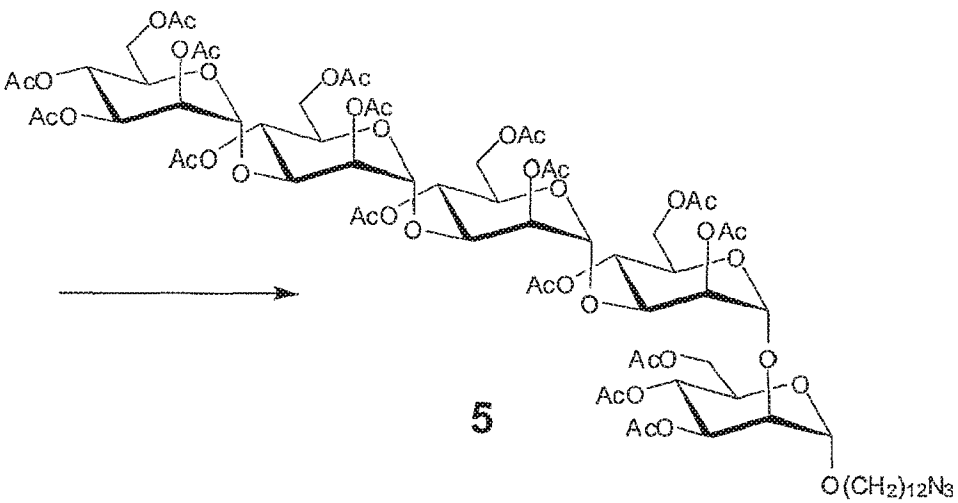
Figure 11B:
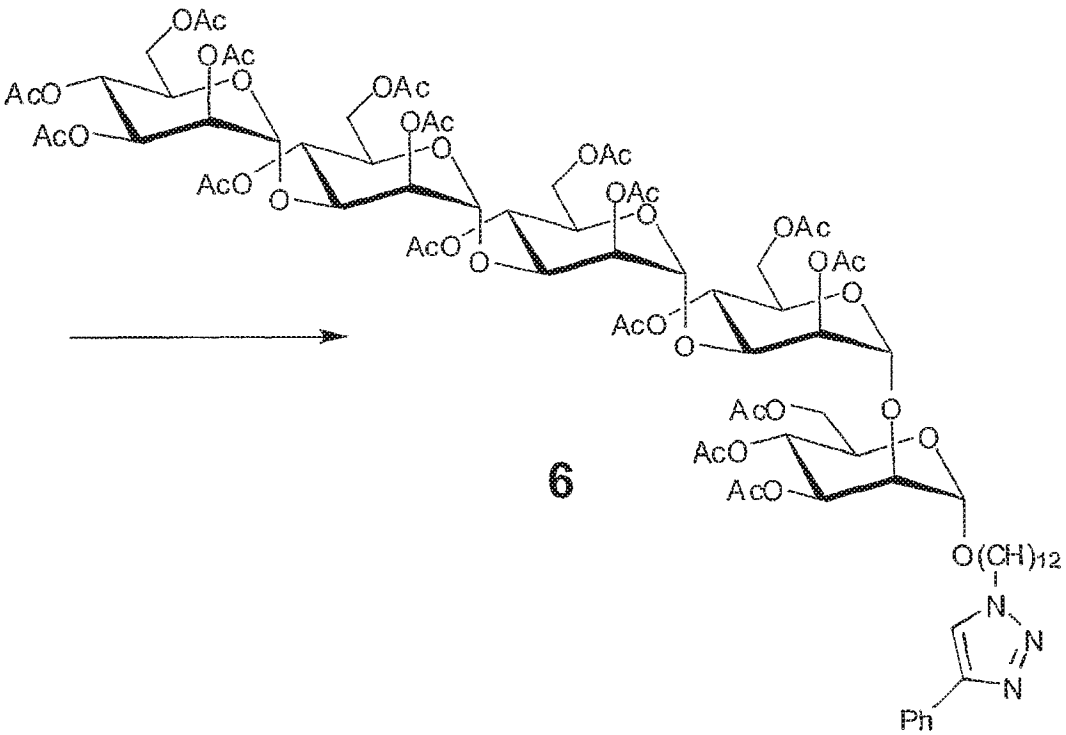
Figure 11C:
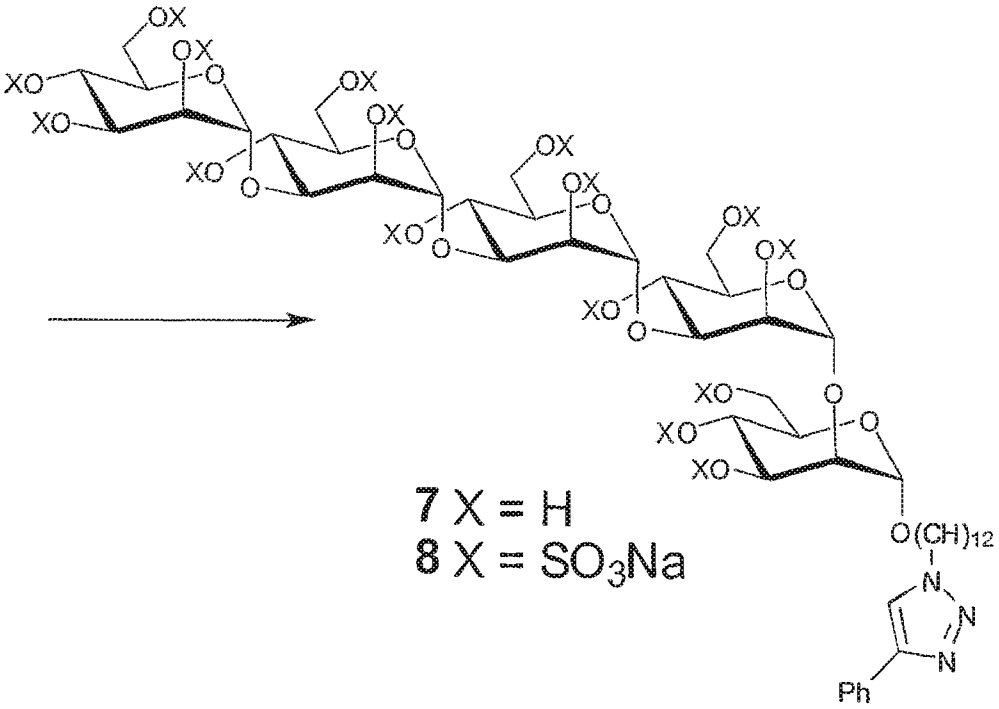
Figure 12A:
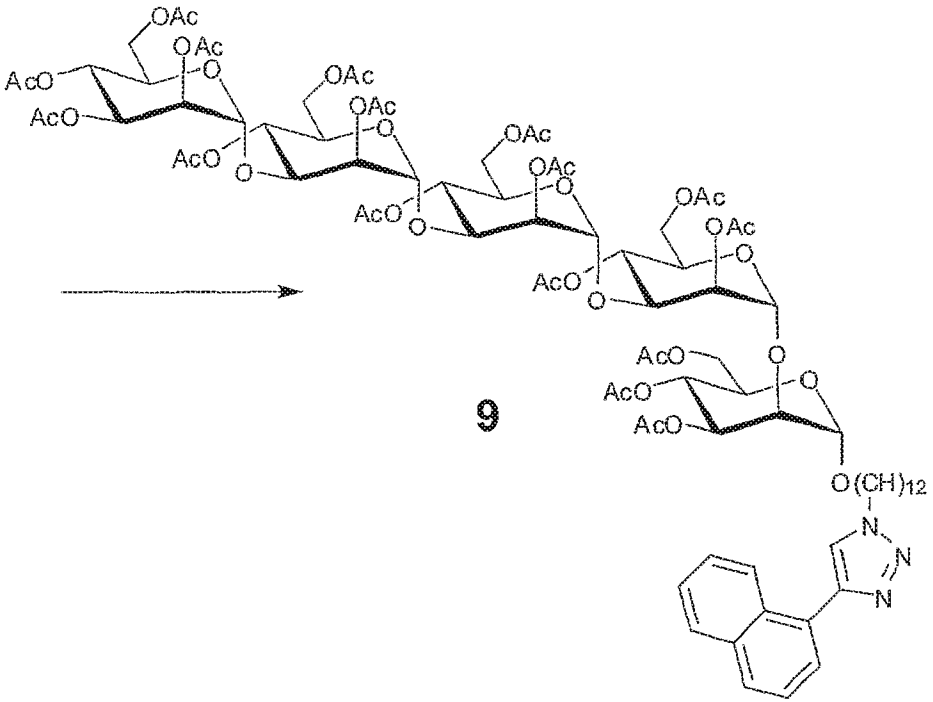
Figure 12B:
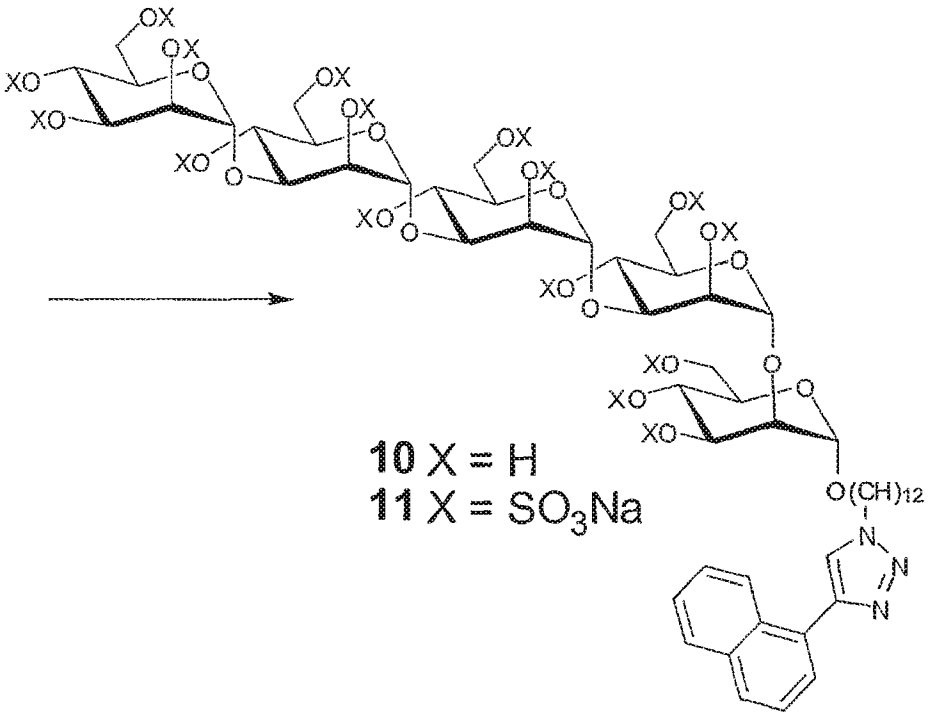
Figure 13A:
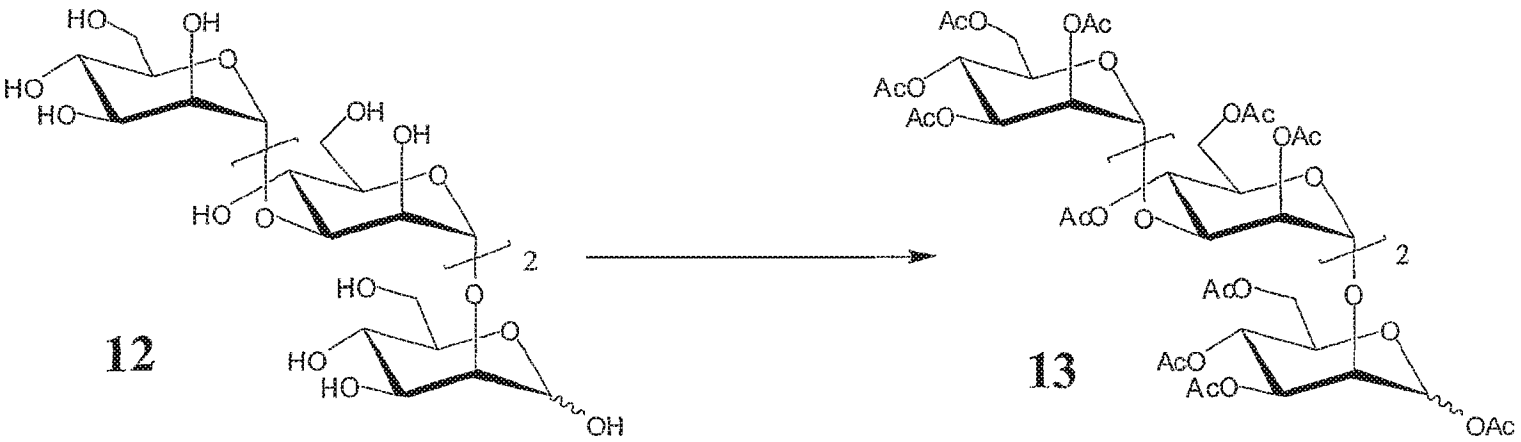
Figure 13B:
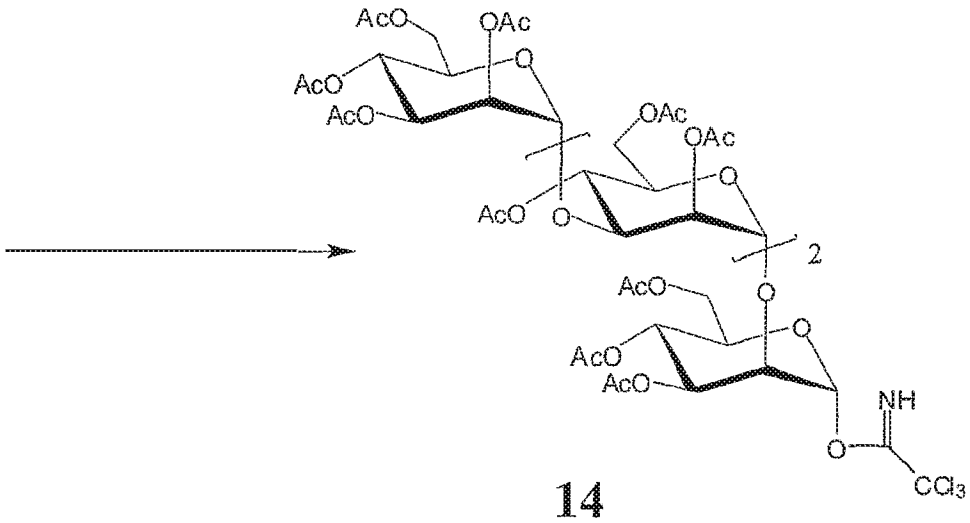
Figure 13C:
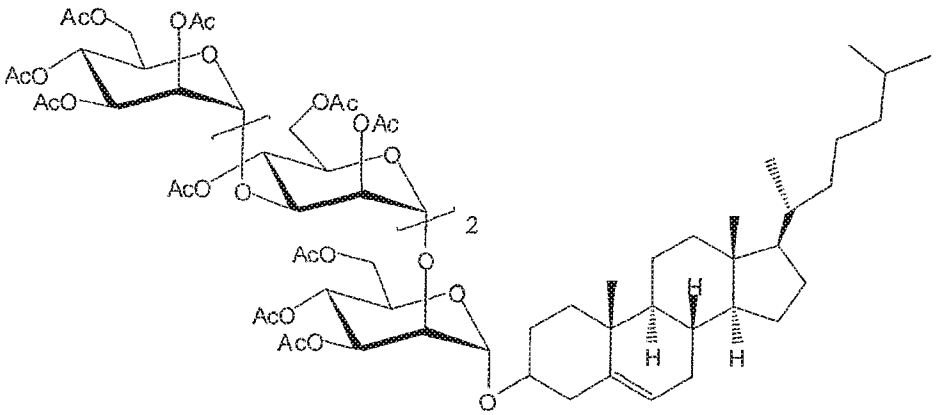
Figure 13D:
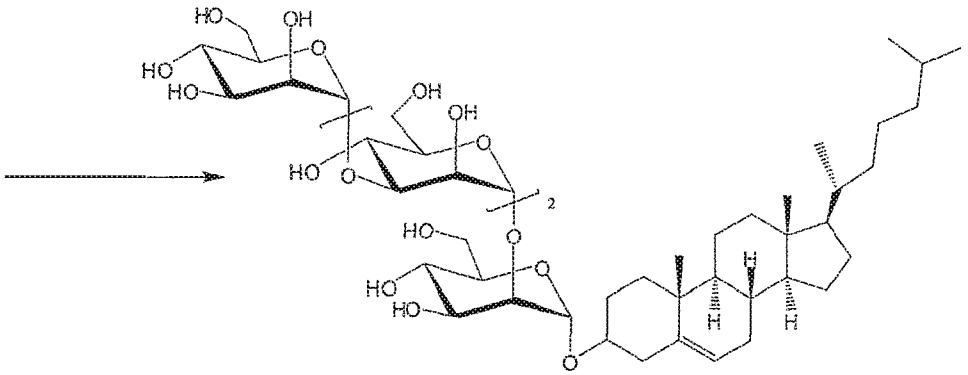
Figure 13E:
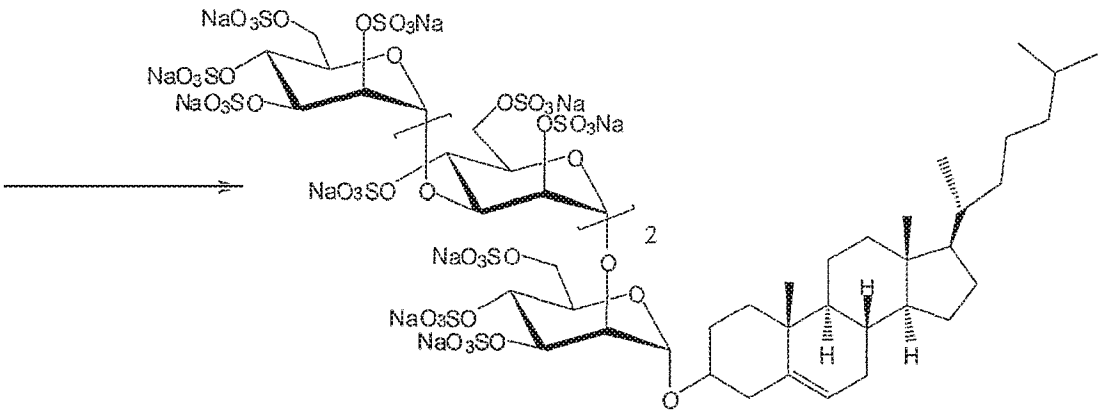
Figure 14A:
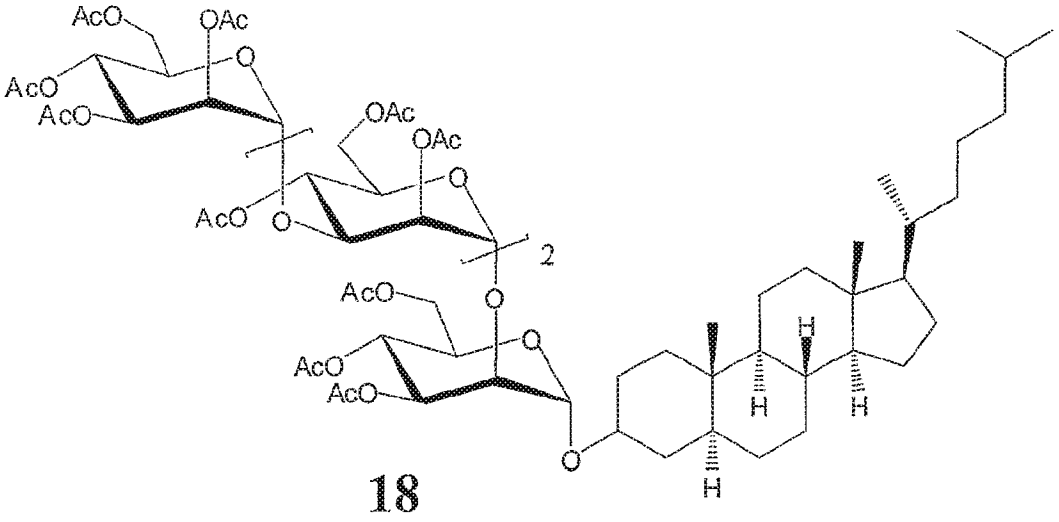
Figure 14B:
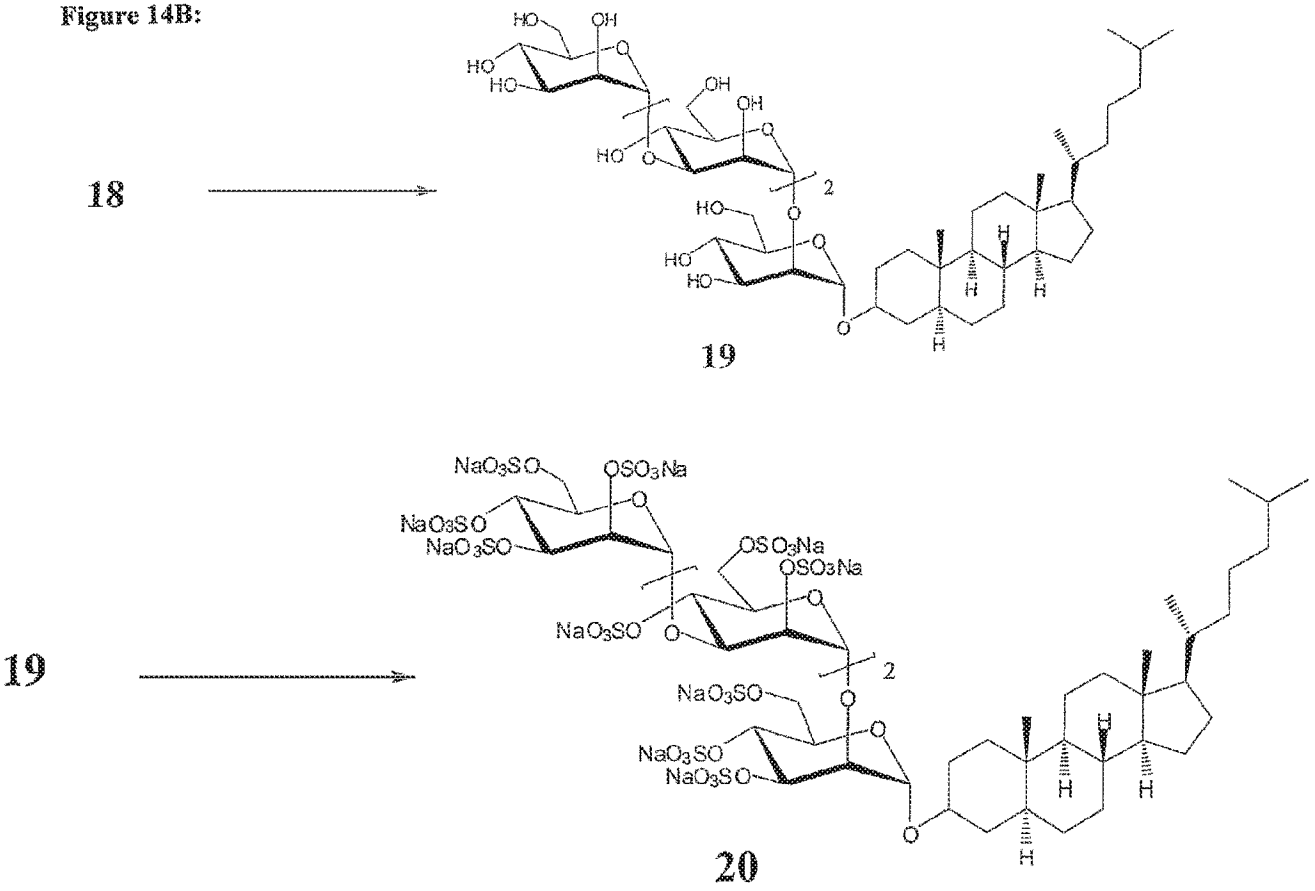
Figure 15A:
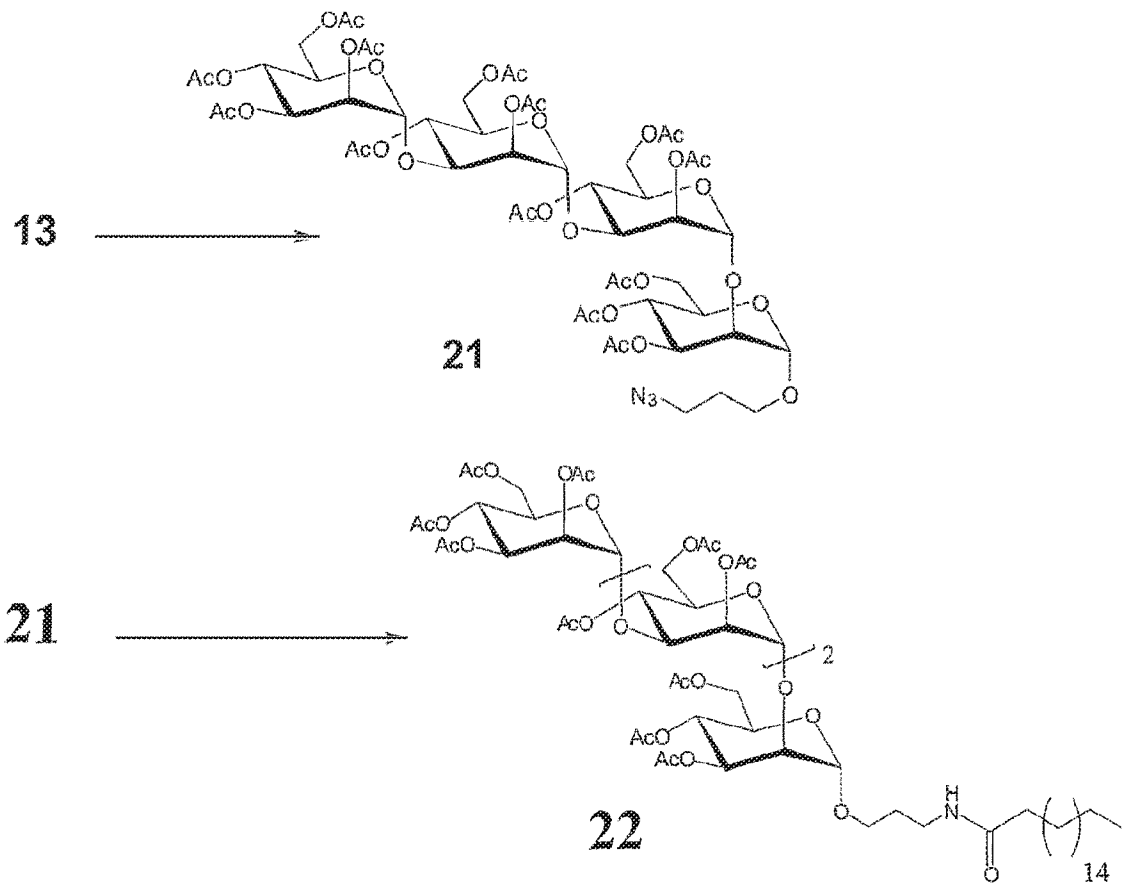
Figure 15B:
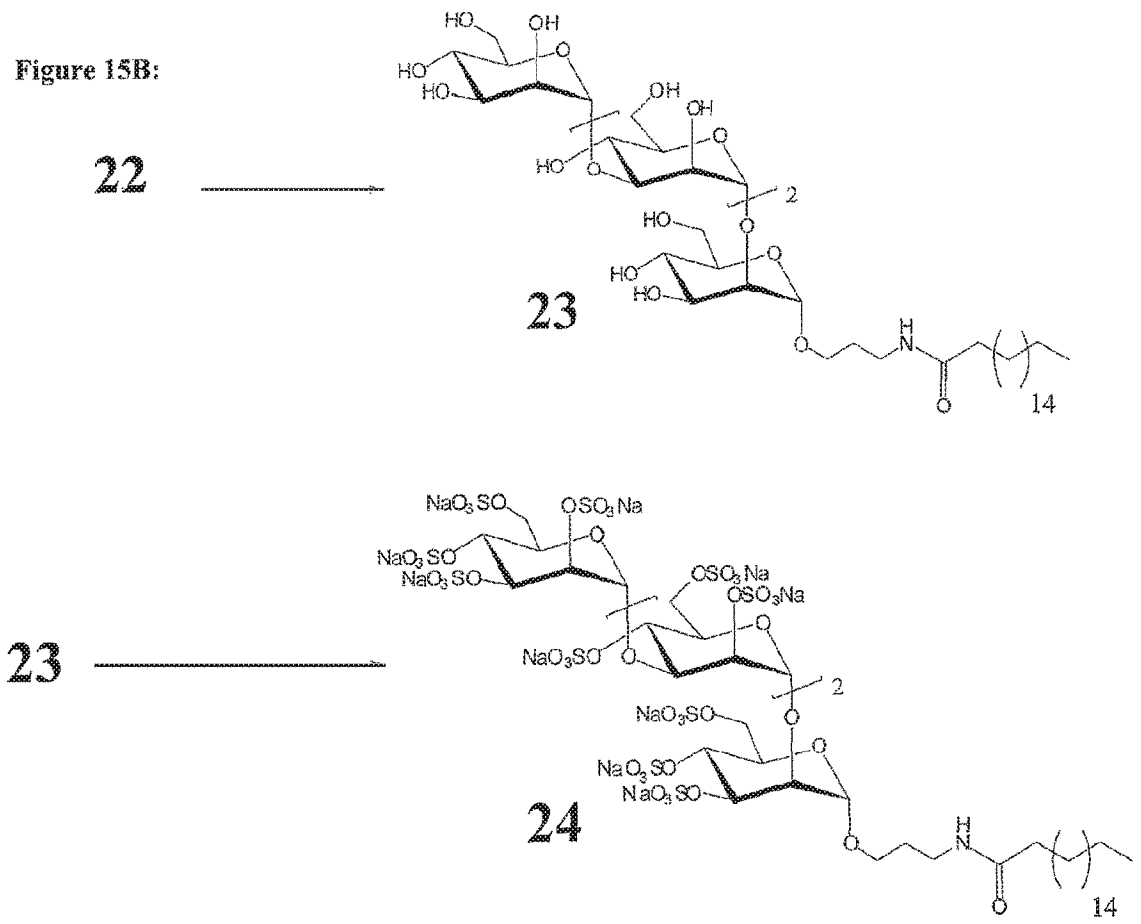
Figure 16A:
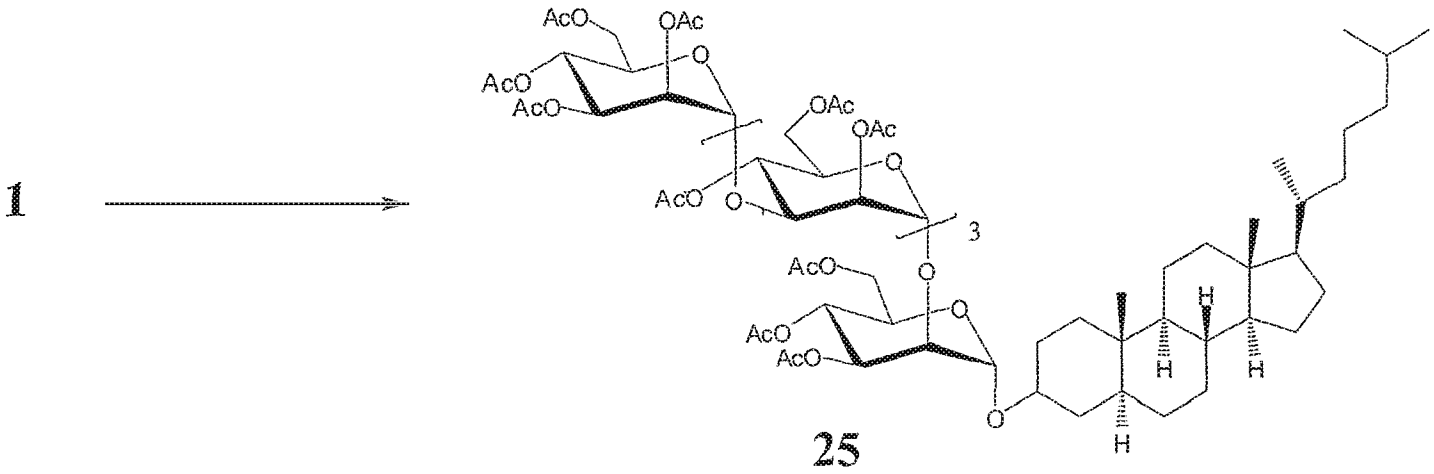
Figure 16B:
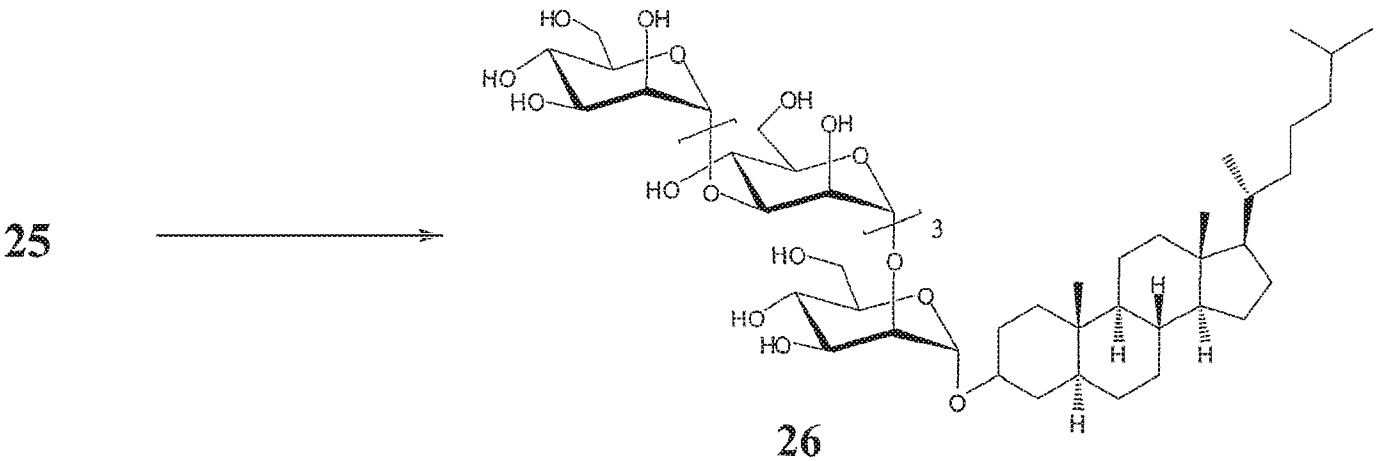
Figure 16C:
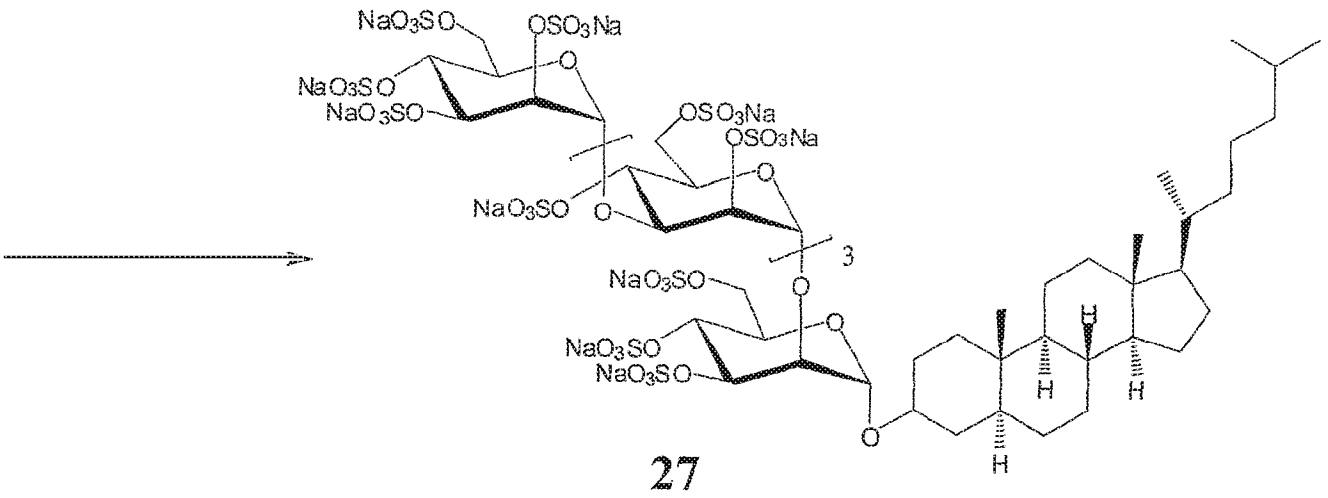
Figure 17A:
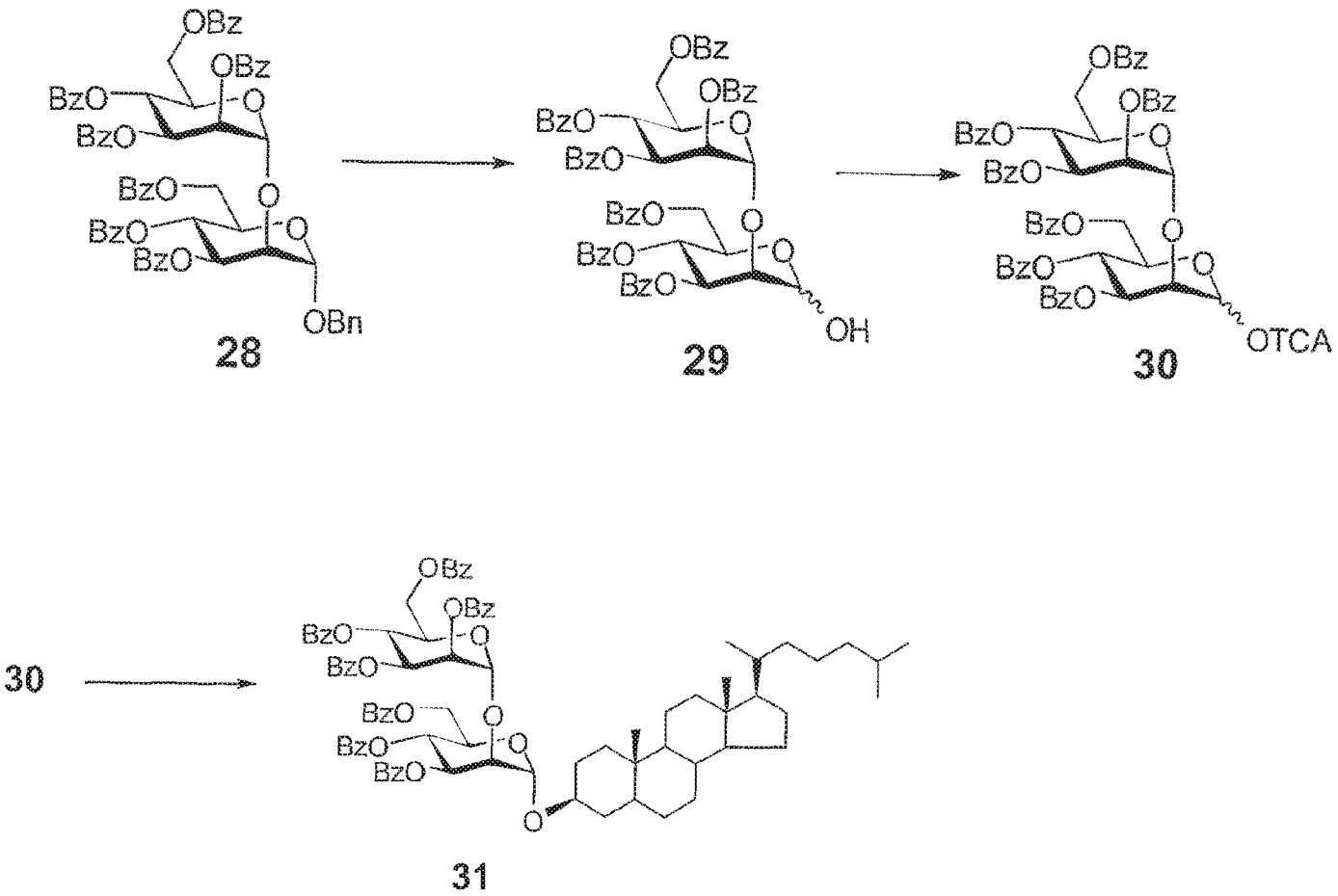
Figure 17B:
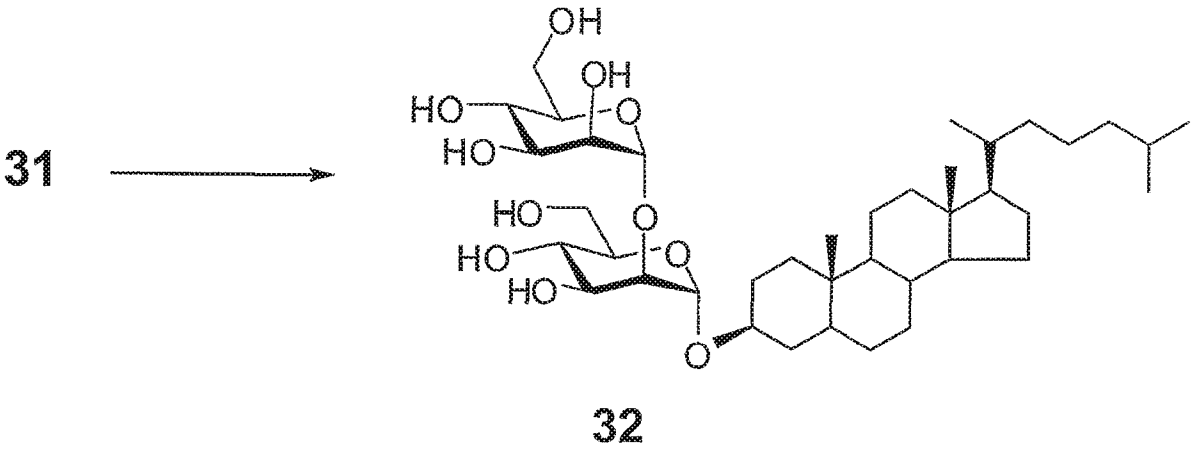
Figure 17C:
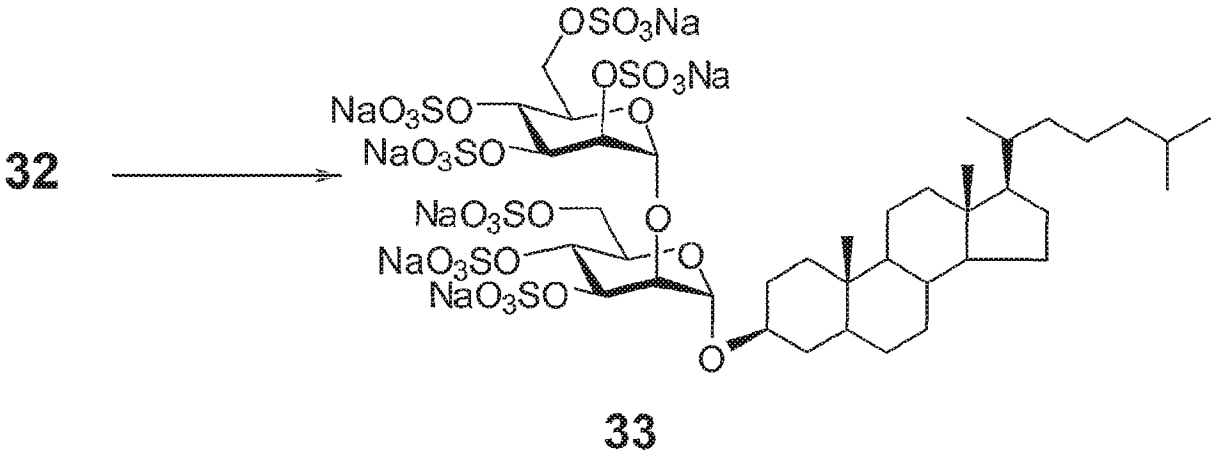
Figure 18A:
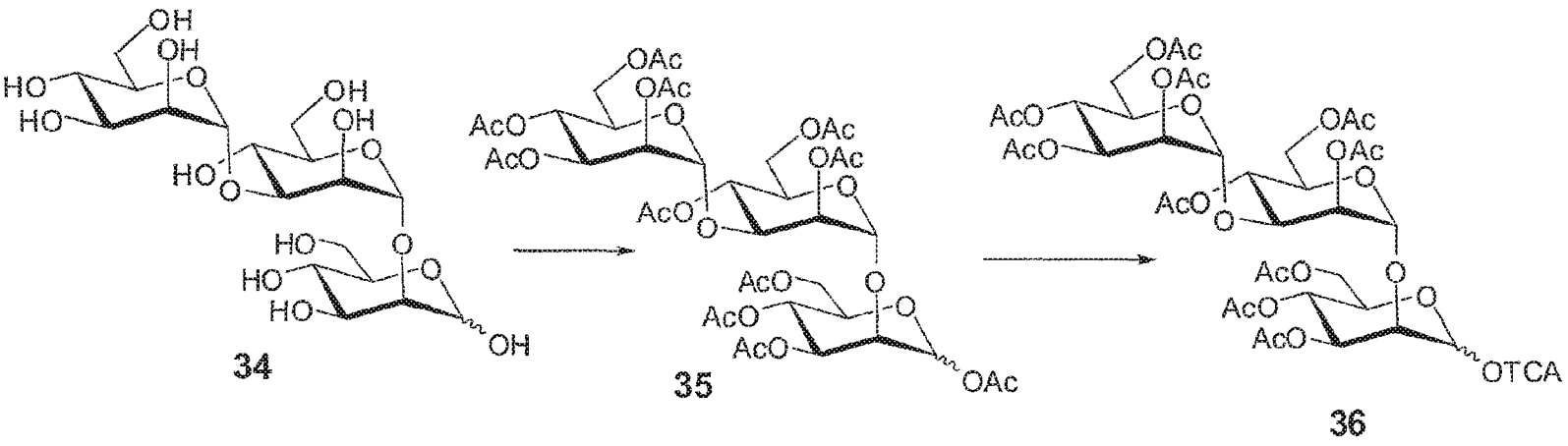
Figure 18B:
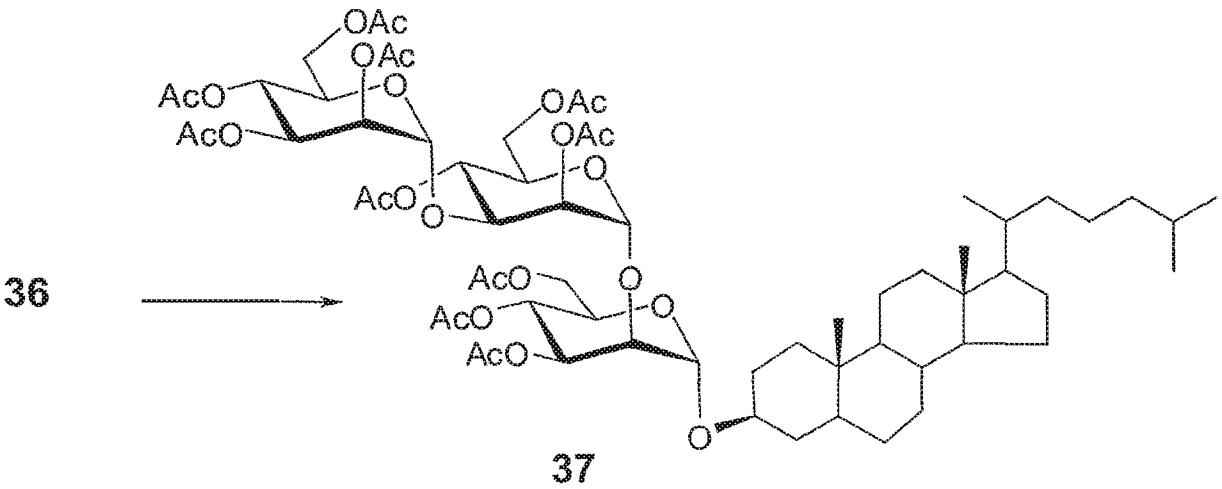
Figure 18C:
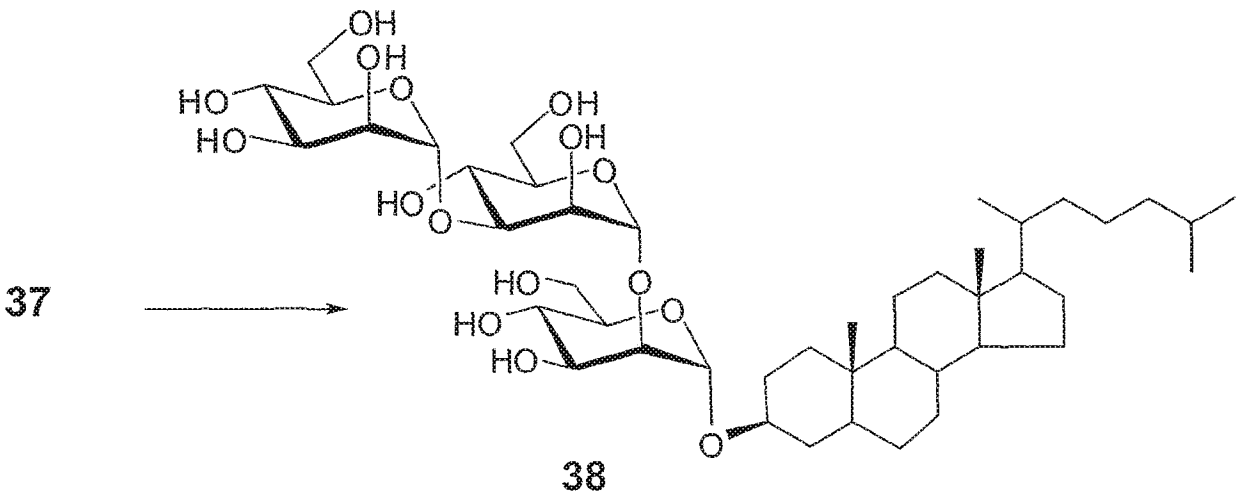
Figure 18D:
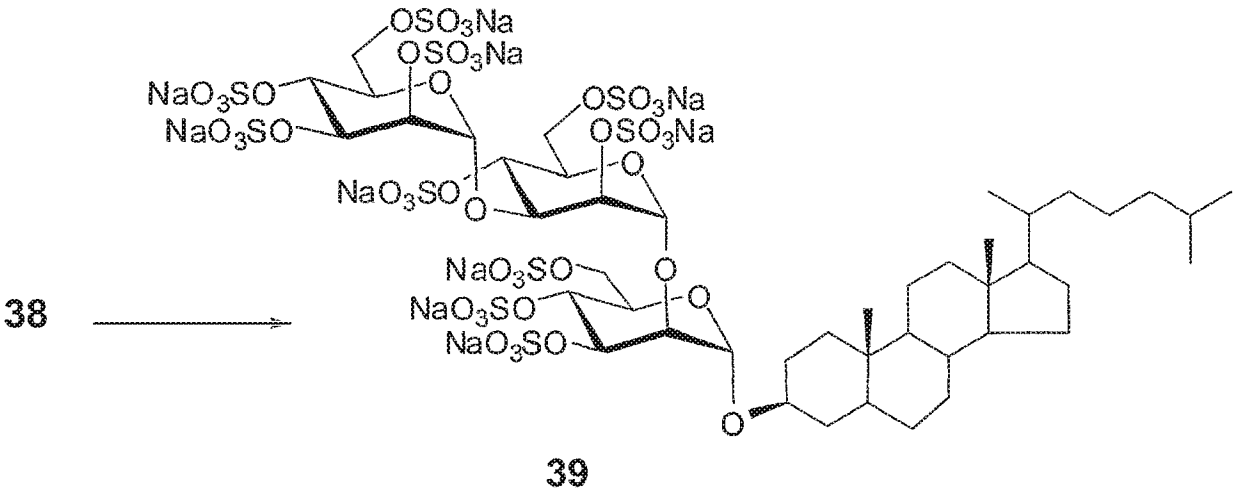
Figure 19A:
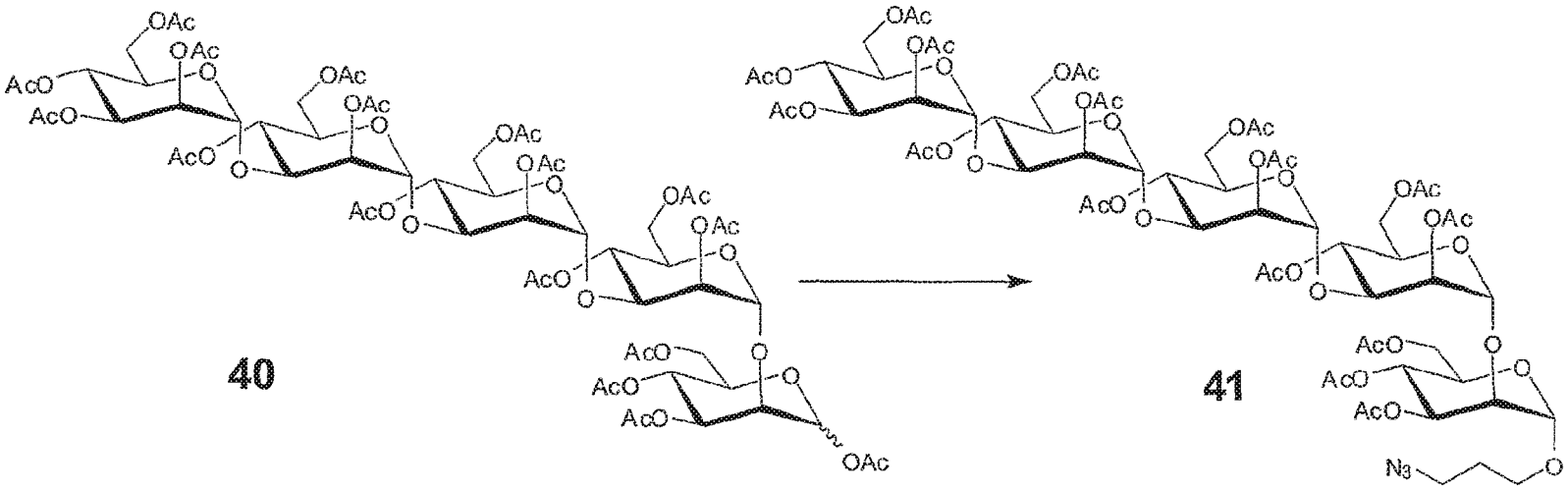
Figure 19B:
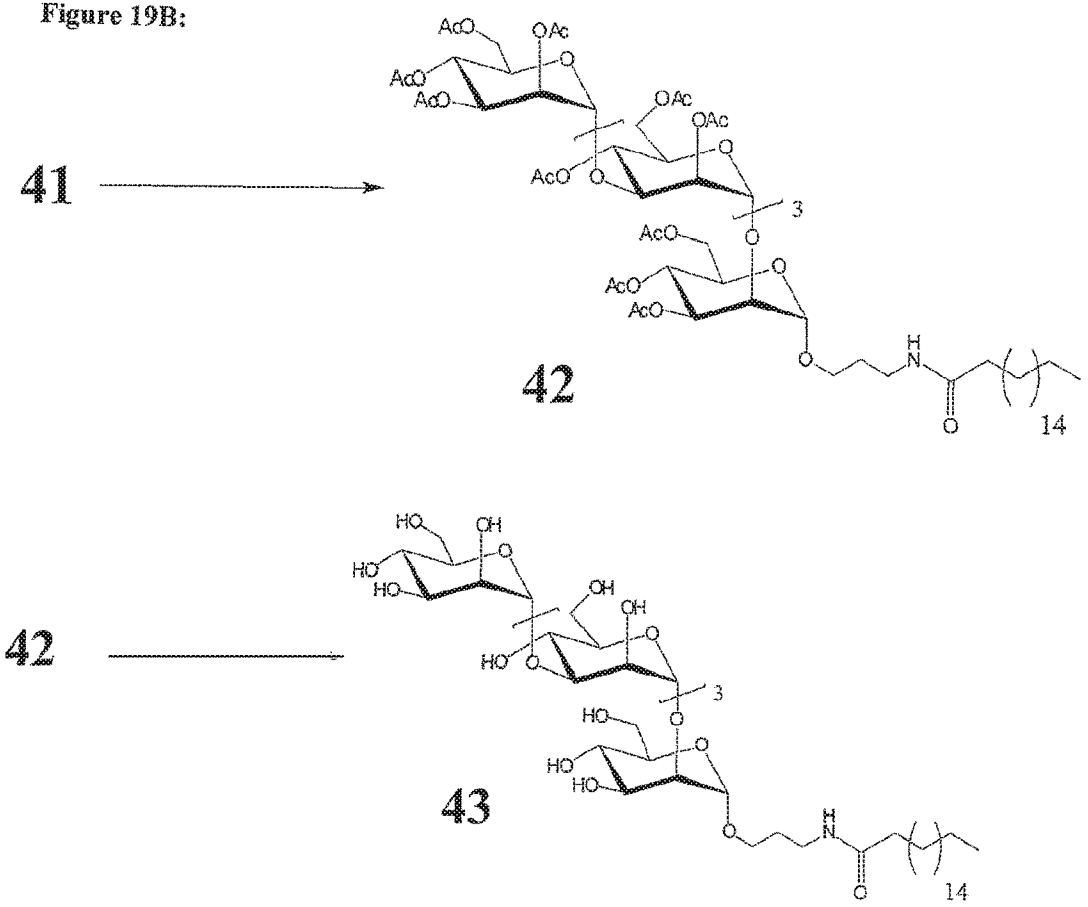
Figure 19C:
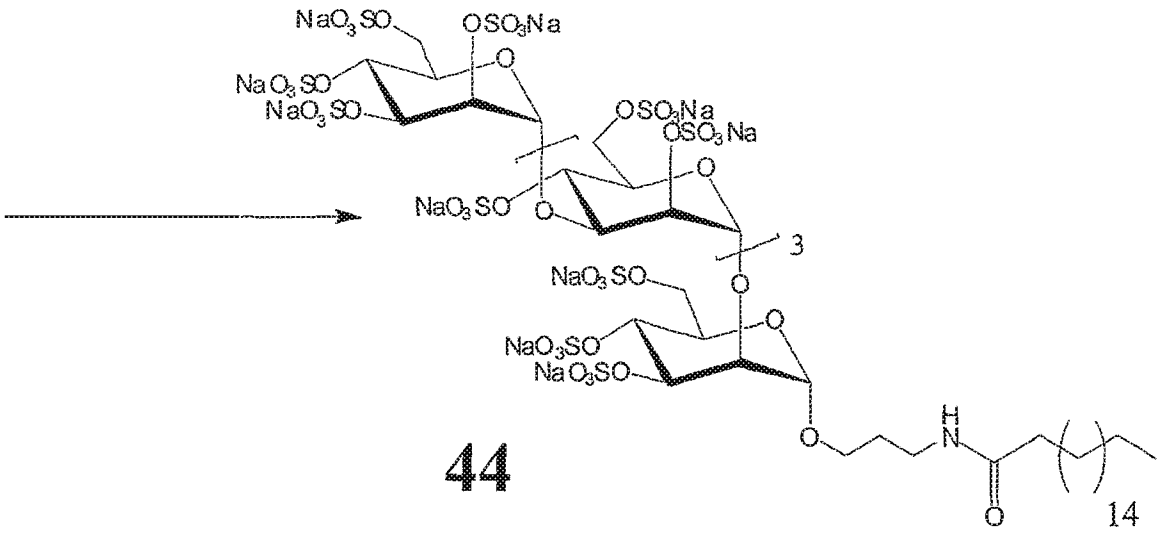
Figure 20A:
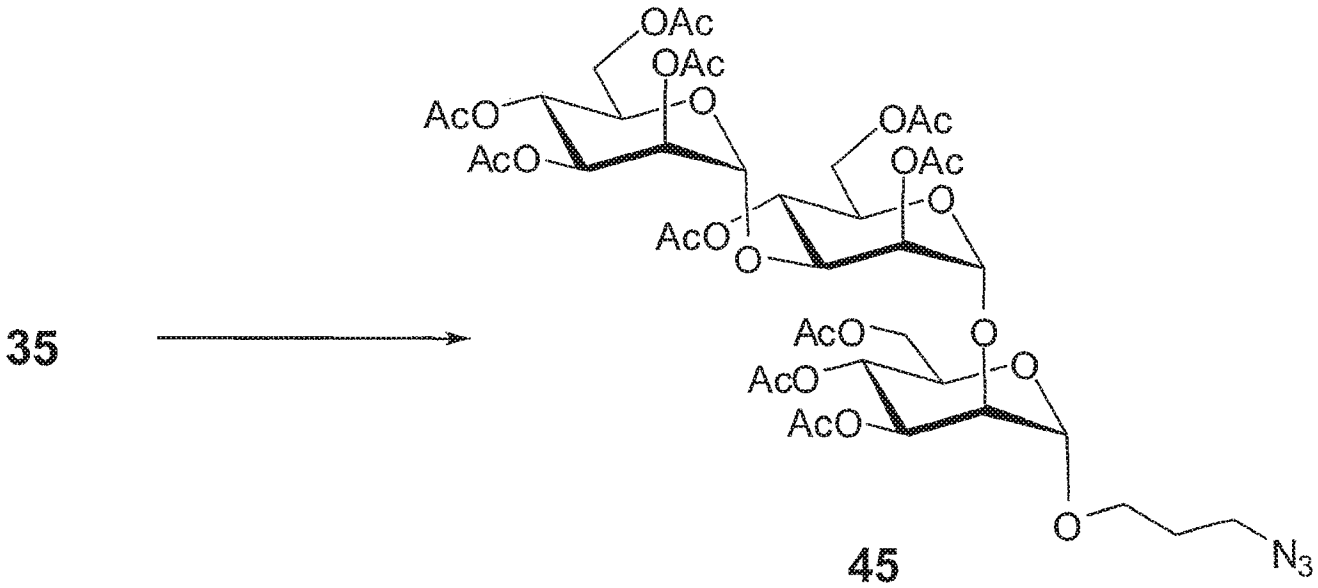
Figure 20B:
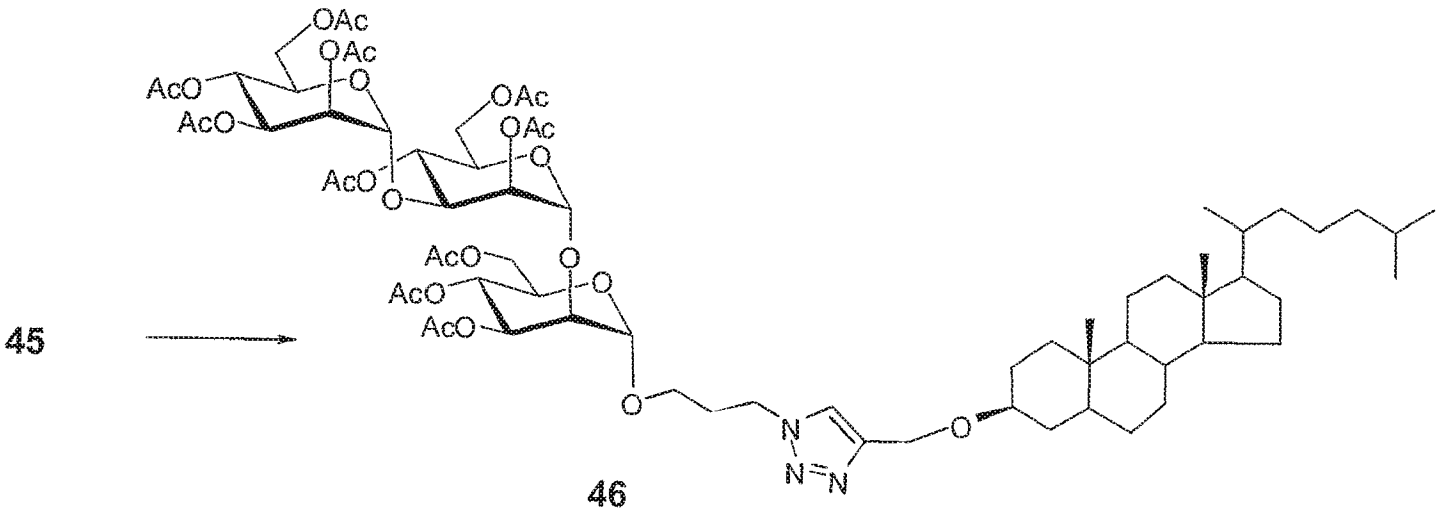
Figure 20C:
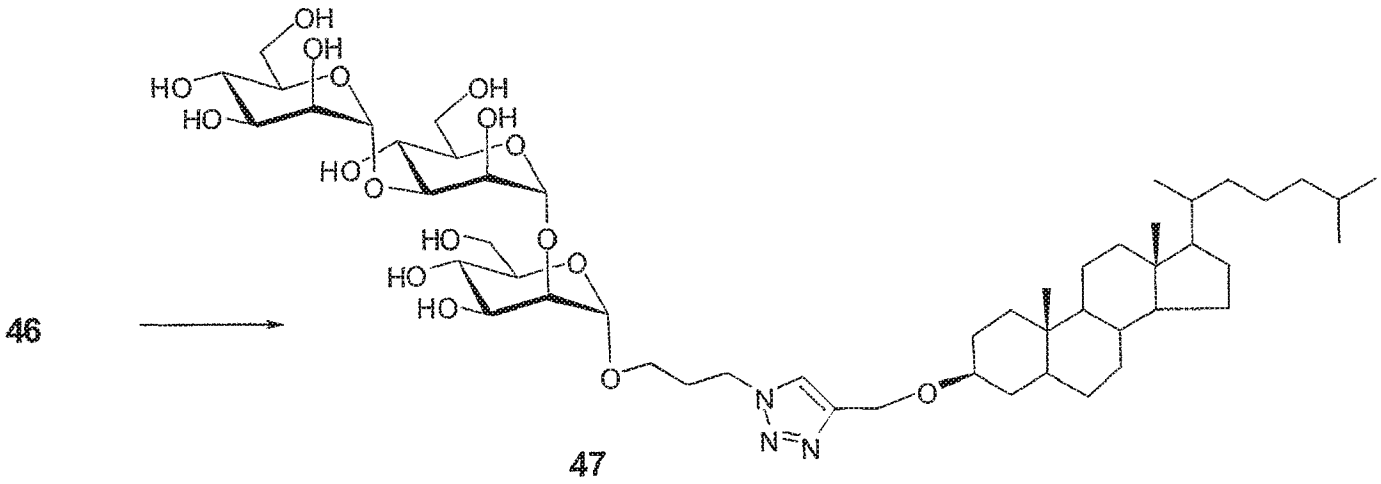
Figure 20D:
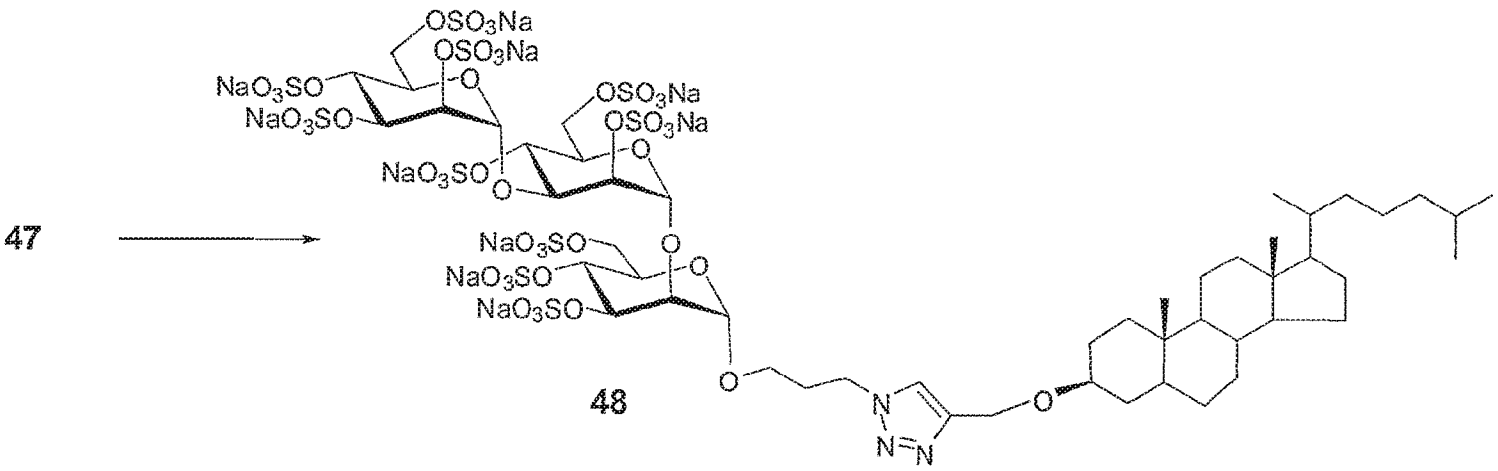
Figure 21A:
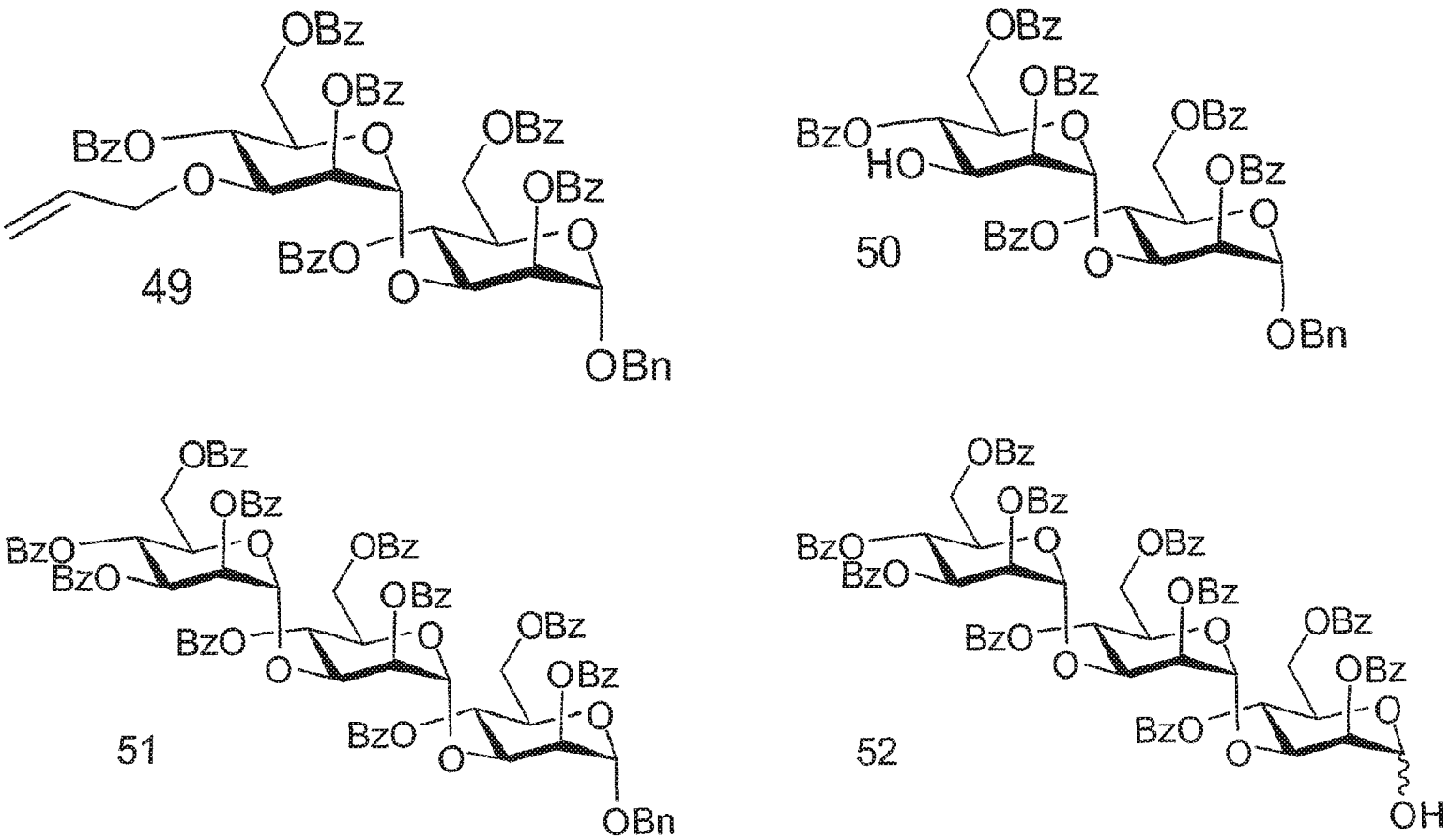
Figure 21B:
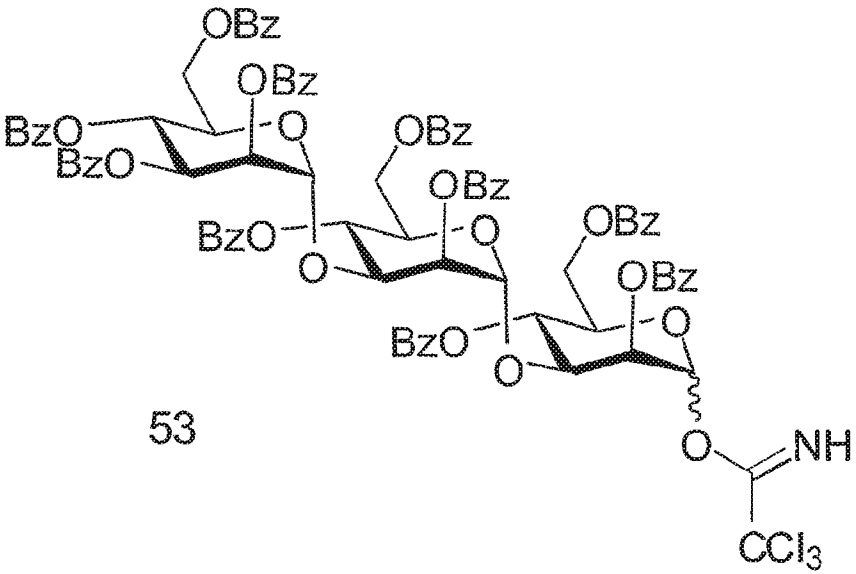
Figure 21C:
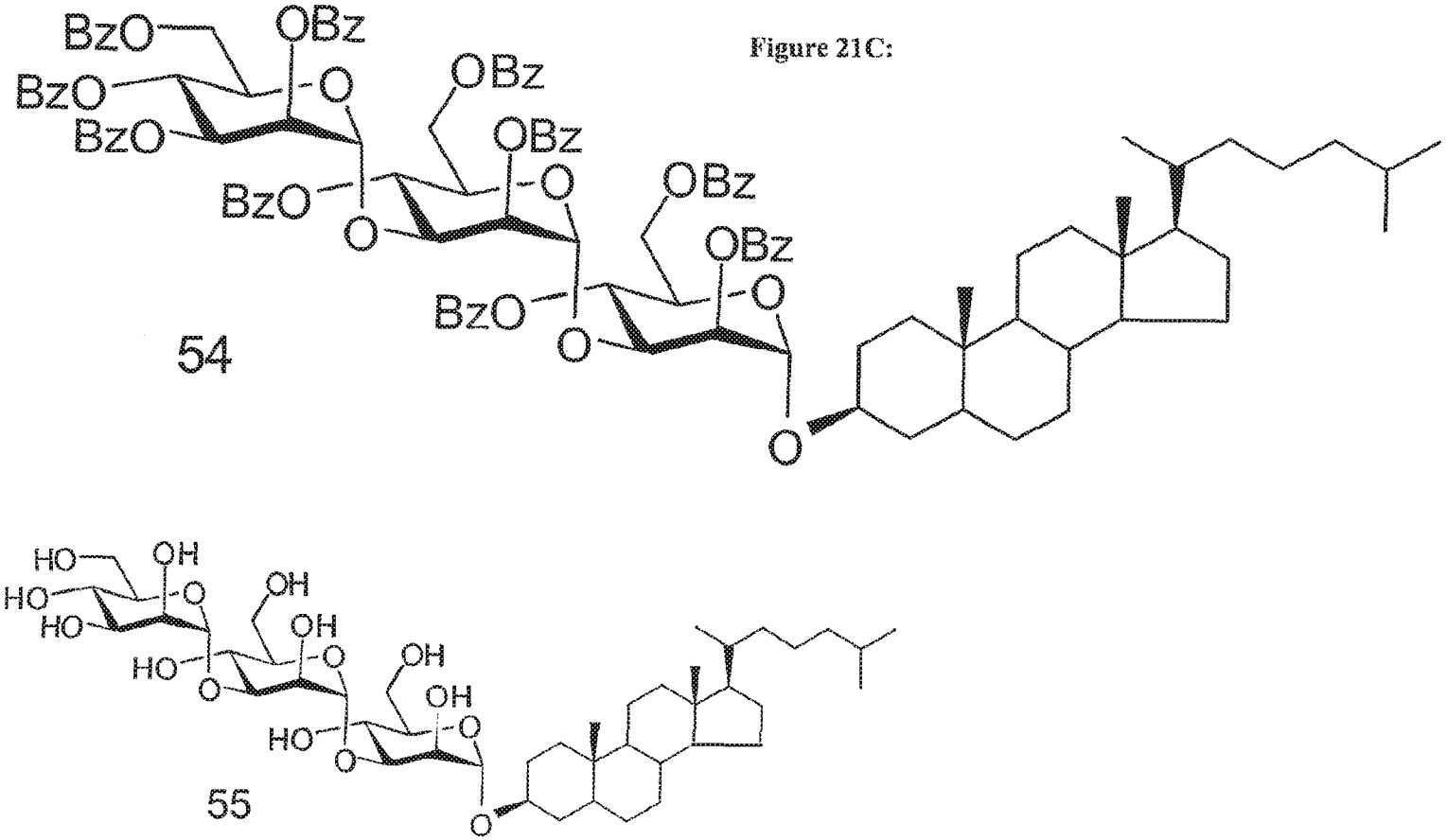
Figure 21D:
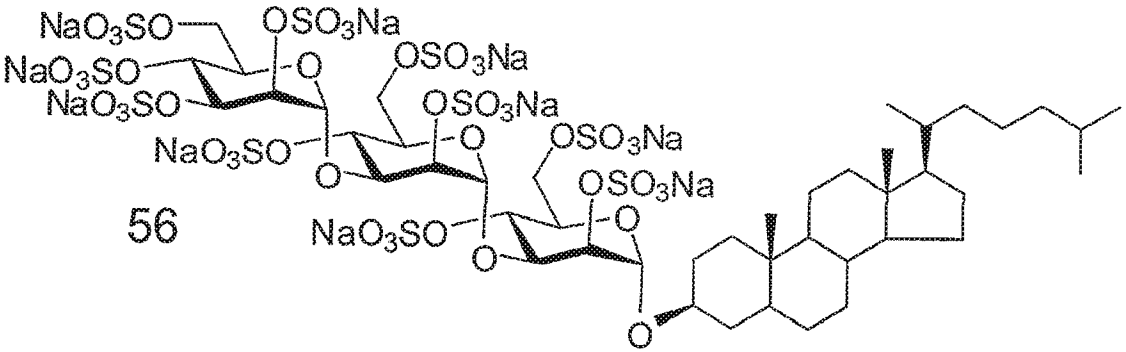
Figure 22A:
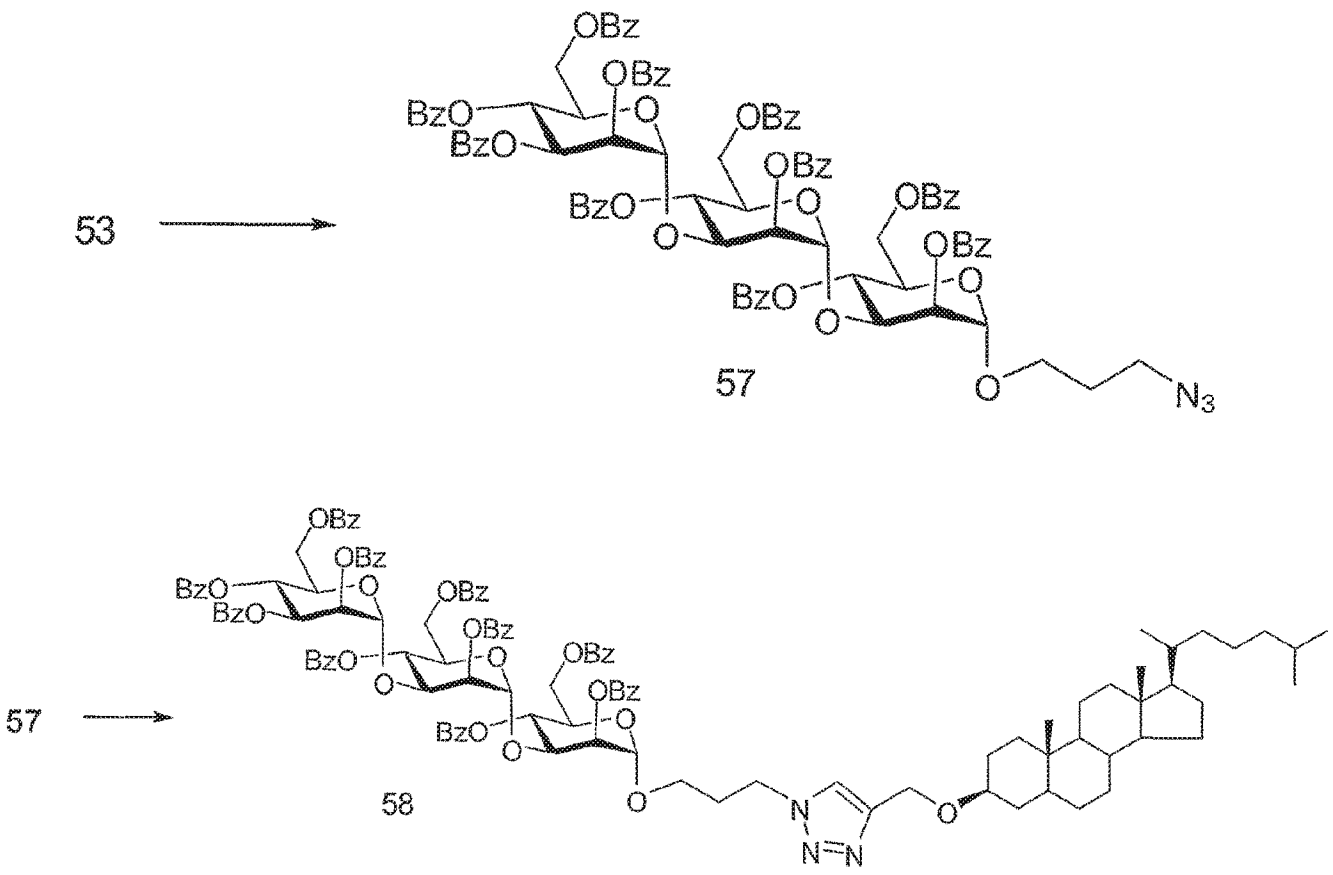
Figure 22B:
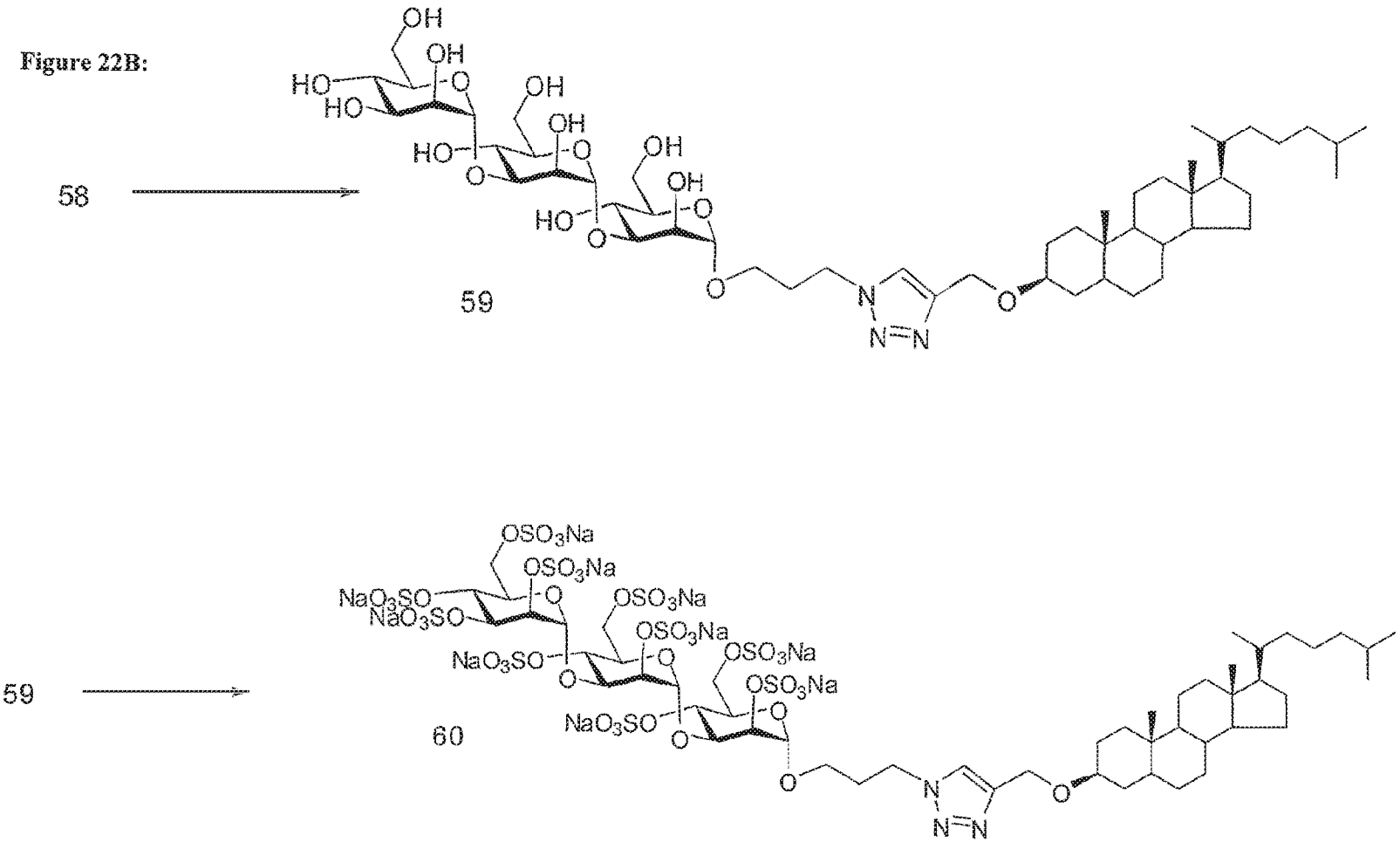
Figure 23A:
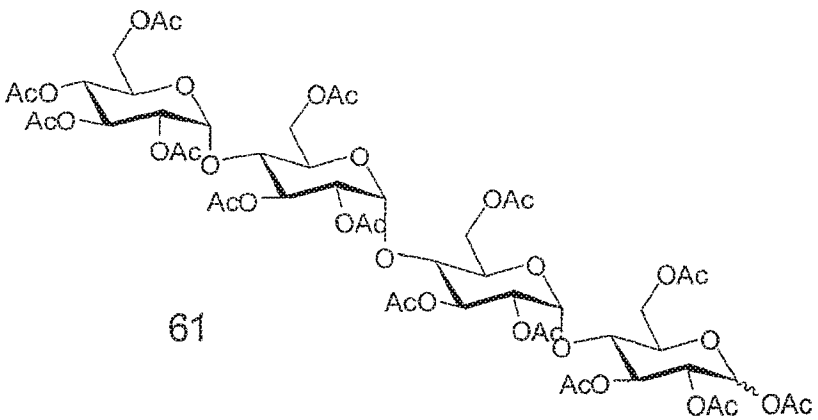
Figure 23B:
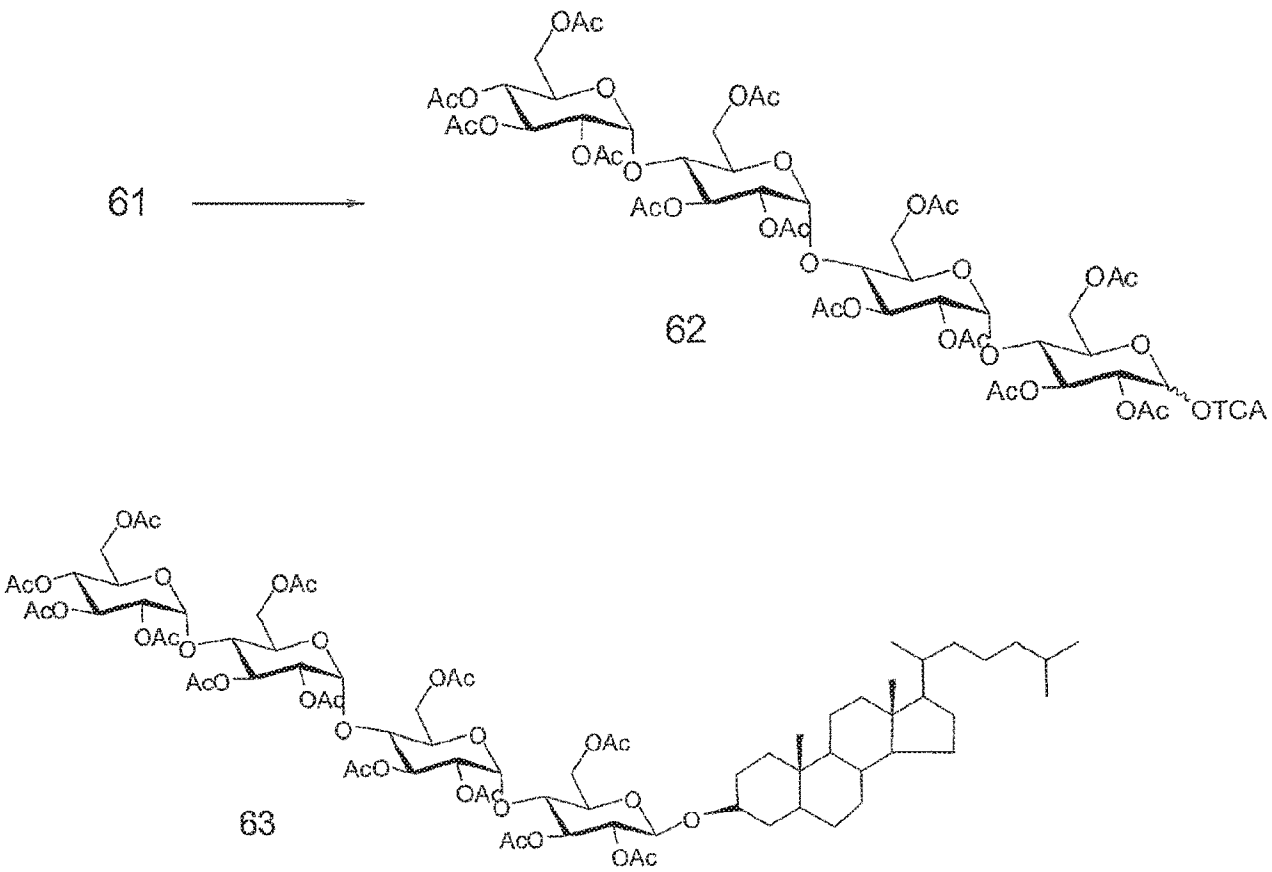
Figure 23C:
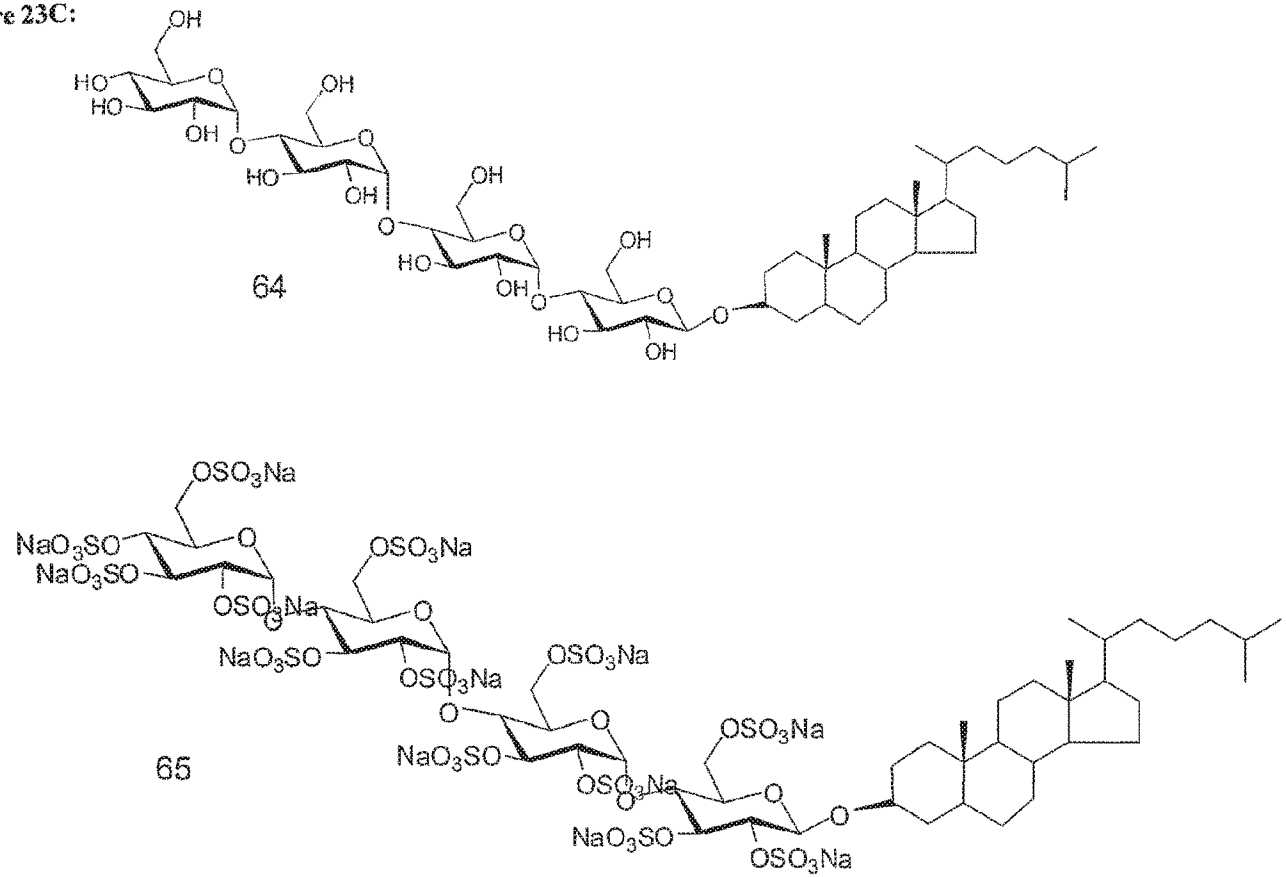
Figure 24A:
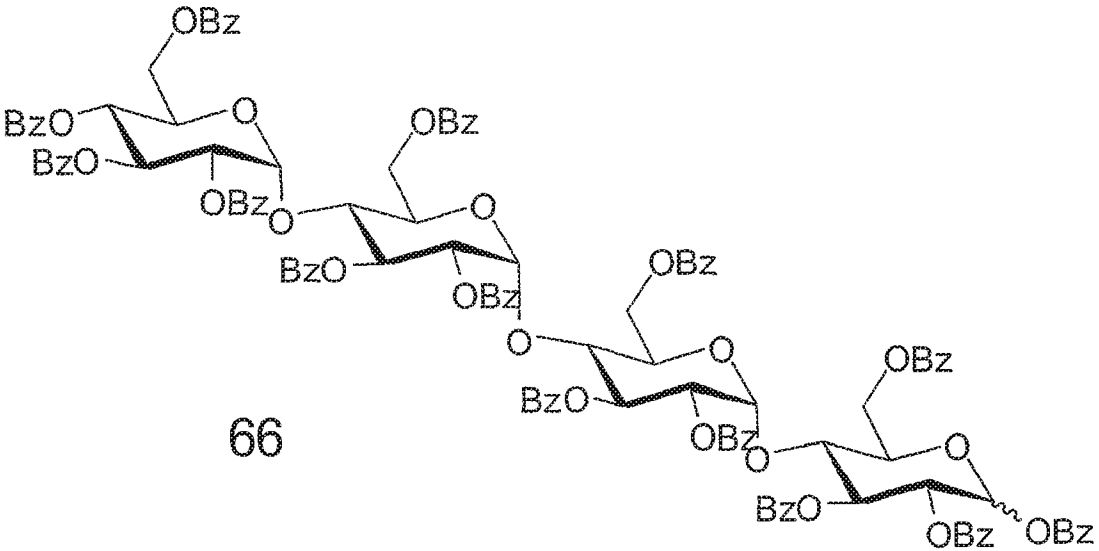
Figure 24B:
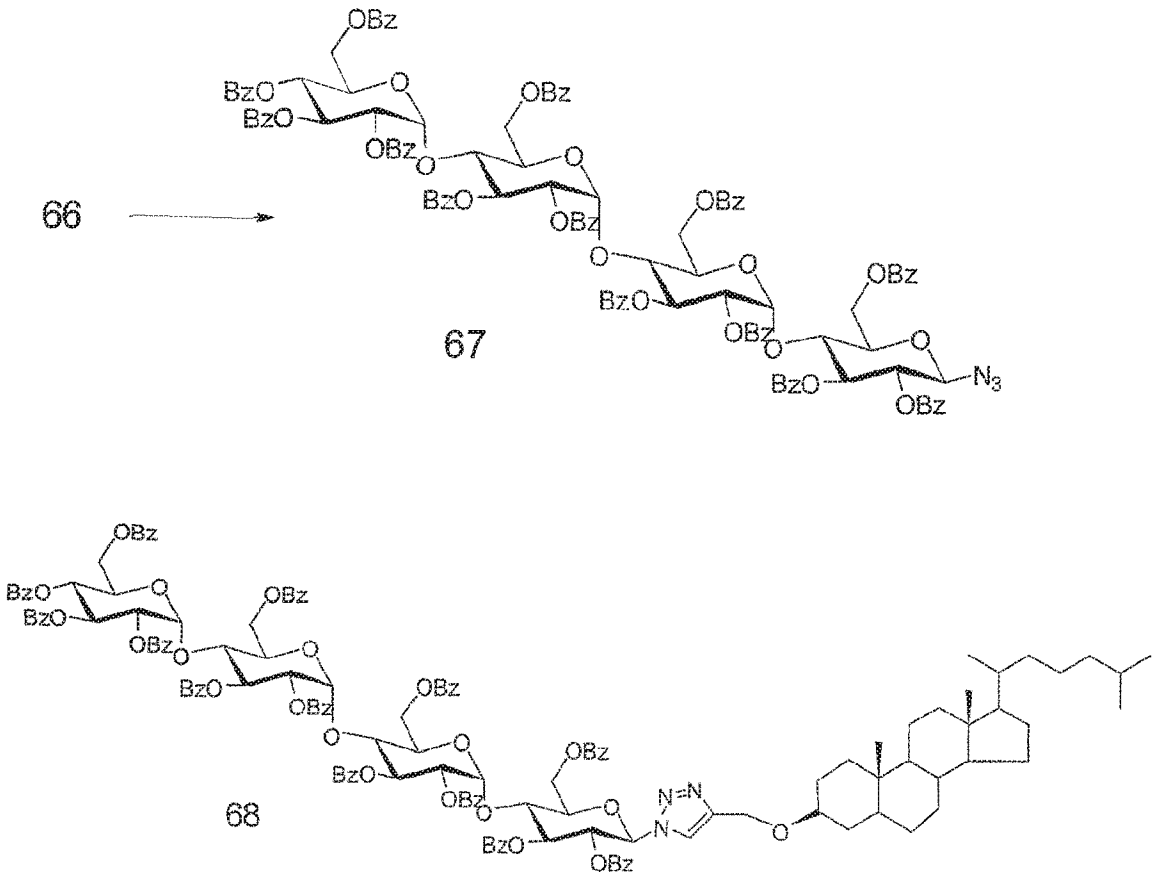
Figure 24C:
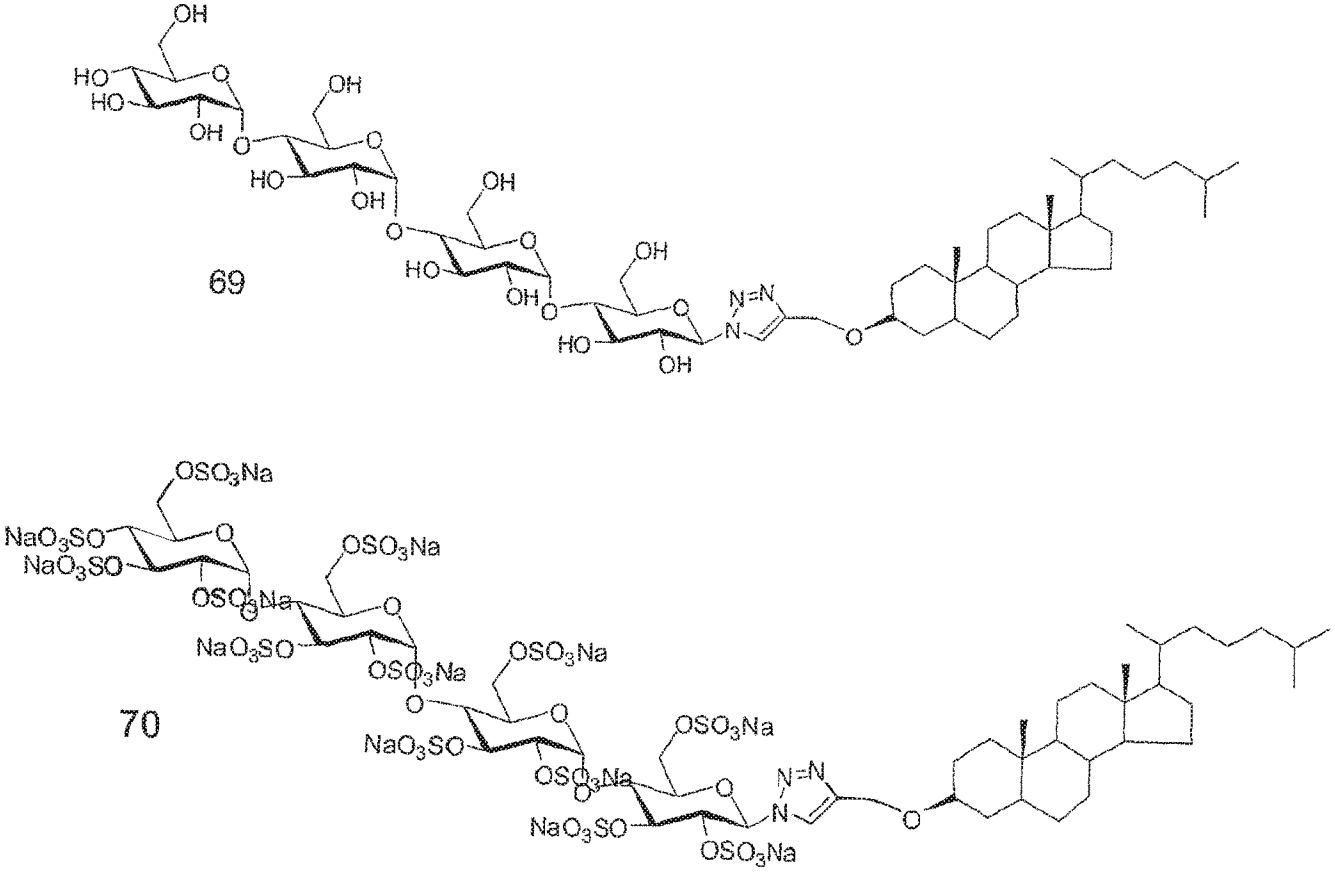
Figure 25A:
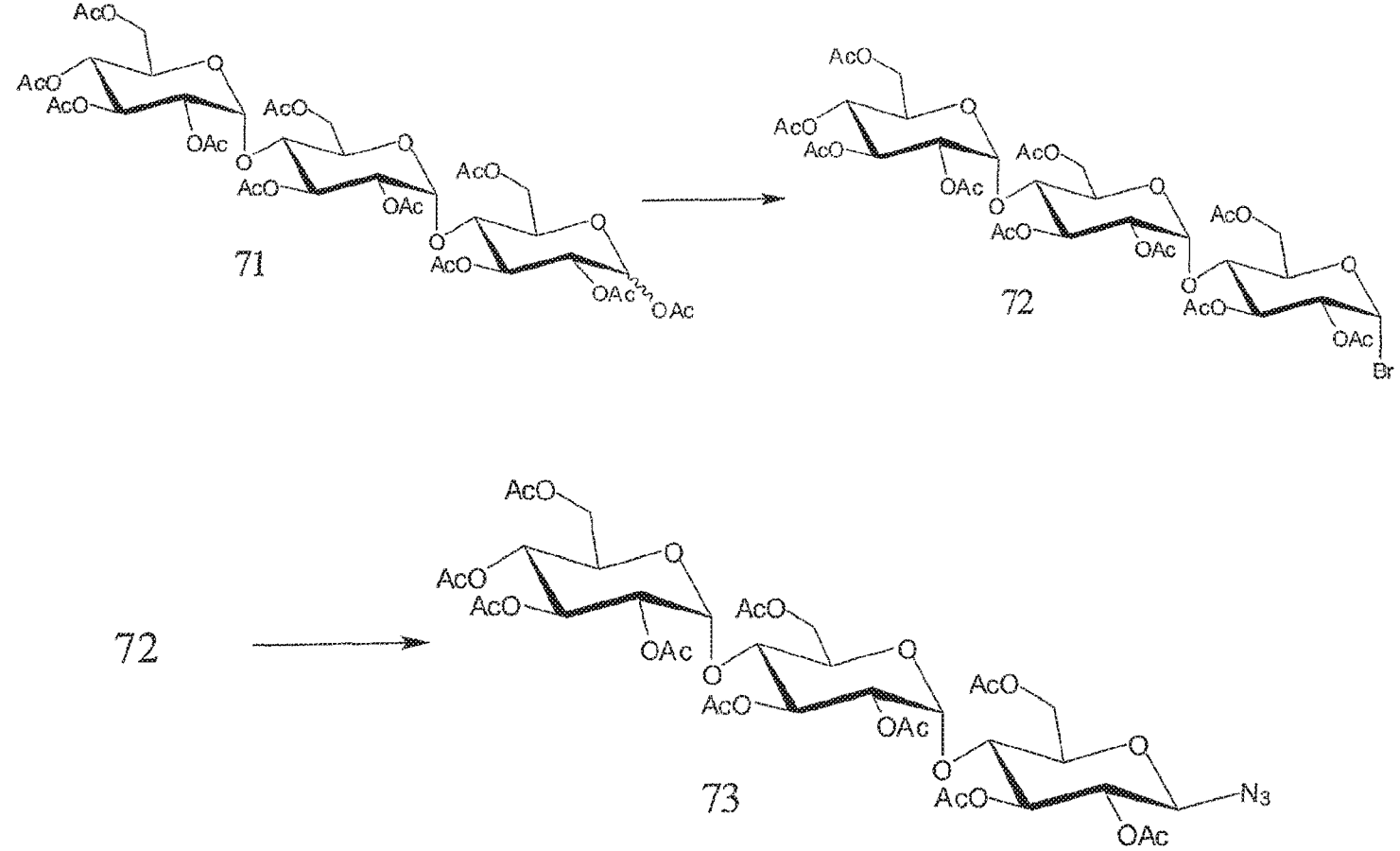
Figure 25B:
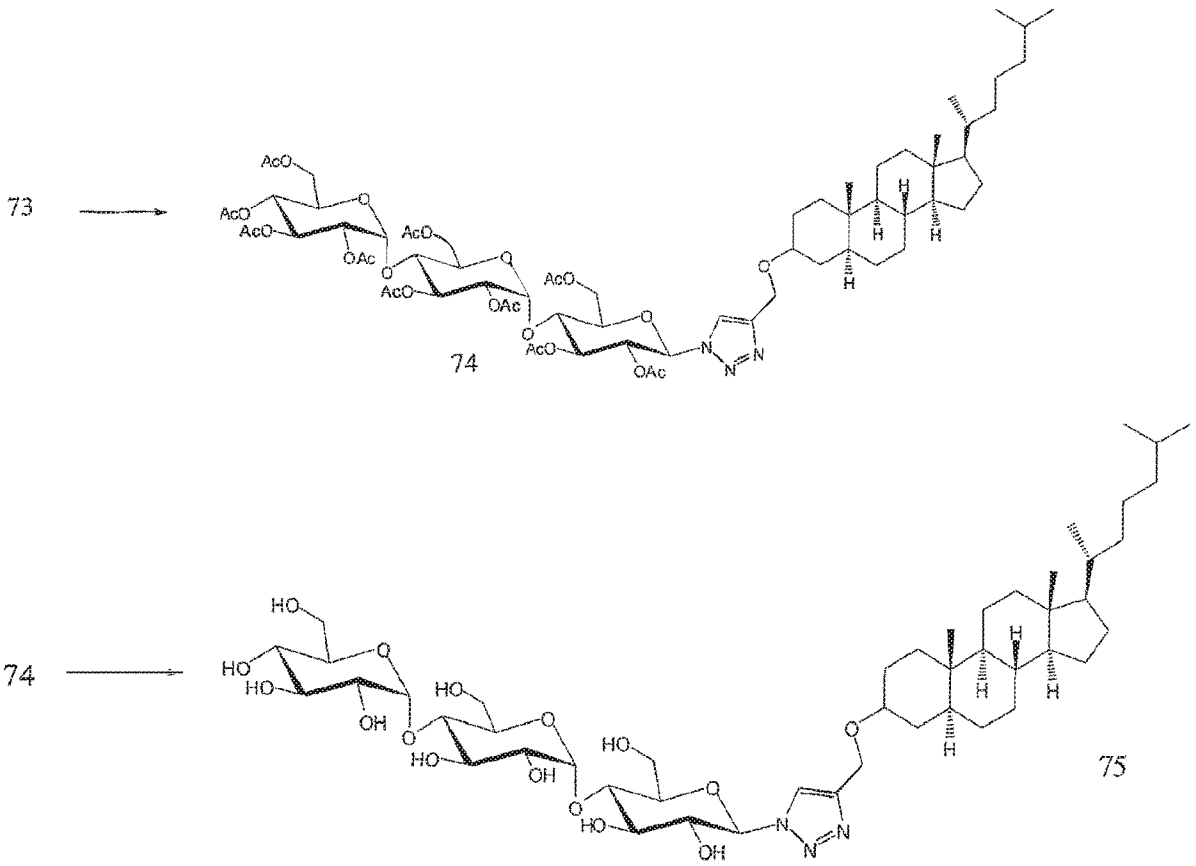
Figure 25C:
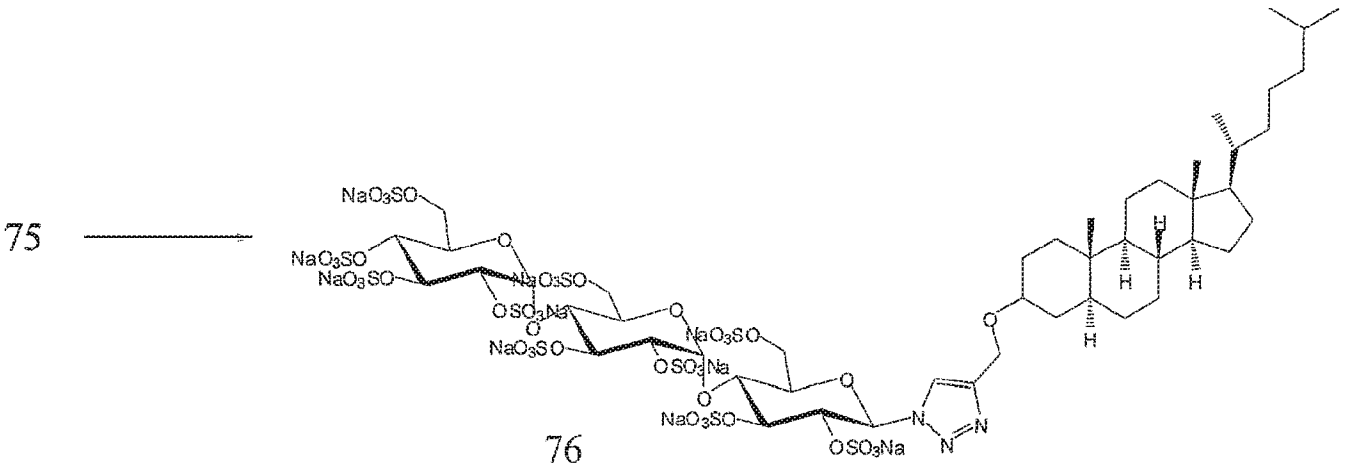
Figure 26A:
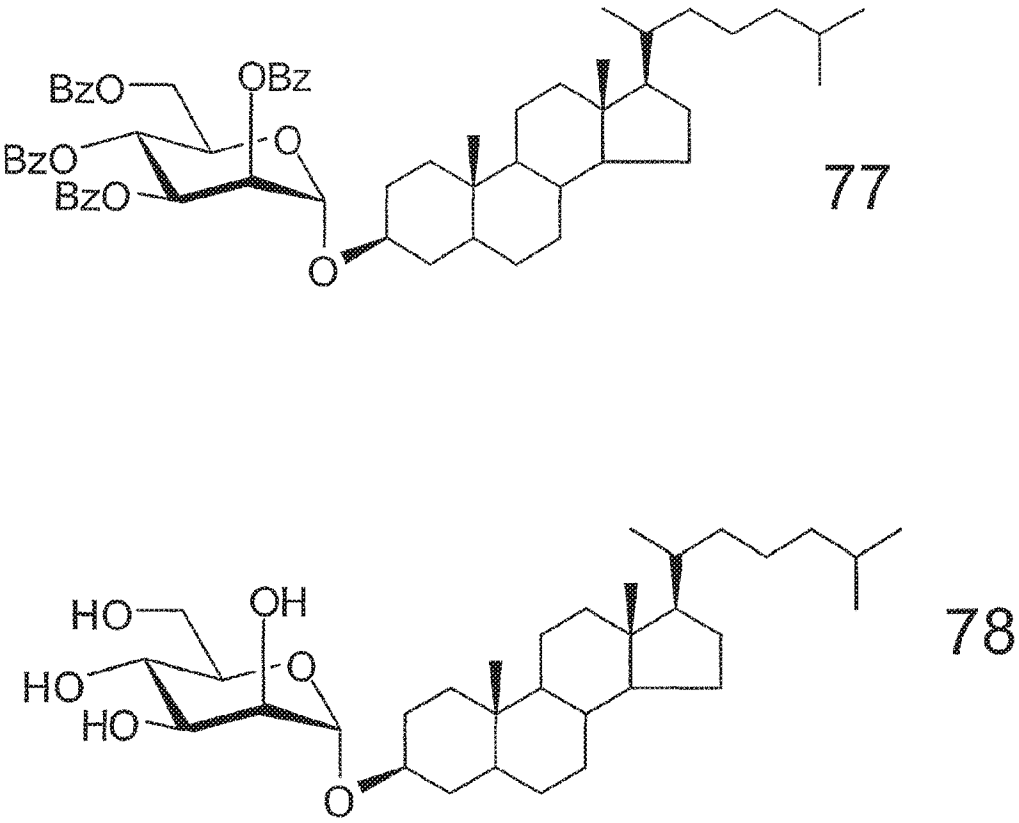
Figure 26B:
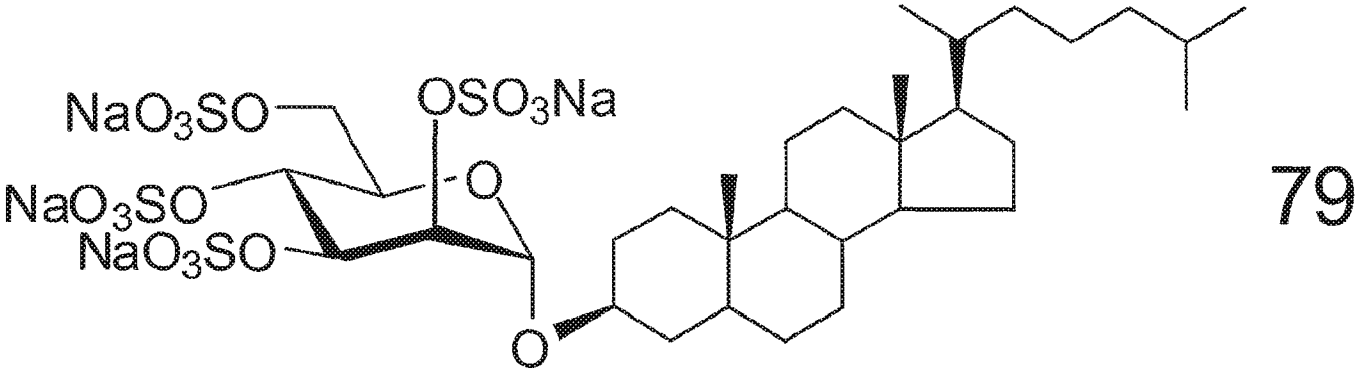
Figure 27A:
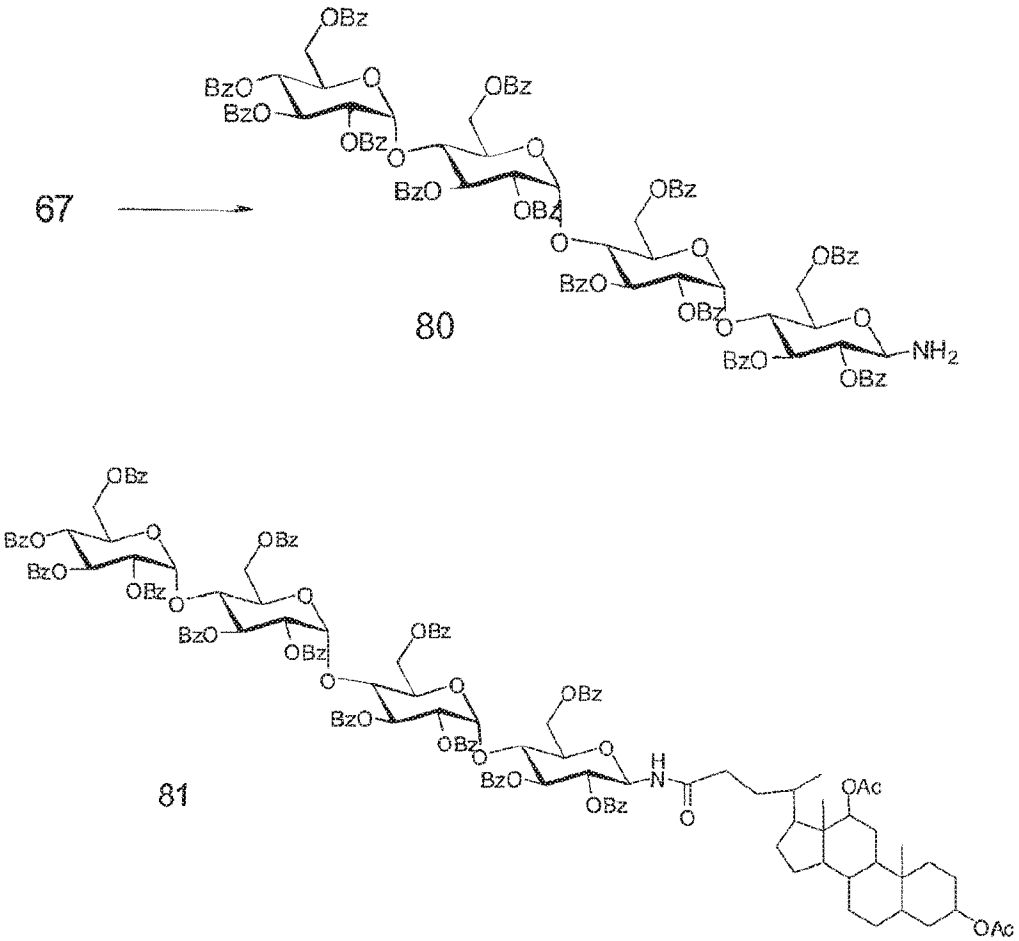
Figure 27B:
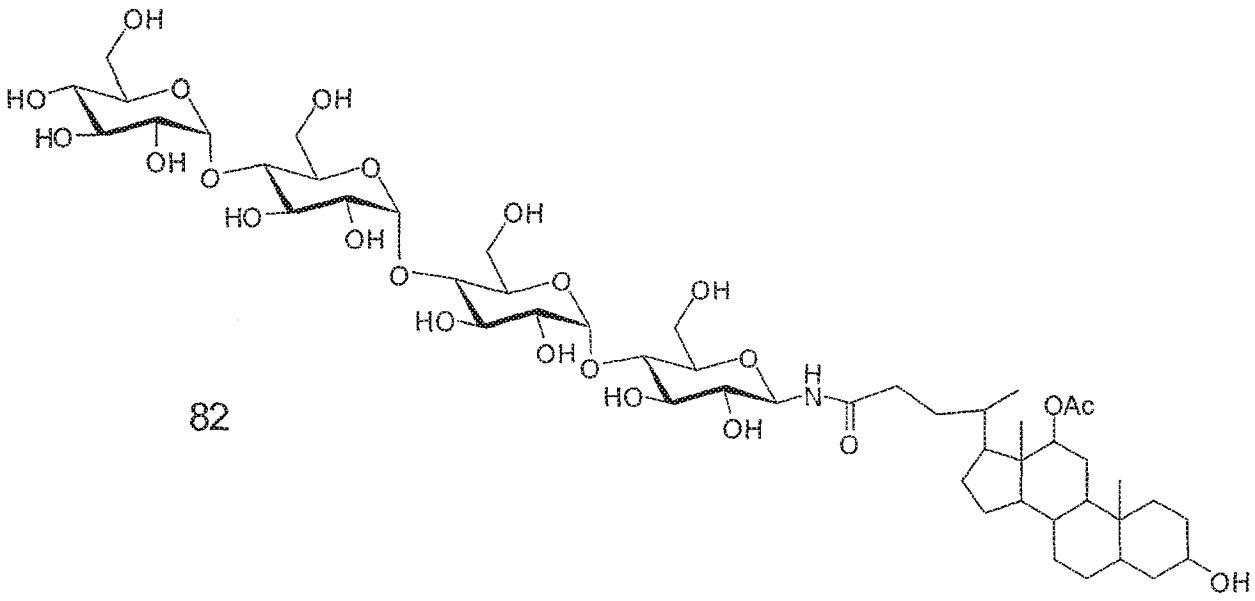
Figure 27C:
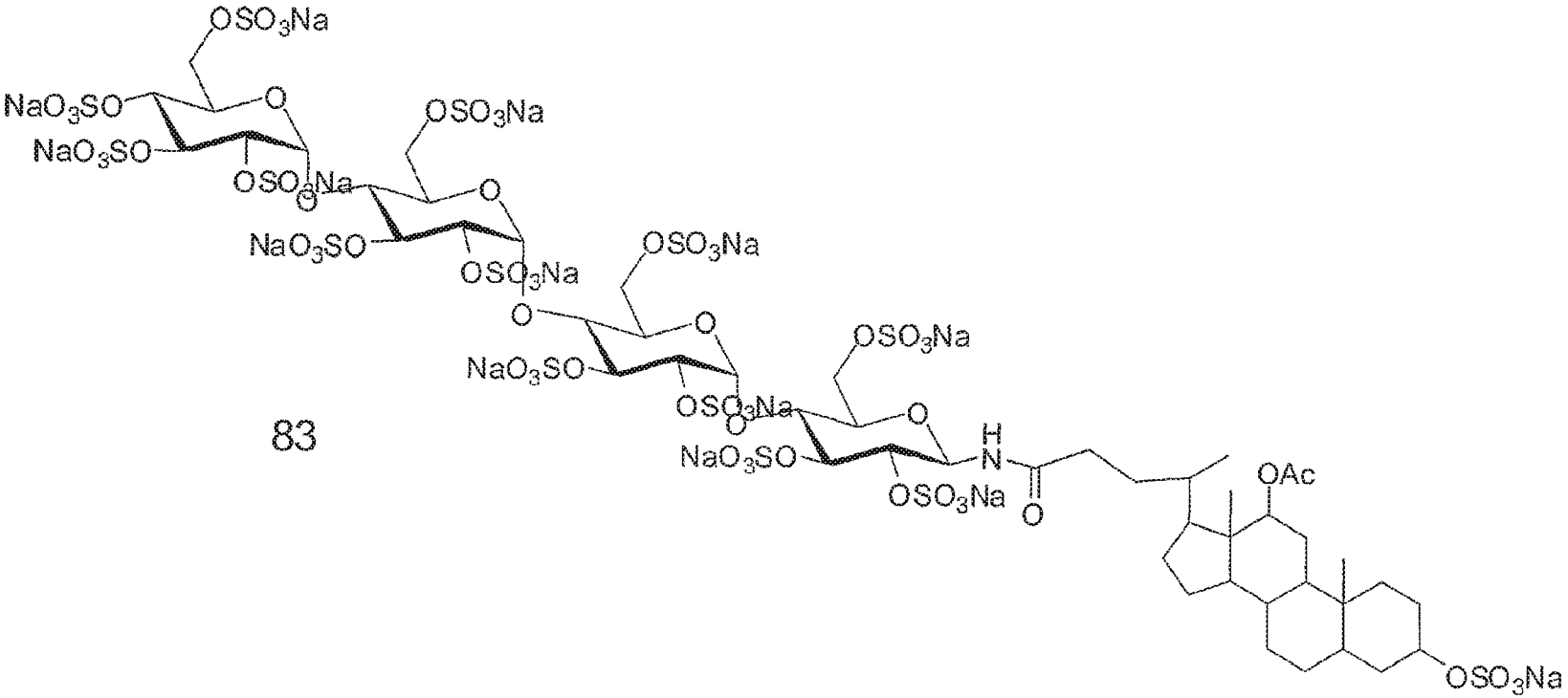
Figure 28A:
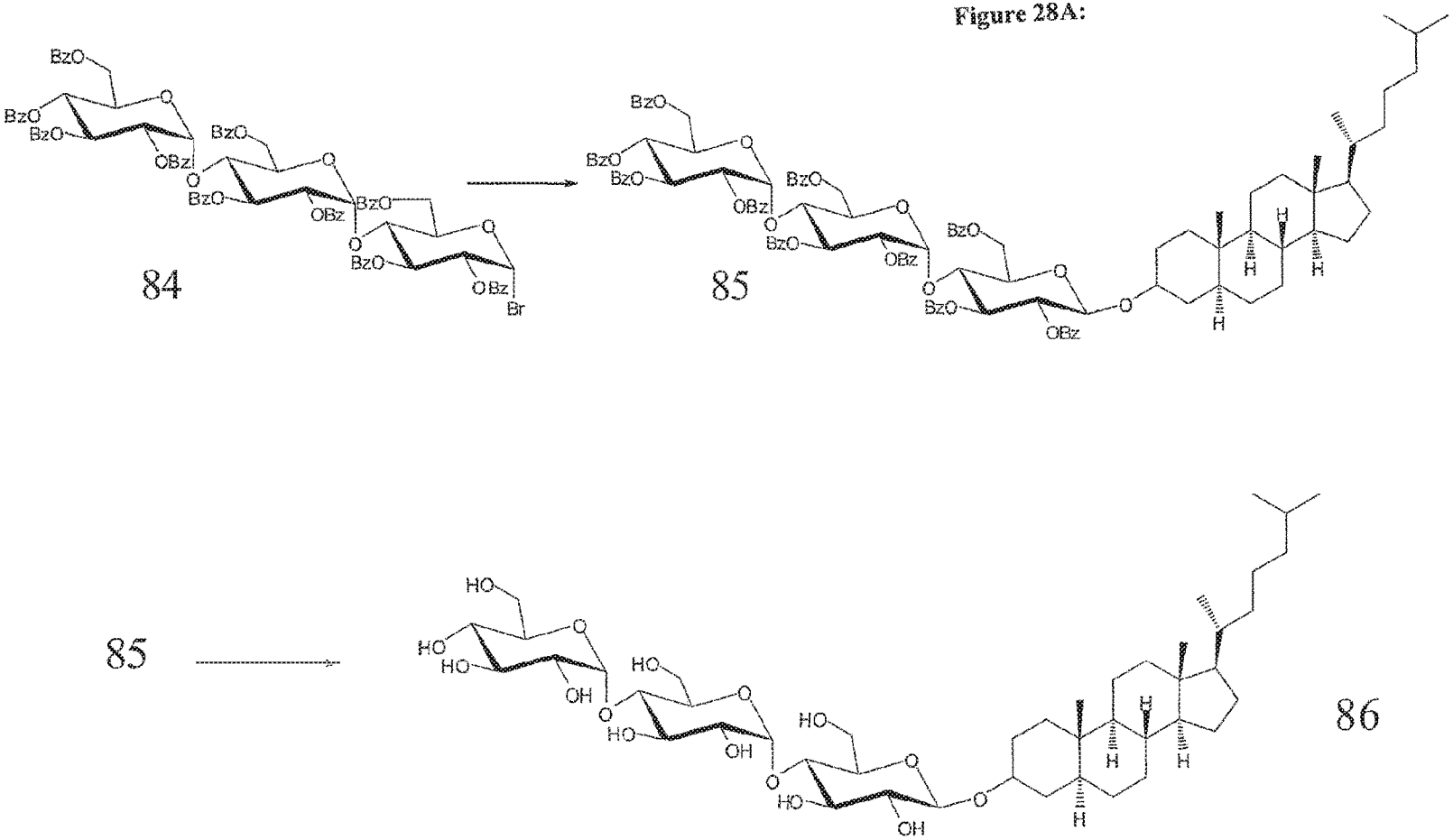
Figure 28B:
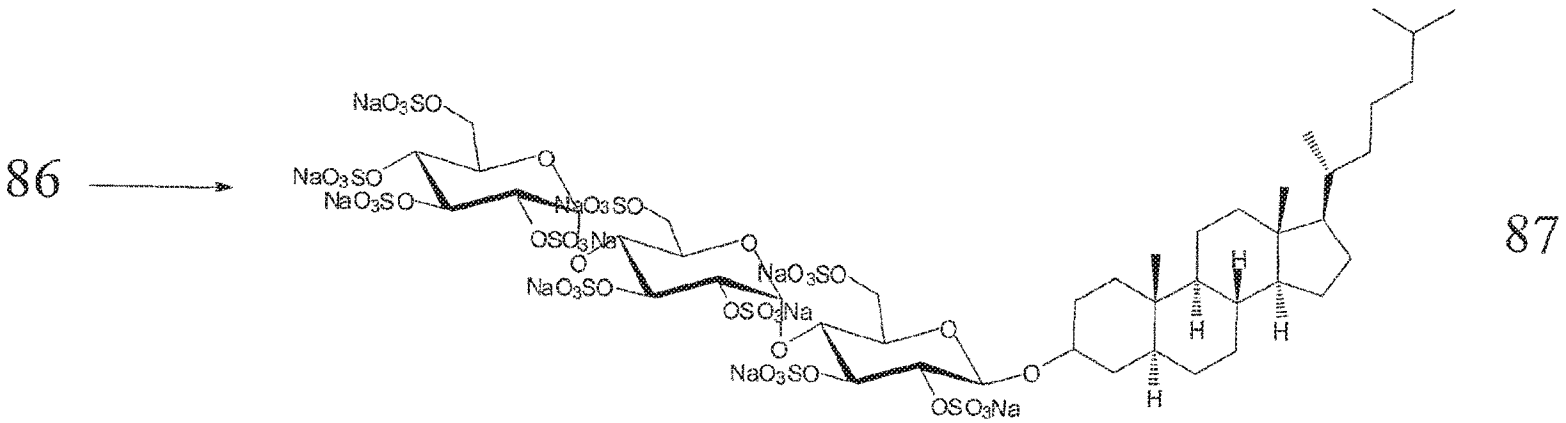
Figure 29A:
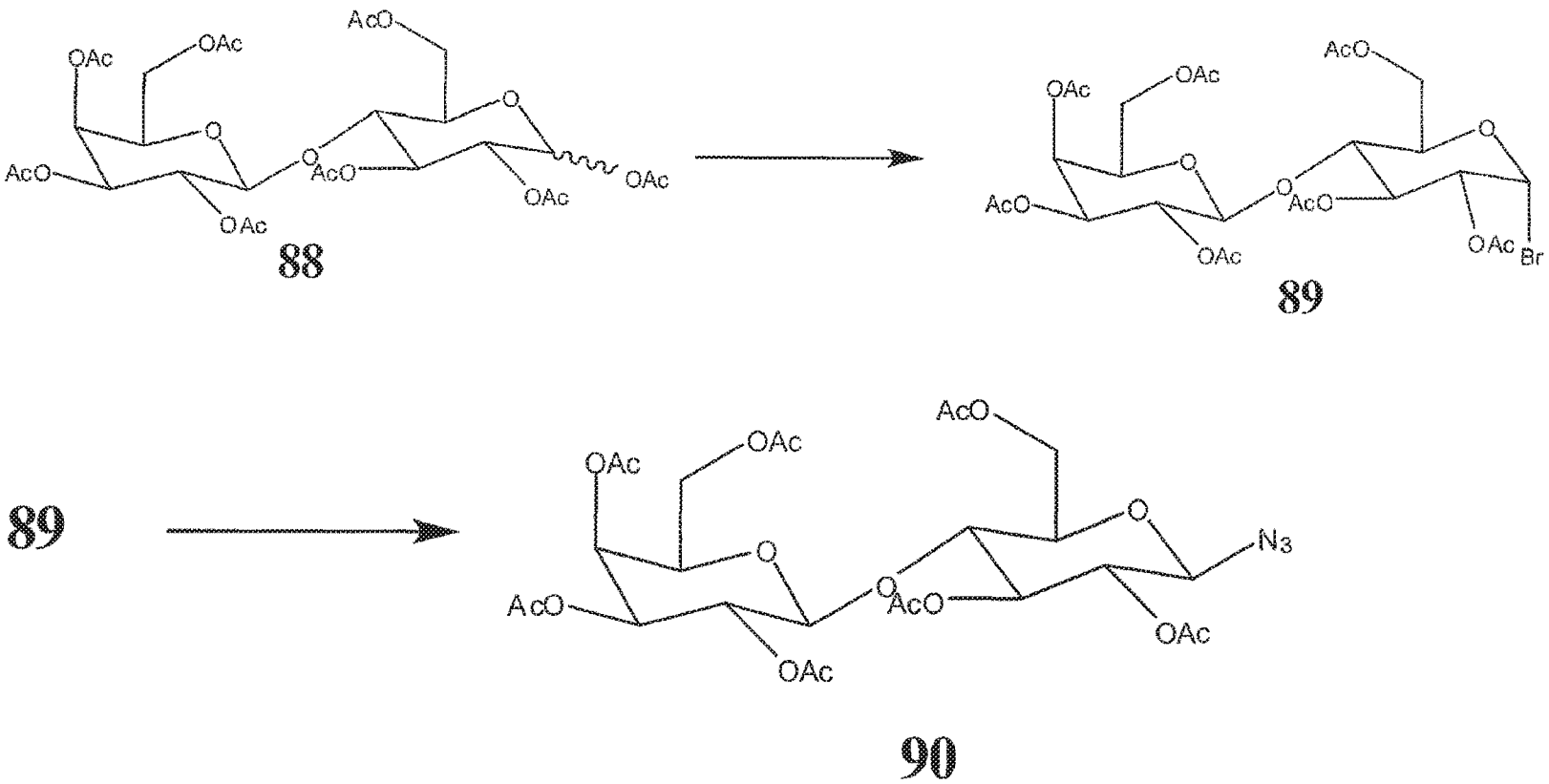
Figure 29B:
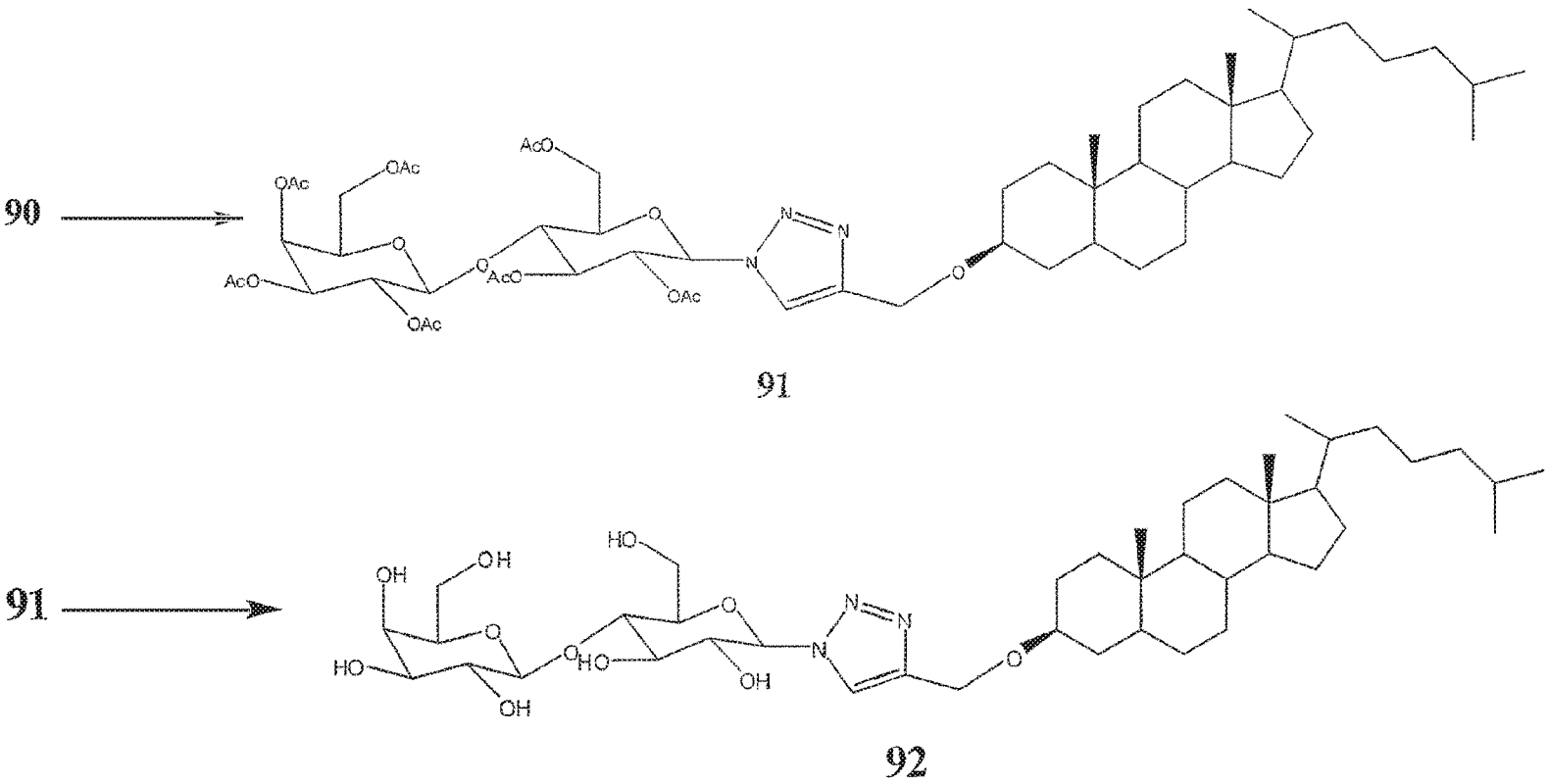
Figure 29C:
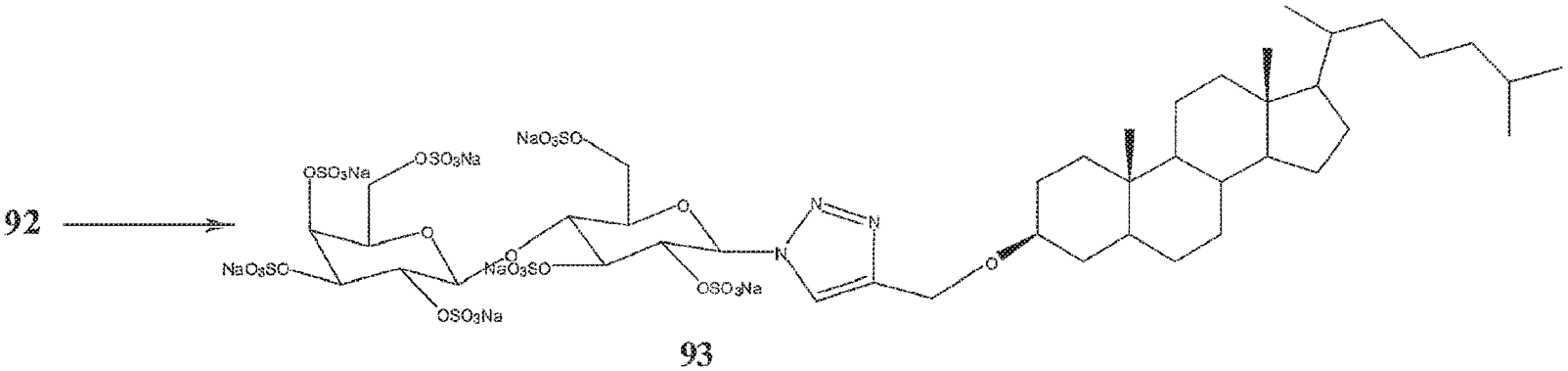
Figure 30A:
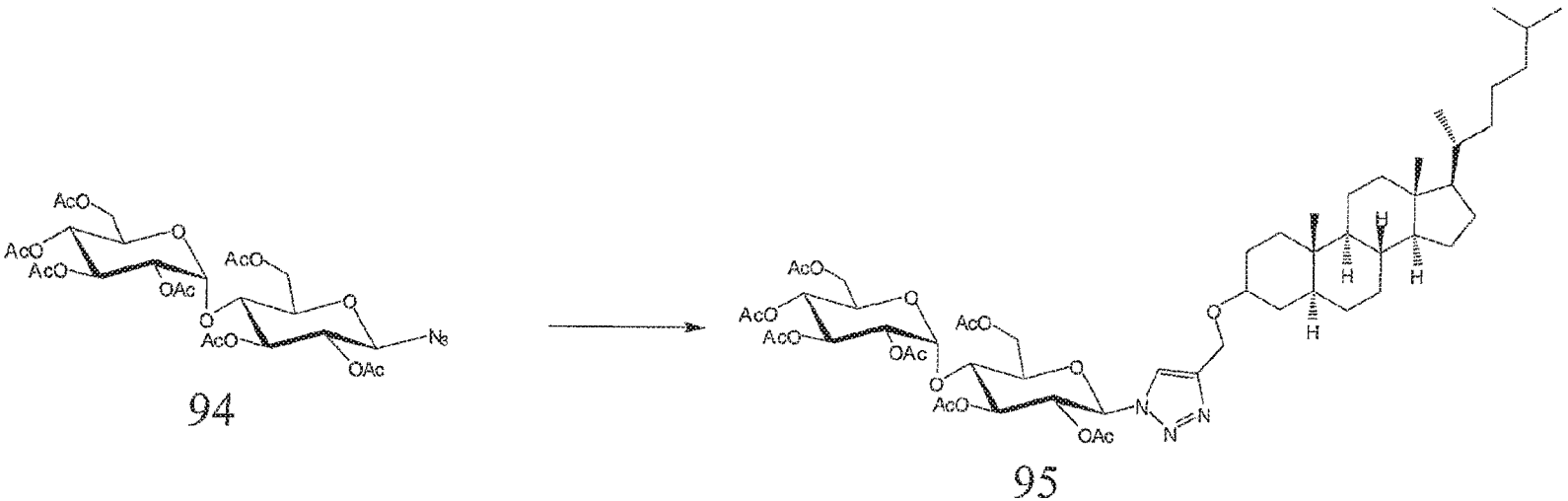
Figure 30B:
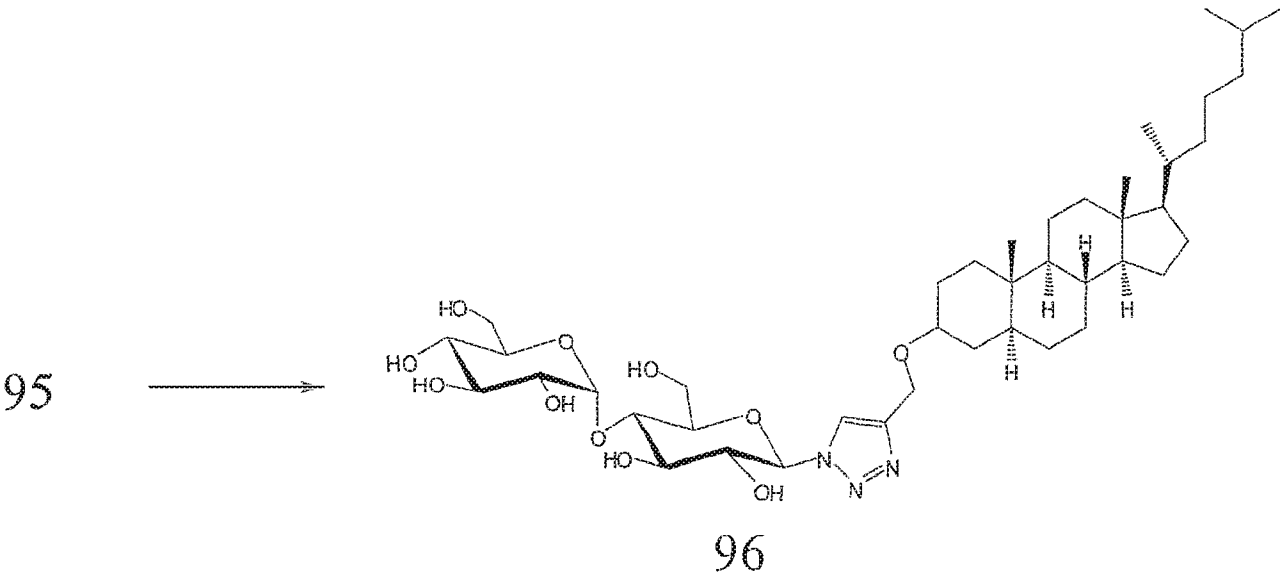
Figure 30C:
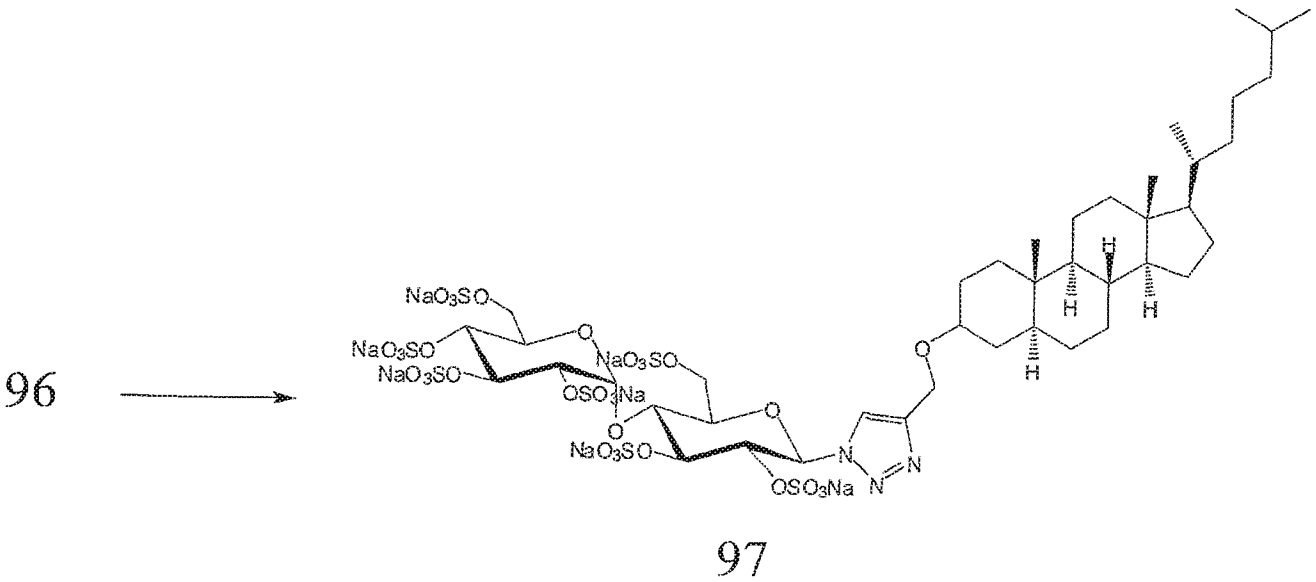
Figure 31A:
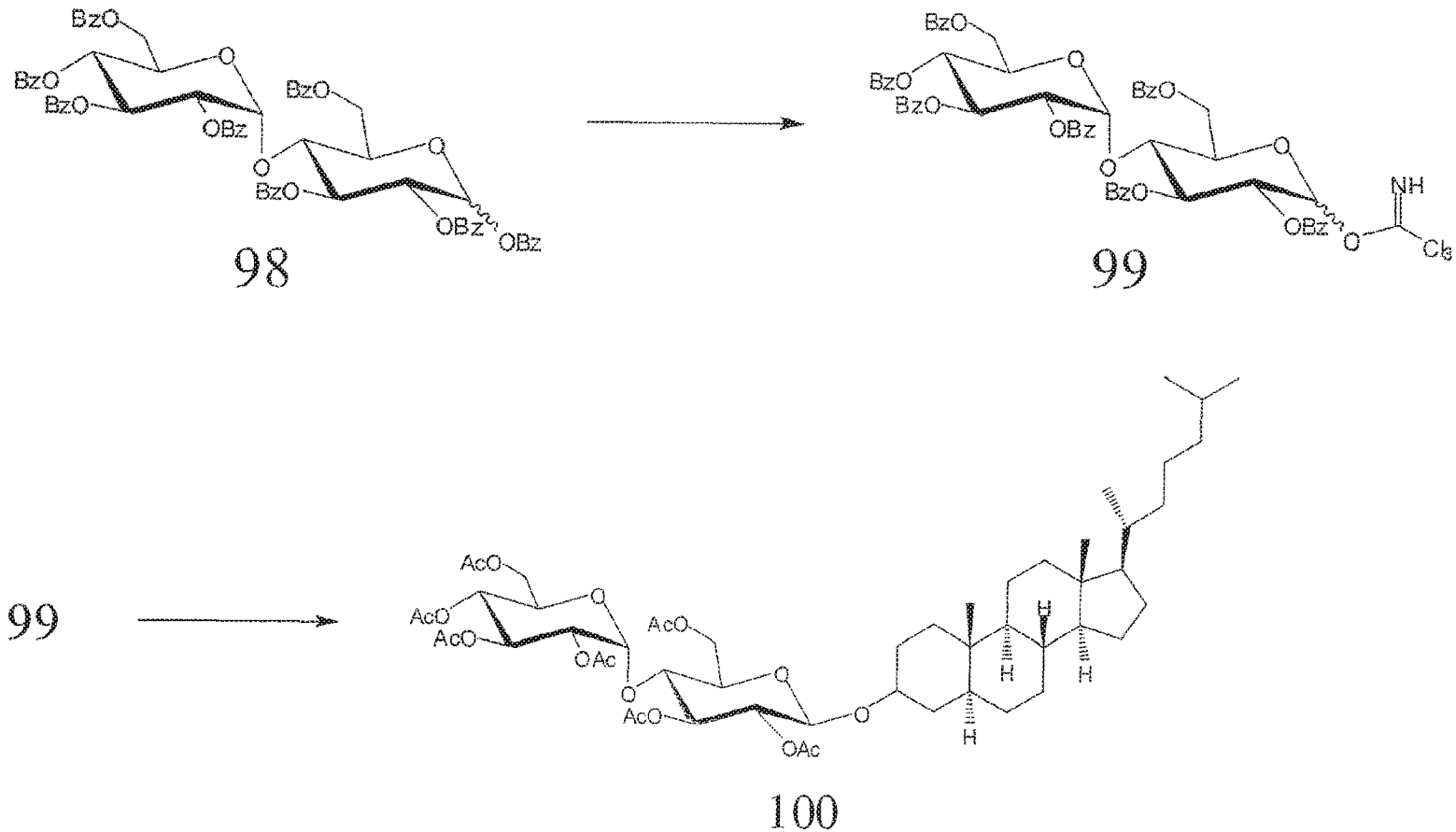
Figure 31B:
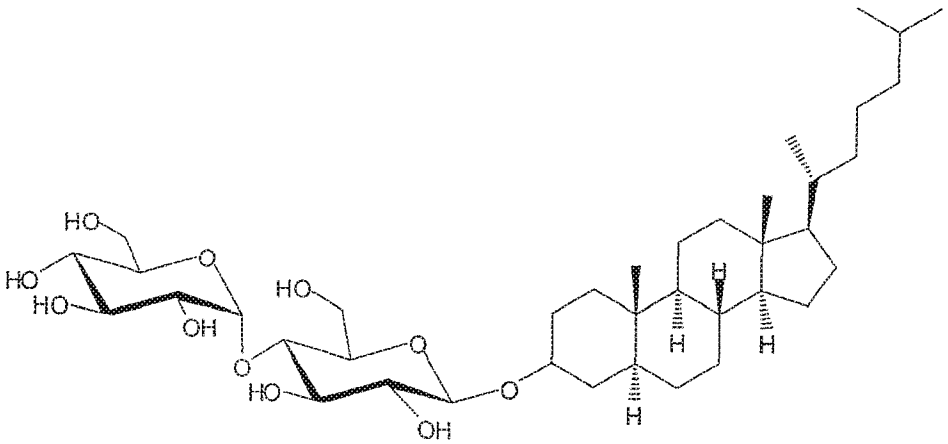
Figure 31C:
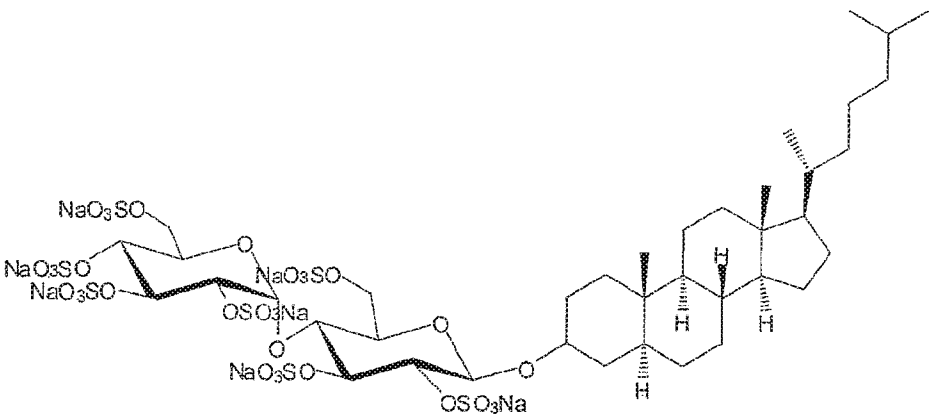
Figure 32A:
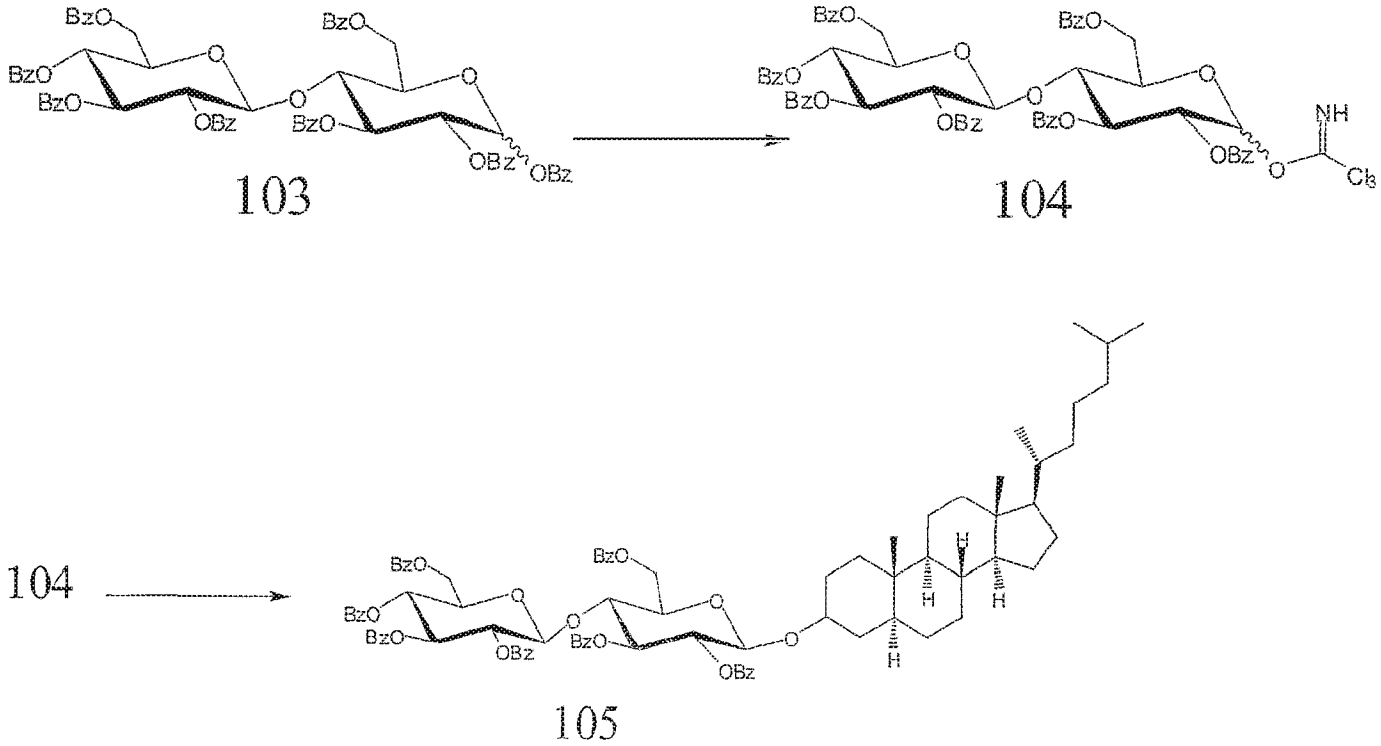
Figure 32B:
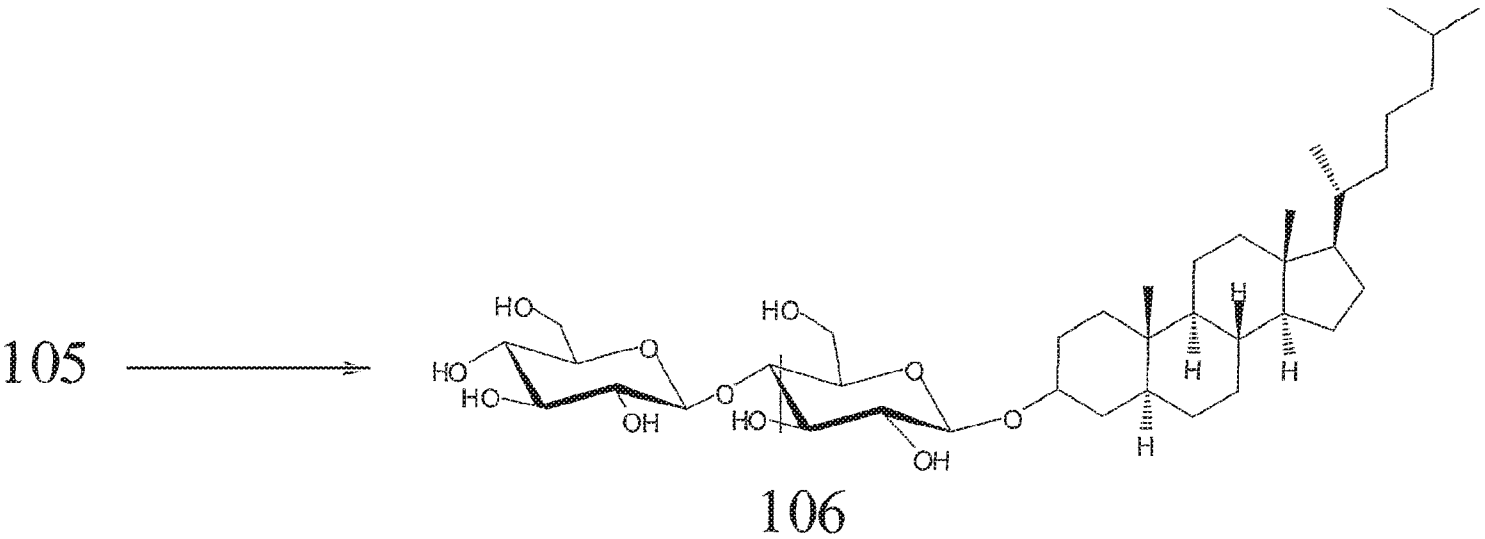
Figure 32C:
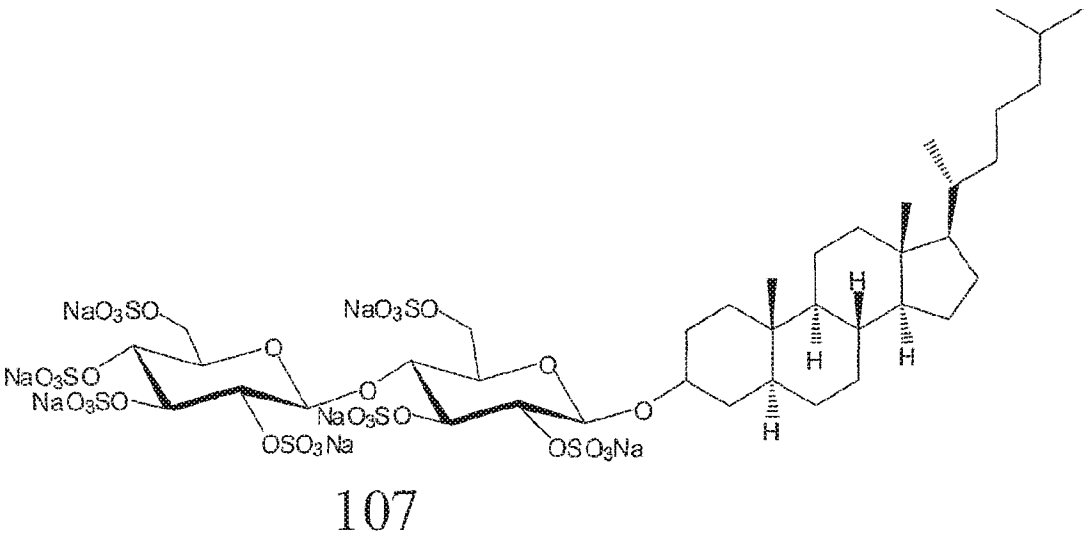
Figure 33A:
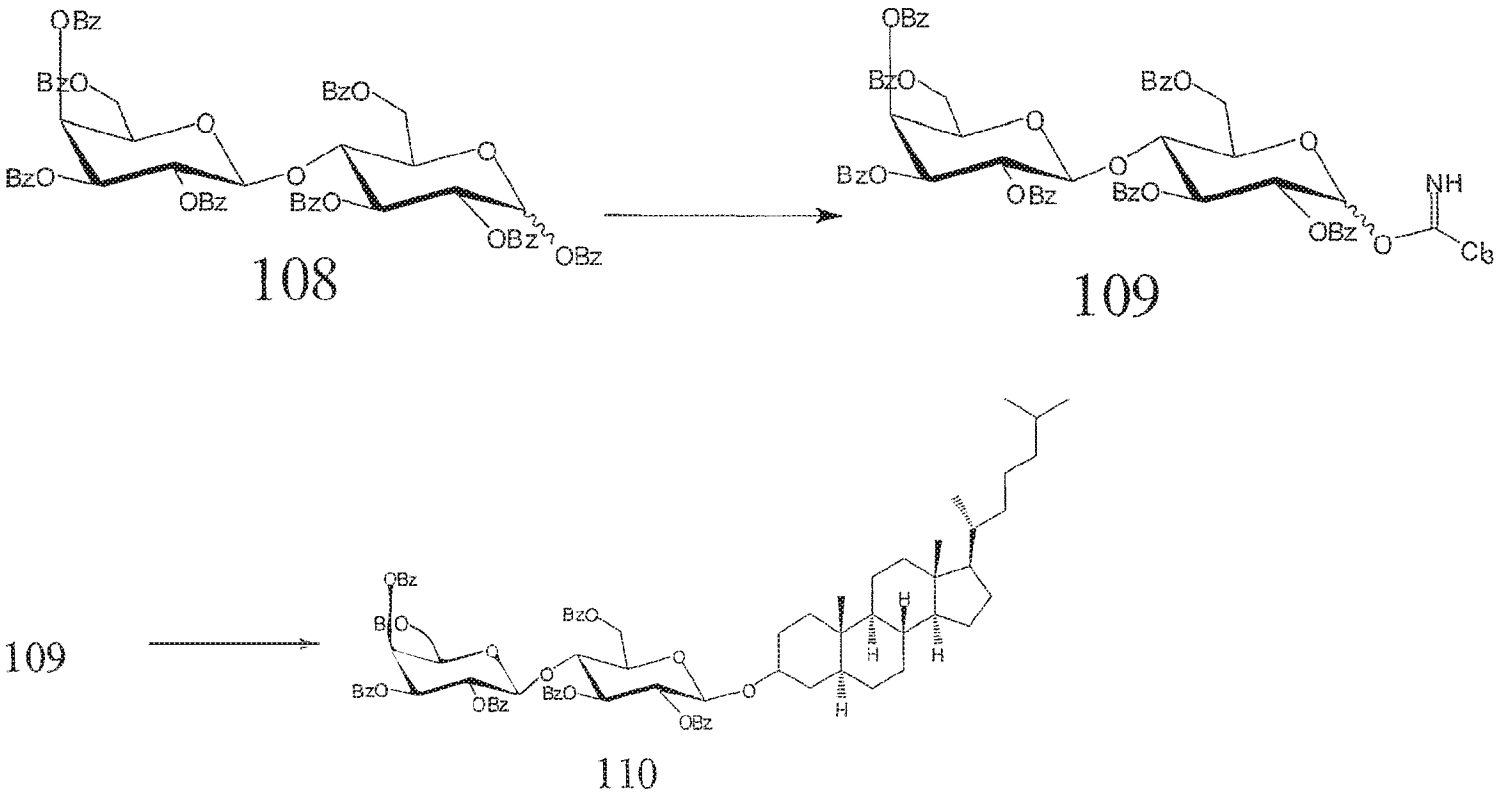
Figure 33B:
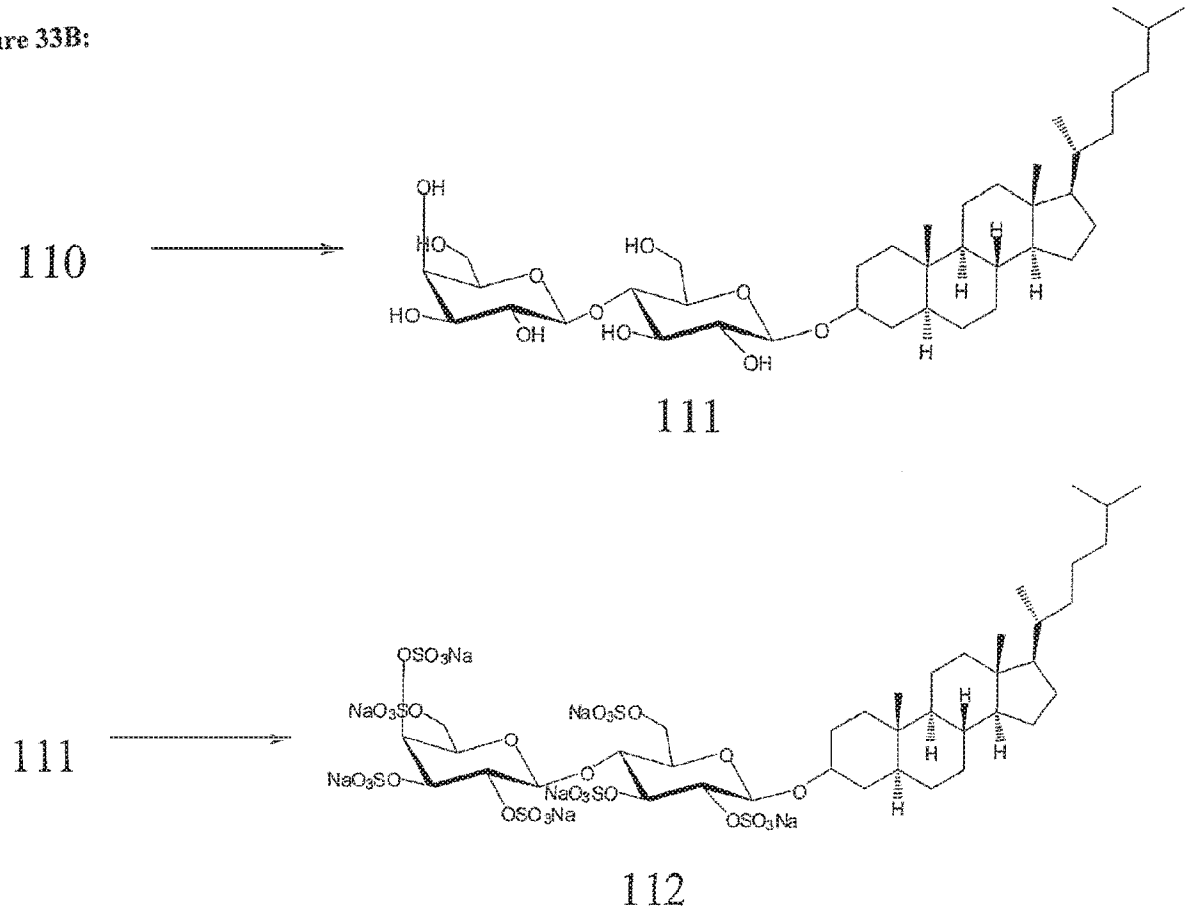
Figure 34A:
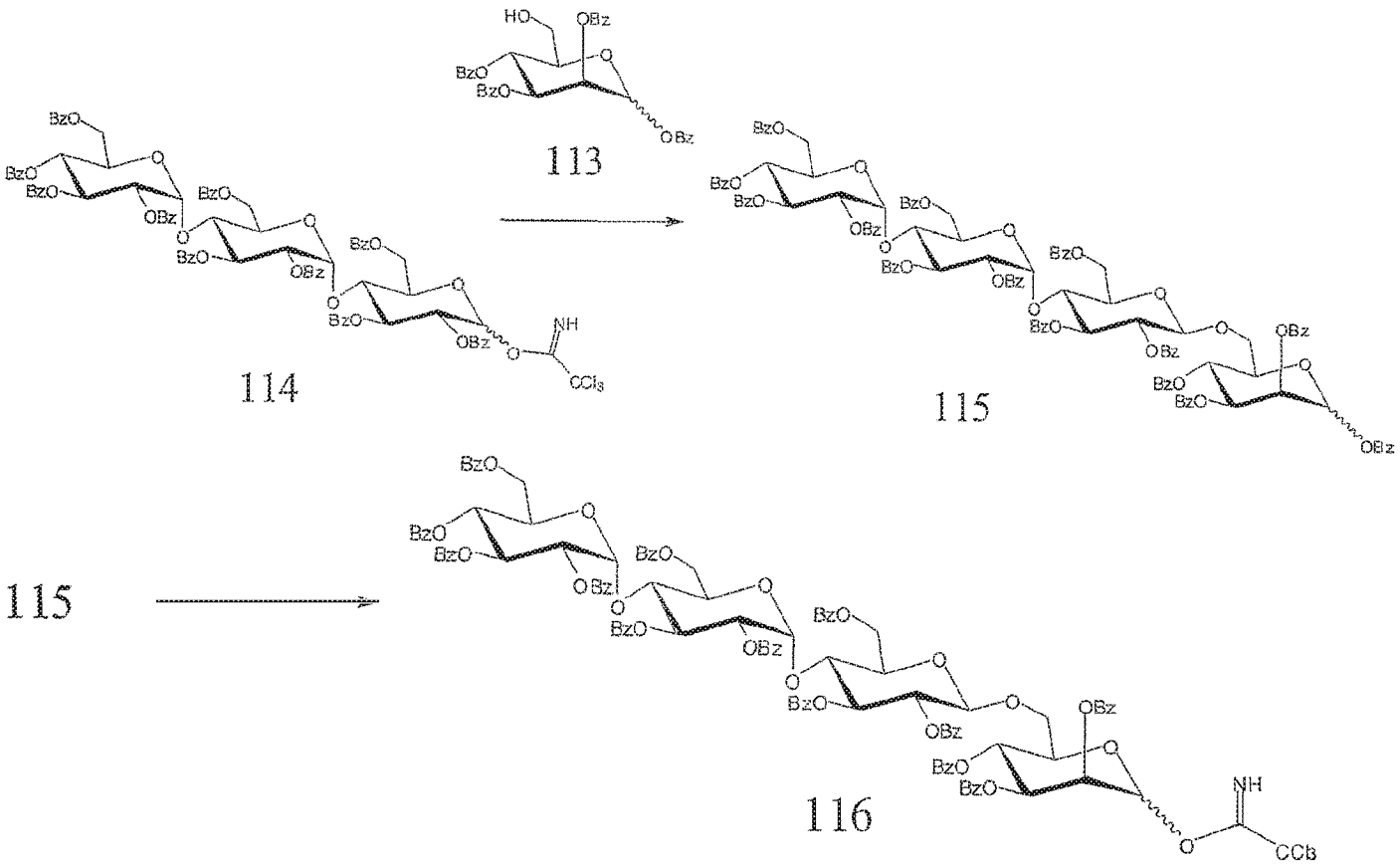
Figure 34B:
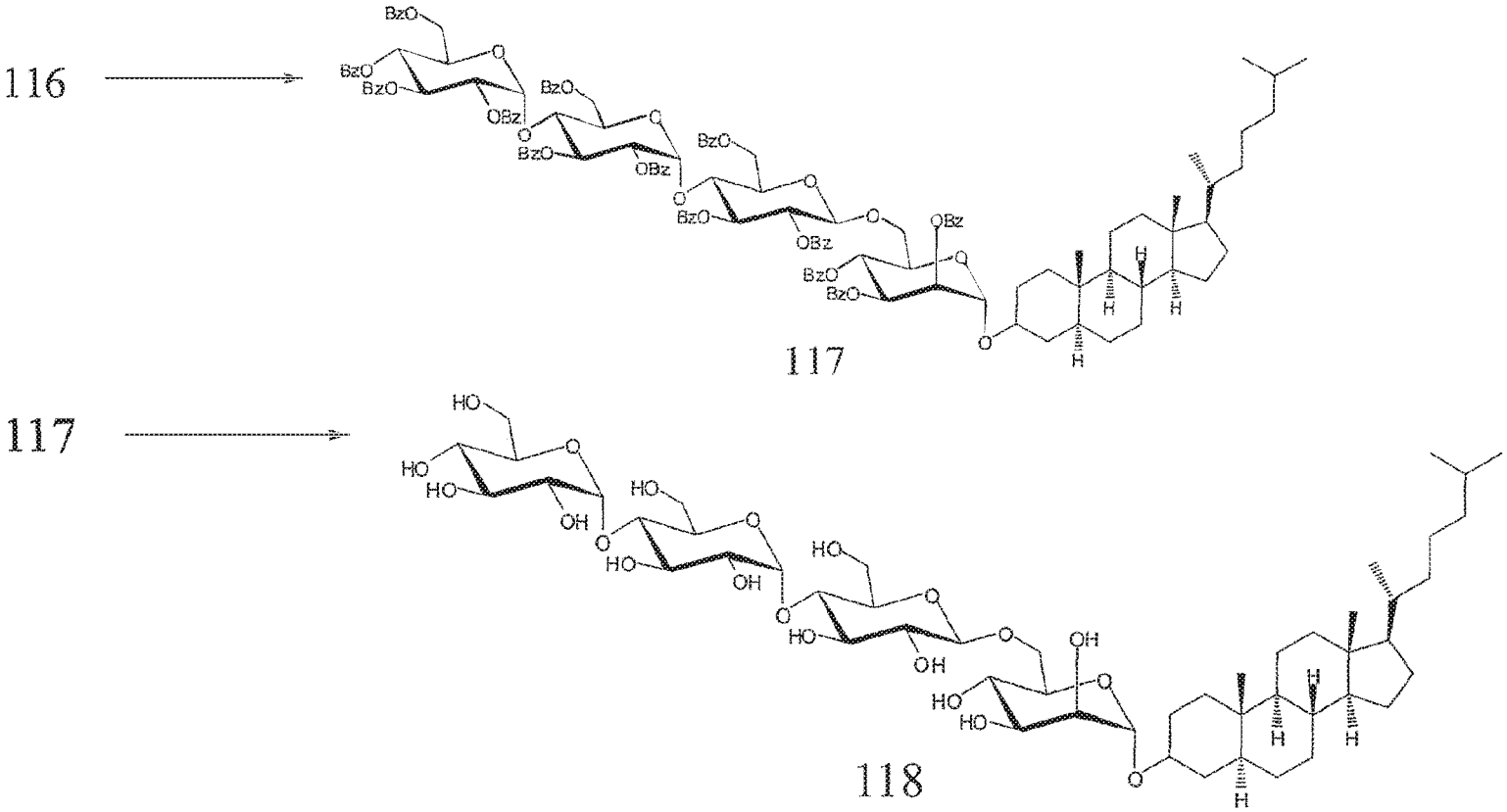
Figure 34C:
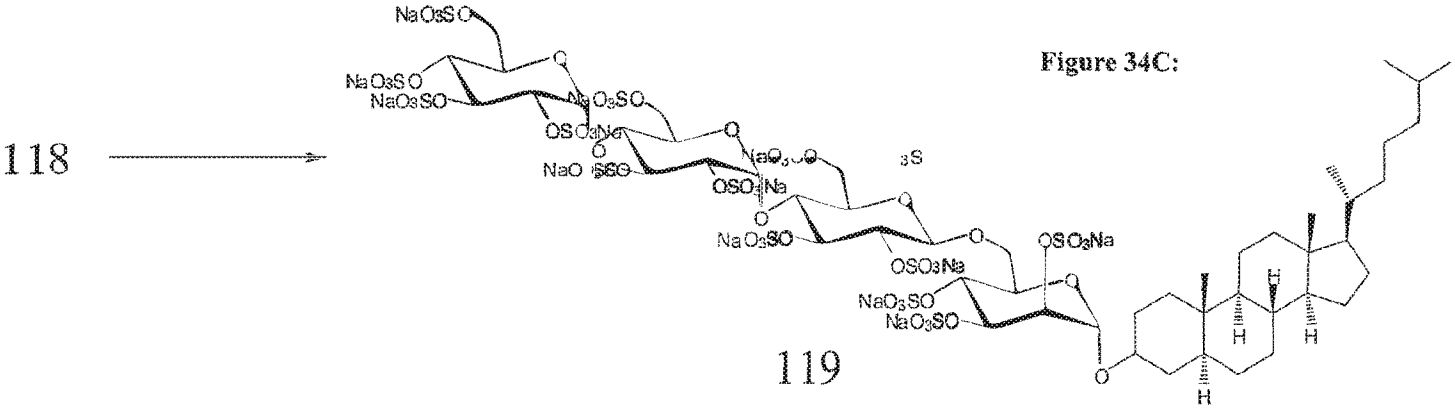
Figure 35A:
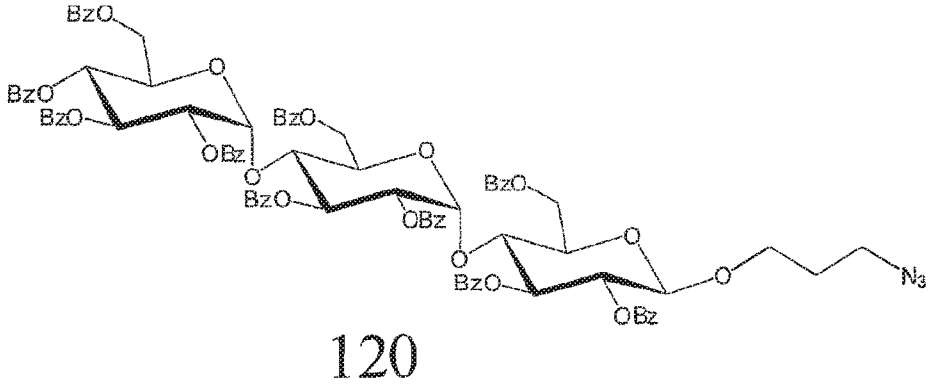
Figure 35B:
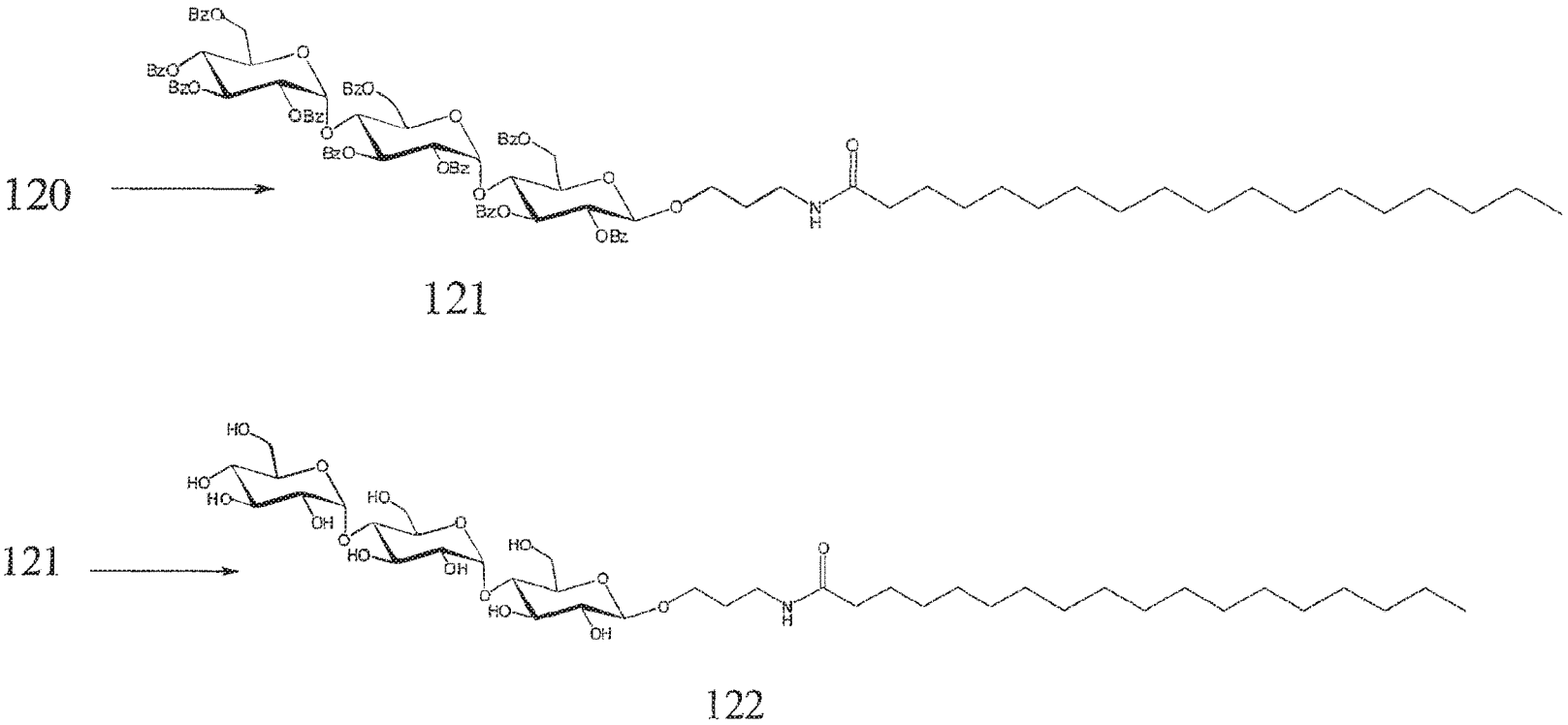
Figure 35C:
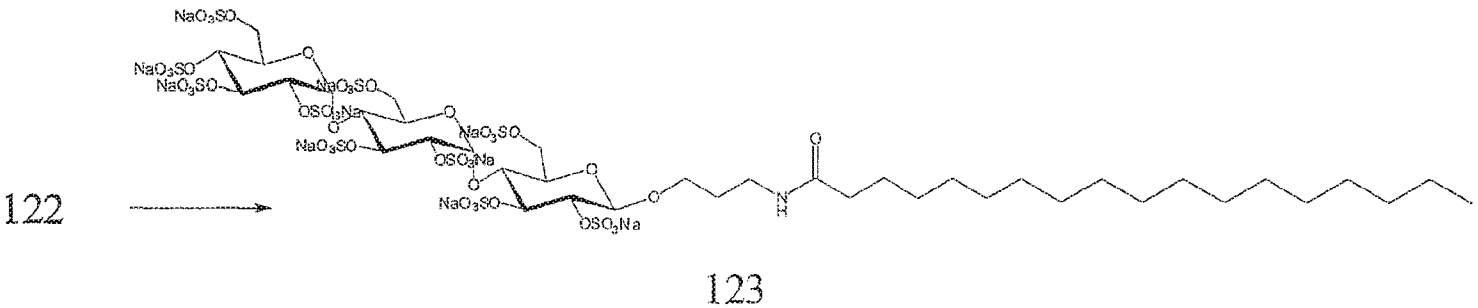
Figure 36A:
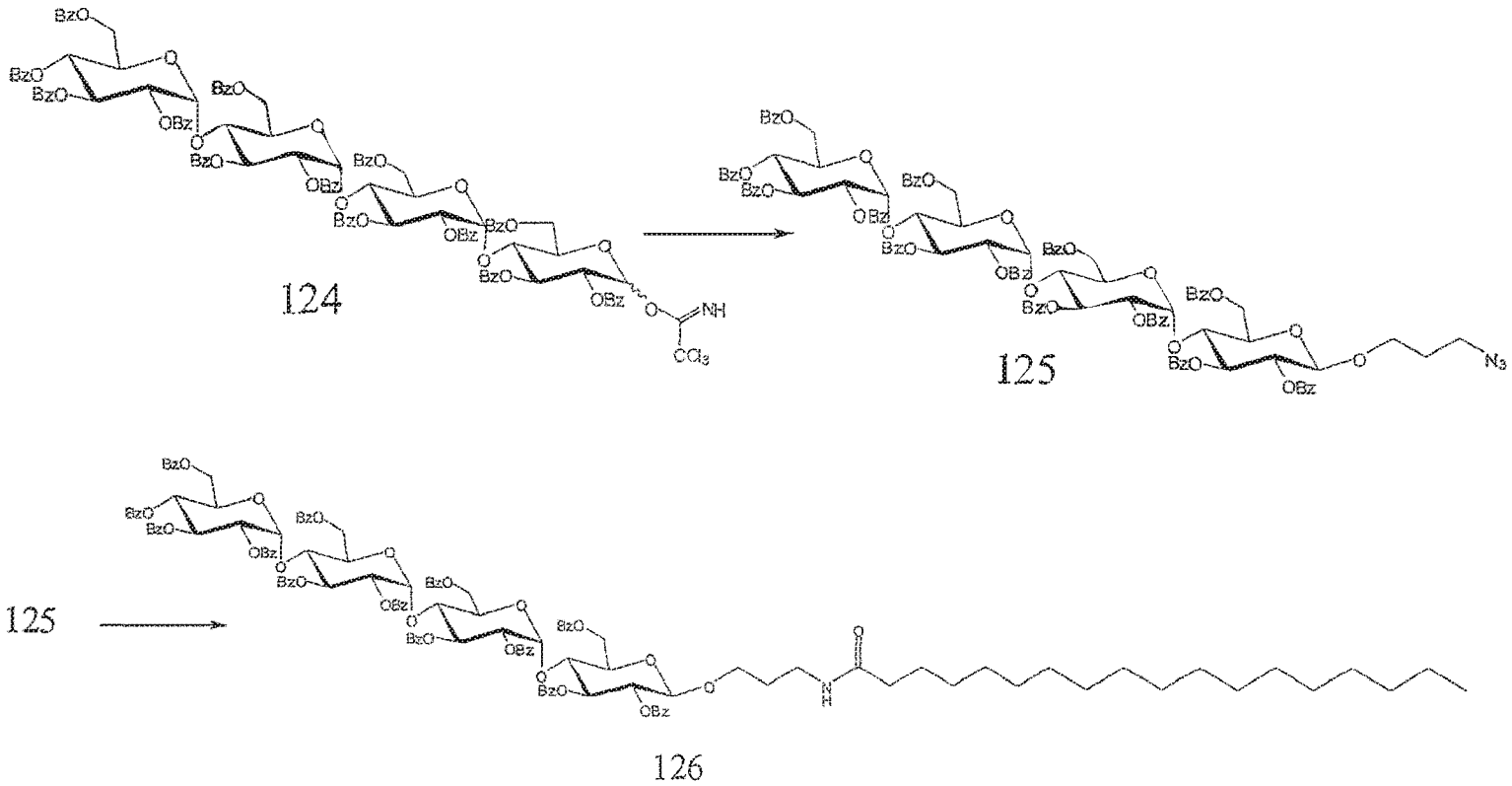
Figure 36B:
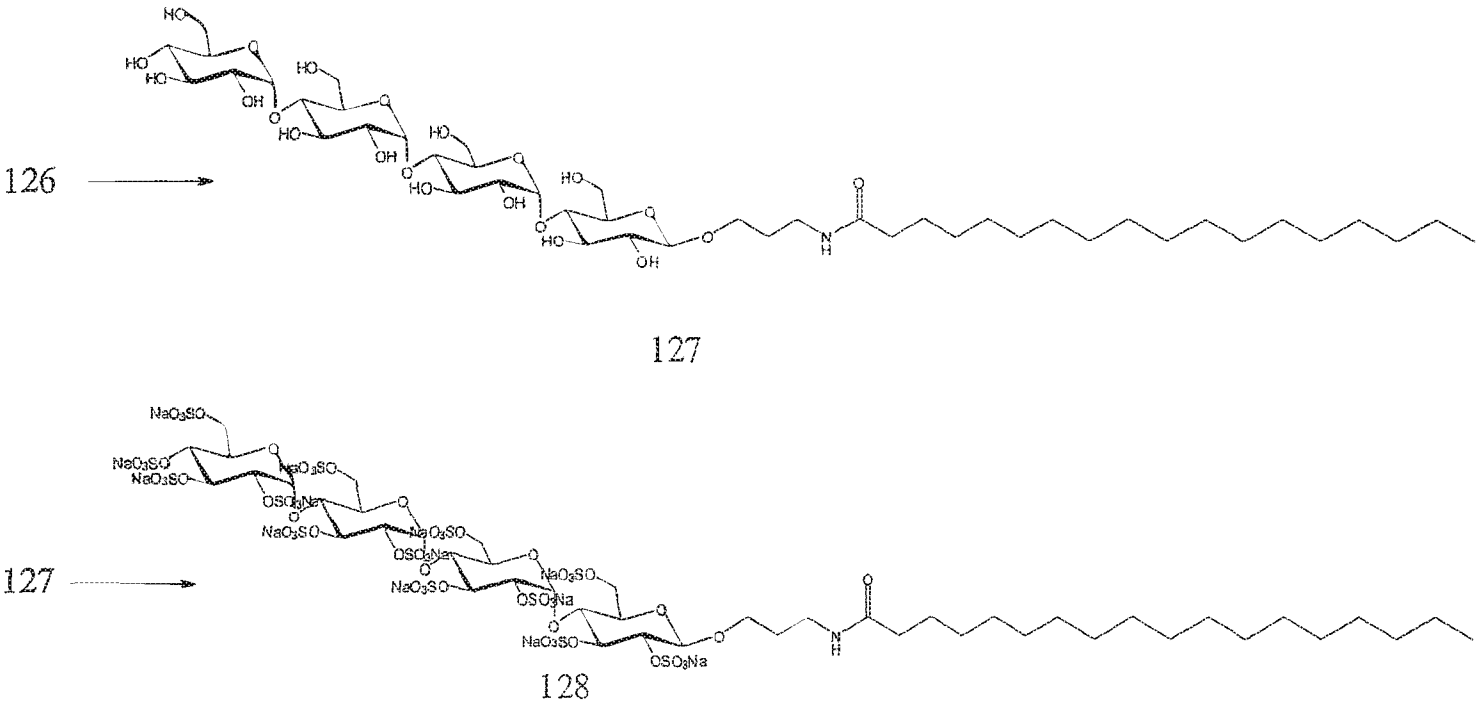
Figure 37A:
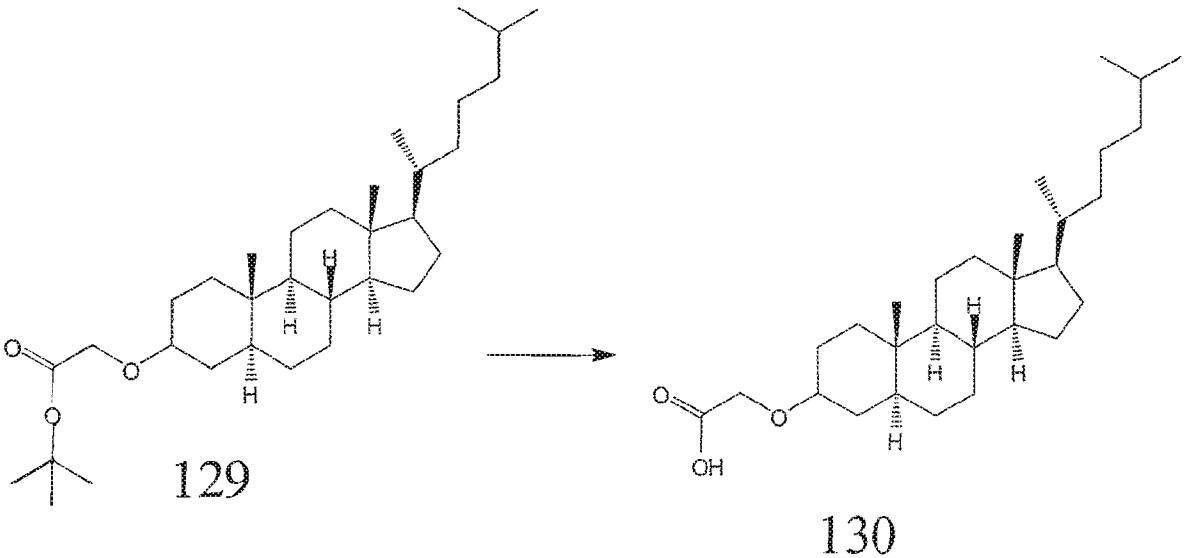
Figure 37B:
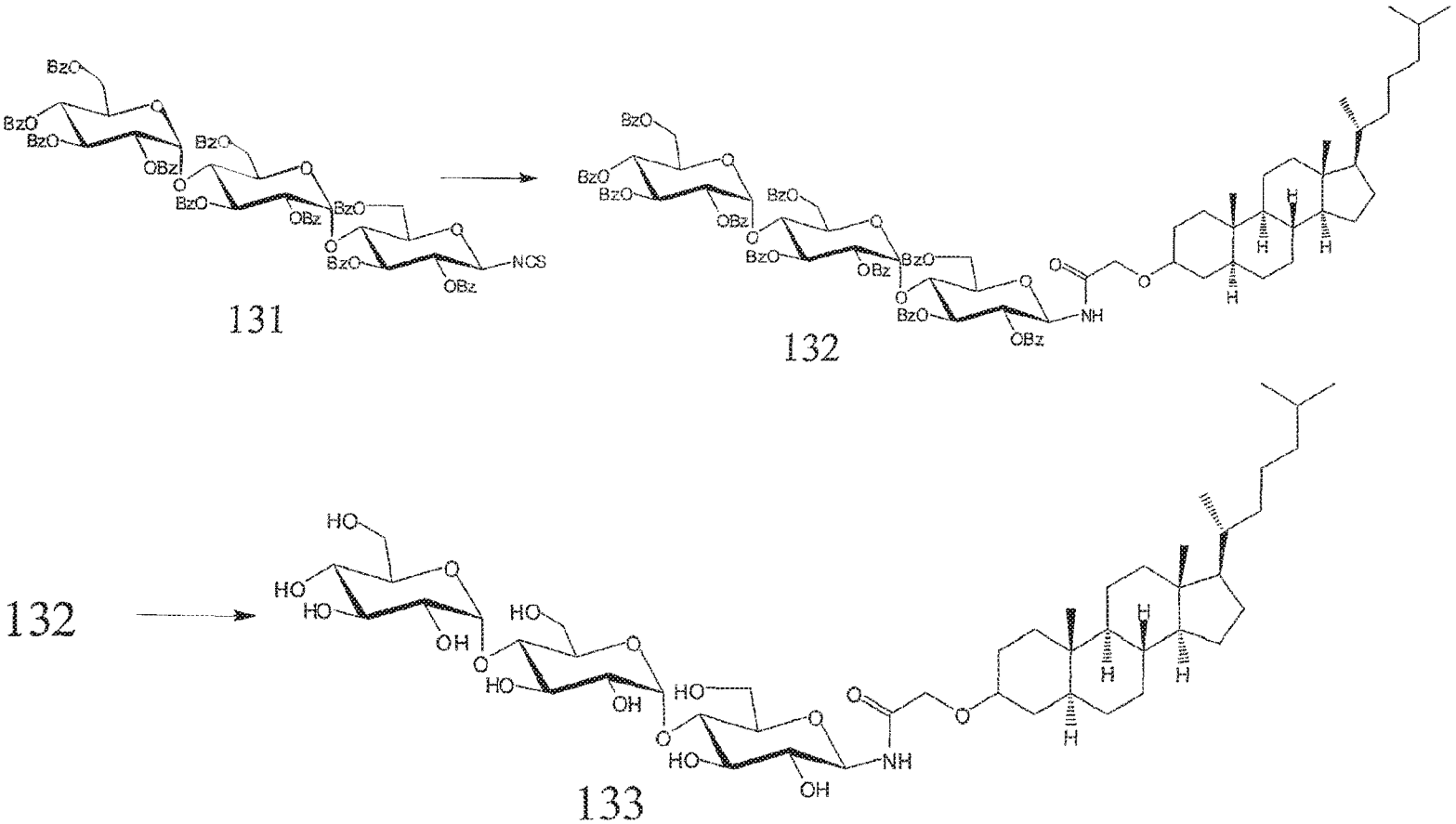
Figure 38A:
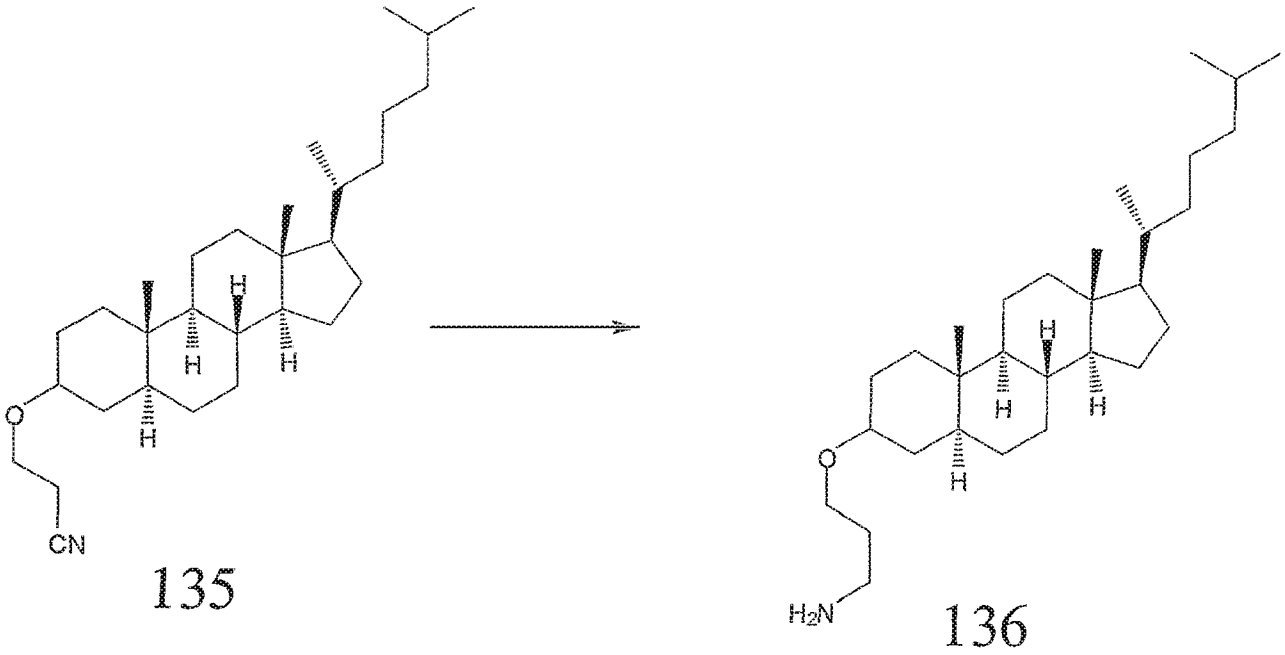
Figure 38B:
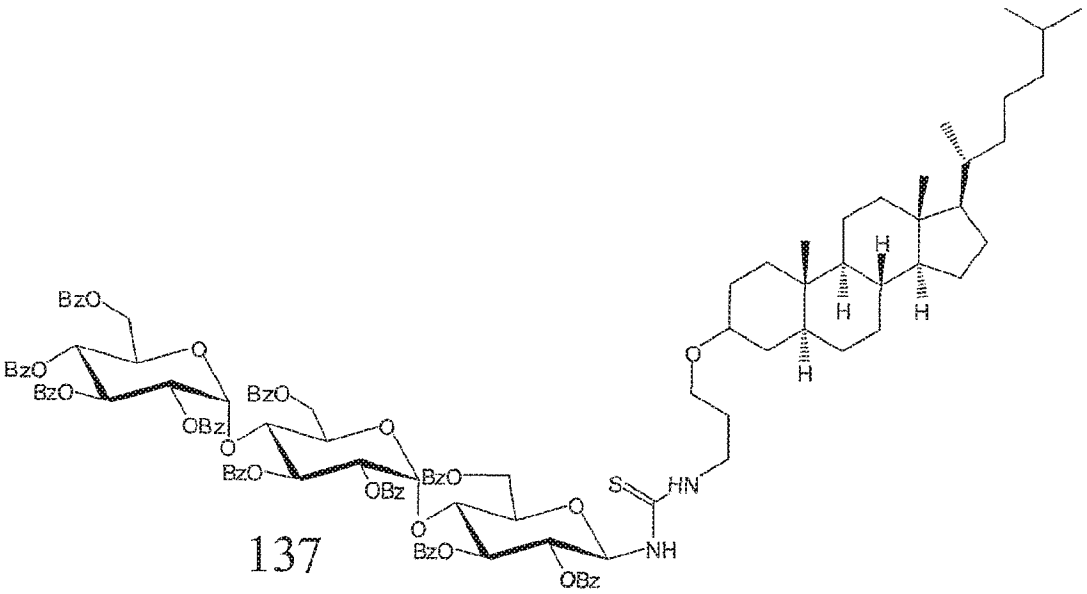
Figure 38C:
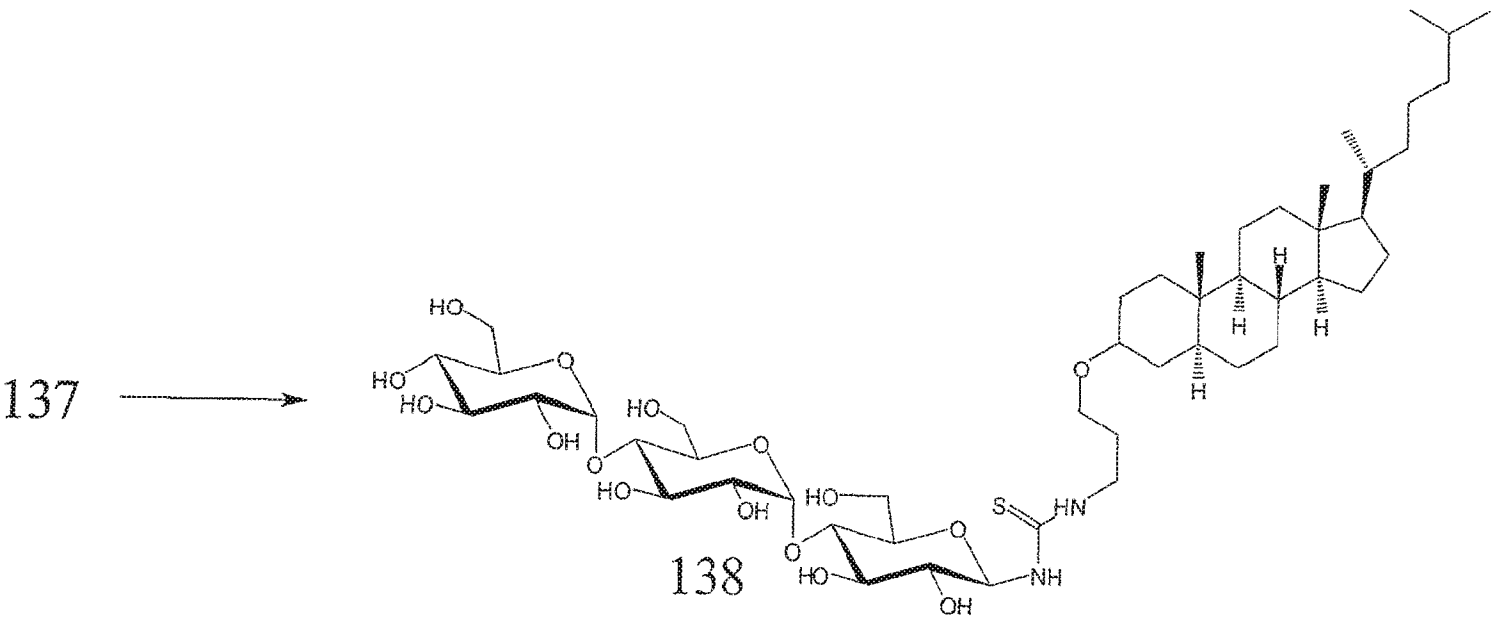
Figure 38D:
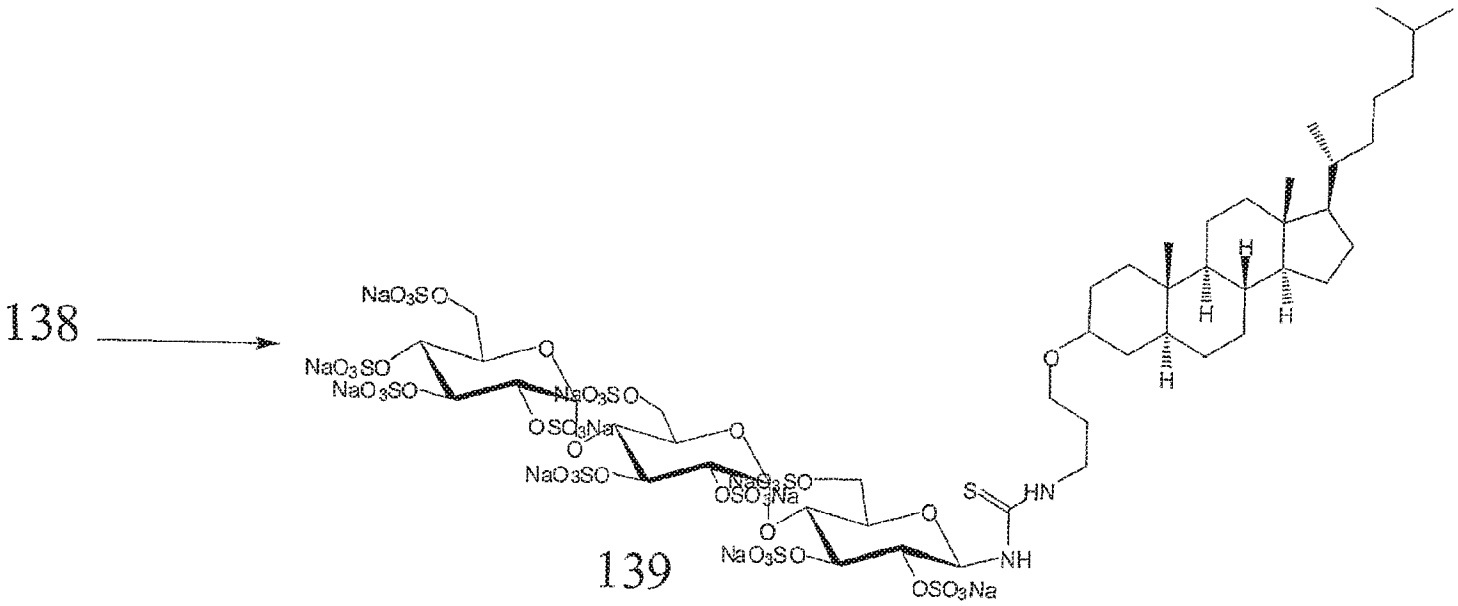
Figure 39:
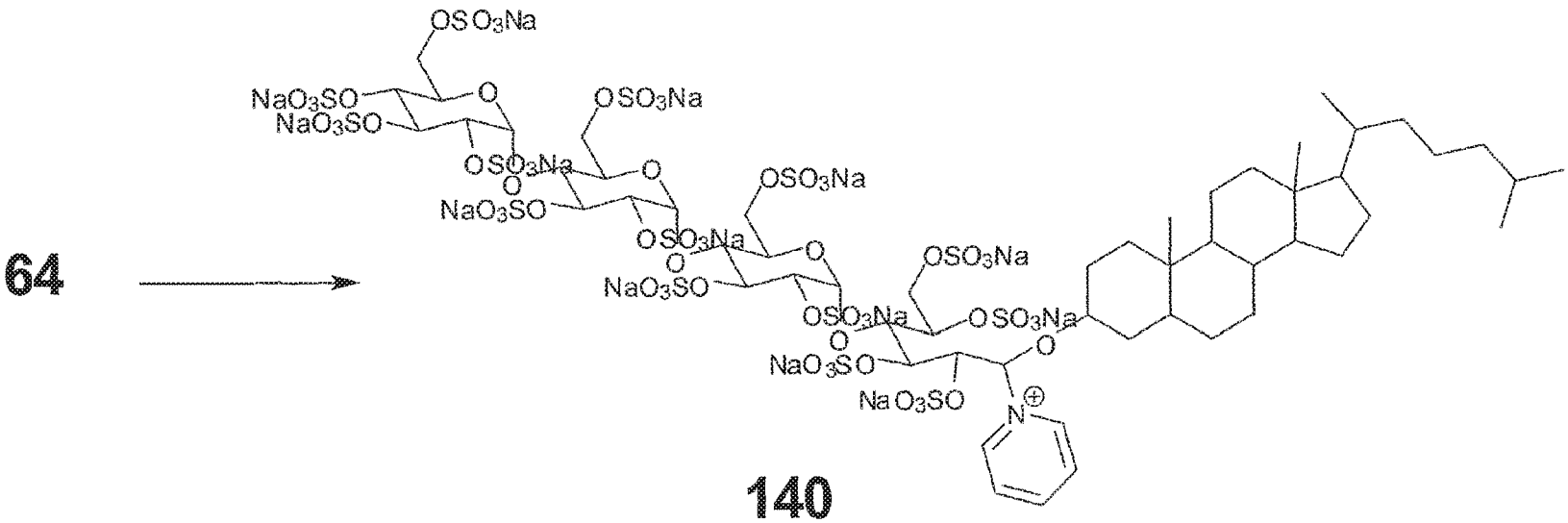
Figure 40A:
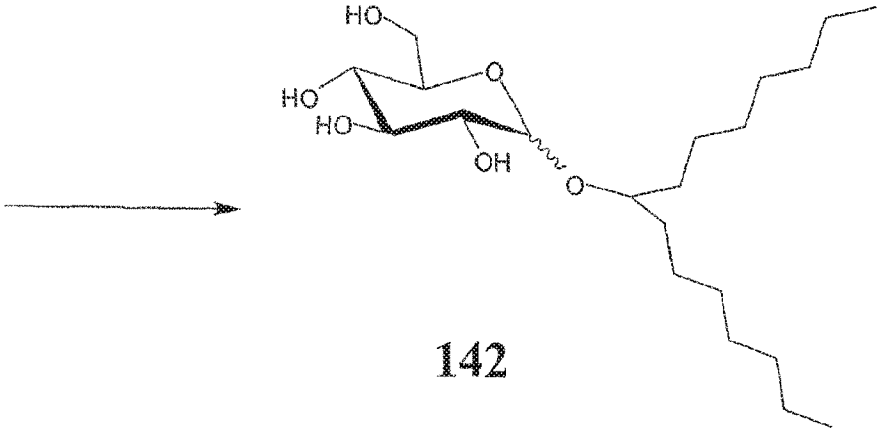
Figure 40B:
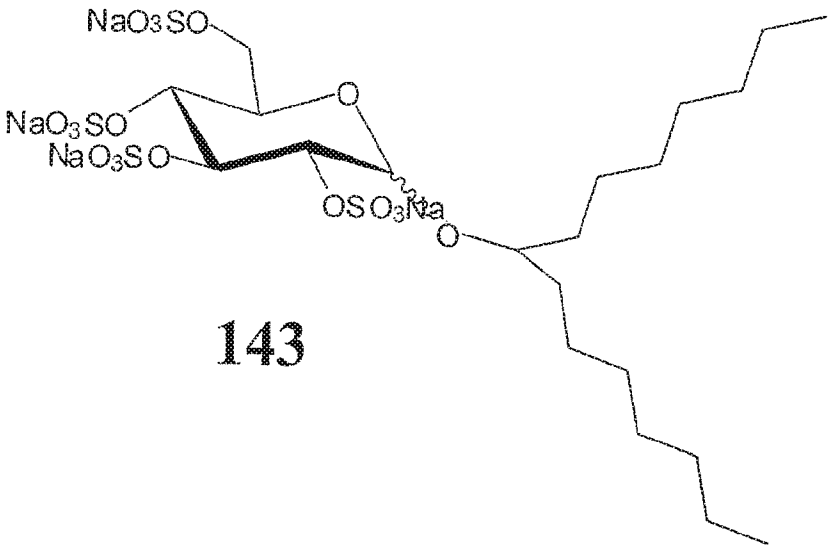

The sulfated oligosaccharide derivatives described in WO 2005/085264 are good inhibitors of angiogenesis and other processes mediated by HS-binding proteins. Such compounds have utility in the prevention or treatment in mammalian subjects of a disorder resulting from angiogenesis, metastasis, inflammation, coagulation, thrombosis, elevated blood triglyceride levels, microbial infection and/or cardiovascular disease. This utility results from the ability of the compounds to inhibit the activity of HS-binding proteins such as the growth factors FGF-2 and VEGF, and the enzyme heparanase. The inventors have found that if sulfated oligosaccharides are modified with highly lipophilic groups, e.g., cholestanol or stearic acid, said groups being attached to carbohydrate directly or via a linker, then the new compounds generated have significantly increased potency as antiangiogenic agents and improved pharmacokinetic properties. This is demonstrated by their activity in various in vitro and ex vivo angiogenesis assays such as growth factor-induced endothelial cell proliferation and migration assays, the endothelial tube formation assay on Matrigel™ and the rat aorta assay. This increased potency is also manifested in animal models of tumour growth. Of particular note is the fact that smaller sulfated saccharides (e.g., mono- to trisaccharides), which generally are inactive or have only mild antiangiogenic activity (or other HS-mimetic activity) compared with longer homologues, once modified have significantly increased activity similar to or better than their longer but unmodified congeners.

Some of the compounds also display increased potency as antiviral agents. For example, lipophilic modification resulted in enhanced capability to inhibit the infection of cells and the cell-to-cell transmission of herpes simplex virus (HSV), respiratory syncytial virus (RSV), or HIV. In addition, the modifications provided some compounds with the ability to completely inactivate the virus particles thus making them more potent antivirals than unmodified sulfated oligosaccharides (such as PI-88) which can inhibit virus binding/entry steps without inactivating the virions.

One of the side effects of unmodified sulfated oligosaccharides is anticoagulant activity. The lipophilic modifications described here result in new compounds with significantly reduced anticoagulant activity compared with PI-88, which may result in broader therapeutic windows. The injection site bruising commonly seen in animals treated with PI-88 is also eliminated, thus potentially improving patient compliance.

The sulfated oligosaccharide derivatives described in this specification can be synthesised using a number of different strategies as broadly described below and as illustrated in the examples.

With regard to the subject compounds of Formula I and Formula II, the monosaccharide units X and Y can be, for example, any hexose or pentose and can be either a D or L isomer. Such hexoses include glucose, mannose, altrose, allose, talose, galactose, idose and gulose. Such pentoses include ribose, arabinose, xylose and lyxose. The glycosidic linkages of the monosaccharide units can be exclusively of one type or of different types in terms of configuration and linkage.

The pharmaceutically acceptable cation M can be any such cation, but is preferably sodium.

With regard to integer n, n is an integer from 0-6, preferably 2, 3 or 4, so as to provide a compound which is a tri-, tetra- or pentasaccharide.

The $R^2$ group can be any suitable lipophilic moiety, but is preferably cholestanyl or propyl stearamide.

The anomeric configuration, where applicable, at $ZR^1$ of compounds of formula I can be either α or β or an anomeric α/β mixture.

With regard to the substituents given above in the definition of compounds of Formula I and Formula II, the term "alkyl", when used alone or in compound words such as "arylalkyl" refers to a straight chain, branched or cyclic hydrocarbon group.

The term "aryl", when used alone or in compound words such as "arylalkyl", denotes single, polynuclear, conjugated or fused residues of aromatic hydrocarbons. An aryl group may be optionally substituted by one or more optional substituents.

The term "acyl" refers to a group —C(O)—R wherein R is an alkyl or aryl group. Since the R group may be optionally substituted as described above, "acyl" is taken to refer to optionally substituted acyl.

Optional substituents for alkyl, aryl or acyl include halo (bromo, fluoro, chloro, iodo), hydroxy, $C_{1-6}$alkyl (e.g. methyl, ethyl, propyl (n- and i-isomers)), $C_{1-6}$alkoxy (e.g. methoxy, ethoxy, propoxy (n- and i-isomers), butoxy (n-, sec- and t-isomers), nitro, amino, $C_{1-6}$alkylamino (e.g. methyl amino, ethyl amino, propyl (n- and i-isomers) amino), $C_{1-6}$dialkylamino (e.g. dimethylamino, diethylamino, diisopropylamino), halomethyl (e.g. trifluoromethyl, tribromomethyl, trichloromethyl), halomethoxy (eg trifluoromethoxy, tribromomethoxy, trichloromethoxy) and acetyl.

The degree of sulfation of compounds according to the invention is typically at least 70%. That is, at least 70% of the hydroxyl groups of an oligosaccharide derivative not involved in a glycosidic linkage are substituted by $SO_3M$. The degree of sulfation is typically from 70 to 100% and preferably is at least as high as 90%.

The compounds of Formula I and Formula II can be made via a stepwise synthetic route from carbohydrate building blocks or by starting with an oligosaccharide of the appropriate length and making the desired modifications thereto. Monosaccharides of formula I can be made directly from the monosaccharide starting material. The lipophilic modifications can be introduced to the saccharide by a number of different methods, as will be apparent to those skilled in the art. For example, lipophilic groups can be introduced at the anomeric position of the reducing end sugar via an O-, N-, S- or C-glycosidic linkage and the said group can be directly linked to the anomeric position or may be attached via a linker. Those skilled in the art will recognize that there are numerous types of suitable linkers.

It should be noted that all the derivatives made as describe above are then subject to deprotection (typically, deacetylation with NaOMe) and the resulting polyol sulfonated with a sulfonating reagent such as sulfur trioxide pyridine complex or sulfur trioxide trimethylamine complex.

As indicated above, the compounds according to the invention have utility in the prevention or treatment in mammalian subjects of a disorder resulting from angiogenesis, metastasis, inflammation, coagulation, thrombosis, elevated blood triglyceride levels, microbial infection or cardiovascular disease. The compounds have particular utility in the treatment of the foregoing disorders in humans. The compounds are typically administered as a component of a pharmaceutical composition as described in the following paragraphs.

Pharmaceutical compositions for oral administration can be in tablet, capsule, powder or liquid form. A tablet can include a solid carrier such as gelatine or an adjuvant or an inert diluent. Liquid pharmaceutical compositions generally include a liquid carrier such as water, petroleum, animal or vegetable oils, a mineral oil or a synthetic oil. Physiological saline solution, or glycols such as ethylene glycol, propylene glycol or polyethylene glycol may be included. Such compositions and preparations will generally contain at least 0.1 wt % of the compound.

Parenteral administration includes administration by the following routes: intravenously, cutaneously or subcutaneously, nasally, intramuscularly, intraocularly, transepithelially, intraperitoneally and topically. Topical administration includes dermal, ocular, rectal, nasal, as well as administration by inhalation or by aerosol means. For intravenous, cutaneous or subcutaneous injection, or injection at a site where treatment is desired, the active ingredient will be in the form of a parenterally acceptable aqueous solution which is pyrogen-free and has suitable pH, isotonicity and stability.

Those of skill in the art will be well able to prepare suitable solutions using, for example, solutions of the subject compounds or derivatives thereof.

In addition to the at least one compound and a carrier or diluent, compositions according to the invention can further include a pharmaceutically or veterinarially acceptable excipient, buffer, stabiliser, isotonicising agent, preservative or anti-oxidant or any other material known to those of skill in the art. It will be appreciated by the person of skill that such materials should be non-toxic and should not interfere with the efficacy of the compound(s). The precise nature of any additive may depend on the route of administration of the composition: that is, whether the composition is to be administered orally or parenterally. With regard to buffers, aqueous compositions typically include such substances so as to maintain the composition at a close to physiological pH or at least within a range of about pH 5.0 to 8.0.

Compositions according to the invention can also include active ingredients in addition to the at least one compound. Such ingredients will be principally chosen for their efficacy as anti-angiogenic, anti-metastatic, anti-inflammatory, anti-coagulant, antimicrobial and anti-thrombotic agents, and agents effective against elevated blood triglyceride levels and cardiovascular disease, but can be chosen for their efficacy against any associated condition.

A pharmaceutical or veterinary composition according to the invention will be administered to a subject in either a prophylactically effective or a therapeutically effective amount as necessary for the particular situation under consideration. The actual amount of at least one compound administered by way of a composition, and rate and time-course of administration, will depend on the nature and severity of the condition being treated or the prophylaxis required. Prescription of treatment such as decisions on dosage and the like will be within the skill of the medical practitioner or veterinarian responsible for the care of the subject. Typically however, compositions for administration to a human subject will include between about 0.01 and 100 mg of the compound per kg of body weight and more preferably between about 0.1 and 10 mg/kg of body weight.

The compounds can be included in compositions as pharmaceutically or veterinarially acceptable derivatives thereof. As used herein "derivatives" of the compounds includes salts, coordination complexes with metal ions such as $Mn^{2+}$ and $Zn^{2+}$, esters such as in vivo hydrolysable esters, free acids or bases, hydrates, or prodrugs. Compounds having acidic groups such as phosphates or sulfates can form salts with alkaline or alkaline earth metals such as Na, K, Mg and Ca, and with organic amines such as triethylamine and Tris(2-hydroxyethyl)amine. Salts can also be formed between compounds with basic groups, such as amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques that will be well known to those of skill in the art.

Prodrug derivatives of the compounds of the invention can be transformed in vivo or in vitro into the parent compounds. Typically, at least one of the biological activities of a parent compound may be suppressed in the prodrug form of the compound, and can be activated by conversion of the prodrug to the parent compound or a metabolite thereof. Prodrugs of compounds of the invention include the use of protecting groups which may be removed in vivo to release the active compound or serve to inhibit clearance of the drug. Suitable protecting groups will be known to those of skill in the art.

As also indicated above, compounds according to the invention have utility in the manufacture of a medicament for the prevention or treatment in a mammalian subject of a disorder resulting from angiogenesis, metastasis, inflammation, coagulation/thrombosis, microbial infection, elevated blood triglyceride levels and/or cardiovascular disease. Processes for the manufacture of such medicaments will be known to those of skill in the art and include the processes used to manufacture the pharmaceutical compositions described above.

A general description of the synthetic routes to the compounds according to the invention will now be given.

General Procedures

General Procedure for Deacetylation

A solution of the peracetate in anhydrous MeOH (0.1 M) (or MeOH-THF) was treated with a solution of NaOMe in MeOH (1.35 M, 0.2-0.6 eq). The mixture was stirred at room temperature for 1-3 h (monitored by TLC). Acidic resin AG®-50W-X8 ($H^+$ form) was added to adjust pH=6-7, the mixture was filtered and the resin was rinsed with MeOH. The combined filtrate and washings were concentrated in vacuo and thoroughly dried to give the polyol product.

General Procedure for Sulfonation

A mixture of the polyol and $SO_3$.trimethylamine or $SO_3$.pyridine complex (2 eq. per alcohol) in DMF was heated (60° C., o/n). The cooled (r.t.) reaction mixture was treated with MeOH and then made basic (to pH>10) by the addition of $Na_2CO_3$ (10% w/w). The mixture was filtered and the filtrate evaporated and co-evaporated ($H_2O$). The crude polysulfated material was dissolved in $H_2O$ and subjected to size exclusion chromatography (see below) to yield the sulfated product. When required, after lyophilisation the product was passed through an ion-exchange resin column (AG®-50W-X8, $Na^+$ form, 1×4 cm, deionized $H_2O$, 15 mL) in order to transfer the product uniformly into the sodium salt form. The solution collected was evaporated and lyophilised to give the final product.

Size Exclusion Chromatography

Size exclusion chromatography (SEC) was performed over Bio-Gel P-2 in a 5×100 cm column and a flow rate of 2.8 mL/min of 0.1 M $NH_4^+ \cdot HCO_3^-$, collecting 2.8 min (7.8 mL) fractions. Fractions were analysed for carbohydrate content by spotting onto silica gel plates and visualisation by charring, and/or analysed for poly-charged species by the dimethyl methylene blue (DMB) test.[29] Finally, fractions were checked for purity by CE[8] and those deemed to be free of salt were pooled and lyophilised.

Example 1

Dodecyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (2)

To a solution of the trichloroacetimidate 1[28] (0.469 g, 0.285 mmol) in DCM (15 mL) was added 1-dodecanol (0.849 mmol, 3 eq) and 3 Å MS (50 mg). The mixture was stirred at −20° C. for 20 min. TMSOTf (103 μL, 0.57 mmol, 2 eq) was added and the mixture stirred at −20° C. for 50 min before quenching with $Et_3N$ (38 μL, 0.285 mmol, 1 eq). After warming to room temperature, the mixture was filtered and the solid washed with DCM. The combined filtrate and washings were evaporated onto silica gel and purified by column chromatography (silica 2×20 cm, gradient elution with $CHCl_3$, $CHCl_3$-MeOH 99:1 to 98:2) to give the glycoside 2 as colourless gum. Two fractions were obtained each containing the byproduct BnNHAc (76 mg, 2:BnNHAc=5:3; 179 mg, 2:BnNHAc=5:11). $^1$H NMR ($CDCl_3$, 400 MHz): 5.30-5.16 (m, 8H), 4.99-4.87 (m, 8H), 4.31-3.77 (m, 19H), 3.68-3.61 (m, 1H, $OCH_2$), 3.44-3.36 (m, 1H, $OCH_2$), 2.18, 2.17, 2.15, 2.11, 2.10, 2.09, 2.07, 2.06, 2.05, 2.02, 2.01, 1.97, 1.95 (each s, total 48H, 16×Ac), 1.58 (quintet, 2H, J=6.7, $CH_2$), 1.33-1.22 (m, 18H, 9×$CH_2$), 0.86 (t, 3H, J=6.7, $CH_3$).

Dodecyl α-D-mannopyranosyl-(1→3)-α-D-mannopyranosyl-(1→3)-α-D-mannopyranosyl-(1→3)-α-D-mannopyranosyl-(12)-α-D-mannopyranoside (3)

Following the general procedure for deacetylation, glycoside 2 (72 mg, 0.043 mmol) in MeOH (3 mL) was treated with NaOMe (11 M in MeOH, 5 μL, 0.055 pimp. The mixture was stirred at room temperature for 20 h, neutralized by addition of AG50WX8 resin ($H^+$ form), filtered and rinsed with water. The solution was extracted with EtOAc (×2) in order to remove BnNHAc. The aqueous phase was evaporated to dryness and the residue freeze-dried to give polyol 3 as an amorphous solid, used directly for the next step. $^1$H NMR ($D_2O$, 400 MHz, internal DOH at 4.60 ppm) δ 4.97-4.83 (m, 5H), 4.06-3.21 (m, 32H), 1.41 (br s, 2H), 1.11 (br s, 18H), 0.71 (t, 3H, J=6.7, $CH_3$).

Dodecyl 2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (4)

Following the standard procedure for sulfonation, polyol 3 (0.43 mmol) was sulfonated and purified by SEC to give the product 4 as white powder (77 mg). $^1$H NMR ($D_2O$, 400 MHz, internal DOH at 4.60 ppm) δ 5.19 (s, 1H), 5.15 (d, 1H, J=1.9), 5.10 (d, 1H, J=1.9), 5.07 (d, 1H, J=1.9), 4.89 (m, 1H), 3.77-3.64 (m, 30H, sugar), 3.48-3.41 (m, 1H, $OCH_2$), 3.33-3.27 (m, 1H, $OCH_2$), 1.30 (m, 2H, $CH_2$), 1.10-0.90 (m, 18H, 9×$CH_2$), 0.54 (t, 3H, J=6.7, $CH_3$).

Example 2

12-Azido-1-dodecanol

A mixture of 12-bromo-1-dodecanol (246 mg, 0.927 mmol) in t-butanol (1.8 mL, 0.5 M) was treated with sodium azide (121 mg, 1.855 mmol, 2 eq), tetrabutylammonium iodide (17 mg, 0.0464 mmol, 0.05 eq) and sat. aq. sodium bicarbonate solution (0.9 mL) in that order. The mixture was stirred at room temperature for 4 days. The mixture was filtered through a plug of celite and the cake rinsed with ethyl acetate (20 mL). The combined filtrate and washings were evaporated onto silica gel and purified by flash column (2.5×18 cm, gradient elution with hexane-ethyl acetate 6:1, 4:1 to 2:1) to give 12-Azido-1-dodecanol as a colourless oil (193 mg, 92%). $^1$H NMR ($CDCl_3$, 400 MHz): 3.62 (t, 2H, J=7.0, $OCH_2$), 3.24 (t, 2H, J=7.0, $NCH_2$), 1.61-1.51 (m, 4H), 1.35-1.25 (m, 16H).

12-Azidododecyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (5)

To a solution of the trichloroacetimidate 1 (0.325 g, 0.197 mmol) in DCM (15 mL) was added 12-azidododecanol (1.5 eq) and 3 Å MS (50 mg). The mixture was stirred at −20° C. for 20 min. TMSOTf (54 μL, 0.296 mmol, 1.5 eq) was added and the mixture stirred at −20° C. for 30 min before quenching with $Et_3N$ (1 eq). After warming to room temperature, the mixture was filtered and the solid washed with DCM. The combined filtrate and washings were evaporated onto silica gel and purified by column chromatography (silica 2×20 cm, gradient elution with $CHCl_3$, $CHCl_3$-MeOH 99:1 to 98:2) to give the glycoside 5 as a colourless gum containing the byproduct BnNHAc (71.1 mg, 5:BnNHAc=1:1). $^1$H NMR ($CDCl_3$, 400 MHz) δ 5.29-5.14 (m, 8H), 5.01-4.86 (m, 8H), 4.28-3.75 (m, 19H), 3.64 (dt, 1H, J=9.5, 7.0, $OCH_2$), 3.39 (dt, 1H, J=9.5, 7.0, $OCH_2$), 3.22 (t, 2H, J=7.0, $NCH_2$), 2.16, 2.15, 2.11, 2.10, 2.09, 2.09, 2.09, 2.09, 2.07, 2.06, 2.04, 2.04, 2.01, 1.95 (each s, total 48H, 16×Ac), 1.57 (m, 4H, 2×$CH_2$), 1.36-1.22 (m, 16H, 8×$CH_2$).

12-(4-Phenyl-[1,2,3]triazol-1-yl)dodecyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (6)

In a 1 mL HPLC sample vial was loaded the azide 5 (71 mg, 41.5 μmol), t-butanol (100 μL, 0.4 M), phenylacetylene (83 μmol, 2 eq), copper sulfate solution (0.3 M in water, 14 μL, 4.2 μmol, 10 mol %) and sodium ascorbate solution (1M in water, 12.4 μL, 12.4 μmol, 30 mol %) in that order. The mixture was stirred at room temperature for 2 days. The mixture was then evaporated onto silica gel and purified by flash column chromatography (1×18 cm, gradient elution with hexane-ethyl acetate 6:1, 4:1, 2:1, 1:1, 1:2 to 1:3) to give the phenyltriazole 6 as a colourless gum (46.3 mg, 62%). $^1$H NMR ($CDCl_3$, 400 MHz) δ 7.82 (d, 2H, J=7.2, Ph), 7.75 (s, 1H, triazole), 7.41 (t, 2H, J=7.2, Ph), 7.31 (t, 1H, J=7.2, Ph), 5.30-5.15 (m, 8H), 5.03-4.87 (m, 8H), 4.38 (t, 2H, J=7.2, $NCH_2$), 4.29-3.77 (m, 19H), 3.64 (dt, 1H, J=9.6, 6.8, $OCH_2$), 3.40 (dt, 1H, J=9.6, 6.8, $OCH_2$), 2.17, 2.16, 2.16, 2.13, 2.11, 2.11, 2.11, 2.10, 2.09, 2.07, 2.05, 2.05, 2.02, 2.00, 1.96 (each s, total 48H, 16×Ac), 1.93 (m, 2H, $CH_2$), 1.57 (m, 2H, $CH_2$), 1.34-1.24 (m, 16H, 8×$CH_2$).

12-(4-Phenyl-[1,2,3]triazol-1-yl)dodecyl 2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (8)

(a) Following the general procedure for deacetylation, peracetate 6 (46 mg, 0.0254 mmol) in MeOH (4.5 mL) was treated with NaOMe (11 M in MeOH, 50 μL, 0.55 μmol). The mixture was stirred at room temperature for 18 h, neutralised by addition of AG50WX8 resin ($H^+$ form), filtered and rinsed with MeOH. The filtrate was evaporated and the residue was dried in vacuum desiccators under $P_2O_5$ and used without further purification or characterization. (b)

Following the standard procedure for sulfonation, the above polyol 7 was sulfonated and purified by SEC to give the product 8 as white powder (45 mg). $^1$H NMR ($D_2O$, 400 MHz, internal DOH at 4.60 ppm) δ 7.88 (s, 1H, triazole-CH), 7.47-7.44 (m, 2H), 7.21-7.10 (m, 3H), 5.23 (br s, 1H), 5.19 (d, 1H, J=1.5), 5.12 (d, 1H, J=1.8), 5.10 (d, 1H, J=1.5), 4.91 (m, 1H), 4.76-3.72 (m, 32H, sugar and $NCH_2$), 3.37-3.30 (m, 1H, $OCH_2$), 3.23-3.17 (m, 1H, $OCH_2$), 1.51 (m, 2H, $CH_2$), 1.12 (m, 2H, $CH_2$), 0.90-0.63 (m, 16H, 8×$CH_2$).

Example 3

12-(4-Naphthalen-1-yl-[1,2,3]triazol-1-yl)dodecyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (9)

In a 1 mL HPLC sample vial was loaded the azide 5 (86 mg, 50.3 μmol), t-butanol (100 μL, 0.4 M), 1-ethynylnaphthalene (83 μmol, 2 eq), copper sulfate solution (0.3 M in water, 14 μL, 4.2 μmol, 10 mol %) and sodium ascorbate solution (1 M in water, 12.4 μL, 12.4 μmol, 30 mol %) in that order. The mixture was stirred at room temperature for 11 days. The mixture was then evaporated onto silica gel and purified by flash column chromatography (1×18 cm, gradient elution with hexane-ethyl acetate 6:1, 4:1, 2:1, 1:1, 1:2 to 1:3) to give the naphthyltriazole 9 as a colourless gum (24.2 mg, 26%). $^1$H NMR ($CDCl_3$, 400 MHz) δ 8.38-8.33 (m, 1H), 7.92-7.86 (m, 2H), 7.80 (s, 1H, triazole-CH), 7.72 (dd, 1H, J=7.3, 1.5), 7.54-7.48 (m, 3H), 5.31-5.15 (m, 8H), 5.03-4.87 (m, 8H), 4.47 (t, 2H, J=7.3, N—$CH_2$), 4.30-3.77 (m, 19H), 3.64 (dt, 1H, J=9.7, 6.8, OCH2), 3.40 (dt, 1H, J=9.7, 6.8, $OCH_2$), 2.17, 2.16, 2.16, 2.13, 2.12, 2.11, 2.11, 2.10, 2.09, 2.07, 2.06, 2.05, 2.02, 2.00, 1.97, 1.57 (15 s, each 3H, except 2.100 (6H), 16×Ac), 2.07-1.95 (m, overlapped with Ac singlets, 2H, $CH_2$), 1.57 (m, 1H, $CH_2$), 1.42-1.23 (m, 16H, 8×$CH_2$).

12-(4-Naphthalen-1-yl-[1,2,3]triazol-1-yl)dodecyl 2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (11)

(a) Following the general procedure for deacetylation, glycoside 9 (39.6 mg, 0.0213 mmol) in MeOH (3 mL) was treated with NaOMe (11 M in MeOH, 40 μL, 0.44 μmol). The mixture was stirred at r.t. for 24 h, neutralized by addition of AG50WX8 resin ($H^+$ form), filtered and rinsed with MeOH. The filtrate was evaporated and the residue was dried in a vacuum desiccator under $P_2O_5$. (b) Following the standard procedure for sulfonation, the above polyol 10 was sulfonated and purified by SEC to give the product 11 as white powder (40 mg, 68%). $^1$H NMR ($D_2O$, 400 MHz, internal DOH at 4.60 ppm) δ 8.05 (s, 1H, triazole-CH), 7.97 (d, 1H, J=8.3), 7.90 (d, 2H, J=7.8), 7.55-7.40 (m, 4H), 5.44-5.22 (m, 4H), 5.09-3.82 (m, 33H, sugar and $NCH_2$), 3.41-3.33 (m, 1H, $OCH_2$), 3.25-3.16 (m, 1H, $OCH_2$), 1.78 (quintet, 2H, $CH_2$), 1.14-0.79 (m, 18H, 9×$CH_2$).

Example 4

2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-2,3,4,6-tetra-O-acetyl-D-mannopyranose (13)

The tetrasaccharide 12[30] was peracetylated ($Ac_2O$, pyridine, DMAP, r.t., 4 days) and purified by flash chromatography (silica gel, hexane-EtOAc gradient) to give the peracetate 13 as an oil. $^1$H NMR (400 MHz, $CDCl_3$) δ 6.20 (d, 1H, $J_{1,2}$=1.8, H-1), 5.35-5.15 (m, 7H), 5.05-4.92 (m, 5H), 4.30-3.85 (m, 15H), 2.18 (s, 6H, OAc), 2.14 (s, 6H, OAc), 2.12 (s, 6H, OAc), 2.10 (s, 3H, OAc), 2.08 (s, 6H, OAc), 2.06 (s, 3H, OAc), 2.03 (s, 3H, OAc), 2.02 (s, 6H, OAc), 1.97 (s, 3H, OAc).

2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranosyl trichloroacetimidate (14)

Peracetate 13 (500 mg, 398 μmol) in diethyl ether (3.0 mL) and THF (750 μL) was treated with benzylamine (0.137 g, 1.3 mmol, 139 μL) at 0° C. The mixture was allowed to warm slowly to room temperature and react overnight. The solvent was evaporated and the residue taken up in DCM and washed with cold 0.5 M HCl (×3), followed by brine and the organic solution was dried ($Na_2SO_4$), filtered and evaporated. The residue was taken up in dry DCM and molecular sieves (3 Å, 30 mg), anhydrous cesium carbonate (12.9 mg, 39.8 μmol) and potassium carbonate (110 mg, 796 μmol) were added. The mixture was stirred at 0° C. before trichloroacetonitrile (115 mg, 80 μL, 796 μmol) was added. The mixture was stirred for 5 hours at room temperature until complete conversion by TLC. The mixture was filtered and the solvent was evaporated to give the crude product which was subjected to column chromatography ($SiO_2$, 6:1 Hex:EtOAc to 1:3 Hex:EtOAc, product eluted with 1:2 Hex:EtOAc) to yield the trichloroacetimidate 14 (307.5 mg, 57%) as a clear oil which solidified on standing in the fridge. $^1$H NMR (400 MHz, $CDCl_3$) δ 6.40 (d, 0.7H, $J_{1,2}$=1.5, H-1$^I$α), 6.22 (d, 0.3H, $J_{1,2}$=1.5, H-1$^I$β), 5.40-5.14 (m, 7H), 5.05-4.89 (m, 5H), 4.31-3.84 (m, 15H), 2.19-1.98 (m, 39H, OAc).

3β-Cholesteryl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (15)

A solution of 14 (90 mg, 0.0663 mmol) and cholesterol (39.8 mg, 0.0995 mmol, 1.5 eq) in DCE (dried over 3 Å MS, 0.7 mL, 0.094M) was stirred with 3 Å MS (~50 mg) at −20° C. while TMSOTf (18 mL, 0.0995 mmol, 1.5 eq) was added via a syringe. The temperature (external) was warmed up to −5° C. during a period of 40 min. The yellow colour slowly turned to orange (reddish). $Et_3N$ (50 μL) was added. The colour disappeared immediately. The mixture was diluted with DCM (20 mL) and washed with sat. $Na_2CO_3$-brine, dried ($Na_2SO_4$) and filtered. The filtrate was evaporated onto silica gel and purified by column chromatography (silica 1×18 cm, gradient elution with hexane-EtOAc 4:1, 2:1, 1:1, 1:2 to 1:3) to give the glycoside 15 as a colourless gum (58 mg, 55%). $^1$H NMR ($CDCl_3$, 400 MHz): 5.34-5.14 (m, 8H, sugar and cholesterol-H6), 5.05-4.90 (m, 6H, sugar), 4.30-

3.84 (m, 15H, sugar), 2.34-0.80 (m, 30H, cholesterol), 2.17, 2.16, 2.13, 2.06, 2.05, 2.02, 2.01, 2.01, 1.96 (each s, each 3H, 9×Ac), 2.11, 2.10 (each s, each 6H, 4×Ac), 0.98 (s, 3H, Me), 0.90 (d, 3H, J=6.4, Me), 0.85 (d, 3H, J=6.4, Me), 0.84 (d, 3H, J=6.4, Me), 0.66 (s, 3H, Me); ESMS: m/z 1604 ($[M+Na]^+$).

3β-Cholesteryl α-D-mannopyranosyl-(1→3)-α-D-mannopyranosyl-(1→3)-α-D-mannopyranosyl-(1→2)-α-D-mannopyranoside (16)

A solution of 15 (56 mg, 0.0354 mmol) in MeOH (dried over 3 Å MS, 3 mL) was stirred with 11M NaOMe in MeOH (50 μL) for 40 min. A white precipitate was formed. THF (1 mL) was added without success to improve the solubility. DMF (4 mL) was added. Some precipitate dissolved. The mixture was stirred for a total of 6 h. Water (0.8 mL) was added to make a clear solution. The pH was adjusted to 6-7 with addition of AG50W-X8 resin ($H^+$ form). The mixture was filtered and the resin washed with MeOH (1 mL). Attempted evaporation on a rotary evaporator was stopped as serious foaming occurred. The mixture was evaporated by air-flow and lyophilized for 8 h to give the polyol 16 as a white solid which was dried in a vacuum desiccator under $P_2O_5$ overnight and used directly for the next step.

3β-Cholesteryl 2,3,4,6-tetra-O-sodium sulfonato-α-D-mannopyranosyl-(1→3)-2,4,6-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (17)

Following the standard procedure for sulfonation, polyol 16 (0.0354 mmol) was sulfonated. The cooled crude mixture was basified by addition of 5 M NaOH (561 μL, 2.81 mmol, 2.05 eq based on $SO_3$ pyridine complex). After evaporation, the residue was dissolved in water (3 mL) and purified by SEC. Pure fractions were combined and dialysed using a Slide-A-Lyser® Cassette 2K (0.5-3 mL) in purified water with addition with 1M $Na_2CO_3$ overnight. Another load of 1M $Na_2CO_3$ was added and fresh purified water was changed. Dialysis was continued overnight. The yellow solution was removed and lyophilised to give the product 17 as an offwhite powder (34.8 mg, 42%). $^1H$ NMR ($D_2O$, 400 MHz) δ 6.41-6.26 (m, 4H, sugar and cholesteryl-H6), 5.09 (s, 1H), 5.03 (d, 1H, J=2.2), 4.86 (s, 1H), 4.73-3.94 (m, 22H), 3.51 (m, 1H, cholesteryl-H3), 2.35 (dm, 1H, J=11.7, cholesteryl-H4), 2.24 (dm, 1H, J=11.7, cholesteryl-H4), 1.90-0.51 (m, including 0.869 [s, 3H], 0.766 [d, 3H, J=6.6], 0.689 [d, 3H, J=6.6], 0.686 [d, 3H, J=6.6], and 0.533 [s, 3H], 43H, cholesteryl).

Example 5

Cholestanol

Cholesterol (500 mg) was taken up in ethyl acetate. 10% Palladium on carbon (cat.) was added and the mixture was stirred overnight under a balloon of hydrogen. The mixture was filtered and the solvent evaporated to give the product as a white solid in quantitative yield. $^1H$ NMR (400 MHz, $CDCl_3$) δ: 3.58 (m, 1H, CHOH), 2.44 (broad, 1H, OH), 1.97-0.83 (m, 31H), 0.88 (d, 3H, J=6.6, $CH_3$), 0.85 (dd, 6H, J=1.5, J=6.6, $CH_3$), 0.79 (s, 3H, $CH_3$), 0.64 (s, 3H, $CH_3$).

3β-Cholestanyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (18)

To a solution of 14 (600 mg, $4.42\times10^{-4}$ moles) in DCM (32 mL) under argon, was added cholestanol (300 mg). The mixture was stirred at −20° C. for 20 min. TMSOTf (40 μL) was added. The mixture was stirred at −20° C. for 40 min, then warmed to −10° C. for 20 min. Triethylamine (70 μL) was added to the mixture and it was warmed to room temperature. The solvent was evaporated. The crude product was purified using column chromatography ($SiO_2$: 3:1 Hex:EtOAc to 1:2 Hex:EtOAc) to yield the glycoside 18 (220 mg, 31%) as a clear oil. $^1H$ NMR (400 MHz, $CDCl_3$) δ: 5.35-5.15 (m, 7H), 5.03-4.91 (m, 6H), 4.31-3.85 (m, 15H), 3.51 (m, 1H, C-3), 2.18 (s, 311, OAc), 2.17 (s, 3H, OAc), 2.14 (s, 3H, OAc), 2.12 (s, 6H, OAc), 2.11 (s, 3H, OAc), 2.10 (s, 3H, OAc), 2.07 (s, 3H, OAc), 2.06 (s, 3H, OAc), 2.05 (s, 3H, OAc), 2.03 (s, 3H, OAc), 2.00 (s, 3H, OAc), 1.97-0.78 (m, 31H, cholestanol), 1.97 (s, 31-1, OAc), 0.88 (d, 3H, J=6.6, $CH_3$), 0.85 (dd, 6H, J=1.5, J=6.6, $CH_3$), 0.79 (s, 3H, $CH_3$), 0.63 (s, 3H, $CH_3$).

3β-Cholestanyl α-D-mannopyranosyl-(1→3)-α-D-mannopyranosyl-(1→3)-α-D-mannopyranosyl-(1→2)-α-D-mannopyranoside (19)

The glycoside 18 (43.1 mg) was deacetylated according to the general procedure to give the polyol 19 as a white solid (21 mg, 74%) which was reacted on without further purification or characterisation.

3β-Cholestanyl 2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (20)

The polyol 19 (19 mg, 18.3 μmol) was dissolved in DMF (1.3 mL, 0.015 M). $SO_3$.pyridine (6 equiv./OH, 1.43 mmol, 227 mg) was added and the mixture was stirred overnight at 60° C. The mixture was cooled in ice-water before 5M NaOH (613 μL) was added all at once to neutralise the solution. The solvent was evaporated. The residue was decolourized with a C18 SPE cartridge and desalted by dialysis, using a 2000 MWCO dialysis cartridge over 48 hours with three water changes, followed by lyophilisation to yield the product 20 as a white solid (19.2 mg, 44%). $^1H$ NMR (400 MHz, $D_2O$) δ 5.52-5.46 (m, 3H), 5.26-5.20 (m, 2H), 5.04 (m, 1H), 4.88 (m, 1H), 4.84-4.15 (m, 21H), 3.76 (m, 1H, C-3), 2.00-0.81 (m, 31H, cholestanol), 0.91 (d, 3H, $CH_3$), 0.86 (d, 6H, J=6.2, $CH_3$), 0.81 (s, 3H, $CH_3$), 0.66 (s, 3H, $CH_3$).

Example 6

3-Azidoprop-1-yl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (21)

$BF_3{\cdot}Et_2O$ (78 mg, 550 μmol) was added to a solution of peracetate 13 (276 mg, 220 μmol) and 3-azidopropan-1-ol[31] (67 mg, 660 μmol) in anhydrous DCE (8 mL). The solution was stirred at 60° C. in a sealed vessel for 2 h, before a further portion of $BF_3 \cdot Et_2O$ (115 mg, 810 μmol) was added and the solution was heated for a further 3 h. The solution was cooled to r.t. and poured into a mixture of crushed ice, $NaHCO_3$ (sat. aq.) and brine. The mixture was extracted with EtOAc and the organic layer was further washed with 1:1 brine:$NaHCO_3$ (sat. aq.), and then dried ($Na_2SO_4$), evaporated and co-distilled with anhydrous toluene. Anhydrous DCM (5 mL), acetic anhydride (66 mg, 648 μmol), $Et_3N$ (89 mg, 875 μmol) and DMAP (crystal) were added and the solution was stored at −20° C. overnight. The solution was applied directly to a prepared flash chromatography column (17×2 cm silica gel, gradient elution 60:40 to 75:25 EtOAc:Hx) to give the glycoside 21 (176 mg, 61%) as an oil. ESMS: m/z 1319.69 ($[M+Na]^+$). $^1H$ NMR (400 MHz, $CDCl_3$) δ 5.31-5.12 (m, 7H), 5.00-4.87 (m, 6H), 4.26-3.94 (m, 11H), 3.90-3.81 (m, 2H), 3.77 (dt, 1H, J=9.9, 6.0), 3.47 (dt, 1H, J=9.9, 6.0), 3.42-3.32 (m, 2H), 2.14(1), 2.13(5), 2.10, 2.08×2, 2.06×2, 2.05, 2.03(2), 2.02(5), 1.99, 1.98, 1.93 (13×s, 13×3H, OAc×13), 1.84 (quintet, 1H, J=6.2). $^{13}C$ NMR (100 MHz, $CDCl_3$) δ: 170.6, 170.5, 170.4, 170.3, 170.1(4), 170.0 (9), 169.9(2), 169.8 (8), 169.7, 169.6, 169.5(4), 169.4(5), 169.3, 99.4, 98.9, 98.8, 98.1, 76.8, 75.1(5), 75.1 (1), 70.9, 70.8, 70.1, 69.6, 69.5, 69.4, 69.2, 68.5, 68.3, 67.3, 66.6, 66.1, 65.5, 64.7, 62.5, 61.9, 61.7, 48.0, 28.5, 20.8(4), 20.7(6), 20.7, 20.6, 20.5(4), 20.5(2), 20.4(9), 20.4(7).

3-Stearamidopropyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (22)

(a) The glycoside 21 (500 mg, 386 μmol) was dissolved in THF (10 mL). Triphenylphosphine, polymer bound (725 mg) was added and the mixture was stirred at room temperature for 1 hour. Water (210 μL) was added, and the mixture was stirred at 50° C. for 4 hours. The mixture was cooled, filtered, and the solvent evaporated to give a white solid which was used without further purification or characterisation in the next step.

(b) The above amine (250 mg, 197 μmol) was dissolved in DCM (6 mL). Stearoyl chloride (2 equivalents, 394 μmol, 119 mg, 133 μL) was added, followed by triethylamine, and the mixture was stirred at room temperature for 5 hours. The solvent was evaporated, and the residue was taken up in DCM, before being washed with $NaHCO_3$ (sat.), dried ($Na_2SO_4$), and the solvent evaporated. The crude product was purified by column chromatography ($SiO_2$: DCM→4% MeOH/DCM) to give the amide 22 as a clear oil (102 mg, 33%). $^1H$ NMR (400 MHz, $CDCl_3$) δ 5.86 (broad m, 1H, NH), 5.32-5.12 (m, 7H), 5.02-4.88 (m, 6H), 4.28-3.96 (m, 15H), 3.73 (m, 1H, $CH_2O$), 3.45 (m, 1H, $CH_2O$), 3.32 (m, 2H, $CH_2N$), 2.15 (s, 3H, OAc), 2.15 (s, 3H, OAc), 2.12 (m, 2H, $CH_2CO$), 2.11 (s, 3H, OAc), 2.10 (s, 6H, OAc), 2.08 (s, 6H, OAc), 2.06 (s, 3H, OAc), 2.04 (s, 6H, OAc), 2.00 (s, 3H, OAc), 1.99 (s, 3H, OAc), 1.95 (s, 3H, OAc), 1.79 (m, 2H, $CH_2$), 1.58 (m, 2H, $CH_2$), 1.28-1.20 (m, 28H, $CH_2$), 0.84 (t, 3H, $CH_3$).

3-Stearamidopropyl α-D-mannopyranosyl-(1→3)-α-D-mannopyranosyl-(1→3)-α-D-mannopyranosyl-(1→2)-α-D-mannopyranoside (23)

The amide 22 (101.6 mg) was deacetylated according to the general procedure to give the polyol 23 (61 mg, 93%) as a white solid that was reacted on without further purification or characterization.

3-Stearamidopropyl 2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (24)

The polyol 23 (60.9 mg, 62 μmol) was dissolved in DMF (0.02 M, 3.1 mL). $SO_3$.pyridine (3 equiv/OH, 2.42 mmol, 385 mg) was added and the solution was stirred at 60° C. overnight. The mixture was cooled in ice-water and 5M NaOH (2.1 equiv/$SO_3$.pyridine, 5.08 mmol, 1.02 mL) was added all at once before the solvent was evaporated. The compound was taken up in 1% MeOH in water and purified on a C18 SPE cartridge. The compound was then dialysed over two nights using a 2000 MWCO dialysis cartridge, before being lyophilised to yield the product 24 (113 mg, 79%) as a white solid. $^1H$ NMR (400 MHz, $D_2O$) δ 5.56 (m, 1H), 5.48 (m, 2H), 5.28 (m, 1H), 5.11 (m, 1H), 5.06 (m, 1H), 4.91-4.13 (m, 22H), 3.87 (m, 1H, $CH_2O$), 3.70 (m, 1H, $CH_2O$), 3.32 (m, 2H, $CH_2N$), 2.29 (t, 2H, $CH_2CO$), 1.88 (m, 2H, $CH_2$), 1.62 (m, 2H, $CH_2$), 1.33-1.28 (m, 28H, $CH_2$), 0.90 (t, 3H, $CH_3$).

Example 7

3β-Cholestanyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (25)

The trichloroacetimidate 1 (165 mg, 0.1 mmol), cholestanol (78 mg, 2 eq, 0.2 mmol) and 3 Å molecular sieves (100 mg) were stirred in dry DCM for 2 h. A solution TMS-triflate in dry DCM (0.4 M, 0.075 mL, 0.03 mmol, 0.3 eq) was added dropwise at 0° C. and stirring continued for 40 min at the same temperature. The reaction was quenched by adding $Et_3N$ (5 μL), diluted with EtOAc (100 mL), sonicated (3 min) and decanted. The organic solution was washed with satd. $NaHCO_3$-solution (3×20 mL), the organic phase was re-extracted with EtOAc (3×20 mL), washed with brine (1×20 mL), dried ($Na_2SO_4$) and concentrated in vacuo to afford the glycoside as colourless foam. The product was purified on a column of silica gel (20×2 cm, toluene:EtOAc, 1:2). The purification gave 2 fractions (A, B) whereby fraction A (90 mg, 48% yield) contained pure product but fraction B was a mixture of pure product and a deacetylated product (1:1, 74 mg). In order to improve the yield of the desired glycoside, the dried fraction B and DMAP (cat) was dissolved in dry pyridine (2 mL) and acetylated by adding dropwise $Ac_2O$ (0.1 mL) at 0° C. and stirring continued at r.t. for 2 h. The mixture was quenched by adding dry MeOH (5 mL) at 0° C. and stirring continued for 30 min. The solution was concentrated in vacuo and co-evaporated with toluene (3×20 mL) to afford pure glycoside 25 (71 mg, 38% yield) to give a total yield of 86%. $^1H$ NMR (400 MHz, $CDCl_3$): δ 5.14-5.32 (m, 9H, 5H-4, 2H-3, H-$2^{IV}$), 4.90-5.05 (m, 8H, 5H-1, 3H-3), 3.90-4.31 (m, 19H, H-2, H-$3^{I}$, H-$3^{II}$, H-$3^{III}$, 5H-5, 5H-$6^{a}$, 5H-$6^{b}$), 3.80 (ddd, 1H, H-5), 3.52 (m, 1H, H-3 Chol.), 2.18, 2.17, 2.14, 2.12, 2.11, 2.10, 2.08, 2.07, 2.06, 2.03, 2.01, 1.98, (s, 48H, 16×Ac), 0.55-1.82 (m, 33H, 12$CH_2$, 9CH), 0.89 (d, 3H, J=6.8, cholestanyl-$CH_3$), 0.857 (d, 3H, J=6.8, cholestanyl-$CH_3$), 0.853 (d, 3H, J=6.6, cholestanyl-$CH_3$), 0.79 (s, 3H, cholestanyl-$CH_3$), 0.64 (s, 3H, cholestanyl-$CH_3$).

3β-Cholestanyl α-D-mannopyranosyl-(1→3)-α-D-mannopyranosyl-(1→3)-α-D-mannopyranosyl-(1→3)-α-D-mannopyranosyl-(1→2)-α-D-mannopyranoside (26)

The glycoside 25 (181 mg, 0.097 mmol) was deacetylated according to the general procedure to give white crystalline polyol 26 (116 mg, 100%), used without further purification or characterization in the next step.

3β-Cholestanyl 2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (27)

The dry polyol 26 (40 mg, 0.033 mmol) was dissolved in dry DMF (0.83 mL) and freshly washed and dried $SO_3$.pyridine (250 mg, 3 eq per OH-group, 1.85 mmol) was added and stirred for 16 h at 60° C. The reaction was quenched by adding dropwise an aqueous NaOH solution (5 M, 2.1 eq $SO_3$, 0.66 mmol) at 0° C. (pH 12) and concentration in vacuo at 40° C. to afford a yellow powder. The powder was dissolved in water (HPLC quality, 12 mL) and dialysed in a 2K cartridge against purified water for 36 h. After 16 h a solution an aqueous solution of $NH_4HCO_3$ (0.1 M, 0.5 mL) was added to the cartridge to ensure pH is higher than 7. The product was purified by reverse phase HPLC using a gradient of 10% MeCN-water→35 MeCN-water and flowrate of 5 mL/min with detection by ELS. Fractions containing pure product were combined and lyophilized to afford 27 as white fluffy powder (23.8 mg, 25% yield). $^1$H NMR (400 MHz, $D_2O$): $^1$H NMR (400 MHz, $CDCl_3$) δ 5.48-5.57 (m, 4H, 4H-2), 5.29, 5.23 (bs, 4H, H-1', H-1'', H-1''', H-1''''), 4.35-4.90 (m, 23H, H-1, 5H-3, 5H-4, 2H-5, 5H-6$^a$, 5H-6$^b$, 4.28 (t, 1H, H-2), 4.15-4.24 (m, 3H, 3H-5), 3.81 (m, 1H, H-3 Chol.), 0.66-2.05 (m, 33H, 12$CH_2$, 9CH), 0.96, 0.94, 0.90, 0.88, 0.85, 0.70 (s, 15H, $CH_3$). 0.85 (d, 3H, J=6.8, cholestanyl-$CH_3$), 0.88 (d, 6H, J=6.8, 2×cholestanyl-$CH_3$), 0.85 (s, 3H, cholestanyl-$CH_3$), 0.70 (s, 3H, cholestanyl-$CH_3$).

Example 8

Benzyl 2,3,4,6-tetra-O-benzoyl-α-D-mannopyranosyl-(1→2)-3,4,6-tri-O-benzoyl-α-D-mannopyranoside (28)

2,3,4,6-Tetra-O-benzoyl-α-D-mannopyranosyl trichloroacetimidate[32] (0.609 g, 0.822 mmol, 1.1 eq) and benzyl 3,4,6-tri-O-benzoyl-α-D-mannopyranoside[33] (0.435 g, 0.747 mmol) was dissolved in anhydrous DCM (6 mL). Powdered MS 3 Å (80 mg freshly activated) were added. The mixture was stirred at 0° C. for 40 min. A solution of TMSOTf (0.027 mL, 0.149 mmol, 0.2 eq) in DCM (1.5 mL) was added dropwise. The mixture was stirred at 0° C. while the reaction was monitored by TLC (hexane-EtOAc=65:35). After 40 min, the reaction was complete and $Et_3N$ (0.3 mL, 2.15 mmol) was added. The crude mixture was combined with the crude from another batch (TCA: 1.42 g, 2.098 mmol; 2-alcohol: 1.22 g, 2.098 mmol, TMSOTf: 0.114 mL, 0.629 mmol, 0.3 eq, 0° C., 40 min). The mixture was filtered through a plug of Celite and rinsed with DCM (3×1 mL). To the combined filtrate and washings were added pyridine (0.121 mL, 1.494 mmol, 2 eq) and benzoyl chloride (0.130 mL, 1.212 mmol, 1.5 eq). The mixture was stirred at r.t. o/n, evaporated onto silica gel and purified by column chromatography (silica gel 3×20 cm, gradient elution with hexane-EtOAc 200:20, 400:80, 200:50, 240:80, 200:90, 200:100) to give the disaccharide 28 as a colourless gum (594 mg, 68%). $^1$H NMR ($CDCl_3$, 400 MHz) δ 8.15-7.88 (m, 14H, Ph), 7.59-7.25 (m, 26H, Ph), 6.16-5.94 (m, 5H), 5.30-5.27 (m, 2H), 4.82 (d, 1H, J=11.7), 4.68-4.39 (m, 8H).

2,3,4,6-tetra-O-benzoyl-α-D-mannopyranosyl-(1→2)-3,4,6-tri-O-benzoyl-D-mannopyranose (29)

The disaccharide 28 (670 mg, 0.577 mmol) was dissolved in MeOH (3 mL) and EtOAc (30 mL). Palladium on charcoal (5%, 80 mg) was added. The mixture was stirred under 50 psi of hydrogen at r.t. o/n. TLC indicated ~60% conversion. More palladium on charcoal (5%, 80 mg) was added. Stirring was continued at 50 psi for 3 days. TLC indicated complete conversion. The mixture was filtered through a plug of Celite and rinsed with EtOAc (5×1 mL). The combined filtrate and washings were evaporated to dryness to give the title compound 29 as a colourless foam (609 mg, 99%). The product was used directly for the next step without purification.

2,3,4,6-Tetra-O-benzoyl-α-D-mannopyranosyl-(1→2)-3,4,6-tri-O-benzoyl-D-mannopyranosyl trichloroacetimidate (30)

To a pre-cooled (0° C.) solution of 29 (609 mg, 0.569 mmol) in anhydrous DCM (2.8 mL, 0.2 M) was added trichloroacetonitrile (114 μL, 1.138 mmol, 2 eq). A solution of DBU (4.3 μL, 0.05 eq, 0.0285 mmol) in anhydrous DCM (0.3 mL) was added. The mixture was stirred at 0° C. for 4 h and TLC (hexane-EtOAc=65:35) indicated complete conversion. The crude mixture was evaporated onto silica gel and purified by silica column chromatography (2.5×14 cm, gradient elution with hexane-EtOAc-$Et_3N$ 210:20:0.5, 200:50:0.5, 180:60:0.5, 150:70:0.5). The product fractions were combined, evaporated and dried in a vacuum desiccator over $P_2O_5$ o/n to give the trichloroacetimidate 30 as white foam (530 mg, 77%), used without further purification in the next step.

3β-Cholestanyl 2,3,4,6-tetra-O-benzoyl-α-D-mannopyranosyl-(1→2)-3,4,6-tri-O-benzoyl-α-D-mannopyranoside (31)

To a solution of the trichloroacetimidate 30 (260 mg, 0.214 mmol) and 3β-cholestanol (166 mg, 0.428 mmol, 2 eq) in anhydrous DCM (3.8 mL) was added freshly activated, powdered molecular sieves 3 Å (50 mg). The mixture was stirred at 0° C. for 0.5 h and a solution of TMSOTf (7.7 μL, 0.0428 mmol, 0.2 eq) in anhydrous DCM (0.3 mL) was added dropwise at 0° C. The mixture was stirred at 0° C. for 1.5 h and TLC indicated the completion of the reaction. $Et_3N$ (150 μL) was added and the mixture was evaporated onto silica gel and purified by silica column chromatography (2×15 cm, gradient elution with hexane-EtOAc 210:20, 200:50, 180:60, 180:90) to give the glycoside 31 as white foam (301 mg, 98%). $^1$H NMR ($CDCl_3$, 400 MHz) δ 8.11-7.28 (m, 35H, Bz), 6.09 (dd or t, 1H, $J_{H3(II)-H4(II)}$=10.3, $J_{H4(II)-H5(II)}$=9.6, H4$^{II}$), 5.97-5.87 (m, 3H, H2$^{II}$, H3$^{I}$ and H4$^{I}$), 5.28 (d, 1H, $J_{HI-H2}$=2.2, H1), 5.28 (d, 1H, $J_{HI-H2}$=1.5, H1), 4.69-4.44 (m, 6H, H5$^{I}$, H5$^{II}$, H6$^{I}$ and H6$^{II}$), 4.33 (br s, 1H, H2$^{I}$), 3.59 (m, 1H, OCH-chol), 3.02 (dd, 1H, $J_{H2(II)-H3(II)}$=2.9, H3$^{II}$), 1.99-0.47 (m, 31H, cholestanyl), 0.91 (d, 3H, J=6.6, cholestanyl-$CH_3$), 0.872 (d, 3H, J=6.6, cholestanyl-$CH_3$), 0.867 (d, 3H, J=6.6, cholestanyl-$CH_3$), 0.75 (s, 3H, cholestanyl-$CH_3$), 0.65 (s, 3H, cholestanyl-$CH_3$).

3β-Cholestanyl α-D-mannopyranosyl-(1→2)-α-D-mannopyranoside (32)

A solution of 31 (293 mg, 0.203 mmol) in anhydrous THF (4 mL) and MeOH (6 mL) was treated with a solution of 11 M NaOMe in MeOH (0.1 mL, 1.1 mmol, 5.4 eq). The mixture was stirred at r.t. o/n. The suspension was treated with AcOH (50 μL) to give an instant clear solution. AG50WX8 resin ($H^+$ form) was added to adjust the pH to 6. The mixture was filtered and the resin washed with MeOH (2×2 mL). The combined filtrate and washings were evaporated to dryness and dried in vacuum dessicator o/n to give the polyol 32 as a pale-yellow powder (171 mg, 118%), used without further purification in the next step.

3β-Cholestanyl 2,3,4,6-tetra-O-sodium sulfonato-α-D-mannopyranosyl-(1→2)-3,4,6-tri-O-sodium sulfonato-α-D-mannopyranoside (33)

The polyol 32 (96 mg, 0.135 mmol) was dissolved in anhydrous DMF (3.4 mL, 0.04 M). Sulfur trioxide-pyridine complex (451 mg, 2.835 mmol, 3 eq per hydroxyl, freshly washed with water, toluene, EtOH, DCM and dried under $P_2O_5$ in a vacuum dessicator for 1 h) was added. The mixture was stirred at 60° C. o/n and cooled to 0° C. 5 M NaOH (794 μL, 3.969 mmol, 1.4 eq based on $SO_3$) and sat. $Na_2CO_3$ (2.5 M, 690 mL, 1.701 mmol, 0.6 eq based on $SO_3$) was added. The colour turned slightly darker (yellow-orange). The mixture was evaporated to dryness. The residue was dissolved in 4 mL of water (pH>9) and purified by Bio-Gel P-2 column chromatography (eluted with 0.1 M $NH_4HCO_3$ at 196 mL/h, 6 min per collection). The product fractions were identified by MBT and CE. Lyophilisation gave the product 33 as pale-yellow powder (33 mg, 20% for two steps). $^1$H NMR ($D_2O$, 300 MHz) δ 5.27 (s, 1H), 4.98 (s, 1H), 4.81 (s, 1H), 4.64-4.48 (m, 4H), 4.38-4.18 (m, 4H), 4.08-3.85 (m, 4H), 3.50 (m, 1H, OCH), 1.75-0.49 (m, 46H, cholestanyl).

Example 9

2,3,4,6-tetra-O-acetyl-α-D-mannopyranosyl-(1→3)-2,4,6-tri-O-acetyl-α-D-mannopyranosyl-(1→2)-3,4,6-tri-O-acetyl-α-D-mannopyranosyl trichloroacetimidate (36)

The trisaccharide 34[30] was peracetylated ($Ac_2O$, pyridine, DMAP, r.t., 4 days) and purified by flash chromatography (silica gel, hexane-EtOAc gradient) to give the peracetate 35 as an oil. Glacial acetic acid (0.65 mmol, 0.038 mL) was added dropwise to a solution of ethylendiamine (1.2 mmol, 0.08 mL) in dry THF (15 mL) at 0° C., resulting in immediate formation of a precipitate, which remains present until aqueous work-up. The peracetate 35 (500 mg, 0.52 mmol) was added at 0° C. and the mixture was stirred 2.5 h at r.t. and stored overnight at −20° C. TLC (toluene/EtOAc, 1:2) then showed the absence of the starting material and the presence of a slower moving product, which appears mostly as an anomeric mixture. The solution was neutralized by adding acetic acid (0.12 mL) to reach pH 6. The solvent was evaporated under a stream of air, the residue was dissolved in EtOAc (100 mL), washed with satd. $NaHCO_3$-solution (3×50 mL), water (3×10 mL), brine (30 mL), dried ($Na_2SO_4$) and concentrated in vacuo to obtain the hemiacetal as yellow foam (500 mg), used without further purification. The hemiacetal (500 mg, ~0.54 mmol)) was dissolved in dry DCM (4 mL), $K_2CO_3$ (0.95 g, 6.81 mmol) and trichloroacetonitrile (0.67 mL, 6.63 mmol) was added at 0° C. and stirring continued at r.t. for 120 min. The mixture was directly purified on a column of silicagel (30×2.5 cm, toluene—EtOAc, 1:1→1:2→EtOAc) and the trichloroacetimidate 36 was obtained as white fluffy powder (300 mg, 65%). The compound was dried over $P_2O_5$ overnight at stored at −20° C.

3β-Cholestanyl 2,3,4,6-tetra-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (37)

The imidate 36 (295 mg, 0.28 mmol), cholestanol (210 mg, 2 eq, 0.56 mmol) and 3 Å molecular sieves (100 mg) were stirred in dry DCM for 0.5 h. A solution of TMS-triflate in dry DCM (0.4 M, 0.21 mL, 0.084 mmol, 0.3 eq) was added dropwise at 0° C. and stirring continued for 30 min at r.t. The reaction was quenched by adding $Et_3N$ (0.02 mL) at 0° C. (pH 5), diluted with DCM (25 mL), sonicated (3 min) and decanted. The organic solution was washed with satd. $NaHCO_3$-solution (3×20 mL), the aqueous phase was re-extracted with EtOAc (50 mL), washed with brine (20 mL), dried ($Na_2SO_4$) and concentrated in vacuo to afford the crude glycoside as white solid (564 mg). The product was purified on a column of silica gel (20×2 cm, toluene:EtOAc 3:2→1:1→1:2). The purification gave a mixture fraction A (56 mg, ~80% glycoside) and fraction B containing pure glycoside 37 as a white solid (170 mg, 58% yield). $^1$H NMR ($CDCl_3$, 400 MHz) δ 5.26-5.34 (m, 3H, 2×H4, H3), 5.17-5.24 (m, 3H, $H2^I$, $H3^{II}$, H4), 5.28 (dd, 1H, $J_{HI-H2}$=2.0, $H2^{II}$), 5.05 (d, 1H, $J_{HI-H2}$=2.0, H1), 5.02 (d, 1H, $H1^{II}$), 4.93 (d, 1H, $J_{HI-H2}$=2.0, $H1^I$), 4.30 (dd, 1H, $J_{H6a-H6b}$=−12.7, $J_{H6-H5}$=3.9, H6a), 3.97-4.22 (m, 9H, 2×H6a, 3×H6b, $H3^I$, 3×H5, 3.95 (dd, 1H, H2), 3.53 (m, 1H, cholestanyl-H3), 2.19, 2.15, 2.14, 2.11, 2.10, 2.08, 2.07, 2.03, 2.03, 2.02, 1.99 (s, 30H, 10×Ac), 0.55-1.85 (m, 33H, 12$CH_2$, 9CH), 0.89 (d, 3H, J=6.8, cholestanyl-$CH_3$), 0.860 (d, 3H, J=6.8, cholestanyl-$CH_3$), 0.854 (d, 3H, J=6.6, cholestanyl-$CH_3$), 0.80 (s, 3H, cholestanyl-$CH_3$), 0.64 (s, 3H, cholestanyl-$CH_3$).

3β-Cholestanyl α-D-mannopyranosyl-(1→3)-α-D-mannopyranosyl-(1→2)-α-D-mannopyranoside (38)

The peracetate 37 (165 mg, 0.127 mmol) was deacetylated according to the general procedure to yield white crystalline polyol 38 (107 mg, 96% yield), used without further purification or characterization in the next step.

3β-Cholestanyl 2,3,4,6-tetra-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (39)

Dry polyol 38 (50 mg, 0.058 mmol) was dissolved in dry DMF (2.9 mL, 0.02 M) and freshly washed and dried $SO_3$.pyridine (1:1, 277 mg, 3 eq per OH-group, 1.74 mmol) added. The mixture was stirred for 16 h at 60° C. and then was cooled to 0° C. for 15 min and neutralized by adding ice-cold aqueous NaOH-solution (5 M, 2.1 eq/$SO_3$, 0.731 mL, 3.65 mmol) at 0° C. in one portion (to pH 12). The suspension was stirred for 15 min at 0° C., diluted with water (10 mL) transferred into a 500 mL-round bottom flask and concentrated in vacuo at 40° C. A pale yellow powder was afforded, which was dissolved in water (10 mL) obtaining a solution with pH 10. The solution was set to pH 12 by adding an aqueous solution of NaOH (5 M, 5 drops), dialysed against water (4 L) using a Slide-A-Lyzer® cassette (2000 MWCO, 4-12 mL) for 16 h at r.t. The dialysis was continued at 0° C. against water (4 L) for 3 d, whereby after each 24 h an aqueous solution of $NH_4HCO_3$ (3 M, 0.6 mL) was added to the water to set the pH to ~6.5. The desalted solution was then lyophilized to afford the persulfate 39 as a white fluffy powder (91 mg, 83%). $^1$H NMR (400 MHz, $D_2O$) δ 5.50 (m, 2H, H1 or H2), 5.23, 5 (m, 2H, H1 or H2), 4.12-4.92 (m, 17H, H1, 1×1H, 3×H-3, 3×H-4, 3×H-5, 3H-6$^a$, 3H-6$^b$) 3.80 (m, 1H, H-3 Chol.), 0.66-2.04 (m, 33H, 12$CH_2$, 9CH), 0.95 (d, 3H, J=6.8, cholestanyl-$CH_3$), 0.887 (d, 3H, J=6.8, cholestanyl-$CH_3$), 0.882 (d, 3H, J=6.8, cholestanyl-$CH_3$), 0.85 (s, 3H, cholestanyl-$CH_3$), 0.70 (s, 3H, cholestanyl-$CH_3$).

Example 10

3-Azidopropyl 2,3,4,6-tetra-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (41)

$BF_3{\cdot}Et_2O$ (115 mg, 810 μmol was added to a solution of pentasaccharide peracetate 40[28] (500 mg, 324 μmol) and 3-azidopropan-1-ol (98 mg, 972 μmol) in anh. DCE (8 mL). The solution was stirred at 60° C. in a sealed vessel for 2 h, before a further portion of $BF_3{\cdot}Et_2O$ (115 mg, 810 μmol) was added and the solution was heated for a further 3 h. The solution was cooled to r.t. and poured into a mixture of crushed ice, $NaHCO_3$ (sat. aq.) and brine. The mixture was extracted with EtOAc and the organic layer was further washed with 1:1 brine:$NaHCO_3$ (sat. aq.), and then dried ($Na_2SO_4$), evaporated and co-distilled with anh. toluene. Anh. DCM (5 mL), acetic anhydride (66 mg, 648 μmol), $Et_3N$ (89 mg, 875 μmol) and DMAP (crystal) were added and the solution was stored at −20° C. overnight. The solution was applied directly to a prepared flash chromatography column (17×2 cm silica gel, gradient elution 60:40 to 75:25 EtOAc:Hx) to give the glycoside 41 (387 mg, 75%) as an oil. ESMS: 1601.81, $[M+NH_4]^+$. $^1$H NMR (400 MHz, $CDCl_3$) δ: 5.30-5.13 (m, 8H), 5.02-4.88 (m, 8H), 4.28-3.75 (m, 20H), 3.49 (dt, 1H, J=9.8, 6.1, $OCH_2CH_2B$), 3.42-3.35 (m, 2H, $CH_2N_3$), 2.16, 2.14(9), 2.14 (7), 2.11, 2.10, 2.09(2), 2.08 (8), 2.08 (7), 2.08, 2.07, 2.06, 2.05, 2.04, 2.00, 1.99, 1.95 (16 s, 16×3H, AcO×16), 1.89-1.84 (m, 2H, $CCH_2C$). $^{13}$C NMR (100 MHz, $CDCl_3$) δ: 170.4, 170.3, 170.2, 170.1, 169.9, 169.8(2), 169.7 (7), 169.6, 169.5, 169.4, 169.3, 169.2, 99.1(2), 99.1(0), 98.8 (4), 98.7(7), 98.1, 76.7, 75.0, 74.9, 74.7, 71.0, 70.8, 70.7, 70.0, 69.5, 69.3, 69.2, 68.5, 68.2, 67.2, 66.7, 66.6, 66.0, 65.4, 64.6, 62.4, 62.3, 61.9, 61.5, 47.9, 28.5, 20.7(4), 20.7(2), 20.6(9), 20.6, 20.4(9), 20.4(6), 20.4.

3-Stearamidopropyl 2,3,4,6-tetra-D-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (42)

The azide 41 (460.5 mg, 291 μmol) was dissolved in THF (10 mL). Triphenylphosphine, polymer bound (725 mg) was added and the mixture was stirred at room temperature for 1 hour. Water (200 μL) was added, and the mixture was stirred at 50° C. for 4 hours. The mixture was cooled, filtered, and the solvent evaporated to give a white solid (APCIMS: 1558.25 $[M+H]^+$). The product was dissolved in DCM (10 mL). Stearoyl chloride (2 equivalents, 580 μmol, 176 mg, 196 μL) was added, followed by triethylamine (2 equiv, 580 μmol, 80 μL), and the mixture was stirred at room temperature for 6 hours. The solvent was evaporated, and the residue was taken up in DCM, before being washed with $NaHCO_3$ (sat.), dried ($Na_2SO_4$), and the solvent evaporated. The crude product was purified by column chromatography ($SiO_2$: DCM→2% MeOH/DCM) to yield the amide 42 as a clear oil (232 mg, 44%, two steps). $^1$H NMR (400 MHz, $CDCl_3$) δ 6.10 (broad m, 1H, NH), 5.24-5.09 (m, 8H), 4.96-4.83 (m, 8H), 4.22-3.71 (m, 19H), 3.68 (m, 1H, $CH_2O$), 3.40 (m, 1H, $CH_2O$), 3.26 (m, 2H, $CH_2NH$), 2.12-2.09 (m, 2H, $CH_2CO$), 2.11 (s, 3H, OAc), 2.10 (s, 6H, OAc), 2.06 (s, 3H, OAc), 2.04 (s, 3H, OAc), 2.03 (s, 12H, OAc), 2.02 (s, 3H, OAc), 2.01 (s, 3H, OAc), 1.99 (s, 6H, OAc), 1.95 (s, 3H, OAc), 1.94 (s, 3H, OAc), 1.90 (s, 3H, OAc), 1.74 (m, 2H, $CH_2CH_2N$), 1.53 (m, 2H, $CH_2CH_2CO$), 1.23-1.16 (m, 28H, $CH_2$), 0.79 (t, 3H, $CH_3$).

3-Stearamidopropyl α-D-mannopyranosyl-(1→3)-α-D-mannopyranosyl-(1→3)-α-D-mannopyranosyl-(1→3)-α-D-mannopyranosyl-(1→2)-α-D-mannopyranoside (43)

The amide 42 (231.5 mg) was deacetylated according to the general procedure to give the polyol 43 (140 mg, 96%) as a white solid that was reacted on without further purification or characterisation.

3-Stearamidopropyl 2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (44)

The polyol 43 (140 mg, 122 μmol) was dissolved in DMF (0.02 M, 6.1 mL). $SO_3$.pyridine (3 equiv/OH, 5.83 mmol, 928 mg) was added and the solution was stirred at 60° C. overnight. The mixture was cooled in ice-water and 5M NaOH (2.1 equiv/$SO_3$.pyridine, 2.45 mL) was added all at once before the solvent was evaporated. The compound was taken up in 1% MeOH in water and purified on a C18 SPE cartridge. The compound was then dialysed over two nights using a 2000 MWCO dialysis cartridge, before being lyophilised to yield the product 44 (220 mg, 65%) as a white solid. $^1$H NMR (400 MHz, $D_2O$) δ 5.55 (d, 1H, H-1), 5.53 (d, 1H, H-1), 5.50 (d, 1H, $J_{1,2}$=1.8, H-1), 5.49 (d, 1H, H-1), 5.28 (m, 1H), 5.12 (m, 1H), 5.08 (m, 1H), 4.90-4.12 (m, 28H), 3.85 (ddd, 1H, J=6.2, J=7.0, J=10.5, $CH_2O$), 3.68 (ddd, 1H, J=6.2, J=6.2, J=9.7, $CH_2O$), 3.31 (m, 2H, $CH_2N$), 2.29 (t, 2H, J=7.0, $CH_2CO$), 1.88 (t, 2H, J=6.2, $CH_2CH_2N$), 1.62 (m, 2H, $CH_2CH_2CO$), 1.31 (m, 28H, $CH_2$), 0.90 (t, 3H, J=7.0, $CH_3$).

Example 11

3β-(Prop-2-ynyloxy)cholestanol

3β-cholestanol (1.23 g, 3.16 mmol) was completely dissolved in anhydrous toluene (7 mL, 0.45 M) at r.t. Powdered potassium t-butoxide (1.06 g, 9.49 mmol, 3 eq) was added in one portion. The mixture was stirred at r.t. for 3 h. A solution of propargyl bromide (80 wt % in toluene, 0.94 g, 6.32 mmol, 2 eq) was added. The mixture was stirred at r.t. for 3 days. The mixture was diluted with hexane (30 mL) and EtOAc (10 mL), washed with water (2×60 mL) and brine (60 mL). The aqueous phase was extracted once with EtOAc (20 mL). The combined organic phases were dried ($Na_2SO_4$), filtered and the filtrate was evaporated onto silica gel and purified by column chromatography (silica gel 2.5×24 cm, gradient elution with hexane 250 mL, hexane-EtOAc 125:5) to give the product as a yellow solid. Recrystallization from EtOAc (3 mL) gave off-white crystals (736 mg, 55%). $^1$H NMR ($CDCl_3$, 400 MHz) δ 4.18 (d, 2H, J=2.2), 3.45 (m, 1H), 2.38 (t, 1H, J=2.2), 1.99-0.57 (m, 31H), 0.89 (d, 3H, J=6.6), 0.86 (d, 3H, J=6.6), 0.86 (d, 3H, J=6.6), 0.79 (s, 3H), 0.64 (s, 3H).

3-Azidopropyl 2,3,4,6-tetra-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (45)

The peracetate 35 (1000 mg, 1.03 mmol) and 3-azidopropanol (1.2 eq., 124 mg, 1.24 mmol) was dissolved in dry DCM (5 mL) and then at 0° C. $BF_3$-etherate (5 eq., 0.546 mL, 5.17 mmol) was added dropwise and the mixture stirred for 3 h at 60° C. The reaction was stopped by adding $Et_3N$ (2.2 mL, 15.5 mmol) at 0° C. The crude reaction mixture was then acetylated by adding pyridine (1 mL), DMAP (cat.) and $Ac_2O$ (0.585 mL) at 0° C. and stirring continued o/n at rt. The dark red solution was quenched by adding dry MeOH (5 mL) at 0° C. and stirred for 2 h at r.t. After co-evaporation with toluene (50 mL), the residue was dissolved in EtOAc (100 mL), washed with satd. $NaHCO_3$-solution (3×20 mL), water (50 mL), the aqueous phase was re-extracted with EtOAc (3×20 mL), combined with the other organic extract, washed with brine (20 mL), dried ($Na_2SO_4$) and concentrated in vacuo to afford the crude glycoside as a gum (~1 g). The crude product was purified on a column of silica gel (20×2 cm, toluene—EtOAc, 2:1→1:1→1:2) and the desired glycoside 45 was obtained as an off-white foam (374 mg, 36%). $^1$H NMR ($CDCl_3$, 400 MHz) δ 5.19-5.38 (m, 6H, 3×H4, $H2^{II}$, $H3^{I}$, $H3^{III}$), 5.08 (dd 1H, $J_{H2-H3}$=3.3, $H2^{II}$), 5.04 (d, 1H, $J_{HI-H2}$=1.7, $H1^{III}$), 4.94 (m, 2H, $H1^{I}$, $H\text{-}1^{II}$), 4.31 (dd, 1H, $J_{H6a-H6b}$=12.5, $J_{H6-H5}$=4.2, H6a), 3.93-4.26 (m, 9H, 2×H6a, 3×H6b, $H2^{I}$, $H3^{II}$, $H5^{I}$, $H5^{II}$ or $H5^{III}$), 3.93 (ddd, 1H, $H5^{II}$ or $H5^{III}$), 3.82 (dt, 1H, $J_{gem}$=10.0, J=6.6, $OCH_2$), 3.53 (dt, 1H, J=6.6, $OCH_2$), 3.43 (t, 2H, J=6.6, $CH_2N_3$), 2.20, 2.161, 2.157, 2.12, 2.11, 2.10, 2.19, 2.05, 2.04, 2.00 (s, 30H, 10×Ac), 1.90 (quintet, 2H, J=6.6, $CH_2$).

3-{4-(Cholestan-3β-yl-oxymethyl)-[1,2,3]triazol-1-yl}propyl 2,3,4,6-tetra-O-acetyl-α-D-mannopyranosyl-(1→3)-2,4,6-tri-O-acetyl-α-D-mannopyranosyl-(1→2)-3,4,6-tri-O-acetyl-α-D-mannopyranoside (46)

3β-(Prop-2-ynyloxy)cholestanol (156 mg, 2 eq., 0.367 mmol) and the azide 45 (185 mg, 0.183 mmol) were dissolved in a mixture of DCM/t-BuOH (3:2, w/w, 0.4 M, 0.562 mL). To the mixture were added an aqueous solution of $CuSO_4$ (0.3 M, 0.1 eq., 0.061 mL) and a aqueous solution of sodium ascorbate (1 M, 0.3 eq., 0.055 mL) and the mixture was vigorously stirred without light for 48 h. TLC analysis (toluene:EtOAc, 1:1) showed the end of the reaction with the appearance of a more polar product than the starting azide. The mixture was diluted with DCM (50 mL) and washed with satd. $NaHCO_3$-solution (3×30 mL). The aqueous phase was re-extracted with EtOAc (3×20 mL), organic extracts were combined, washed with brine (20 mL), dried ($Na_2SO_4$) and concentrated in vacuo to afford the crude product as a yellow foam (475 mg). The crude product was purified on a column of silica gel (25×2.5 cm, toluene—EtOAc, 1:2→1:3→1:4) to yield the triazole 46 as white foam (214 mg, 81%). $^1$H NMR ($CDCl_3$, 400 MHz) δ 7.76 (s, 1H, =CH), 5.18-5.36 (m, 6H, 3×H4, $H2^{II}$, $H3^{I}$, $H3^{III}$), 5.06 (dd 1H, $J_{H2-H3}$=3.2, $H2^{III}$), 5.02 (d, 1H, $J_{HI-H2}$=1.7, $H1^{III}$), 4.94 (d, 2H, $J_{HI-H2}$=1.6, $H\text{-}1^{II}$), 4.92 (d, 1H, $J_{HI-H2}$=1.6, $H1^{I}$), 4.71 (s, 2H, $OCH_2$), 4.49 (t, 2H, J=6.6, $CH_2N$), 4.30 (dd, 1H, $J_{H6a-H6b}$=−11.9, $J_{H6-H5}$=4.0, H6a), 3.96-4.26 (m, 9H, 2×H6a, 3×H6b, $H2^{I}$, $H3^{II}$, $H5^{I}$, $H5^{II}$ or $\underline{H5^{III}}$), 3.92 (ddd, 1H, $\underline{H5^{II}}$ or $H5^{III}$), 3.43 (m, 2H, $OCH_2$, H-3 Chol), 2.31 (m, 2H, $\overline{CH_2}$), 2.19, 2.145, 2.142, 2.11, 2.09, 2.08, 2.06, 2.04, 1.99 (s, 30H, 10×Ac), 1.90 (quintet, 2H, J=6.6, $CH_2$), 0.56-2.04 (m, 33H, $12CH_2$, 9CH), 0.89 (d, 3H, J=6.8, cholestanyl-$CH_3$), 0.858 (d, 3H, J=6.8, cholestanyl-$CH_3$), 0.855 (d, 3H, J=6.8, cholestanyl-$CH_3$), 0.79 (s, 3H, cholestanyl-$CH_3$), 0.64 (s, 3H, cholestanyl-$CH_3$).

3-{4-(Cholestan-3β-yl-oxymethyl)-[1,2,3]triazol-1-yl}propyl α-D-mannopyranosyl-(1→3)-α-D-mannopyranosyl-(1→2)-α-D-mannopyranoside (47)

Dry peracetate 46 (202 mg, 0.141 mmol) was deacetylated according to the general procedure to yield the polyol 47 as a white crystalline solid (138 mg, 97%), used without further purification or characterization in the next step.

3-{4-(Cholestan-3β-yl-oxymethyl)-[1,2,3]triazol-1-yl}propyl 2,3,4,6-tetra-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (48)

Dry polyol 47 (50 mg, 0.049 mmol) was dissolved in dry DMF (2.45 mL, 0.02 M) and freshly washed and dried $SO_3$.pyridine complex (234 mg, 3 eq per OH-group, 1.47 mmol) was added and the mixture stirred for 16 h at 60° C. The reaction mixture was cooled to 0° C. for 15 min, then neutralized by adding ice-cold aqueous NaOH solution (5 M, 2.1 eq/$SO_3$, 0.617 mL, 3.09 mmol) at 0° C. in one portion (to pH 12). The suspension was stirred for 15 min at 0° C., diluted with water (10 mL) and co-evaporated with water (3×20 mL) in vacuo at 40° C. The yellow solid was dissolved in water (9 mL, →pH10.5), then the solution was set to pH 12 by adding an aqueous solution of NaOH (5 M, 5 drops) and dialysed against water (4 L) for 16 h at r.t. using a Slide-A-Lyzer® cassette (2000 MWCO, 4-12 mL). The dialysis was continued at 0° C. against water (4 L) for 2 d, whereby after each 24 h an aqueous solution $NH_4HCO_3$ (3 M, 0.6 mL) was added to the changed water (4 L) to set the pH to 6-6.5. The desalted solution was then lyophilized to afford the product 48 as a white fluffy powder (94 mg, 94%). $^1$H NMR (400 MHz, $D_2O$) δ 8.08 (s, 1H, =CH), 5.50 (m, 2H, $H2^{II}$, $H2^{III}$), 5.22, 5 (m, 1H, $H1^{II}$ or $H1^{III}$), 5.07 (m, 1H, $H1^{I}$), 4.33-4.93 (m, 19H, $H1^{II}$ or $H1^{III}$, 3×H3, 3×H4, 3×H4, $CH_2N$, 4H6, H2, $OCH_2$), 4.15 (m, 4H, 2×H6, 2×H-5), 4.02 (m, 1H, H-5), 3.83 (m, 1H, $OCH_2$), 3.71 (m, 1H, $OCH_2$), 3.51 (m, 1H, H-3 Chol), 2.28 (m, 2H, $CH_2$), 0.62-2.06 (m, 33H, $12CH_2$, 9CH), 0.94 (d, 3H, J=5.8, cholestanyl-$CH_3$), 0.86 (d, 9H, J=6.7, cholestanyl-$CH_3$), 0.70 (s, 3H, cholestanyl-$CH_3$).

Example 12

Benzyl 3-O-allyl-2,4,6-tri-O-benzoyl-α-D-mannopyranosyl-(1→3)-2,4,6-tri-O-benzoyl-α-D-mannopyranoside (49)

3-O-allyl-2,4,6-tri-O-benzoyl-α-D-mannopyranosyl trichloroacetimidate[34] (0.504 g, 0.744 mmol, 1.05 eq) and benzyl 2,4,6-tri-O-benzoyl-α-D-mannopyranoside (0.413 g, 0.709 mmol) was dissolved in anhydrous DCM (6.4 mL, 0.11 M). Powdered MS 3 Å (70 mg freshly activated) were added. The mixture was stirred at 0° C. for 30 min. A solution of TMSOTf (26 μL, 0.142 mmol, 0.2 eq) in DCM (0.6 mL) was added dropwise (final concentration: 1 M). The mixture was stirred at 0° C. while the reaction was monitored by TLC (hexane-EtOAc=65:35). After 60 min, the conversion was complete and $Et_3N$ (0.15 mL) was added. The crude mixture was treated with pyridine (0.115 mL, 1.418 mmol, 2 eq) and benzoyl chloride (0.124 mL, 1.064 mmol, 1.5 eq). The mixture was stirred at r.t. o/n and filtered. The solid was washed with DCM (6×1 mL). The combined filtrate and washings were evaporated onto silica gel and purified by column chromatography (silica gel 2.5×24 cm, gradient elution with hexane-EtOAc 200:20, 210:40, 200:50, 180:60, 170:85) to give pure product 49 as a pale-yellow gum (0.738 g, 95%). $^1$H NMR ($CDCl_3$, 400 MHz) δ 8.20-8.06 (m, 8H, Ph), 7.90-7.80 (m, 4H, Ph), 7.67-7.23 (m, 23H, Ph), 5.98 (dd or t, 1H, $J_{H3(I)-H4(I)}$=9.8, $J_{H4(I)-H5(I)}$=9.8, H4$^I$), 5.75 (dd or t, 1H, $J_{H3(II)-H4(II)}$=9.8, $J_{H4(II)-H5(II)}$=9.8, H4$^{II}$), 5.41 (m, 1H, allyl-2'), 5.23 (d, 1H, J=2.0), 5.18-5.15 (m, 2H), 4.87-4.71 (m, 3H), 4.64-4.56 (m, 4H), 4.48 (dd or t, 1H, J=12.7, J=4.9), 4.34-4.27 (M, 2H), 4.22 (dd, 1H, J=12.7, J=3.9), 3.87 (dd, 1H, J=9.8, J=2.9), 3.74 (dd, 1H, J=12.7, J=5.9), 3.59 (dd, 1H, J=12.7, J=5.9).

Benzyl 2,4,6-tri-O-benzoyl-α-D-mannopyranosyl-(1→3)-2,4,6-tri-O-benzoyl-α-D-mannopyranoside (50)

A solution of the allyl ether 49 (688 mg, 0.627 mmol) in MeOH (6 mL) and 1,2-dichloroethane (6 mL) (0.05 M) was treated with solid palladium chloride (25 mg). The mixture was stirred at 70° C. (external oil bath) for 2 h. TLC indicated complete conversion. The mixture was evaporated onto silica and purified by column chromatography (silica 2.7×17 cm, gradient elution with hexane-EtOAc 200:20, 200:40, 200:50, 210:70, 200:100) to give the alcohol 50 as a colourless gum (0.539 mg, 81%). $^1$H NMR ($CDCl_3$, 400 MHz) δ 8.18-8.03 (m, 8H, Ph), 7.85-7.81 (m, 4H, Ph), 7.68-7.25 (m, 23H, Ph), 5.97 (dd or t, 1H, $J_{H3(I)H4(I)}$=9.8, $J_{H4(I)-H5(I)}$=9.8, H4$^I$), 5.68 (dd, 1H, J $J_{H1(I)-H2(I)}$=2.0, $J_{H2(I)-H3(I)}$=2.9, H2$^I$), 5.60 (dd or t, 1H, J $J_{H3(II)-H4(II)}$=9.8, J $J_{H4(II)-H5(II)}$=9.8, H4$^{II}$), 5.28 (br s, 1H, H1$^{II}$), 5.15 (d, 1H, J $J_{H1(II)-H2(II)}$=2.0, H1$^I$), 5.05 (dd, 1H, $J_{H1(II)-H2(II)}$=2.0, $J_{H2(II)-H3(II)}$=2.9, H2$^{II}$), 4.77 (d, 1H, $J_{gem}$=11.7, $CH_2$), 4.65-4.56 (m, 4H, $CH_2$, H6$^I$eq, H3$^I$ and H6$^{II}$), 4.44 (dd, 1H, $J_{gem}$=12.7, $J_{H5(I)-H6(I)ax}$=4.9, H6$^I$ax), 4.34 (m, 1H, H5$^{II}$), 4.32 (dd, 1H, $J_{gem}$=10.7, $J_{H5(II)-H6(II)}$=2.9, H6$^{II}$), 4.28 (ddd, 1H, $J_{H5(I)-H6(I)ax}$=4.9, $J_{H5(I)-H6(I)eq}$=2.9, H5$^I$), 4.17 (dd, 1H, H3$^{II}$).

Benzyl 2,3,4,6-tetra-O-benzoyl-α-D-mannopyranosyl-(1→3)-2,4,6-tri-O-benzoyl-α-D-mannopyranosyl-(1→3)-2,4,6-tri-O-benzoyl-α-D-mannopyranoside (51)

A solution of the alcohol 50 (424 mg, 0.401 mmol) and 2,3,4,6-tetra-O-benzoyl-α-D-mannopyranosyl trichloroacetimidate (357 mg, 0.481 mmol, 1.2 eq) in anhydrous DCM (7.5 mL) was stirred with powdered molecular sieves 3 Å (50 mg) at 0° C. for 1 h. A solution of TMSOTf (15 μL, 0.0802 mmol, 0.2 eq) in DCM (0.5 mL) was added dropwise via a syringe. The mixture was stirred at 0° C. for 2 h and TLC indicated complete conversion. $Et_3N$ (100 μL) was added. Pyridine (65 μL, 0.802 mmol) and benzoyl chloride (47 μL, 0.401 mmol) were added. The mixture was stirred at room temperature o/n and evaporated onto silica gel. Purification by column chromatography (silica 2.5×17 cm, gradient elution with hexane-EtOAc 210:30, 200:50, 180:60, 160:80 and 150:100) gave the trisaccharide 51 as a colourless gum (392 mg, 60%). $^1$H NMR ($CDCl_3$, 400 MHz) δ 8.19-7.89 (m, 16H, Ph), 7.68-7.63 (m, 4H, Ph), 7.61-7.15 (m, 35H, Ph), 6.00 (dd or t, 1H, $J_{H3-H4}$=10.7, $J_{H4-H5}$=9.8, H4), 5.98 (dd or t, 1H, $J_{H3-H4}$=9.8, J=9.8, H4), 5.92 (dd or t, 1H, J=10.7, J=9.8, H4), 5.72 (dd, 1H, $J_{H1-H2}$=2.0, $J_{H2-H3}$=3.9, H2), 5.56 (dd, 1H, $J_{H2-H3}$=2.9, H3), 5.33 (d, 1H, J=2.0, H1), 5.26 (dd, 1H, J=2.0, H2), 5.19 (d, 1H, J=2.0, J=3.9, H2), 5.16 (d, 1H, J=2.0, H1), 4.90 (d, 1H, H1), 4.78 and 4.62 (AB quartet, 2H, $J_{gem}$=11.7, $CH_2$), 4.65-4.56 (m, 3H), 4.45 (dd, 1H, $J_{gem}$=12.7, $J_{H5-H6}$=3.9, H6), 4.35 (dd, 1H, H3), 4.34-4.28 (m, 2H), 4.24 (dd, 1H, J=12.7, $J_{H5-H6}$=2.9, H6), 4.10 (dt or dm, 1H, H5), 4.01 (dd, 1H, J=12.7, H6), 3.95 (dd, 1H, $J_{H5-H6}$=2.0, H6).

2,3,4,6-tetra-O-benzoyl-α-D-mannopyranosyl-(1→3)-2,4,6-tri-O-benzoyl-α-D-mannopyranosyl-(1→3)-2,4,6-tri-O-benzoyl-D-mannopyranose (52)

The benzyl glycoside 51 (385 mg, 0.235 mmol) was dissolved in MeOH (5 mL) and chloroform (5 mL). Palladium on charcoal (5%, 538 mg) was added. The mixture was stirred under hydrogen at 100 psi for 3 days. TLC indicated complete conversion. The mixture was filtered through a plug of Celite and rinsed with EtOAc (5×1 mL). The combined filtrate and washings were evaporated to dryness, co-evaporated with DCM (3 mL) to give the hemiacetal 52 as pale-yellow foam (338 mg, 93%), used without further purification or characterization in the next step.

2,3,4,6-tetra-O-benzoyl-α-D-mannopyranosyl-(1→3)-2,4,6-tri-O-benzoyl-α-D-mannopyranosyl-(1→3)-2,4,6-tri-O-benzoyl-D-mannopyranosyl trichloroacetimidate (53)

The hemiacetal 52 (330 mg, 0.214 mmol) was dissolved in anhydrous DCM (1.1 mL, 0.2 M). To the solution was added trichloroacetonitrile (43 μL, 0.427 mmol, 2 eq). The mixture was stirred at 0° C. while a solution of DBU (1.6 μL, 0.05 eq, 0.0107 mmol) in anhydrous DCM (0.15 mL) was added. The mixture was stirred at 0° C. for 4 h and TLC (hexane-EtOAc=65:35) indicated the complete conversion. The crude was evaporated onto silica gel and purified by silica column chromatography (2×14 cm, gradient elution with hexane-EtOAc 200:20, 150:30, 120:30, 150:50 and hexane-EtOAc-$Et_3N$ 140:70:0.3) to give the trichloroacetimidate 53 as white foam (261 mg, 72%) which was used directly in the next step without further characterization.

3β-Cholestanyl 2,3,4,6-tetra-O-benzoyl-α-D-mannopyranosyl-(1→3)-2,4,6-tri-O-benzoyl-α-D-mannopyranosyl-(1→3)-2,4,6-tri-O-benzoyl-α-D-mannopyranoside (54)

To a solution of the trichloroacetimidate 53 (128 mg, 0.0757 mmol) and 3β-cholestanol (59 mg, 0.151 mmol, 2 eq) in anhydrous DCM (2 mL) was added freshly activated, powdered molecular sieves 3 Å (50 mg). The mixture was stirred at 0° C. for 0.5 h and a solution of TMSOTf (2.7 μL, 0.0151 mmol, 0.2 eq) in anhydrous DCM (0.15 mL) was added dropwise at 0° C. The mixture was stirred at 0° C. for 2 h and TLC indicated the completion of the reaction. $Et_3N$ (150 μL) was added. The mixture was evaporated onto silica gel and purified by silica column chromatography (2×14 cm, gradient elution with hexane-EtOAc 180:20, 150:30, 120:30, 120:40 and 120:60) to give the glycoside 54 as colourless gum (74 mg, 51%). $^1$H NMR ($CDCl_3$, 300 MHz) δ 8.21-7.15 (m, 50H, Bz), 6.00 (dd or t, 1H, $J_{H3(I)-H4(II)}$=10.0, $J_{H4(II)-H5(II)}$=10.0, H4$^{II}$), 5.93 (dd or t, 1H, $J_{H3-H4}$=10.0, $J_{H4-H5}$=10.0, H4$^{I}$ and H4$^{III}$), 5.61 (dd, 1H, $J_{H2(I)-H3(I)}$=3.0, $J_{H1(II)-H2(II)}$=1.5, H2$^{I}$), 5.57 (dd, 1H, $J_{H3(III)-H4(III)}$=10.0, $J_{H2(III)-H3(III)}$=3.0, H3$^{III}$), 5.36 (d, 1H, $J_{H1(II)-H2(II)}$=1.5, H1$^{II}$), 5.26 (dd, 1H, $J_{H2(II)-H3(II)}$=3.0, H2$^{II}$), 5.21 (m, 2H, H1$^{I}$ and H2$^{III}$), 4.91 (s, 1H, H1$^{III}$), 4.68-3.90 (m, 11H), 3.62 (m, 1H, OCH-chol), 1.99-0.50 (m, 31H, cholestanyl), 0.90 (d, 3H, J=6.9, cholestanyl-$CH_3$), 0.87 (d, 3H, J=6.9, cholestanyl-$CH_3$), 0.86 (d, 3H, J=6.9, cholestanyl-$CH_3$), 0.80 (s, 3H, cholestanyl-$CH_3$), 0.65 (s, 3H, cholestanyl-$CH_3$).

3β-Cholestanyl α-D-mannopyranosyl-(1→3)-α-D-mannopyranosyl-(1→3)-α-D-mannopyranoside (55)

The glycoside 54 (70 mg, 0.0365 mmol) was deacetylated according to the general procedure to give the polyol 55 as pale yellow powder, used directly in the next step.

3'-Cholestanyl 2,3,4,6-tetra-O-sodium sulfonato-α-D-mannopyranosyl-(1→3)-2,4,6-tri-O-sodium sulfonato-α-D-mannopyranosyl-(1→3)-3,4,6-tri-O-sodium sulfonato-α-D-mannopyranoside (56)

The above powder (55) was dissolved in anhydrous DMF (1.8 mL, 0.02 M). $SO_3$.pyridine complex (174 mg, 1.096 mmol, 3 eq per hydroxyl, freshly washed with water, toluene, EtOH, DCM and dried under $P_2O_5$ in vacuum dessicator for 1 h) was added. The mixture was stirred at 60° C. o/n (18 h) and cooled to 0° C. 5 M NaOH was added until pH>10. EtOH (6 mL) was added and the mixture stirred at 0° C. for 20 min. The precipitate was isolated by centrifugation and evaporated to dryness on a rotary evaporator. The residue was redissolved in water (1.5 mL). The solution was loaded into a Slide-A-Lyzer® dialysis cassette (2000 MWCO, 0.5-3.0 mL capacity). The flask was rinsed with water (2×0.5 mL) and the washings were also loaded into the cassette. Dialysis was carried out in 10 L of purified water at room temperature for 4 h. The water was changed (10 L) and dialysis was continued at 0° C. o/n. The water was changed (4 L) and dialysis continued for another day. The slightly yellow solution was removed and lyophilized to give the persulfate 56 as a slightly orange powder (46.8 mg). $^1$H NMR ($D_2O$, 300 MHz) δ 5.28 (s, 1H), 5.21 (s, 1H), 5.16 (s, 1H), 5.05 (br s, 1H), 4.76 (br s, 1H), 4.67-3.88 (m, 16H), 3.53 (m, 1H, OCH), 1.82-0.44 (m, 31H, cholestanyl), 0.74 (d, 3H, cholestanyl-$CH_3$), 0.67 (d, 6H, cholestanyl-$CH_3$), 0.65 (s, 3H, cholestanyl-$CH_3$), 0.49 (s, 3H, cholestanyl-$CH_3$).

Example 13

3-Azidopropyl 2,3,4,6-tetra-O-benzoyl-α-D-mannopyranosyl-(1→3)-2,4,6-tri-O-benzoyl-α-D-mannopyranosyl-(1→3)- 2,4,6-tri-O-benzoyl-α-D-mannopyranoside (57)

To a solution of trichloroacetimidate 53 (128 mg, 0.0757 mmol) and 3-azidopropanol (15 mg, 0.151 mmol, 2 eq) in anhydrous DCM (2 mL) was added freshly activated, powdered molecular sieves 3 Å (50 mg). The mixture was stirred at 0° C. for 0.5 h and a solution of TMSOTf (2.7 μL, 0.0151 mmol, 0.2 eq) in anhydrous DCM (0.15 mL) was added dropwise at 0° C. The mixture was stirred at 0° C. for 2 h and TLC indicated the completion of the reaction. $Et_3N$ (150 μL) was added. The mixture was evaporated onto silica gel and purified by silica column chromatography (2×14 cm, gradient elution with hexane-EtOAc 150:20, 150:30, 120:30, 120:40, 120:60 and 120:80) to give the glycoside 57 as colourless gum (86 mg, 70%). $^1$H NMR ($CDCl_3$, 300 MHz) δ 8.22-7.16 (m, 50H, Bz), 6.02 (dd or t, 1H, $J_{H3(I)-H4(II)}$=10.0, $J_{H4(II)-H5(II)}$=9.5, H4$^{II}$), 6.00 (dd or t, 1H, $J_{H3(I)-H4(I)}$=10.0, $J_{H4(I)-H5(I)}$=9.5, H4$^{I}$), 5.96 (dd or t, 1H, $J_{H3(III)-H4(III)}$=10.0, $J_{H4(III)-H5(III)}$=9.5, H4$^{III}$), 5.69 (dd, 1H, $J_{H2(I)-H3(I)}$=3.2, $J_{H1(II)-H2(II)}$=1.6, H2$^{I}$), 5.59 (dd, 1H, $J_{H3(III)-H4(III)}$=10.3, $J_{H2(III)-H3(III)}$=3.2, H3$^{III}$), 5.37 (d, 1H, $J_{H1(II)H2(II)}$= 2.4, H1$^{II}$), 5.29 (dd, 1H, $J_{H1(II)-H2(II)}$=1.6, $J_{H2(II)-H3(II)}$=2.4, H2$^{II}$), 5.23 (dd, 1H, $J_{H1(III)-H2(III)}$=1.6, H2$^{III}$), 5.09 (d, 1H, $J_{H1(I)-H2(I)}$=1.6, H1$^{I}$), 4.94 (d, 1H, $J_{H1(III)-H2(III)}$=1.6, H1$^{III}$), 4.71 (dd, 1H, $J_{gem}$=11.9, J32 2.4, H6), 4.60 (dd, 1H, J=11.9, J=2.4, H6), 4.58 (dd, 1H, H3$^{I}$), 4.50 (dd, 1H, J=4.8, H6), 4.38 (dd, 1H, $J_{H2(II)-H3(II)}$=3.2, H3$^{II}$), 4.34-4.22 (m, 3H), 4.14-3.94 (m, 3H), 3.91 (dt, 1H, $J_{gem}$=9.5, J=6.4, J=6.4, $OCH_2$), 3.59 (dt, 1H, J=6.4, J=6.4, $OCH_2$), 3.44 (t, 2H, J=6.4, $NCH_2$), 1.91 (quintet, 2H, J=6.4, $CH_2$).

3-{4-(Cholestan-3β-yl-oxymethyl)[1,2,3]triazol-1-yl}propyl 2,3,4,6-tetra-O-benzoyl-α-D-mannopyranosyl-(1→3)-2,4,6-tri-O-benzoyl-α-D-mannopyranosyl-(1→3)-2,4,6-tri-O-benzoyl-α-D-mannopyranoside (58)

To a mixture of 57 (81 mg, 0.0497 mol), 3β-(prop-2-ynyloxy)cholestanol (43 mg, 0.0994 mmol, 2 eq) in DCM (64 μL) and t-butanol (60 μL) (0.4 M) was added a solution of $CuSO_4$ (0.3 M in water, 33 μL, 0.00994 mmol, 0.2 eq) and a solution of sodium ascorbate (1M in water, 20 μL, 0.0199 mmol, 0.4 eq). The mixture was vigorously stirred at r.t. for 3 days. The mixture was evaporated onto silica gel and purified by silica column chromatography (2×14 cm, gradient elution with hexane-EtOAc 170:20, 150:30, 120:30, 120:40, 120:60, 120:80 and 100:100) to give the triazole 58 as a colourless gum (74 mg, 72%). $^1$H NMR ($CDCl_3$, 300 MHz) δ 8.19-7.88 (m, 16H, Bz), 7.69-7.15 (m, 35H, Bz and triazole-CH), 5.99 (dd or t, 1H, $J_{H3-H4}$=9.9, $J_{H4-H5}$=9.9, H4), 5.98 (dd or t, 1H, J=9.9, J=9.9, H4), 5.94 (dd or t, 1H, H4), 5.66 (dd, 1H, $J_{H2(I)-H3(I)}$=3.1, $J_{H1(I)H2(I)}$=1.6, H2$^{I}$), 5.57 (dd, 1H, $J_{3(III)-H4(III)}$=10.0, $J_{H2(III)-H3(III)}$=3.1, H3$^{III}$), 5.36 (d, 1H, $J_{H1(II)-H2(II)}$=1.6, H1$^{II}$), 5.28 (dd, 1H, $J_{H2(II)-H3(II)}$=3.1, H2$^{II}$), 5.21 (dd, 1H, $J_{H1(III)-H2(III)}$=1.6, H2$^{III}$), 5.04 (d, 1H, H1$^{I}$), 4.94 (d, 1H, H1$^{III}$), 4.70 (s, 2H, $OCH_2$), 4.70-3.92 (m, 11H), 3.84 (dt or ddd, 1H, $J_{gem}$=9.9, J=6.3, J=6.3, $OCH_2$), 3.50 (dt or ddd, 1H, J=5.5, J=5.5, $OCH_2$), 3.37 (m, 1H, OCH-chol), 2.26 (m, 2H, $CH_2$), 1.99-0.53 (m, 31H, cholestanyl), 0.90 (d, 3H, J=6.8, cholestanyl-$CH_3$), 0.87 (d, 3H, J=6.8, cholestanyl-$CH_3$), 0.86 (d, 3H, J=6.8, cholestanyl-$CH_3$), 0.76 (s, 3H, cholestanyl-$CH_3$), 0.64 (s, 3H, cholestanyl-$CH_3$).

3-{4-(Cholestan-3β-yl-oxymethyl)-[1,2,3]triazol-1-yl}propyl α-D-mannopyranosyl-(1→3)-α-D-mannopyranosyl-(1→3)-α-D-mannopyranoside (59)

The perbenzoate 58 (70 mg, 0.0341 mmol) was dissolved in anhydrous THF (2 mL) and MeOH (2 mL). The mixture was treated with a solution of 11M NaOMe in MeOH (0.2 mL, 2.2 mmol). After stirring at r.t for 2 days, the white suspension was neutralized by addition of AG50WX8 resin ($H^+$ form). The clear solution was separated from the resin by filtration. The resin was washed with MeOH (3×2 mL).

The combined filtrate and washings were evaporated to dryness and dried in vacuum dessicator under $P_2O_5$ o/n to give the polyol 59, used directly in the next step.

3-{4-(Cholestan-3β-yl-oxymethyl)-[1,2,3]triazol-1-yl}propyl 2,3,4,6-tetra-O-sodium sulfonato-α-D-mannopyranosyl-(1→3)-2,4,6-tri-O-sodium sulfonato-α-D-mannopyranosyl-(1→3)-3,4,6-tri-O-sodium sulfonato-α-D-mannopyranoside (60)

The polyol 59 was dissolved in anhydrous DMF (1.7 mL, 0.02 M). $SO_3$.pyridine complex (163 mg, 1.023 mmol, 3 eq per hydroxyl, freshly washed with water, toluene, EtOH, DCM and dried under $P_2O_5$ in vacuum dessicator for 1 h) was added. The mixture was stirred at 60° C. o/n (19 h) and cooled to 0° C. 5 M NaOH was added until pH>10. EtOH (6 mL) was added and the mixture stirred at 0° C. for 20 min. The precipitate was isolated by centrifugation and was washed with EtOH (1 mL) and re-dissolved in water (1.5 mL). The orange solution was loaded onto a Waters® C18 SPE (200 mg, pre-conditioned by gravity elution with MeOH, MeOH—$H_2O$ 50:50, 10:90, 5:95 and 1:99, 3 mL each) and eluted with MeOH—$H_2O$ (1:99). The product fractions were loaded into a Slide-A-Lyzer® dialysis cassette (2000 MWCO, 0.5-3.0 mL capacity). Dialysis was carried out in 10 L of purified water at r.t. for 1 day. The water was changed (10 L) and dialysis was continued at 0° C. for another day. The slightly yellow solution was removed and lyophilized to give the persulfate 60 as a slightly yellow powder (43 mg, 62%). $^1$H NMR ($D_2O$, 300 MHz) δ 7.92 (s, 1H, triazole), 5.27 (d, 1H, J=1.8), 5.20 (d, 1H, J=1.4), 5.04 (m, 1H), 4.89 (br s, 1H), 4.72 (m, 1H), 4.65-3.28 (m, 23H), 2.07 (m, 2H, CH2), 1.83-0.45 (m, 31H, cholestanyl), 0.73 (d, 3H, J=6.4, $CH_3$), 0.66 (d, 6H, J=6.4, 2×$CH_3$), 0.63 (s, 3H, $CH_3$), 0.49 (s, 3H, $CH_3$).

Example 14

2,3,4,6-tetra-O-acetyl-α-D-glucopyranosyl-(1→4)-2,3,6-tri-O-acetyl-α-D-glucopyranosyl-(1→4)-2,3,6-tri-O-acetyl-α-D-glucopyranosyl-(1→4)-1,2,3,6-tetra-O-acetyl-D-glucopyranose (61)

Dry maltotetraose (502 mg, 0.753 mmol) and DMAP (cat.) was dissolved in dry pyridine (10 mL) then at 0° C. a solution of $Ac_2O$ (2.8 g) in pyridine (5 mL) was added drop-wise at 0° C., stirred for 4 h at 0° C. and left for 48 h at −20° C. The reaction was not completed, therefore additional $Ac_2O$ (1 g, mmol) was added at 0° C. and after 16 h at r.t., the reaction was quenched by adding dry MeOH (10 mL) at 0° C. and stirring continued for 2 h at r.t. The solution was co-evaporated with toluene (3×30 mL) to give the peracetate 61[35] as white solid (920 mg, 97%).

2,3,4,6-tetra-O-acetyl-α-D-glucopyranosyl-(1→4)-2,3,6-tri-O-acetyl-α-D-glucopyranosyl-(1→4)-2,3,6-tri-O-acetyl-α-D-glucopyranosyl-(1→4)-2,3,6-tri-O-acetyl-α-D-glucopyranosyl trichloroacetimidate (62)

To a solution of ethylenediamine (1.66 mmol, 0.11 mL) in dry THF (15 mL), glacial acetic acid (0.90 mmol, 0.053 mL) was added drop-wise at 0° C. resulting immediate formation of a precipitate, which remains present until aqueous workup. The peracetate 61 (900 mg, 0.717 mmol) was added at 0° C. and the mixture was stirred 2 h at r.t. TLC (toluene/EtOAc, 1:2) then showed the absence of the starting material and the presence of a slower moving product, which appears mostly as an anomeric mixture. The solution was neutralized by adding acetic acid (0.15 mL) drop-wise to reach pH 6. The solvent was blown out with a stream of air, the residue was dissolved in EtOAc (100 mL), washed with satd. $NaHCO_3$-solution (3×50 mL), water (3×10 mL), brine (30 mL), dried ($Na_2SO_4$) and concentrated in vacuo to give the hemiacetal as a yellow foam (830 mg). The dry hemiacetal (830 mg, 0.684 mmol) was dissolved in dry DCM (5 mL), $K_2CO_3$ (1.20 g, 8.60 mmol) and trichloroacetonitrile (0.849 mL, 8.40 mmol) was added at 0° C. and stirring continued at r.t. for 2 h. The mixture was purified on a column of silica gel (20×1.5 cm, toluene—EtOAc, 1:2→EtOAc, containing 0.2% (v/v) $Et_3N$) and the desired trichloroacetimidate 62[35] was obtained as white fluffy powder (795 mg, 86%). The compound was dried over $P_2O_5$ over-night and stored at −20° C.

Cholestanyl 2,3,4,6-tetra-O-acetyl-α-D-glucopyranosyl-(1→4)-2,3,6-tri-O-acetyl-α-D-glucopyranosyl-(1→4)-2,3,6-tri-O-acetyl-α-D-glucopyranosyl-(1→4)-2,3,6-tri-O-acetyl-β-D-glucopyranoside (63)

The trichloroacetimidate 62 (300 mg, 0.221 mmol), cholestanol (2 eq, 172 mg, 0.442 mmol) and 3 Å molecular sieves (100 mg) were stirred in dry DCM (1.5 mL) for 0.5 h. A solution TMS-triflate in dry DCM (0.5 eq., 0.4 M, 0.275 mL, 0.11 mmol,) was added dropwise at 0° C. After 30 min at r.t. another portion of TMS-triflate in dry DCM (0.36 eq., 0.4 M, 0.2 mL, 0.08 mmol) was added and stirring continued for 30 min at r.t. The reaction was quenched by adding $Et_3N$ (0.025 mL) at 0° C. for 10 min, filtered through a plug of celite (0.5 cm), washed with DCM (5×25 mL) and EtOAc (3×25 mL). Both organic phases were washed separately with satd. $NaHCO_3$-solution (3×25 mL) and brine (25 mL). Aqueous extracts were combined and re-extracted with EtOAc (3×30 mL), washed with brine (30 mL), combined with the other organic extracts, dried ($Na_2SO_4$) and concentrated in vacuo to afford the crude yellow foam (480 mg). The product was purified on a column of silica gel (30×5 cm, toluene:EtOAc 3:2→1:1→1:2→EtOAc, containing 0.2% $Et_3N$ (v/v)). The purification resulted in the desired β-linked glycoside 63 in 5 fraction A as a white foam (81 mg, 23%) and fraction B containing 77% partially deacetylated α-linked glycoside and 23% partially deacetylated β-linked glycoside (118 mg). $^1$H NMR ($CDCl_3$, 400 MHz) δ 5.24-5.45 (m, 7H, 3×H1,4×H3), 5.08 (t, 3H, $J_{H3\text{-}H4}$=$J_{H4\text{-}H5}$ 9.80, $H4^{III}$,) 4.86 (dd, 1H, $J_{H1\text{-}H2}$=4.1, $J_{H2\text{-}H3}$=10.4, $H2^{IIII}$), 4.70-4.80 (m, 3H, 3×H2), 4.63 (d, 1H, JH1-H2=7.7, $H1^{I}$), 4.33-4.54 (m, 4H, 4×H6), 3.86-4.31 (m, 10H, 3×H4, 3×H5, 4×H6), 3.70 (ddd, 1H, $H5^{I}$), 3.56 (m, 1H, cholesteryl-H3), 2.20, 2.19, 2.16, 2.11, 2.07, 2.04, 2.03, 2.02, 2.015, 2.010, 2.00, 1.99 (s, 39H, 13×Ac), 0.55-2.00 (m, 33H, 12$CH_2$, 9CH), 0.90 (d, 3H, J=6.6, cholestanyl-$CH_3$), 0.871 (d, 3H, J=6.6, cholestanyl-$CH_3$), 0.867 (d, 3H, J=6.6, cholestanyl-$CH_3$), 0.78 (s, 3H, cholestanyl-$CH_3$), 0.65 (s, 3H, cholestanyl-$CH_3$).

3β-Cholestanyl α-D-glucopyranosyl-(1→4)-α-D-glucopyranosyl-(1→4)-α-D-glucopyranosyl-(1→4)-β-D-glucopyranoside (64)

The peracetate 63 (75 mg, 0.047 mmol) was deacetylated according to the general procedure to yield the polyol 64 as a white solid (48 mg, 98%), used without further purification or characterization in the next step.

3β-Cholestanyl 2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (65)

The polyol 64 (48 mg, 0.046 mmol) was dissolved in dry DMF (2.3 mL, 0.02 M) and freshly washed and dried $SO_3$.pyridine complex (285 mg, 3 eq per OH-group, 1.79 mmol) added and the mixture was stirred for 16 h at 60° C. The reaction mixture was cooled to 0° C. for 10 min, then neutralized by adding ice-cold aqueous NaOH solution (5 M, 2.1 eq/$SO_3$, 0.752 mL, 3.76 mmol) at 0° C. in one portion (to pH 12). The suspension was stirred for 15 min 0° C., diluted with water (10 mL) and concentrated in vacuo at 40° C. A pale yellow powder was afforded, which was dissolved in water (10 mL) obtaining a solution with pH 11.5. The solution was set to pH 12.5 by adding a aqueous solution of NaOH (5 M, 5 drops) and dialyzed against water (4 L) using a Slide-A-Lyzer® cassette (2000 MWCO, 4-12 mL) for 16 h at r.t. The dialysis against water (4 L) was continued at 0° C. for 3 d, whereby the water was changed after each 24 h, as well as an aqueous solution $NH_4HCO_3$ (3 M, 0.6 mL) was added to the water to set pH ~6.0-6.5. The desalted solution was then lyophilized to afford the persulfate 65 as a white fluffy powder (97 mg, 89%). $^1$H NMR (400 MHz, $D_2O$) δ 5.72 (d, 1H, $J_{HI-H2}$=3.3, 1H1), 5.69 (d, 1H, $J_{HI-H2}$=3.6, H1), 5.59 (d, 1H, $J_{HI-H2}$=3.6, H1), 5.10 (d, 1H, $J_{HI-H2}$=4.8, $H1^I$), 4.19-5.02 (m, 23H, 4×H2, 4×H3, 4×H-4, 3×H5, 8×H6), 4.14 (m, 1H, $H5^I$), 3.85 (m, 1H, H-3 Chol.), 0.63-2.06 (m, 33H, 12$CH_2$, 9CH), 0.95 (d, 3H, J=6.5, cholestanyl-$CH_3$), 0.885 (d, 3H, J=6.6, cholestanyl-$CH_3$), 0.882 (d, 3H, J=6.6, cholestanyl-$CH_3$), 0.85 (s, 3H, cholestanyl-$CH_3$), 0.70 (s, 3H, cholestanyl-$CH_3$).

Example 15

2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-1,2,3,6-tetra-O-benzoyl-D-glucopyranose (66)

G4 syrup (1.8 g, lyophilized, containing ~72% Maltotetraose (w/w), ~1.94 mmol), and DMAP (75 mg) was dissolved in dry pyridine (36 mL) and at 0° C. a solution of benzoyl chloride (94.7 mmol, 11 mL) in pyridine (8 mL) was added dropwise and stirring continued at r.t. for 16 h. The mixture was quenched by adding MeOH (50 mL) at 0° C. and stirring continued for 2 h. The mixture was co-evaporated with toluene (3×50 mL) to afford a yellow syrup. The syrup was suspended in EtOAc (150 mL), washed with satd sodium bicarbonate solution (5×50 mL), aqueous HCl (5%, 5×50 mL), and water (5×50 mL). The aqueous phase waste re-extracted with EtOAc (2×50 mL), combined with the main organic extract, washed with brine (50 mL), dried ($Na_2SO_4$), filtered and concentrated in vacuo. To remove most of the aromatic impurities, the syrup was washed with boiling n-hexane (5×50 mL), sonicated and dried at high-vacuum o/n to yield a mixture of perbenzoylated maltooligosaccharides as slightly beige foam (6.0 g). The residue was dissolved in a minimum volume of a mixture of toluene/ethylacetate (15:1, 25 mL) at 50° C. and applied on a column of silica gel (21×5.5 cm, preconditioned with toluene) eluting with a gradient of toluene/ethylacetate 15:1, ~1 column volumes) to 10:1 (1.5 column volumes) to 5:1 (1.5 column volumes). Fractions were checked on TLC by UV and chemical staining and pure fractions of maltotetraose perbenzoate were combined, concentrated in vacuo and dried at high-vacuum to yield the pure product 66 as a white foam (3.04 g, 76%, based on 72% maltotetraose in dry syrup). $^1$H-NMR shows the presence of a anomeric mixture (α; β=1:1) and full benzoylation of all OH-groups (purity>95%). $^1$H NMR (400 MHz, $CDCl_3$): β-anomer: 8.26-7.09 (m, 65H, 13×Bz), 6.33 (d, 1H, $J_{1(I)-2(I)}$=7.5, $H1^I$), 6.19 (dd or t, 1H, $J_{2(IV)-3(IV)}$=10.2, $J_{3(IV)-4(IV)}$=10.2, $H3^{IV}$), 6.07 (dd, 1H, $J_{2(II)-3(II)}$=10.2, $J_{3(II)-4(II)}$=8.9, $H3^{II}$), 5.96 (dd, 1H, $J_{2(III)-3(III)}$=10.2, $J_{3(III)-4(III)}$=8.2, $H3^{III}$), 5.83 (d, 1H, $J_{1(IV)-2(IV)}$=4.1, $H1^{IV}$), 5.82 (dd or t, 1H, $J_{2(I)-3(I)}$=6.8, $J_{3(I)-4(I)}$=8.2, $H3^I$), 5.76 (dd or t, 1H, $J_{4(IV)-5(IV)}$=9.6, $H4^{IV}$), 5.71 (d, 1H, $J_{1(II)-2(II)}$=4.1, $H1^{II}$), 5.69 (d, 1H, $J_{1(III)-2(III)}$=4.1, $H1^{III}$), 5.65 (dd, 1H, $H2^I$), 5.34 (dd, 1H, $H2^{IV}$), 5.20 (dd, 1H, $H2^{II}$), 5.14 (dd, 1H, $H2^{III}$), 5.03-4.22 (m, 15H, 3×H4 at 4.70, 4.52 and 4.40 ppm, respectively, and 4×H5 and 8×H6). Note: assignment for sugar rings II and III were ambiguous. α-anomer: 6.84 (d, 1H, $J_{1(I)-2(I)}$==3.6, $H1^I$) 5.46 (dd, 1H, $J_{1(I)-2(I)}$=10.2, $J_{2(I)-3(I)}$=3.6, $H2^I$).

2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranosyl azide (67)

The perbenzoate 66 (500 mg, 0.235 mmol) was dissolved in dry DCM (2 mL) then at 0° C. a solution of 30% HBr in acetic acid (0.5 mL) was added and stirred under Ar for 2 h. The reaction was quenched by pouring the solution onto ice-water-DCM (100 mL), the organic phase was washed with ice-water (3×50 mL), satd. $NaHCO_3$-solution (3×30 mL), brine (25 mL), dried ($Na_2SO_4$) and concentrated in vacuo at r.t. to afford the crude bromide. The crude bromide was dissolved in chloroform (2 mL), then $NaN_3$ (130 mg, 2 mmol), tetrabutylammonium bromide (129 mg, 0.4 mmol), and finally a satd. $NaHCO_3$-solution (3.5 mL) was added and stirred vigorously at r.t. for 24 h. The solvent was blown out with a stream of air. The residue was then dissolved in EtOAc (10 mL), washed with water (3×50 mL), satd. $NaHCO_3$-solution (4×25 mL). The aqueous phase was re-extracted with EtOAc (2×50 mL), organic extracts were combined, washed with brine (2×25 mL), dried ($Na_2SO_4$) and concentrated in vacuo. The glycosyl azide 67 was obtained as a yellow foam (466 mg, 97%), used without further purification in the next step. $^1$H NMR ($CDCl_3$, 400 MHz) δ 7.03-8.24 (m, 65H, 13×Bz), 6.10 (dd, 1H, $J_{H2-H3}$=10.4, $J_{H3-H4}$ 9.9, $H3^{III}$,) 5.99 (dd, 1H, $J_{H2-H3}$=10.1, $J_{H3-H4}$ 8.7, $H3^{III}$), 5.84 (dd, 1H, $J_{H2-H3}$=9.9, $J_{H2-H3}$=8.2, $H3^{II}$), 5.75 (d, 1H, $J_{HI-H2}$=3.9, $H1^{III}$), 5.67 (m, 2H, H3, $H4^{III}$), 5.63 (d, 1H, $J_{HI-H2}$=4.1, $H1^{III}$), 5.58 (d, 1H, $J_{HI-H2}$=3.9, $H1^{II}$), 5.26 (dd, 1H, $J_{HI-H2}$=4.1, $J_{H2-H3}$=10.4, $H2^{III}$), 5.20 (dd, 1H, $J_{HI-H2}$=8.4, $J_{H2-H3}$=9.2, H2), 5.10 (dd, 1H, $J_{H2-H3}$=10.1, $H2^{III}$), 5.04 (dd, 1H, $H2^{II}$), 4.98 (dd, 1H, $J_{H6b-H5}$=2.1, $J_{H6bH6a}$=−12.0, H6b), 4.88 (d, 1H, $J_{HI-H2}$=8.4, H1), 4.82 (dd, 1H, $J_{H6b-H5}$=1.7, $J_{H6bH6a}$=−12.0, H6b), 4.67-4.76 (m, 2H, H-6a, H-6b), 4.53-4.63 (m, 2H, H-6a, H-6b), 4.30-4.47 (m, 7H, 3×H4, 2×H6, 2×H5), 4.10-4.21 (m, 2H, 2×H5).

4-(Cholestan-3β-yl-oxymethyl)[1,2,3]triazol-1-yl 2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranoside (68)

3β-(Prop-2-ynyloxy)cholestanol (84 mg, 2 eq., 0.196 mmol) and the azide 67 (200 mg, 0.098 mmol) was dissolved in a mixture of DCM/t-BuOH (3:2, w/w, 0.21 M, 0.200 mL). An aqueous solution of $CuSO_4$ (0.3 M, 0.1 eq., 0.033 mL) and an aqueous solution of sodium ascorbate (1 M, 0.3 eq., 0.029 mL) were added and the mixture was vigorously stirred without light for 48 h. TLC analyses (toluene: EtOAc, 1:1) showed the end of the reaction with the appearance of a more polar product than the starting azide. The mixture was diluted with DCM (100 mL), washed with satd. $NaHCO_3$-solution (3×50 mL). The aqueous phase was re-extracted with DCM (3×20 mL), organic extracts were combined, washed with brine (50 mL), dried ($Na_2SO_4$) and concentrated in vacuo to afford the crude product as a yellow foam (279 mg). The crude product was purified on a column of silica gel (30×5 cm, toluene—EtOAc, 7:1→5:1→3:1) to give the triazole 68 as a slightly yellow foam (153 mg, 63%). $^1$H NMR ($CDCl_3$, 400 MHz) δ 7.05-8.24 (m, 65H, 13×Bz), 6.14 (d, 1H, $J_{H1-H2}$=8.9, H1$^I$), 6.11 (dd, 1H, $J_{H2-H3}$=10.6, $J_{H3-H4}$ 9.8, H3$^{IIII}$), 6.00 (dd, 1H, $J_{H2-H3}$=10.1, $J_{H3-H4}$=8.6, H3$^{III}$), 5.86 (m, 2H, H3$^I$, H1$^{II}$), 5.76 (d, 1H, $J_{HI-H2}$=3.8, H1$^{IIII}$), 5.64-5.71 (m, 3H, H1$^{III}$, H2$^I$, H4$^{IIII}$), 5.63 (d, 1H, $J_{HI-H2}$=3.8, H1$^{II}$), 5.26 (dd, 1H, H2$^{IIII}$), 5.12 (dd, 1H, $J_{HI-H2}$=3.8, H2$^{III}$), 5.08 (dd, 1H, $J_{H2-H3}$=9.8, H2$^{II}$), 4.98 (dd, 1H, $J_{H6b-H5}$=1.7, $J_{H6bH6a}$=−12.5, H6b), 4.87 (dd, 1H, H6b), 4.69-4.77 (m, 2H, H6a, H6b), 4.53-4.66 (m, 4H, 2×H6, $OCH_2$, H4$^I$), 4.29-4.50 (m, 7H, 2×H4, 2H6, 3×H5), 4.18 (m, 1H, H5), 4.10-4.21 (m, 2H, 2×H5), 3.26 (m, 1H, H-3 Chol), 0.52-2.00 (m, 33H, 12$CH_2$, 9CH), 0.90 (d, 3H, J=6.5, cholestanyl-$CH_3$), 0.869 (d, 3H, J=6.7, cholestanyl-$CH_3$), 0.864 (d, 3H, J=6.6, cholestanyl-$CH_3$), 0.77 (s, 3H, cholestanyl-$CH_3$), 0.65 (s, 3H, cholestanyl-$CH_3$).

4-(Cholestan-3β-yl-oxymethyl)[1,2,3]triazol-1-yl α-D-glucopyranosyl-(1→4)-α-D-glucopyranosyl-(1→4)-1-deoxy-β-D-glucopyranoside (69)

The perbenzoate 68 (95 mg, 0.038 mmol) was dissolved in mixture of MeOH/THF (4:1 (w/w), 7.5 mL) then at 0° C. a solution of NaOMe in MeOH (11 M, 0.040 mL) was added and stirring continued at r.t. After 16 h still partially benzoylated compounds were present (TLC: MeOH:EtOAc, 3:1), so more NaOMe in MeOH (11 M, 0.040 mL) was added and stirring continued for another 3 h. The solution was neutralized by adding strongly acidic cation exchange resin (BioRad AG-X8, $H^+$) to adjust the pH to 7, before the solution was filtered, washed with MeOH (5×20 mL) and concentrated in vacuo. The residue was purified on a column of silicagel (15×1 cm, EtOAc, →MeOH—EtOAc, 3:1→MeOH, containing 0.2% $Et_3N$) to yield the polyol 69 as a white solid (47 mg, 100%).

4-(Cholestan-3-yl-oxymethyl)[1,2,3]triazol-1-yl 2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (70)

The polyol 69 (45 mg, 0.040 mmol) was dissolved in dry DMF (2 mL, 0.02 M) and freshly washed and dried $SO_3$.pyridine complex (248 mg, 3 eq per OH-group, 1.56 mmol) added and the mixture was stirred for 16 h at 60° C. The reaction mixture was cooled to 0° C. for 10 min, then neutralized by adding ice-cold aqueous NaOH solution (5 M, 2.1 eq/$SO_3$, 0.656 mL, 3.28 mmol) at 0° C. in one portion (to pH 12). The suspension was stirred for 15 min at 0° C., diluted with water (20 mL) and concentrated in vacuo at 40° C. The solid was dissolved in water (11 mL) obtaining a solution with pH 10.5. The solution was set to pH 12 by adding an aqueous solution of NaOH (5 M, 5 drops) and dialyzed against water (4 L) using a Slide-A-Lyzer® cassette (2000 MWCO, 4-12 mL) for 16 h at r.t. The dialysis was continued at 0° C. against water (4 L) for 3 d, whereby the water (4 L) was changed after each 24 h as well as a aqueous solution $NH_4HCO_3$ (3 M, 0.6 mL) was added to the water to set pH ~6.0-6.5. The desalted solution was then lyophilized to afford the persulfate 70 as white fluffy powder (80 mg, 82%). $^1$H NMR (400 MHz, $D_2O$) δ 8.31 (s, 1H, =CH), 6.25 (d, 1H, $J_{HI-H2}$=6.9, 1H, H1$^I$), 5.70 (m, 2H, 2×H1), 5.65 (d, 1H, $J_{HI-H2}$=3.6, H1), 4.72-5.03 (m, 11H, 4×H2, 4×H3, H4$^{IIII}$, $OCH_2$), 4.13-4.69 (m, 15H, 3×H4, 4×H5, 8×H6), 3.58 (m, 1H, H-3 Chol.), 0.63-2.05 (m, 33H, 12$CH_2$, 9CH), 0.95 (d, 3H, J=6.3, cholestanyl-$CH_3$), 0.87 (d, 6H, 2×cholestanyl-$CH_3$), 0.84 (s, 3H, cholestanyl-$CH_3$), 0.70 (s, 3H, cholestanyl-$CH_3$).

Example 16

2,3,4,6-tetra-O-acetyl-α-D-glucopyranosyl-(1→4)-2,3,6-tri-O-acetyl-α-D-glucopyranosyl-(1→4)-2,3,6-tri-O-acetyl-α-D-glucopyranosyl bromide (72)

Maltotriose peracetate (71)[36] (200 mg, 207 μmol) was taken up in DCM (1 mL) and 33% HBr/HOAc (0.7 mL) at 0° C. The mixture was stirred at 0° C. for four hours. The solution was diluted with DCM and washed with ice-water (×2), $NaHCO_3$ (sat.) (×2) and brine (×1), before being dried ($Na_2SO_4$) and the solvent evaporated to yield the bromide 72 as white solid which was reacted on without further purification or characterisation.

2,3,4,6-tetra-O-acetyl-α-D-glucopyranosyl-(1→4)-2,3,6-tri-O-acetyl-α-D-glucopyranosyl-(1→4)-2,3,6-tri-O-acetyl-β-D-glucopyranosyl azide (73)

The bromide 72 (~200 mg) was taken up in a mixture of EtOAc (5 mL) and $NaHCO_3$ (sat.) (5 mL). $NaN_3$ (500 mg) was added, followed by $Bu_4NBr$ (cat.). The mixture was stirred vigorously overnight at r.t. The solution was diluted with EtOAc and washed with $NaHCO_3$(sat.) (×2) and brine (×1), before being dried ($Na_2SO_4$) and the solvent evaporated to yield the azide 73 as white solid (198.9 mg, 100%, two steps) which was reacted on without further purification or characterisation.

4-(Cholestan-3β-yloxymethyl)[1,2,3]triazol-1-yl 2,3,4,6-tetra-O-acetyl-α-D-glucopyranosyl-(1→4)-2,3,6-tri-O-acetyl-α-D-glucopyranosyl-(1→4)-2,3,6-tri-O-acetyl-1-deoxy-β-D-glucopyranoside (74)

The azide 73 (200 mg, 211 μmol), 3-(prop-2-ynyloxy) cholestanol (3 equiv., 267 mg), $CHCl_3$ (2 mL), t-BuOH (2 mL), $CuSO_4$ (50 μL of a 0.3 M aqueous solution) and sodium ascorbate (62.5 μL of a 1M aqueous solution) was stirred vigorously overnight at r.t. The solvent was evaporated and the residue purified by column chromatography ($SiO_2$: Hexane to 2:3 Hexane:EtOAc) to yield the triazole 74 (197 mg, 68%). $^1$H NMR (300 MHz, $CDCl_3$) δ 7.66 (s, 1H, triazol-H), 5.85 (d, 1H, $J_{1,2}$=9.3, H-1$^I$), 5.46-5.27 (m, 6H, H-1$^{II}$, H-1$^I$, H-2$^I$, H-4$^{III}$, H-3$^{II}$, H-3$^{III}$), 5.03 (dd, 1H, $J_{3,2}$=9.8, $J_{3,4}$=9.8, H-3$^I$), 4.82 (dd, 1H, $J_{2,1}$=4.1, $J_{2,3}$=10.3, H-2), 4.72 (dd, 1H, H-2), 4.63 (s, 2H, $CH_2O$), 4.47-4.41 (m, 2H), 4.32-3.88 (m, 9H), 3.31 (m, 1H, CHO), 2.12 (s, 6H, OAc), 2.06 (s, 3H, OAc), 2.03 (s, 3H, OAc), 2.00 (s, 3H, OAc), 1.99 (s, 3H, OAc), 1.98 (s, 3H, OAc), 1.96 (s, 3H, OAc), 1.96-0.83 (m, 31H), 1.82 (s, 3H, OAc), 0.85 (d, 3H, J=6.7, $CH_3$), 0.82 (m, 6H, $CH_3$), 0.76 (s, 3H, $CH_3$), 0.60 (s, 3H, $CH_3$).

4-(Cholestan-3-yl-oxymethyl)[1,2,3]triazol-1-yl α-D-glucopyranosyl-(1→4)-α-D-glucopyranosyl-(1→4)-1-deoxy-β-D-glucopyranoside (75)

The peracetate 74 (197.2 mg) was deacetylated according to the general procedure to give the polyol 75 as a white solid (131 mg, 96%) which was reacted on without further purification or characterisation.

4-(Cholestan-3β-yl-oxymethyl)[1,2,3]triazol-1-yl 2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (76)

The polyol 75 (131.2 mg, 137 μmol) was dissolved in DMF (0.02M, 6.9 mL). $SO_3$.pyridine (3 equiv. per hydroxyl group, 4.12 mmol, 655 mg) was added and the solution stirred overnight at 60° C. The solution was cooled in ice-water before being neutralized with 5 M NaOH (2.1 equiv./$SO_3$.pyridine, 1.73 mL). The solvent was evaporated and the crude product was purified on a C18 SPE cartridge (2×1 g cartridges) followed by dialysis (48 h, 2000 MWCO cartridge). The off-white solution was freeze-dried to yield the persulfate 76 as an off-white solid (156 mg, 58%). $^1$H NMR (400 MHz, $D_2O$) δ 8.32 (s, 1H, triazol-H), 6.22 (d, 1H, $J_{1,2}$=7.5, H-1$^I$), 5.69 (d, 1H, $J_{1,2}$=3.4, H-1), 5.63 (d, 1H, H-1), 5.04-4.17 (m, 18H), 3.58 (m, 1H, CHO), 2.03-0.85 (m, 31H), 0.95 (d, 3H, J=6.2, $CH_3$), 0.88 (d, 6H, $CH_3$), 0.85 (s, 3H, $CH_3$), 0.71 (s, 3H, $CH_3$).

Example 17

3β-Cholestanyl 2,3,4,6-tetra-O-benzoyl-α-D-mannopyranoside (77)

2,3,4,6-tetra-O-benzoyl-α-D-mannopyranosyl trichloroacetimidate (0.372 g, 0.502 mmol) and 3β-cholestanol (0.390 g, 1.004 mmol, 2 eq) was dissolved in anhydrous DCM (5 mL, 0.1 M). Powdered MS 3 Å (120 mg freshly activated) were added. The mixture was stirred at 0° C. for 30 min. A solution of TMSOTf (0.018 mL, 0.100 mmol, 0.2 eq) in DCM (0.3 mL) was added dropwise via a syringe. The mixture was stirred at 0° C. while the reaction was monitored by TLC (hexane-EtOAc=83:17). After 1.5 h, the conversion was complete and $Et_3N$ (0.2 mL) was added. The crude mixture was filtered and the solid rinsed with DCM (5×1.5 mL). The combined filtrate and washings were evaporated onto silica gel and purified by column chromatography (silica gel 2.5×22 cm, gradient elution with hexane-EtOAc 200:20, 210:30, 400:80) to give the glycoside 77 as a colourless foam (368 mg, 76%).

3β-Cholestanyl α-D-mannopyranoside (78)

The above colourless foam (358 mg, 0.370 mg) was dissolved in anhydrous THF (5 mL) and MeOH (3 mL) and a solution of 11 M NaOMe in MeOH (0.4 mL) was added. A white precipitate formed immediately. The mixture was stirred at r.t. o/n. More THF (3 mL) was added and the thick suspension was stirred at r.t. for another day. The mixture was neutralized by addition of AG50WX8 resin ($H^+$ form) resulting in the suspension becoming a clear solution. The resin was removed by filtration and washed with MeOH (4×1.5 mL). The combined filtrate and washings turned into a gel within 5 min (semi-transparent). The mixture was evaporated to a small volume and crystallized from EtOH (10 mL). The whole mixture turned into a gel at r.t., which was filtered and pressed to drain the liquid. The residue was washed with EtOH (1.5 mL), air-dried, and dried under $P_2O_5$ under vacuum o/n to give the tetrol 78 as a white powder (131 mg). The filtrate gave a precipitate and was heated to reflux. The resulting clear solution was evaporated onto silica gel and purified by silica column chromatography (3×8 cm, gradient elution with $CHCl_3$ 200 mL and MeOH—$CHCl_3$ 20:200, 20:160, 30:150). The product fractions were pooled, evaporated and dried under $P_2O_5$ under vacuum for 3 days to give a second crop of product as a white powder (79 mg). $^1$H NMR (DMSO-$d_6$, 300 MHz) δ 4.73 (d, 1H, J=1.5, H1), 4.64 (d, exchangeable with $D_2O$, 1H, J=4.6, OH), 4.61 (br d, exchangeable with $D_2O$, 1H, J=4.1, OH), 4.48 (d, exchangeable with $D_2O$, 1H, J=5.7, OH), 4.37 (t, exchangeable with $D_2O$, 1H, J=6.0, OH), 3.62 (dd, 1H, J=10.3, 5.7), 3.56-3.29 (m, 6H, sugar 5×H and H3 for cholestanyl), 1.95-0.56 (m, 46H, cholestanyl).

3β-Cholestanyl 2,3,4,6-tetra-O-sulfonato-α-D-mannopyranoside tetrasodium salt (79)

The tetrol 78 (102.8 mg, 0.187 mmol) was dissolved in anhydrous DMF (4.67 mL, 0.04 M). $SO_3$.pyridine complex (357 mg, 2.244 mmol, 3 eq per hydroxyl, freshly washed with water, toluene, EtOH, DCM and dried under $P_2O_5$ in vacuum dessicator for 1 h) was added. The mixture was stirred at 60° C. for 18 h and cooled to 0° C. 5 M NaOH (3×0.45 mL) was added. The colour of the mixture (pH>10) turned yellow-orange. The mixture was evaporated to dryness. The residue (pale-yellow powder) was dissolved in 4 mL of water (pH>10) and purified by SPE-C18 cartridge (800 mg, pre-conditioned by eluting with MeCN, MeCN-water 1:1, 1:9, 1:99, 4 mL each). After loading, the SPE was eluted with waster (12 mL), 1% MeCN in water (4.04 mL), 5% (4.2 mL), 10% (4.4 mL), 20% (4.8 mL), 30% (5.2 mL), 40% (5.6 mL), 50% (6 mL), 60% (4.8 mL) and 70% (5.1 mL). The fractions were checked by MBT, Char Test, CE and then were pooled and lyophilized. A small amount of product 79 (25 mg of brownish powder) was obtained from 1%-5% MeCN-water. The majority of the product was eluted with 10%, 20% and 30% of MeCN in water (pale-yellow powder, 120 mg, 67%). Another small amount of product eluted with 40% of MeCN in water (pale-yellow powder, 4 mg). $^1$H NMR ($D_2O$, 400 MHz) δ 5.16 (br s, 1H, H1), 4.70 (br s, 1H, H2), 4.6 (overlapped with HOD, 1H, H3), 4.35 (br m, 1H, H4), 4.22 (br m, 1H, H6), 4.14 (br m, 1H, H6), 3.96 (br m, 1H, H5), 3.54 (br m, 1H, cholestanyl-H3), 1.90-0.50 (m, 46H, cholestanyl).

Example 18

2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranosylamine (80)

The azide 67 (201 mg, 0.098 mmol) was dissolved in EtOAc (10 mL) and stirred with Pd—C (10%, (w/w), 100 mg) under $H_2$ atmosphere for 3 h (TLC: toluene:EtOAc, 7:1). $H_2$ was replaced by Ar then the mixture was filtered through celite (prewashed with MeOH and EtOAc, 5 mL), washed with EtOAc (5×20 mL, +sonication) and finally concentrated in vacuo at r.t. to obtain the amine 80 as a white solid (200 mg, 100%), used without further purification or characterization in the next step.

N-(2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranosyl)-4-((3R,10S,12S,13R)-3,12-di-O-acetyl-10,13-dimethylhexadecahydro-1H-cyclopenta[a]phenanthren-17-yl)pentanamide (81)

Diacetyl deoxycholic acid[37] (53 mg, 0.111 mmol) and DMAP (cat.) were dissolved in dry DCM (3 mL) then at 0° C. a solution of DCC in DCM (1 M, 1 eq, 0.111 mL) and HOBt (17 mg, 0.111 mmol) was added and the mixture was stirred at r.t. for 30 min. The solution was basified by the addition of $Et_3N$ (2 drops) to set pH to 8 and afterwards at 0° C. a solution of the amine 80 (150 mg, 0.074 mmol) in a mixture of DCM/DMF (5:1, (w/w), 2.5 mL) was added and stirring continued at r.t. for 16 h (pH 8). TLC (toluene: EtOAc, 3:1) showed no progress so additional diacetyl deoxycholic acid (53 mg, 0.111 mmol), DCC in DCM (1 M, 1 eq, 0.111 mL), HOBt (17 mg, 0.111 mmol) and $Et_3N$ (3 drops) were added and stirring continued for 56 h. TLC indicated end of reaction, so the solution was filtered through celite (pre-washed, 2 mm) and washed with DCM (3×40 mL). The clear solution was washed with satd $NaHCO_3$-solution (4×30 mL). The aqueous phase was re-extracted with DCM (2×20 mL), organic extracts were combined, washed with aqueous HCl (3%, 5×30 mL), satd $NaHCO_3$-solution (20 mL), dried ($Na_2SO_4$) and concentrated in vacuo. The residue was purified on a column of silicagel (30×5 cm, toluene—EtOAc, 7:1→5:1→1:1) to afford the amide 81 as a slightly yellow solid (58 mg, 32%). $^1$H NMR ($CDCl_3$, 400 MHz) δ7.01-8.28 (m, 65H, 13×Bz), 6.31 (d, 1H, $J_{H1\text{-}NH}$=9.3, NH), 6.10 (dd, 1H, $J_{H2\text{-}H3}$=$J_{H3\text{-}H4}$ 10.1, H3$^{III}$), 6.00 (dd, 1H, $J_{H2\text{-}H3}$=10.2, $J_{H3\text{-}H4}$=8.9, H3$^{I}$), 5.82 (m, 2H, H3$^{II}$, H3$^{III}$), 5.74 (d, 1H, $J_{HI\text{-}H2}$=3.9, H1$^{III}$), 5.67 (t, 1H, H4$^{III}$), 5.61 (d, 1H, $J_{HI\text{-}H2}$=4.0, H1$^{III}$), 5.57 (d, 1H, $J_{HI\text{-}H2}$=4.0, H1$^{II}$), 5.48 (t, 1H, $J_{H1\text{-}H2}$=9.4H1$^{I}$), 5.25 (dd, 1H, $J_{H2\text{-}H3}$=10.6, H2$^{III}$), 4.99-5.15 (m, 4H, 3×H2, H3-Deoxycholic.), 4.92 (dd, 1H, $J_{H6b\text{-}H5}$=1.7, $J_{H6bH6a}$=−12.4, H6b), 4.63-4.81 (m, 4H, 3×H6, H12-Deoxycholic), 4.56 (dd, 1H, $J_{H6b\text{-}H5}$=1.7, $J_{H6bH6a}$=−12.6, H6b), 4.08-4.52 (m, 10H, 3×H4, 4×H5, 3 H6), 2.07 (s, 3H, Ac), 2.03 (s, 3H, Ac), 0.8-2.15 (m, 26H, 10×CH2, 6×CH), 0.89 (s, 3H, $CH_3$), 0.70 (d, 3H, J=6.4, CH—C$\underline{H}_3$), 0.63 (s, 3H, $CH_3$).

N-(α-D-glucopyranosyl-(1→4)-α-D-glucopyranosyl-(1→4)-α-D-glucopyranosyl-(1→4)-β-D-glucopyranosyl)-4-((3R,10S,12S,13R)-12-O-acetyl-10,13-dimethylhexadecahydro-1H-cyclopenta[a]phenanthren-17-yl)pentanamide (82)

Compound 81 (53 mg, 0.021 mmol) was dissolved in mixture of MeOH/THF (7:1 (w/w), 4 mL) then at 0° C. a solution of NaOMe in MeOH (11 M, 0.040 mL) was added and stirring continued at r.t. After 16 h still 10% of a partially benzoylated unpolar compound was present (TLC: MeOH: EtOAc, 2:1) so more NaOMe in MeOH (11 M, 0.050 mL) was added and stirring continued for 1 h (pH 12). The solution was neutralized by adding strongly acidic cation exchange resin (BioRad AG-X8, $H^+$) to adjust the pH to 7, before the solution was filtered, washed with MeOH (3×30 mL, +sonication) and concentrated in vacuo. The residue, bearing a strong aromatic smell, was purified on a column of silicagel (10×1 cm, EtOAc, →MeOH-EtOAc, 2:1→MeOH, containing 0.2% $Et_3N$) to afford the polyol 82 as white solid (23 mg, 100%).

N-(2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranosyl)-4-((3R,10S,12S,13R)-3-O-sodium sulfonato-12-O-acetyl-10,13-dimethylhexadecahydro-1H-cyclopenta[a]phenanthren-17-yl)pentanamide (83)

The polyol 82 (22 mg, 0.020 mmol) was dissolved in dry DMF (0.02 M, 1.05 mL) and freshly washed and dried $SO_3$.pyridine complex (3 eq per OH-group, 150 mg, 0.945 mmol) was added and the mixture stirred for 16 h at 60° C. The reaction was quenched by adding aqueous NaOH solution (5 M, 2.1 eq $SO_3$, 0.397 mL, 1.985 mmol) in one portion at 0° C. (pH 12) and stirred for 15 min 0° C. The suspension was concentrated in vacuo at 40° C. to afford a yellow powder. The powder was dissolved in water (11 mL) (pH 11.5) and dialyzed against water (4 L) using a Slide-A-Lyzer® cassette (2000 MWCO, 4-12 mL) for 2 h at r.t. The dialysis against water (4 L, containing 0.6 mL of a 3 M aq. $NH_4HCO_3$, pH 6) was continued at r.t. for 16 h. The dialysis was continued at 0° C. for 46 h, whereby the water (4 L) was changed after each 24 has well as an aqueous solution of $NH_4HCO_3$ (3 M, 0.6 mL) was added to the water to set the pH to ~6.0-6.5. The desalted solution was then lyophilized to afford a white fluffy powder. CE analysis showed the appearance of 3 compounds, corresponding to 1 major peak at 5.228 min (80%) and 2 minor peaks at 5.121 (5%) and 5.278 min (10%). The mixture (~54 mg) was purified on a C18 HPLC column: solvent A: 100% water; solvent B: 100% acetonitrile; flowrate: 10 mL/min; fraction size: 5 mL; detector: ELS; gradient: 5% B. The product bound only weakly to the C18 matrix but pure fractions of 83 were collected and analysed by CE. Lyophilisation afforded persulfate 83 as a white fluffy powder (12.1 mg, 24%, 98% pure by CE). $^1$H NMR (400 MHz, $D_2O$) δ 5.96 (d, 1H, NH), 5.79 (d, 2H, 2×H1$^{III}$, H1$^{III}$), 5.68 (d, 1H, H1$^{II}$), 5.19 (s, 1H, H3-Deoxycholic), 5.00-5.10 (m, 3H1, 3×H3), 4.67-4.98 (m, 6H, H1$^{I}$, 4×H2, H3), 4.18-4.60 (m, 16H, 3×H4, 4×H5, 8×H6, H12-Deoxycholic.), 2.46 (m, 2H, $OCH_2$), 2.28 (s, 3H, 12-O Ac-deoxycholic), 1.08-2.13 (m, 24H, 9×$CH_2$, 6×CH), 1.05 (s, 3H, $CH_3$), 0.93 (d, 3H, J=6.2, CH—C$\underline{H}_3$), 0.88 (s, 3H, $CH_3$).

(2,3,4,6-Tetra-O-benzoyl-α-D-glucopyranosyl)-(1→4)-(2,3,6-tri-O-benzoyl-α-D-glucopyranosyl)-(1→4)-(2,3,6-tri-O-benzoyl-α-D-glucopyranosyl) bromide (84)

Maltotriose perbenzoate (200 mg, 207 μmol) was taken up in DCM (1 mL) and HBr/HOAc (0.7 mL) at 0° C. The mixture was stirred at 0° C. for 6 hours. The solution was diluted with DCM and washed with ice-water (×2), $NaHCO_3$ (sat.) (×2) and brine (×1), before being dried ($Na_2SO_4$) and the solvent evaporated to yield the white solid product (quantitative) which was reacted on without further purification. $^1$H NMR ($CDCl_3$, 400 MHz) δ 8.19 (m, 2H, Ar), 8.05 (m, 2H, Ar), 7.95 (m, 2H, Ar), 7.88-7.85 (m, 4H, Ar), 7.74-7.70 (m, 4H, Ar), 7.63-7.09 (m, 36H, Ar), 6.73 (d, 1H, $J_{1,2}$=3.4, H1$^{I}$), 6.13-6.08 (m, 2H, H-3$^{III}$, H-3$^{I}$), 5.95 (m, 1H, H-3$^{II}$), 5.76 (d, 1H, $J_{1,2}$=4.1, H-1$^{III}$), 5.67 (m, 1H, H-4$^{III}$), 5.65 (d, 1H, $J_{1,2}$=3.4, H1$^{II}$), 5.27 (dd, 1H, H-2$^{III}$), 5.11 (dd, 1H, H-2$^{II}$), 5.03 (dd, 1H, H-2$^{I}$), 4.99 (dd, 1H, H-6$^{I}$), 4.76-4.72 (m, 2H, H-6$^{II}$, H-6$^{I}$), 4.66-4.58 (m, 2H, H-6$^{II}$, H-5$^{I}$), 4.55-4.35 (m, 5H, H-4$^{I}$, H-4$^{II}$, H-5$^{II}$, H-5$^{III}$, H-6$^{III}$), 4.23 (dd, 1H, H-6$^{III}$).

Example 19

3β-Cholestanyl 2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranoside (85)

2,3,4,6-Tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl bromide 84 (200 mg, 124 μmol),[38] molecular sieves (~50 mg) and cholestanol (3 equiv., 370 μmol, 145 mg) were taken up in dry DCM under Ar and cooled to 0° C. AgOTf (1.5 equiv., 187 μmol, 48 mg) was added and the solution stirred at 0° C. for 2 hours. Triethylamine (600 μL) was added and the solution was warmed to room temperature. The mixture was passed through a short silica plug (using 1:1 EtOAc:Hex with 0.5% (v/v) triethylamine as the elution solvent). The solvent was evaporated (the water bath temperature was kept at room temperature). The resultant mixture was taken up in dry DCM under Ar with molecular sieves, then cooled to 0° C. before TMSOTf (1.24 mL of a 0.1M solution in DCM) was added slowly over 20 minutes. The solution was stirred at 0° C. for 1 hour, then at room temperature with an extra 0.5 equivalents of TMSOTf added over 15 minutes. After a further 30 minutes, triethylamine (1 mL) was added and the solution was filtered and the solvent evaporated. The crude product was purified by column chromatography ($SiO_2$: Hexane to 35% EtOAc/Hex) to give the pure glycoside 85 as a white solid (91 mg, 38%). $^1$H NMR (300 MHz, $CDCl_3$) δ 8.17 (m, 2H, Ar), 8.06 (m, 2H, Ar), 7.96 (m, 2H, Ar), 7.88 (m, 2H, Ar), 7.82 (m, 2H, Ar), 7.72 (m, 4H, Ar), 7.57 (m, 4H, Ar), 7.52-7.09 (m, 32H, Ar), 6.10 (t, 1H, J=9.7, H-3$^{III}$), 5.92 (t, 1H, H-3$^{II}$), 5.75 (d, 1H, $J_{1,2}$=3.8, H-1$^{III}$), 5.71-5.64 (m, 2H, H-4$^{III}$, H-3$^{I}$), 5.58 (d, 1H, $J_{1,2}$=3.8, H-1$^{II}$), 5.30-5.19 (m, 2H, H-2$^{III}$, H-2$^{I}$), 5.10 (dd, 1H, H-2$^{II}$), 4.95 (m, 1H, H-6$^{II}$), 4.84 (d, 1H, $J_{1,2}$=7.7, H-1$^{I}$), 4.77-4.61 (m, 3H, H-6$^{I}$, H-6$^{I}$, H-6$^{II}$), 4.49-4.34 (m, 5H, H-6$^{III}$, H-5$^{I}$, H-5$^{III}$, H-4$^{I}$, H-4$^{II}$), 4.25 (m, 1H, H-6$^{III}$), 4.06 (m, 1H, H-5$^{II}$), 3.53 (m, 1H, CHO), 1.99-0.47 (m, 31H), 0.91 (d, 3H, $CH_3$), 0.87 (m, 6H, $CH_3$), 0.64 (s, 3H, $CH_3$), 0.62 (s, 3H, $CH_3$).

3β-Cholestanyl α-D-glucopyranosyl-(1→4)-α-D-glucopyranosyl-(1→4)-β-D-glucopyranoside (86)

The glycoside 85 (91 mg, 47.5 μmol) was taken up in 1:1 MeOH:THF and deacetylated according to the general procedure to give the polyol 86 (48 mg) as a white solid (containing traces of methyl benzoate) which was reacted on without further purification or characterisation.

3β-Cholestanyl 2,3,4,6-tetra-O-sodium sulfonato-α-D-glucopyranosyl-(1→4)-2,3,6-tri-O-sodium sulfonato-α-D-glucopyranosyl-(1-94)-2,3,6-tri-O-sodium sulfonato-β-D-glucopyranoside (87)

The polyol 86 (47.8 mg, 54.6 μmol) was dissolved in DMF (0.02M, 2.73 mL). $SO_3$.pyridine (3 equiv. per hydroxy, 1.64 mmol, 261 mg) was added and the solution was stirred at 60° C. overnight. The solution was cooled in ice-water and neutralised with 5 M NaOH (700 μL) before the solvent was evaporated. The residue was taken up in water and purified on a C18 SPE cartridge using MeOH/Water as the mobile phase. Fractions containing the product were pooled and dialysed over 48 hours with a 2000 MWCO dialysis cartridge, before being filtered using a 40 micron syringe filter and lyophilized to give the persulfate 87 as an off-white solid (43 mg, 48% over two steps). $^1$H NMR (400 MHz, $D_2O$) δ 5.68 (d, 1H, H-1), 5.58 (d, 1H, H-1), 5.05-4.03 (m, 19H), 3.82 (m, 1H, Cholestanyl H-3), 2.05-0.65 (m, 31H), 0.96 (d, 3H, J=5.6, $CH_3$), 0.90 (d, 6H, J=6.4, $CH_3$), 0.86 (s, 3H, $CH_3$), 0.71 (s, 3H, $CH_3$).

Example 20

2,3,4,6-Tetra-O-acetyl-β-D-galactopyranosyl-((1→4)-1,2,3,6-tetra-O-acetyl-D-glucopyranose (88)

Lactose (5.0221 g, 13.88 mmol) was suspended in dry pyridine (40 mL) and DMAP (50 mg) was added. Acetic anhydride (26.24 mL, 277.6 mmol) was added dropwise to the suspension at 0° C. over 15 minutes and the mixture stirred at room temperature overnight. The reaction was quenched with the dropwise addition of anhydrous methanol at 0° C. and the solution stirred. The solvent was evaporated followed by coelution with anhydrous toluene (3×50 mL) and the remaining solvent was reduced overnight under vacuum to yield a white solid (9 g, 13.26 mmol, 95%) which was reacted on without further purification or characterization.

2,3,4,6-Tetra-O-acetyl-β-D-galactopyranosyl-(1→4)-2,3,6-tri-O-acetyl-α-D-glucopyranosyl bromide (89)

Peracetate 88 (510.3 mg, 0.75 mmol) was dissolved in anhydrous DCM (1.5 mL) and HBr/acetic acid (30%, 1 mL) added dropwise at 0° C. The mixture was stirred at room temperature for 3 hrs then diluted with DCM (30 mL), washed with ice-water (2×40 mL), ice-cold sat'd $NaHCO_3$ solution (3×30 mL) and brine (2×30 mL). the solution was dried over $Na_2SO_4$ and concentrated under vacuum to produce the crude bromide. The next reaction proceeded immediately after concentration.

2,3,4,6-Tetra-O-acetyl-β-D-galactopyranosyl-((1→4)-2,3,6-tri-O-acetyl-β-D-glucopyranosyl azide (90)

Crude glycosyl bromide 89 (0.75 mmol) was dissolved in $CHCl_3$ (4 mL) and $Bu_4NHBr$ (193.42 mg, 0.6 mmol), $NaN_3$ (195.03 mg, 3.0 mmol) and sat'd $NaHCO_3$ solution (7 mL) were added. The reaction was stirred vigorously overnight at room temperature. The reaction was reduced, diluted in EtOAc and washed with sat'd $NaHCO_3$ solution (3×30 mL) and brine (3×30 mL). The organic layer was dried over $Na_2SO_4$ and concentrated in vacuo and purified by flash chromatography using EtOAc/Hexane (1:1) with 0.2% $Et_3N$ to yield the azide (348 mg, 70% over 2 steps). $^1$H NMR (300 MHz, $CDCl_3$) δ5.33 (dd, 1H, $J_{H4',H3'}$=3.4 Hz, $J_{H4',H5'}$=1.1 Hz, H-4'), 5.19 (dd, 1H, $J_{H3,H4}$=9.4 Hz, $J_{H2,H3}$=9.0 Hz, H-3), 5.09 (dd, 1H, $J_{H2',H3'}$=10.4 Hz, $J_{H2',H1'}$=7.8 Hz, H-2'), 4.94 (dd, 1H, $J_{H2',H3'}$=10.4 Hz, $J_{H3',H4'}$=3.4 Hz, H-3'), 4.84 (dd, 1H, $J_{H2,H3}$=9.5 Hz, $J_{H2,H1}$=8.8 Hz, H-2), 4.61 (d, 1H, $J_{H2,H1}$=8.8 Hz, 1H), 4.49 (dd, 1H, $J_{H6a,H6b}$=11.9 Hz, $J_{H6a,H5}$=2.2 Hz, H-6a), 4.46 (d, 1H, $J_{H1',H2'}$=7.8 Hz, H-1'), 4.14-4.03 (m, 3H, H-6b, H-6a', H-6b'), 3.87 (dd, 1H, $J_{H5',H4'}$=1.1 Hz, H-5'), 3.80 (t, 1H, $J_{H4,H5\ and\ H4,H3}$=9.4 Hz, H-4), 3.68 (ddd, 1H, $H_{H6a,H5}$=2.0 Hz, $J_{H6b,H5}$=5.0 Hz, $J_{H4,H5}$=9.9 Hz, H-5), 2.13 (s, 3H, OAc), 2.12 (s, 3H, OAc), 2.05 (s, 3H, OAc), 2.05 (s, 3H, OAc), 2.03 (s, 311, OAc), 2.03 (s, 3H, OAc), 2.02 (s, 3H, OAc), 1.95 (s, 3H, OAc).

4-(Cholestan-3β-yl-oxymethyl)[1,2,3]triazol-1-yl 2,3,4,6-tetra-O-acetyl-β-D-galactopyranosyl-(1→4)-2,3,6-tri-O-acetyl-β-D-glucopyranoside (91)

Dry azide 90 (100 mg, 0.15 mmol) and 3β-(prop-2-ynyloxy) cholestanol (129 mg, 0.302 mmol, 2 eq) were dissolved in DCM/t-BuOH (3:2, 0.21M). An aqueous solution of CuSO4 (0.3M, 0.1 eq, 0.015 mmol, 50 μL) was added to the mixture followed by an aqueous solution of Na-ascorbate (1M, 0.3 eq, 0.045 mmol, 45.3 μL). The reaction was sheltered from light and stirred vigorously overnight. The mixture was diluted in DCM (100 mL) and washed with sat'd $NaHCO_3$ sol (3×30 mL). The aqueous phase was re-extracted with DCM (20 mL) and combined organic layers were then washed with brine (2×30 mL) and dried over $Na_2SO4$. The solvent was evaporated in vacuo to yield the crude product. The crude product was purified by flash chromatography using Hexane/EtOAc (3:2) with 0.2% $Et_3N$ to yield the product as a white solid (135.3 mg, 82%). $^1H$ NMR (300 MHz, $CDCl_3$) δ 7.67 (s, 1H, CH—N), 5.79 (d, 1H, $J_{H1,H2}$=9.2, H-1), 5.43-5.37 (m, 2H, H-2, H-3), 5.35 (dd, 1H, $J_{H3',H4'}$=3.4, $J_{H4',H5'}$=0.8, H-4'), 5.11 (dd, 1H, $J_{H2',H3'}$=10.4, $J_{H2',H1'}$=7.8, H-2'), 4.95 (dd, 1H, $J_{H2',H3'}$=10.4, $J_{H3',H4'}$=3.4, H-3'), 4.64 (s, 2H, $CH_2$—N), 4.50 (d, 1H, $J_{H1',H2'}$=7.9, H-1'), 4.46 (dd, 1H, $J_{H6a',H6b'}$=12.4, H6a', H5'=1.6, H-6a'), 4.16-4.04 (m, 3H, H-6b', H-6a, H-6b), 3.96-3.85 (m, 3H, H-4, H-5, H-5'), 3.39-3.28 (m, 1H, H-Chol), 2.14 (s, 3H, OAc), 2.09 (s, 3H, OAc), 2.06 (s, 3H, OAc), 2.05 (s, 3H, OAc), 2.04 (s, 3H, OAc), 1.95 (s, 3H, OAc), 1.88-1.80 (m, 31H), 1.85 (s, 3H, OAc), 0.88-0.80 (m, 3H, $CH_3$—CH), 0.85 (d, 3H, J=1.3, $CH_3$—CH), 0.83 (d, 3H, J=1.2, $CH_3$—CH), 0.77 (s, 3H, $CH_3$), 0.62 (s, 3H, $CH_3$).

4-(Cholestan-3β-yl-oxymethyl)[1,2,3]triazol-1-yl β-D-galactopyranosyl-(1→4)-β-D-glucopyranoside (92)

Dry N-glycoside 91 (100 mg, 0.092 mmol) was dissolved in anhydrous $CH_3OH$ and a solution of NaOMe/$CH_3OH$ (11M, 30 μL) was added dropwise to the mixture at 0° C. under argon. The solution was allowed to stir at RT overnight. After monitoring by TLC, additional anhydrous $CH_3OH$ (2 mL) and NaOMe/$CH_3OH$ (11M, 50 μL) was added and the reaction mixture found to be pH 11. Upon completion, the reaction was neutralised to pH 6 by the addition of Dowex H+ ion-exchange resin, and the resulting suspension dissolved in $CHCl_3$/$CH_3OH$ (1:1) at 40° C. The solution was filtered, concentrated and dried over $P_2O_5$ to yield the crude product.

4-(Cholestan-3β-yl-oxymethyl)[1,2,3]triazol-1-yl 2,3,4,6-tetra-O-sulfo-β-D-galactopyranosyl-(1→4)-2,3,6-tri-O-sulfo-β-D-glucopyranoside, heptasodium salt (93)

$SO_3$-Pyr (124.89 mg, 0.785 mmol, 3 eq/OH, prewashed and dried) was added in one portion to dry polyol 92 (29.7 mg, 0.037 mmol) in anhydrous DMF (0.02M, 1.85 mL) at 60° C. The reaction was allowed to stir overnight. The reaction was cooled to 0° C. and cooled solution of 5M NaOH (329.7 μL, 1.65 mmol, 2.1 eq of $SO_3$-Pyr) was added in one portion with stirring. The pH was checked immediately and found to be only slightly basic. An additional solution of cooled 5M NaOH (50 μL) was added to the reaction and the pH found to be approximately 13. The suspension was stirred at 0° C. for 15 minutes, then diluted in HPLC grade $H_2O$ (100 mL) and the solvent evaporated slowly. The product was de-salted on a C18 Solid phase extraction cartridge (WatersSepPak, 1 g) by a gradient elution from 100% HPLC grade $H_2O$ to ACN/$H_2O$ (1:1). The fractions were kept basic by the addition of 0.1 M $NH_4HCO_3$ and a char test performed on all fractions. The char positive fractions were analysed by CE and the fractions containing JR245_33 combined and separated on C18 Liquid Chromatography using a gradient elution from 5-50% ACN in $H_2O$ over 35 mins. All fractions were tested for sugar using 10 μL of sample with 40 μL of 1,9-dimethylmethylene blue aqueous solution, and the sugar-positive fractions were analysed by CE. Pure fractions were collected and lyophilised to yield the product as an off-white powder (21.1 mg, 37% yield) 98% pure by CE. $^1H$ NMR (300 MHz, $D_2O$) δ: 8.29 (s, 1H, CH═C—), 6.27 (d, 1H, $J_{H1,H2}$=8.1 Hz, H-1), 5.14 (d, 1H, $J_{H3',H4'}$=3.0 Hz, H-4'), 4.98 (t, 1H, $J_{H1,H2}$=7.8 Hz, H-2), 4.91-4.82 (m, 1H, H-3), 4.89 (d, 1H, $J_{H1',H2'}$=7.5 Hz, H-1'), 4.74 (s, 2H, $CH_2$), 4.57 (dd, 2H, $J_{H2',H3'}$=10.2 Hz, $J_{H3',H4'}$=3.0 Hz, H-3', H-5'), 4.46 (dd, 1H, $J_{H2',H3'}$=9.9, $J_{H1',H2'}$=7.5, H-2'), 4.36 (m, 5H, H-4, H-5, H-6a, H-6a', H-6b'), 4.18-4.14 (m, 1H, H-6b), 3.63-3.49 (m, 1H, Chol-H), 2.04-0.98 (m, 31H, Chol), 0.97-0.83 (m, 12H, $CH_3$), 0.70 (s, 3H, $CH_3$).

Example 21

2,3,4,6-Tetra-O-acetyl-α-D-glucopyranosyl-(1→4)-2,3,6-tri-O-acetyl-β-D-glucopyranosyl azide (94)

Maltose peracetate (200 mg, 295 μmol) was taken up in DCM (1 mL) and HBr/HOAc (0.7 mL) at 0° C. The mixture was stirred at 0° C. for four hours. The solution was diluted with DCM and washed with ice-water (×2), $NaHCO_3$(sat.) (×2) and brine (×1), before being dried ($Na_2SO_4$) and the solvent evaporated to yield the white solid bromide product which was taken up in a mixture of EtOAc (5 mL) and $NaHCO_3$(sat.) (5 mL). $NaN_3$ (2.0 g) was added, followed by $Bu_4NBr$ (cat.). The mixture was stirred vigorously overnight at room temperature. The solution was diluted with EtOAc and washed with $NaHCO_3$(sat.) (×2) and brine (×1), before being dried ($Na_2SO_4$) and the solvent evaporated to yield the crude product which was purified using column chromatography ($SiO_2$: Hexane to 50% EtOAc/Hexane; loaded with toluene) to yield 170.6 mg of the white solid product (87%, two steps) which was reacted on without further characterisation.

4-(Cholestan-3β-yl-oxymethyl)[1,2,3]triazol-1-yl 2,3,4,6-tetra-O-acetyl-α-D-glucopyranosyl-(1→4)-2,3,6-tri-O-acetyl-β-D-glucopyranoside (95)

Azide 94 (170 mg, 257 μmol), 3β-(prop-2-ynyloxy) cholestanol (2 equiv., 219 mg), $CHCl_3$ (2 mL), t-BuOH (2 mL), $CuSO_4$ (50 μL of a 0.3 M aqueous solution) and sodium ascorbate (62.5 μL of a 1M aqueous solution) was stirred vigorously overnight at room temperature. The solvent was evaporated and the residue loaded onto a silica column ($SiO_2$: Hexane to 50% EtOAc/Hexane) to yield 190 mg of the pure material 95 (68%). $^1H$ NMR (300 MHz, $CDCl_3$) δ: 7.67 (s, 1H, Triazol-H), 5.85 (d, 1H, $J_{1,2}$=9.3, $H1^I$), 5.46-5.29 (m, 4H, $H\text{-}1^{II}$, $H\text{-}2^I$, $H\text{-}4^{II}$, $H\text{-}3^{II}$), 5.04 (t, 1H, $J_{2,3}$=10.3, $J_{3,4}$=10.3, $H\text{-}3^I$), 4.85 (dd, 1H, $J_{1,2}$=4.1, $J_{2,3}$=10.8, $H\text{-}2^{II}$), 4.63 (s, 2H, $CH_2$), 4.45 (ddd, 1H, $H\text{-}6^I$), 4.25-4.19 (m, 2H, $H\text{-}5^I$, $H\text{-}6^{II}$), 4.14-3.92 (m, 4H, $H\text{-}5^{II}$, $H\text{-}6^I$, $H\text{-}6^{II}$, $H\text{-}4^I$), 3.32 (m, 1H, CHO), 2.31-0.53 (m, 31H), 2.10 (s, 3H, OAc), 2.08 (s, 3H, OAc), 2.03 (s, 3H, OAc), 2.00 (s, 6H, OAc), 1.98 (s, 3H, OAc), 1.82 (s, 3H, OAc), 0.83 (d, 3H, J=1.0, $CH_3$), 0.81 (d, 3H, J=1.5, $CH_3$), 0.76 (s, 3H, $CH_3$), 0.61 (s, 3H, $CH_3$).

4-(Cholestan-3β-yl-oxymethyl)[1,2,3]triazol-1-yl α-D-glucopyranosyl-(1→4)-β-D-glucopyranoside (96)

Peracetate 95 (190 mg) was dissolved in THF/MeOH (1:1). NaOMe in MeOH (11M, 20 μL) was added and the solution was stirred at room temperature for 3 hours. The solution was neutralised with $H^+$ resin, filtered and the solvent evaporated to give 125 mg (90%) of the off-white solid product which was reacted on without further purification or characterisation.

4-(Cholestan-3β-yl-oxymethyl)[1,2,3]triazol-1-yl 2,3,4,6-tetra-O-sulfo-α-D-glucopyranosyl-(1→4)-2,3,6-tri-O-sulfo-β-D-glucopyranoside, heptasodium salt (97)

Polyol 96 (124.5 mg, 157 μmol) was dissolved in DMF (0.02 M, 7.84 mL). $SO_3$.pyridine (3 equiv./OH, 3.3 mmol, 525 mg) was added and the solution stirred at 60° C. overnight. The solution was cooled to 0° C. and neutralized with 5M NaOH (2.1 equiv./$SO_3$.pyridine, 1.4 mL). The mixture was transferred to a large round-bottomed flask with water, evaporated and dialysed (2000 MWCO cartridge, Pierce) against purified water (5 L, water changes every 12 hours) for 24 hours. The solution was lyophilized and taken up in water before being purified on a prep C18 RP-HPLC system (5% to 95% acetonitrile in water over 20 minutes). CE was used to determine the purity of each fraction collected after HPLC purification. Greater than 90% purity fractions were combined and lyophilized to give the product as a white solid (55 mg, 23%). $^1$H NMR (300 MHz, $D_2O$) δ: 8.25 (s, 1H, triazol), 6.20 (d, 1H, $J_{1,2}$=6.0, H1$^I$), 5.65 (d, 1H, H-1$^{II}$), 5.04-4.94 (m, 3H, H-3$^I$, H-3$^{II}$, H-2$^I$), 4.80 (s, 2H, $CH_2$), 4.73 (m, 1H, H-2$^{II}$), 4.58 (dd, 1H, H-4$^{II}$), 4.49-4.23 (m, 7H, H-4$^I$, H-5$^I$, H-5$^{II}$, 4×H-6), 3.57 (m, 1H, CHO), 2.09-0.56 (m, 46H).

Example 22

2,3,4,6-Tetra-O-benzoyl-α-D-glucopyranosyl-(1→4)-1,2,3,6-tetra-O-benzoyl-D-glucopyranose (98)

Maltose (2.0 g, 5.84 mmol) was dissolved in dry pyridine (40 mL) at 0° C. DMAP (cat.) was added. Benzoyl chloride (2.5 equiv., 14.6 mmol, 16.4 g, 13.6 mL) was added dropwise and the solution stirred at room temperature overnight. The solution was poured onto a mixture of ice-water and DCM. The organic layer was washed with $NaHCO_3$(sat.) (×7), brine, $H_2SO_4$ (5%) (×2), followed by brine. The solution was dried ($Na_2SO_4$) and the solvent evaporated. The product was passed through a short silica plug to remove the remaining benzoyl chloride and the solvent was evaporated to yield 3.5 g (51%) of the white solid product which was reacted on without further purification or characterisation.

2,3,4,6-Tetra-O-benzoyl-α-D-glucopyranosyl-(1→4)-2,3,6-tri-O-benzoyl-D-glucopyranosyl trichloroacetimidate (99)

Perbenzoate 98 (0.5 g) was dissolved in pyridine (5 mL). Dimethylamine (3.5 mL; 5.6 M in EtOH) was added. The reaction mixture was stirred at room temperature for 1 hour. Toluene (10 mL) was added and the solution washed with brine, $H_2SO_4$ (5%) (×2), brine, $NaHCO_3$ (sat.) and brine. The solution was dried ($Na_2SO_4$) and the solvent was evaporated. The crude hemiacetal was taken up in dry DCM with molecular sieves, potassium carbonate (200 mg) and caesium carbonate (70 mg). The solution was cooled to 0° C. before trichloroacetonitrile (120 μL) was added. The mixture was stirred at room temperature for 3 hours. The mixture was filtered and the solvent evaporated. The crude product was purified using column chromatography ($SiO_2$: Hexane to 50% EtOAc/Hexane) to yield the product as a white solid (336 mg, 66% over two steps) which was reacted on without further characterisation.

3'-Cholestanyl 2,3,4,6-tetra-O-acetyl-α-D-glucopyranosyl-(1→4)-2,3,6-tri-O-acetyl-β-D-glucopyranoside (100)

Trichloroacetimidate 99 (336.2 mg, 280 μmol), cholestanol (3 equiv., 326 mg) and molecular sieves were taken up in dry DCM under Ar. The solution was stirred for 15 minutes before TMSOTf (0.1 M solution in DCM, 0.33 equiv., 924 μL) was added slowly. After 30 minutes a further one equivalent of TMSOTf (2.77 mL of 0.1 M solution in DCM) was added slowly and the solution was allowed to stir for a further 40 minutes. Triethylamine (200 μL) was added and the solvent was evaporated. The crude product was purified by column chromatography ($SiO_2$: Hexane to 15% EtOAc/Hexane) but eluted close to the excess cholestanol starting material. Thus the mixture was debenzoylated, acetylated and re-purified to afford adequate separation. The compound was taken up in MeOH/THF (1:1). 11M NaOMe in MeOH (50 μL) was added and the solution was stirred at room temperature for 5 hours. The solution was neutralised with H+ resin, filtered and the solvent evaporated. The crude polyol product was taken up in pyridine (5 mL) and acetic anhydride (5 mL). DMAP (cat.) was added and the solution stirred overnight at room temperature. The mixture was added to ice-water and extracted with DCM before being washed with 5% $H_2SO_4$, followed by brine. The solution was dried ($Na_2SO_4$) and the solvent evaporated, before the crude sample was purified using column chromatography ($SiO_2$: Hexane to 50% EtOAc/Hexane) to yield 118 mg of the white solid peracetylated product (42%). $^1$H NMR (300 MHz, $CDCl_3$) δ: 5.40 (d, 1H, $J_{1,2}$=4.1, H-1$^{II}$), 5.35 (dd, 1H, $J_{3,2}$=10.6, $J_{3,4}$=9.5, H-3$^{II}$), 5.23 (dd, 1H, $J_{3,2}$=9.0, $J_{3,4}$=9.0, H-3$^I$), 5.03 (dd, 1H, $J_{4,3}$=10.0, $J_{4,5}$=10.0, H-4$^{II}$), 4.83 (dd, 1H, $J_{2,1}$=3.9, $J_{2,3}$=10.3, H-2$^{II}$), 4.76 (dd, 1H, $J_{2,1}$=8.0, $J_{2,3}$=9.3, H-2$^I$), 4.60 (d, 1H, $J_{1,2}$=8.0, H-1$^I$), 4.42 (dd, 1H, H-6$^I$), 4.26-4.20 (m, 2H, H-6$^I$, H-6$^{II}$), 4.04-3.92 (m, 3H, H-4$^I$, H-5$^{II}$, H-6$^{II}$), 3.64 (ddd, 1H, H-5$^I$), 3.53 (m, 1H, CHO), 2.12 (s, 3H, OAc), 2.09 (s, 3H, OAc), 2.03 (s, 3H, OAc), 2.01 (s, 3H, OAc), 2.00 (s, 3H, OAc), 1.99 (s, 3H, OAc), 1.98 (s, 3H, OAc), 1.96-0.52 (m, 31H), 0.87 (d, 3H, J=6.4, $CH_3$), 0.86 (d, 3H, J=1.5, $CH_3$), 0.83 (d, 3H, J=1.3, $CH_3$), 0.76 (s, 3H, $CH_3$), 0.63 (s, 3H, $CH_3$).

3'-Cholestanyl α-D-glucopyranosyl-(1→4)-β-D-glucopyranoside (101)

Glycoside 100 (118 mg) was dissolved in THF/MeOH (1:1). NaOMe in MeOH (11M, 30 μL) was added and the solution was stirred at room temperature for 3 hours. The solution was neutralised with $H^+$ resin, filtered and the solvent evaporated to give a quantitative yield of the off-white solid which was reacted on without further purification or characterisation.

3'-Cholestanyl 2,3,4,6-tetra-O-sulfo-α-D-glucopyranosyl-(1→4)-2,3,6-tri-O-sulfo-β-D-glucopyranoside, heptasodium salt (102)

Polyol 101 (99.5 mg, 140 μmol) was dissolved in DMF (0.02 M, 7 mL). $SO_3$.pyridine (3 equiv./OH, 2.9 mmol, 467 mg) was added and the solution stirred at 60° C. overnight. The solution was cooled to 0° C. and neutralized with 5M NaOH (2.1 equiv./$SO_3$.pyridine, 1.23 mL). The mixture was transferred to a large round-bottomed flask with water, evaporated and dialysed (2000 MWCO cartridge, Pierce) against purified water (5 L, water changes every 12 hours) for 48 hours. The solution was lyophilized and taken up in water before being purified on a prep C18 RP-HPLC system (5% to 95% acetonitrile in water over 20 minutes). CE was used to determine the purity of each fraction collected after HPLC purification. Greater than 90% purity fractions were combined and lyophilized to give the product as a white solid (27 mg, 14%). $^1$H NMR (400 MHz, $D_2O$) δ: 5.59 (d, 1H, $J_{1,2}$=3.4, H-1$^{II}$), 5.09 (d, 1H, $J_{1,2}$=5.0, H-1$^{I}$), 4.89 (m, 1H, H-3$^{II}$), 4.73 (m, 1H, H-3$^{I}$), 4.61 (dd, 1H, H-2$^{II}$), 4.53-4.42 (m, 3H, H-2$^{I}$, H-4$^{II}$, H-6$^{II}$), 4.37-4.14 (m, 6H, H-4$^{I}$, H-5$^{II}$, H-5$^{I}$, 3×H-6), 185 (m, 1H, CHO), 2.08-0.64 (m, 46H).

Example 23

2,3,4,6-Tetra-O-benzoyl-β-D-glucopyranosyl-(1→4)-1,2,3,6-tetra-O-benzoyl-D-glucopyranose (103)

Cellobiose (1.0 g, 2.92 mmol) was dissolved in dry pyridine (20 mL) at 0° C. DMAP (cat.) was added. Benzoyl chloride (2.5 equiv., 58 mmol, 6.8 mL) was added dropwise and the solution stirred at room temperature overnight. The solution was poured onto a mixture of ice-water and DCM. The organic layer was washed with $NaHCO_3$(sat.) (×7), brine, $H_2SO_4$ (5%) (×2), followed by brine. The solution was dried ($Na_2SO_4$) and the solvent evaporated. The product was passed through a short silica plug to remove the remaining benzoyl chloride and the solvent was evaporated to yield 740 mg (22%) of the white solid product which was reacted on without further purification or characterisation.

2,3,4,6-Tetra-O-benzoyl-β-D-glucopyranosyl-(1→4)-2,3,6-tri-O-benzoyl-D-glucopyranosyl trichloroacetimidate (104)

Perbenzoate 103 (740 mg, 0.63 mmol) was dissolved in pyridine (5 mL). The solution was cooled to 0° C., before dimethylamine (3.1 mL; 5.6 M in EtOH) was added. The reaction mixture was stirred at room temperature for 2 hours. Toluene (20 mL) was added and the solution washed with brine, $H_2SO_4$ (5%) (×2), brine, $NaHCO_3$ (sat.) and brine. The solution was dried ($Na_2SO_4$) and the solvent was evaporated. The crude hemiacetal was taken up in dry DCM (5 mL) with molecular sieves and potassium carbonate (1.17 g). The solution was cooled to 0° C. before trichloroacetonitrile (782 μL) was added. The mixture was stirred at room temperature for 2 hours. The mixture was filtered and the solvent evaporated. The crude product was purified using column chromatography ($SiO_2$; Toluene:EtOAc (5:1) to 100% EtOAc) to yield the product as a white foam (566 mg, 75% over two steps) which was reacted on without further characterisation.

3'-Cholestanyl 2,3,4,6-tetra-O-benzoyl-β-D-glucopyranosyl-(1→4)-2,3,6-tri-O-benzoyl-β-D-glucopyranoside (105)

Trichloroacetimidate 104 (250 mg, 210 μmol), cholestanol (2 equiv., 163 mg) and molecular sieves were taken up in dry DCM under Ar. The solution was stirred for 30 minutes at 0° C. before TMSOTf (0.4 M solution in DCM, 0.5 equiv., 260 μL) was added slowly. After 30 minutes a further one equivalent of TMSOTf (130 μL of 0.4 M solution in DCM) was added slowly and the solution was allowed to stir for a further 20 minutes. Triethylamine (15 μL) was added and the solution filtered before the solvent was evaporated. The crude product was purified by column chromatography ($SiO_2$; Toluene:EtOAc, 10:1 to 5:1) to yield 208 mg of the white solid product (69%). 1H nmr (300 MHz, $CDCl_3$) δ: 7.99-7.16 (m, 35H, Ar), 5.73 (m, 2H, H-3$^{I}$, H-3$^{II}$), 5.51 (dd, 1H, $J_{2,1}$=7.9, $J_{2,3}$=9.8, H-2$^{II}$), 5.37 (m, 2H, H-4$^{II}$, H-2$^{I}$), 4.93 (d, 1H, $J_{1,2}$=7.9, H-1$^{II}$), 4.76 (d, 1H, $J_{1,2}$=7.9, H-1$^{I}$), 4.59 (dd, 1H, H-6), 4.45 (dd, 1H, H-6), 4.19 (dd, 1H, $J_{4,3}$=9.5, $J_{4,5}$=9.5, H-4$^{I}$), 4.07 (dd, 1H, H-6), 3.84-3.79 (m, 2H, 2×H-5), 3.72 (dd, 1H, H-6), 3.46 (m, 1H, CHO), 1.95-0.45 (m, 31H), 0.88 (d, 3H, J=7.3, $CH_3$), 0.86 (d, 3H, J=1.4, $CH_3$), 0.84 (d, 3H, J=1.4, $CH_3$), 0.62 (s, 3H, $CH_3$), 0.60 (s, 3H, $CH_3$).

3'-Cholestanyl β-D-glucopyranosyl-(1→4)-β-D-glucopyranoside (106)

Glycoside 105 (152 mg) was dissolved in THF/MeOH (1:1). NaOMe in MeOH (11M, 30 uL) was added and the solution was stirred at room temperature for 24 hours. The solution was neutralised with $H^+$ resin, filtered and the solvent evaporated to give 23 mg (30%) of the off-white solid which was reacted on without further purification or characterisation.

3'-Cholestanyl 2,3,4,6-tetra-O-sulfo-β-D-glucopyranosyl-(1→4)-2,3,6-tri-O-sulfo-β-D-glucopyranoside, heptasodium salt (107)

Polyol 106 (23 mg, 32 μmol) was dissolved in DMF (0.02 M, 1.6 mL). $SO_3$.pyridine (3 equiv./OH, 672 μmol, 107 mg) was added and the solution stirred at 60° C. overnight. The solution was cooled to 0° C. and neutralized with 5M NaOH (2.1 equiv./$SO_3$.pyridine, 0.282 mL). The mixture was transferred to a large round-bottomed flask with water, evaporated and dialysed (2000 MWCO cartridge, Pierce) against purified water (5 L, water changes every 12 hours) for 48 hours. The solution was lyophilized and taken up in water before being purified on a prep C18 RP-HPLC system (5% to 95% acetonitrile in water over 20 minutes). CE was used to determine the purity of each fraction collected after HPLC purification. Greater than 90% purity fractions were combined and lyophilized to give the product as a white solid (11.6 mg, 25%). $^1$H NMR (400 MHz, $D_2O$) δ: 5.06 (d, 1H, $J_{1,2}$=6.3, H-1$^{II}$), 4.86 (d, 1H, $J_{1,2}$=6.3, H-1$^{I}$), 4.72-4.66 (m, 2H, H-3$^{I}$, H-3$^{II}$), 4.57-4.48 (m, 2H, H-4$^{II}$, H-6), 4.40-4.35 (m, 3H, H-2$^{I}$, H-2$^{II}$, H-6), 4.30 (dd, 1H, H-6), 4.24-4.20 (m, 2H, H-4$^{I}$, H-6), 4.08 (m, 2H, H-5$^{I}$, H-5"), 3.62 (m, 1H, CHO), 2.00-0.67 (m, 31H), 0.93 (d, 3H, $CH_3$), 0.87 (d, 3H, $CH_3$), 0.86 (d, 3H, $CH_3$), 0.83 (s, 3H, $CH_3$), 0.68 (s, 3H, $CH_3$).

Example 24

2,3,4,6-Tetra-O-benzoyl-β-D-galactopyranosyl-(1→4)-1,2,3,6-tetra-O-benzoyl-D-glucopyranose (108)

Lactose (1.0 g, 2.92 mmol) was dissolved in dry pyridine (20 mL) at 0° C. DMAP (cat.) was added. Benzoyl chloride (2.5 equiv., 58 mmol, 6.8 mL) was added dropwise and the solution stirred at room temperature overnight. The solution was poured onto a mixture of ice-water and DCM. The organic layer was washed with $NaHCO_3$(sat.) (×7), brine, $H_2SO_4$ (5%) (×2), followed by brine. The solution was dried ($Na_2SO_4$) and the solvent evaporated. The product was passed through a short silica plug to remove the remaining benzoyl chloride and the solvent was evaporated to yield 3.67 g (quantitative) of the white solid product which was reacted on without further purification or characterisation.

2,3,4,6-Tetra-O-benzoyl-β-D-galactopyranosyl-(1→4)-2,3,6-tri-O-benzoyl-D-glucopyranosyl trichloroacetimidate (109)

Perbenzoate 108 (500 mg, 0.43 mmol) was dissolved in pyridine (3.5 mL). The solution was cooled to 0° C., before dimethylamine (2.1 mL; 5.6 M in EtOH) was added. The reaction mixture was stirred at room temperature for 2 hours. Toluene (20 mL) was added and the solution washed with brine, $H_2SO_4$ (5%) (×2), brine, $NaHCO_3$ (sat.) and brine. The solution was dried ($Na_2SO_4$) and the solvent was evaporated. The crude hemiacetal was taken up in dry DCM (5 mL) with molecular sieves and potassium carbonate (871 mg). The solution was cooled to 0° C. before trichloroacetonitrile (582 μL) was added. The mixture was stirred at room temperature for 2 hours. The mixture was filtered and the solvent evaporated. The crude product was purified using column chromatography ($SiO_2$; Toluene:EtOAc (5:1) to 100% EtOAc) to yield the product as a white foam (152 mg, 29% over two steps) which was reacted on without further characterisation.

3'-Cholestanyl 2,3,4,6-Tetra-O-benzoyl-β-D-galactopyranosyl-(1→4)-2,3,6-tri-O-benzoyl-β-D-glucopyranoside (110)

Trichloroacetimidate 109 (250 mg, 210 μmol), cholestanol (2 equiv., 163 mg) and molecular sieves were taken up in dry DCM under Ar. The solution was stirred for 30 minutes at 0° C. before TMSOTf (0.4 M solution in DCM, 0.5 equiv., 260 μL) was added slowly. After 30 minutes a further one equivalent of TMSOTf (130 μL of 0.4 M solution in DCM) was added slowly and the solution was allowed to stir for a further 20 minutes. Triethylamine (12 μL) was added and the solution filtered before the solvent was evaporated. The crude product was purified by column chromatography ($SiO_2$; Toluene:EtOAc, 15:1 to 7:1) to yield 237 mg of the white solid product (78%). 1H nmr (400 MHz, $CDCl_3$) δ 8.02-7.11 (m, 35H, Ar), 5.77 (dd, 1H, $J_{3,2}$=9.6, $J_{3,4}$=9.6, H-3$^{I}$), 5.74-5.69 (m, 2H, H-2$^{II}$, H-4$^{II}$), 5.43-5.35 (m, 2H, H-2$^{I}$, H-3$^{II}$), 4.86 (d, 1H, $J_{1,2}$=7.9, H-1$^{II}$), 4.78 (d, 1H, $J_{1,2}$=7.9, H-1$^{I}$), 4.57 (dd, 1H, H-6$^{I}$), 4.47 (dd, 1H, H-6$^{I}$), 4.20 (dd, 1H, $J_{4,3}$=9.6, $J_{4,5}$=9.6, H-4$^{I}$), 3.89 (ddd, 1H, H-5$^{II}$), 3.83 (ddd, 1H, H-5$^{I}$), 3.75 (dd, 1H, H-6$^{II}$), 3.65 (dd, 1H, H-6$^{II}$), 3.49 (m, 1H, CHO), 1.94-0.47 (m, 31H), 0.88 (d, 3H, J=6.5, $CH_3$), 0.86 (d, 3H, J=1.7, $CH_3$), 0.84 (d, 3H, J=1.9, $CH_3$), 0.63 (s, 3H, $CH_3$), 0.60 (s, 3H, $CH_3$).

3'-Cholestanyl β-D-galactopyranosyl-(1→4)-β-D-glucopyranoside (111)

Glycoside 110 (231 mg) was dissolved in THF/MeOH (1:1). NaOMe in MeOH (11M, 150 μL) was added and the solution was stirred at room temperature for 24 hours. The solution was neutralised with $H^+$ resin, filtered and the solvent evaporated to give 61 mg (54%) of the white solid which was reacted on without further purification or characterisation.

3'-Cholestanyl 2,3,4,6-tetra-O-sulfo-β-D-galactopyranosyl-(1→4)-2,3,6-tri-O-sulfo-β-D-glucopyranoside, heptasodium salt (112)

Polyol 111 (30 mg, 42 μmol) was dissolved in DMF (0.02 M, 2.1 mL). $SO_3$.pyridine (3 equiv./OH, 882 μmol, 140 mg) was added and the solution stirred at 60° C. overnight. The solution was cooled to 0° C. and neutralized with 5M NaOH (2.5 equiv./$SO_3$.pyridine, 0.442 mL). The mixture was transferred to a large round-bottomed flask with water, evaporated and dialysed (2000 MWCO cartridge, Pierce) against purified water (5 L, water changes every 12 hours) for 48 hours. The solution was lyophilized and taken up in water before being purified on a prep C18 RP-HPLC system (5% to 95% acetonitrile in water over 20 minutes). CE was used to determine the purity of each fraction collected after HPLC purification. Greater than 90% purity fractions were combined and lyophilized to give the product as an off-white solid (13 mg, 22%). $^1$H NMR (300 MHz, $D_2O$) δ: 5.15 (d, 1H, H-1), 4.70 (d, 1H, H-1), 4.55-3.88 (m, 12H), 3.50 (m, 1H, CHO), 1.88-0.44 (m, 46H).

Example 25

1,2,3,4-Tetra-O-benzoyl-α-D-mannopyranose (113)

6-O-Trityl-1,2,3,4-tetra-O-benzoyl-α-D-mannopyranose (5 g, 6.0 mmol), was dissolved in MeOH. $H_2SO_4$ (conc.) (150 μL) was carefully added, and the solution was stirred at room temperature overnight. The solution was poured into ice-water (300 mL) and extracted with EtOAc (80 mL). The organic layer was separated and washed with brine (80 mL), followed by $NaHCO_3$ (sat.). The solution was dried ($Na_2SO_4$), filtered and the solvent evaporated. The crude product was purified using column chromatography ($SiO_2$; Hex:EtOAc, 500:50 to 200:200) to yield 1.79 g of the white solid product (50%). $^1$H NMR (300 MHz, $CDCl_3$) δ: 8.20-8.12 (m, 4H, Ar), 8.02-7.98 (m, 2H, Ar), 7.87-7.84 (m, 2H, Ar), 7.70-7.26 (m, 27H, Ar), 6.63 (d, 1H, $J_{1,2}$=2.1, H-1), 6.12 (dd, 1H, $J_{3,2}$=3.3, $J_{3,4}$=10.2, H-3), 6.02 (dd, 1H, $J_{4,3}$=10.0, $J_{4,5}$=10.0, H-4), 5.89 (dd, 1H, $J_{1,2}$=1.8, $J_{2,3}$=3.1, H-2), 4.25 (ddd, 1H, H-5), 3.90-3.76 (m, 2H, H-6).

2,3,4,6-Tetra-O-benzoyl-α-D-glucopyranosyl-(1→4)-2,3,6-tri-O-benzoyl-α-D-glucopyranosyl-(1→4)-2,3,6-tri-O-benzoyl-D-glucopyranosyl trichloroacetimidate (114)

Maltotriose perbenzoate (400 mg) was dissolved in THF (3 mL) at 0° C. A saturated solution of $NH_3$ in MeOH (6 mL) was added and the solution was stirred at 0° C. for 4 hours. The solution was diluted with DCM, washed with cold 0.5 M HCl, then washed with brine before the solvent was evaporated. The crude product was purified using column chromatography ($SiO_2$: 10-50% EtOAc/Hexane) to yield 211 mg of the pure hemiacetal which was taken up in dry DCM with molecular sieves, potassium carbonate (129 mg) and caesium carbonate (45 mg). The mixture was stirred at 0° C., before trichloroacetonitrile (93 μL) was added. The mixture was allowed to warm to room temperature and stirred for 5 hours. The solution was filtered and the solvent evaporated. The crude product was purified using column chromatography ($SiO_2$: Hexane to 50% EtOAC/Hexane) to yield 149.2 mg of the white solid product (36%, two steps) which was reacted on without further characterisation.

2,3,4,6-Tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranosyl-(1→6)-1,2,3,4-tetra-O-benzoyl-D-mannopyranose (115)

Trichloroacetimidate 114 (279 μmol, 435 mg), 1,2,3,4-tetra-O-benzoyl mannopyranose 113 (1.2 equiv., 200 mg, 335 μmol) and molecular sieves were taken up in DCM and stirred at 0° C. for 30 mins before TMSOTf (1.1 equiv., 68.2 mg, 56 μL in 600 μL DCM) was added dropwise slowly. The mixture was stirred at 0° C. for 90 mins, before being neutralised with triethylamine (200 μL), filtered and the solvent was evaporated to yield the crude product, which was purified by column chromatography ($SiO_2$: Hexane to 50% EtOAc/Hexane) to yield 312.8 mg of the white solid product (53%) which was reacted on without further characterisation.

2,3,4,6-Tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranosyl-(1→6)-2,3,4-tri-O-benzoyl-D-mannopyranosyl trichloroacetimidate (116)

Perbenzoate 115 (312.8 mg) was dissolved in pyridine (4.5 mL). Dimethylamine (3 mL; 5.6 M in EtOH) was added. The reaction mixture was stirred at room temperature for 2 hours. DCM (10 mL) was added and the solution washed with brine, $H_2SO_4$ (5%) (×2), brine and $NaHCO_3$ (sat.). The solution was dried ($Na_2SO_4$) and the solvent was evaporated. The crude hemiacetal was taken up in dry DCM with molecular sieves, potassium carbonate (600 mg) and caesium carbonate (100 mg). The solution was cooled to 0° C. before trichloroacetonitrile (200 μL) was added. The mixture was stirred at room temperature for 4 hours. The mixture was filtered and the solvent evaporated. The crude product was purified using column chromatography ($SiO_2$: Hexane to 60% EtOAc/Hexane) to yield the product as a white solid (153.9 mg, 48% over two steps) which was reacted on without further characterisation.

3'-Cholestanyl 2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranosyl-(1→6)-2,3,4-tri-O-benzoyl-α-D-mannopyranoside (117)

Trichloroacetimidate 116 (153.9 mg, 71.1 μmol), cholestanol (3 equiv., 83 mg) and molecular sieves were taken up in dry DCM under Ar. The solution was stirred at 0° C. for 15 minutes before TMSOTf (1.1 equiv., 17.4 μL in 200 uL DCM) was added slowly. The solution was allowed to stir for 90 minutes at 0° C. Triethylamine (20 μL) was added and the solvent was evaporated. The crude product was purified by column chromatography ($SiO_2$: Hexane to 40% EtOAc/Hexane; loaded with toluene) to yield 71.4 mg of the white solid product (42%). $^1H$ NMR (300 MHz, $CDCl_3$) δ: 8.00-6.94 (m, 65H, Ar), 5.94 (dd, 1H, $J_{3,2}$=9.7, $J_{3,4}$=9.7, H-$3^{IV}$), 5.76 (dd, 1H, $J_{3,2}$=10.0, $J_{3,4}$=7.9, H-$3^{III}$), 5.68 (dd, 1H, $J_{3,2}$=3.3, $J_{3,4}$=10.0, H-$3^{I}$), 5.59 (d, 1H, $J_{1,2}$=3.8, H-$1^{IV}$), 5.57-5.49 (m, 3H, H-$3^{II}$, H-$4^{IV}$, H-$4^{I}$), 5.42 (d, 1H, $J_{1,2}$=3.8, H-$1^{III}$), 5.35 (dd, 1H, $J_{2,1}$=1.8, $J_{2,3}$=3.3, H-$2^{I}$), 5.16 (dd, 1H, $J_{2,1}$=7.4, $J_{2,3}$=9.5, H-$2^{II}$), 5.12 (dd, 1H, $J_{2,1}$=3.8, $J_{2,3}$=10.5, H-$2^{IV}$), 4.93 (dd, 1H, $J_{2,1}$=3.8, $J_{2,3}$=10.0, H-$2^{III}$), 4.76 (dd, 1H, H-$6^{III}$), 4.73 (d, 1H, $J_{1,2}$=1.8, H-$1^{I}$), 4.71 (d, 1H, $J_{1,2}$=7.7, H-$1^{II}$), 4.53 (dd, 1H, H-$6^{II}$), 4.48-4.41 (m, 2H, H-$6^{II}$, H-$6^{III}$), 4.32-4.16 (m, 6H, H-$5^{IV}$, H-$5^{II}$, H-$5^{I}$, H-$4^{II}$, H-$4^{III}$, H-$6^{IV}$), 4.11-4.03 (m, 2H, H-$6^{I}$, H-$6^{IV}$), 3.88 (ddd, 1H, H-$5^{III}$), 3.60 (dd, 1H, H-$6^{I}$), 3.23 (m, 11-1, CHO), 1.87-0.38 (m, 3111), 0.77 (d, 3H, J=6.4, $CH_3$), 0.74 (d, 3H, J=1.3, $CH_3$), 0.72 (d, 3H, J=1.5, $CH_3$), 0.61 (s, 3H, $CH_3$), 0.51 (s, 3H, $CH_3$).

3'-Cholestanyl α-D-glucopyranosyl-(1→4)-α-D-glucopyranosyl-(1→4)-β-D-glucopyranosyl-(1→6)-α-D-mannopyranoside (118)

Glycoside 117 (80 mg) was dissolved in MeOH/THF 1:1. NaOMe (200 μL of an 11M solution) was added and the solution was stirred at room temperature overnight. The mixture was neutralized with acidic resin and the solution filtered before the solvent was evaporated to yield the white solid product which was triturated with EtOAc and the solvent decanted (×3). The solid was dried under vacuum to yield a quantitative amount of the white solid product which was reacted on without further purification or characterisation.

3'-Cholestanyl 2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranosyl-(1→6)-2,3,4-tri-O-sulfo-α-D-mannopyranoside, tridecasodium salt (119)

Polyol 118 (72.8 mg, 70.2 μmol) was dissolved in DMF (0.02 M, 3.5 mL). $SO_3$.pyridine (3 equiv./OH, 2.7 mmol, 436 mg) was added and the solution stirred at 60° C. overnight. The solution was cooled to 0° C. and neutralized with 5M NaOH (2.1 equiv./$SO_3$.pyridine, 1.15 mL). The mixture was transferred to a large round-bottomed flask with water, evaporated and dialysed (2000 MWCO cartridge, Pierce) against purified water (5 L, water changes every 12 hours) for 24 hours. The solution was lyophilized and taken up in water before being purified on a prep C18 RP-HPLC system (5% to 95% acetonitrile in water over 20 minutes). CE was used to determine the purity of each fraction collected after HPLC purification. Greater than 90% purity fractions were combined and lyophilized to give the product as a white solid (25 mg, 15%). $^1H$ NMR (300 MHz, $D_2O$) δ: 5.70 (d, 1H, $J_{1,2}$=3.5, H-1), 5.55 (d, 1H, H-1), 5.36 (m, 2H, H2×H-1), 5.03-4.05 (m, 24H), 3.88 (m, 1H, CHO), 2.00-0.70 (m, 31H), 0.94 (d, 3H, J=6.4, $CH_3$), 0.89 (d, 3H, J=1.3, $CH_3$), 0.86 (s, 3H, $CH_3$), 0.86 (d, 3H, J=1.3, $CH_3$), 0.70 (s, 3H, $CH_3$).

Example 26

3-Azidopropyl 2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranoside (120)

Trichloroacetimidate 114 (2 g, 1.3 mmol), 3-azidopropanol (2 equiv., 260 mg) and molecular sieves were taken up in DCM (10 mL) and cooled to 0° C. TMSOTf (1.1 equiv., 318 mg, 260 μL) was added dropwise (⅓ at a time each 30 mins, drop-wise, in 2.6 mL DCM). The solution was stirred for 90 mins at 0° C., before being neutralised with triethylamine (300 μL), filtered, washed with water, dried ($Na_2SO_4$) and the solvent was evaporated to give the crude product. This was purified by column chromatography ($SiO_2$: toluene to 5% EtOAc/toluene, loaded with toluene) to yield 2.06 g of the clear oil product 120 (97%). $^1$H NMR (400 MHz, $CDCl_3$) δ: 8.18 (m, 2H, Ar), 8.04 (m, 2H, Ar), 7.95 (m, 2H, Ar), 7.87 (m, 2H, Ar), 7.84 (m, 2H, Ar), 7.74-7.70 (m, 4H, Ar), 7.61-7.10 (m, 36H, Ar), 6.09 (t, 1H, $J_{3,2}$=10.2, $J_{3,4}$=10.2, H-3$^{III}$), 5.92 (dd, 1H, $J_{3,2}$=9.9, $J_{3,4}$=8.2, H-3$^{II}$), 5.75 (d, 1H, $J_{1,2}$=3.8, H-1$^{III}$), 5.70-5.64 (m, 2H, H-3$^{I}$, H-4$^{III}$), 5.60 (d, 1H, $J_{1,2}$=4.1, H-1$^{II}$), 5.30-5.23 (m, 2H, H-2$^{III}$, H-2$^{I}$), 5.08 (dd, 1H, $J_{2,1}$=3.8, $J_{2,3}$=9.9, H-2$^{II}$), 4.99 (dd, 1H, H-6$^{I}$), 4.75-4.59 (m, 3H, H2×H-6$^{II}$, H-6$^{I}$), 4.74 (d, 1H, $J_{1,2}$=7.5, H-1$^{I}$), 4.48-4.36 (m, 5H, H-5$^{III}$, H-5$^{II}$, H-4$^{I}$, H-4$^{II}$, H-6$^{III}$), 4.23 (dd, 1H, H-6$^{III}$), 4.05 (ddd, 1H, H-5$^{I}$), 3.92 (m, 1H, CH2O), 3.57 (m, 1H, $CH_2O$), 3.19 (m, 2H, $CH_2N_3$), 1.74 (m, 2H, $CH_2$).

3-Stearamidopropyl 2,3,4,6-tetra-O-benzoyl-α-D-glucopyranosyl-(1→4)-2,3,6-tri-O-benzoyl-α-D-glucopyranosyl)-(1→4)-2,3,6-tri-O-benzoyl-β-D-glucopyranoside (121)

Glycoside 120 (2 g, 1.23 mmol) was dissolved in THF (10 mL). Triphenylphosphine (3 equiv., 966 mg) was added and the mixture was stirred at room temperature for 1 hour under Ar. Water (30 equiv., 665 μL) was added and the solution was stirred at 50° C. for 4.5 hours. The solvent was evaporated and the crude amine was taken up in DCM. Stearoyl chloride (3 equiv., 1.18 g, 1.25 mL) was added, followed by triethylamine (3.1 equiv., 386 mg, 532 μL) and the solution was stirred overnight at room temperature. The solvent was evaporated and the crude product purified by column chromatography ($SiO_2$: toluene to 8:1 toluene: EtOAc, loaded with toluene) to yield 1.65 g of the clear oil product 121 (72%, 2 steps). $^1$H NMR (400 MHz, $CDCl_3$) δ: 8.16 (m, 2H, Ar), 8.05 (m, 2H, Ar), 7.95 (m, 2H, Ar), 7.86 (m, 2H, Ar), 7.82 (m, 2H, Ar), 7.74-7.70 (m, 4H, Ar), 7.63-7.10 (m, 36H, Ar), 6.10 (t, 1H, $J_{3,2}$=10.2, $J_{3,4}$=10.2, H-3$^{III}$), 5.98-5.91 (m, 2H, H-3$^{II}$, NH), 5.76 (d, 1H, $J_{1,2}$=4.1, H-1$^{III}$), 5.73-5.65 (m, 2H, H-3$^{I}$, H-4$^{III}$), 5.61 (d, 1H, $J_{1,2}$=4.1, H-1$^{II}$), 5.29-5.20 (m, 2H, H-2$^{III}$, H-2$^{I}$), 5.11-5.05 (m, 2H, H-2$^{II}$, H-6$^{I}$), 4.79 (dd, 1H, H-6$^{II}$), 4.71 (d, 1H, $J_{1,2}$=7.5, H-1$^{I}$), 4.68-4.61 (m, 2H, H-6$^{II}$, H-6$^{I}$), 4.49-4.38 (m, 5H, H-5$^{III}$, H-5$^{II}$, H-4$^{I}$, H-4$^{II}$, H-6$^{III}$), 4.23 (dd, 1H, H-6$^{III}$), 4.04 (ddd, 1H, H-5$^{I}$), 3.92 (m, 1H, $CH_2O$), 3.57 (m, 1H, $CH_2O$), 3.27 (m, 1H, $CH_2N$), 3.13 (m, 1H, $CH_2N$), 2.11 (t, 2H, $CH_2CO$), 1.72 (m, 2H, $CH_2$), 1.56 (m, 2H, $CH_2$), 1.30-1.24 (m, 28H, 14×$CH_2$), 0.88 (t, 3H, $CH_3$).

3-Stearamidopropyl α-D-glucopyranosyl-(1→4)-α-D-glucopyranosyl-(1→4)-β-D-glucopyranoside (122)

Glycoside 121 (1.61 g, 861 pimp was dissolved in MeOH/THF 1:1 (40 mL). NaOMe (1 mL of a 6M solution) was added and the solution was stirred at room temperature for 48 hrs. The mixture was neutralized with acidic resin and the solution filtered before the solvent was evaporated to yield the white solid product which was triturated with EtOAc and the solvent decanted (×3). The solid was dried under vacuum to yield 651 mg of the white solid product (91%) which was reacted on without further purification or characterisation.

3-Stearamidopropyl 2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, decasodium salt (123)

Polyol 122 (200 mg, 242 μmol) was dissolved in DMF (0.02 M, 12.1 mL). $SO_3$.pyridine (3 equiv./OH, 7.26 mmol, 1.16 g) was added and the solution stirred at 60° C. overnight. The solution was cooled to 0° C. and neutralized with 5M NaOH (3 equiv./$SO_3$.pyridine, 4.4 mL). The mixture was cooled at −20° C. for one hour. The supernatant was decanted and discarded. The precipitate was transferred to a large round-bottomed flask with water, evaporated and dialysed (2000 MWCO cartridge, Pierce) against purified water (5 L, containing 1 mL 1.7 M $NH_4HCO_3$) for 72 hours. The solution was lyophilized to give the product as a yellow solid (177 mg, 40%). $^1$H NMR ($D_2O$, 400 MHz) δ 5.69 (d, 1H, $J_{1,2}$=3.4, H-1), 5.59 (d, 1H, $J_{1,2}$=2.7, H-1), 4.99-4.92 (m, 2H), 4.85-4.08 (m, 17H), 4.01 (ddd, 1H, $CH_2O$), 3.75 (ddd, 1H, $CH_2O$), 3.32 (t, 2H, J=6.7, $CH_2N$), 2.27 (t, 2H, $CH_2CO$), 1.87 (m, 2H, $CH_2$), 1.61 (m, 2H, $CH_2$), 1.37-1.29 (m, 28H, $CH_2$), 0.91 (t, 3H, $CH_3$).

Example 27

2,3,4,6-Tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-2,3,6-tri-O-benzoyl-D-glucopyranosyl trichloroacetimidate (124)

Maltotetraose perbenzoate 66 (12.4 g) was dissolved in pyridine (47 mL) at 0° C. Dimethylamine (5.6M in EtOH) (28.3 mL) was added and the solution was stirred at room temperature for 2 hours. The solution was poured onto ice-cold 0.5 M HCl and the resulting precipitate was filtered and washed with water before being dried. The crude product was purified using column chromatography ($SiO_2$: 5-70% EtOAc/Hexane) to yield 6.7 g of the pure hemiacetal which was taken up in dry DCM with molecular sieves and potassium carbonate (6.6 g). The mixture was stirred at 0° C., before trichloroacetonitrile (4.4 mL) was added. The mixture was allowed to warm to room temperature and stirred for 2 hours. The solution was filtered and the solvent evaporated. The crude product (7.2 g, 57%) was reacted on without further purification or characterisation.

3-Azidopropyl 2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranoside (125)

Trichloroacetimidate 124 (1.476 g, 0.682 mmol), 3-azidopropanol (2 equiv., 137 mg) and molecular sieves were taken up in DCM (10 mL) and cooled to 0° C. TMSOTf (0.5 equiv., 62 μL in 850 μL DCM) was added dropwise. The solution was stirred for 90 mins at 0° C., before being neutralised with triethylamine (300 μL), filtered, washed with water, dried ($Na_2SO_4$) and the solvent was evaporated to give the crude product. This was purified by column chromatography ($SiO_2$: toluene to 24:3 toluene:EtOAc, loaded with toluene) to yield 660 mg of the white solid product (46%). $^1$H NMR (400 MHz, $CDCl_3$) δ: 8.25-7.05 (m, 35H, Ar), 6.12 (dd, 1H, $J_{3,2}$=9.9, $J_{3,4}$=9.9, H-3$^{IV}$), 6.00 (dd, 1H, H-3), 5.87 (dd, 1H, H-3), 5.76 (d, 1H, $J_{1,2}$=3.7, H-1$^{IV}$), 5.71-5.64 (m, 3H, H-1, H-3$^{I}$, H-4$^{IV}$), 5.60 (d, 1H, $J_{1,2}$=3.7, H-1), 5.29-5.23 (m, 2H, H-2$^{I}$, H-2$^{IV}$), 5.14-5.05 (m, 2H, 2×H-2), 5.01 (dd, 1H, H-6), 4.85 (dd, 1H, H-6), 4.76-4.69 (m, 2H, 2×H-6), 4.75 (d, 1H, $J_{1,2}$=7.5, H-1$^{I}$), 4.59 (m, 2H, 2×H-6), 4.47-4.33 (m, 7H, 3×H-4, 3×H-5, H-6), 4.19 (dd, 1H, H-6), 4.05 (ddd, 1H, H-5$^{I}$), 3.91 (m, 1H, $CH_2O$), 3.57 (m, 1H, $CH_2O$), 3.19 (m, 2H, $CH_2N$), 1.74 (m, 2H, $CH_2$).

3-Stearamidopropyl 2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranoside (126)

Glycoside 125 (660 mg, 0.314 mmol) was dissolved in ACN (21 mL). Triphenylphosphine (3 equiv., 247 mg) was added and the mixture was stirred at room temperature for 1 hour under Ar. Water (30 equiv., 169 μL) was added and the solution was stirred at 50° C. for 7 hours. The solvent was evaporated and the crude amine was taken up in DCM. Stearoyl chloride (3 equiv., 317 μL) was added, followed by triethylamine (3 equiv., 131 μL) and the solution was stirred for 3 days at room temperature. The solvent was evaporated and the crude product purified by column chromatography ($SiO_2$: toluene to 15:3 toluene:EtOAc, loaded with toluene) to yield 403 mg of the clear oil product (55%, 2 steps). $^1$H NMR (400 MHz, $CDCl_3$) δ: 8.21-7.05 (m, 35H, Ar), 6.09 (dd, 1H, $J_{3,2}$=9.8, $J_{3,4}$=9.8, H-3$^{IV}$), 6.02 (t, 1H, NH), 5.97 (dd, 1H, H-3), 5.90 (dd, 1H, H-6), 5.86 (dd, 1H, H-3), 5.75 (d, 1H, $J_{1,2}$=3.9, H-1$^{IV}$), 5.71-5.63 (m, 3H, H-1, H-3$^{I}$, H-4$^{IV}$), 5.59 (d, 1H, $J_{1,2}$=3.9, H-1), 5.27-5.18 (m, 2H, H-2$^{I}$, H-2$^{IV}$), 5.12-5.04 (m, 3H, H-6$^{I}$, 2×H-2), 4.72-4.66 (m, 2H, 2×H-6), 4.70 (d, 1H, $J_{1,2}$=7.8, H-1$^{I}$), 4.58 (m, 2H, H2×H-6), 4.45-4.31 (m, 6H, 3×H-4, 3×H-5, H-6), 4.17 (dd, 1H, H-6), 4.02 (ddd, 1H, H-5$^{I}$), 3.91 (m, 1H, $CH_2O$), 3.56 (m, 1H, $CH_2O$), 3.28 (m, 1H, $CH_2N$), 3.13 (m, 1H, $CH_2N$), 2.13 (m, 2H, $CH_2CO$), 1.76-1.58 (m, 4H, $CH_2$), 1.26-1.24 (m, 28H, $CH_2$), 0.88 (t, 3H, $CH_3$).

3-Stearamidopropyl α-D-glucopyranosyl-(1→4)-α-D-glucopyranosyl-(1→4)-α-D-glucopyranosyl-(1→4)-β-D-glucopyranoside (127)

Glycoside 126 (377 mg, 161 μmol) was dissolved in MeOH/THF 1:1 (10 mL). NaOMe (60 μL of an 11M solution) was added and the solution was stirred at room temperature for 24 hrs. The mixture was neutralized with acidic resin and the solution filtered before the solvent was evaporated to yield the white solid product which was triturated with EtOAc and the solvent decanted (×3). The solid was dried under vacuum to yield 159 mg of the white solid product (quantitative) which was reacted on without further purification or characterisation.

3-Stearamidopropyl 2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, tridecasodium salt (128)

Polyol 127 (159 mg, 161 μmol) was dissolved in DMF (0.02 M, 8.1 mL). $SO_3$.pyridine (3 equiv./OH, 6.3 mmol, 1.0 g) was added and the solution stirred at 60° C. overnight. The solution was cooled to 0° C. and neutralized with 5M NaOH (3 equiv./$SO_3$.pyridine, 3.8 mL). The mixture was cooled at −20° C. for one hour. The supernatant was decanted and discarded. The precipitate was transferred to a large round-bottomed flask with water, evaporated and dialysed (2000 MWCO cartridge, Pierce) against purified water (5 L, containing 1 mL 1.7 M $NH_4HCO_3$) for 72 hours. The solution was lyophilized to give the product as a yellow solid (227 mg, 61%). $^1$H NMR ($D_2O$, 400 MHz) δ 5.89 (d, 1H, $J_{1,2}$=3.4, H-1), 5.72 (d, 1H, $J_{1,2}$=2.7, H-1), 5.67 (d, 1H, H-1), 5.06-4.09 (m, 18H), 4.01 (ddd, 1H, $CH_2O$), 3.75 (ddd, 1H, $CH_2O$), 3.33 (t, 2H, J=6.1, $CH_2N$), 2.28 (t, 2H, J=7.4, $CH_2CO$), 1.87 (m, 2H, $CH_2$), 1.62 (m, 2H, $CH_2$), 1.37-1.29 (m, 28H, $CH_2$), 0.91 (t, 3H, $CH_3$).

Example 28 tert-Butyl 2-(cholestan-3-yloxy)acetate (129)

Cholestanol (0.662 g, 1.703 mmol) was dissolved in toluene (13 mL). Potassium tert-butoxide (573 mg, 5.11 mmol) was added in one portion. The mixture was stirred at room temperature for 3 hours. tert-Butyl bromoacetate (503 μL, 3.406 mmol) was added drop-wise and the mixture was stirred overnight at room temperature. Toluene (20 mL) was added and the solution was washed with brine (50 mL). The aqueous phase was extracted with toluene (30 mL) before all organic phases were combined, dried ($Na_2SO_4$) and the solvent evaporated. The crude product was purified using column chromatography ($SiO_2$; Hexane:EtOAc, 200:1 to 200:20) to yield the white solid product (0.65 g, 76% yield). $^1$H NMR (400 MHz, $CDCl_3$) δ: 3.98 (s, 2H, $CH_2O$), 3.30 (m, 1H, CHO), 1.97-0.56 (m, 31H), 1.46 (s, 9H, $CH_3$), 0.89 (d, 3H, J=6.1, $CH_3$), 0.85 (d, 3H, J=2.0, $CH_3$), 0.84 (d, 3H, J=1.4, $CH_3$), 0.79 (s, 3H, $CH_3$), 0.64 (s, 3H, $CH_3$).

2-(Cholestan-3-yloxy)acetic acid (130)

tert-Butyl 2-(cholestan-3-yloxy)acetate 129 (634 mg, 1.26 mmol) was taken up in DCM (4 mL) before TFA (1 mL) was added. The solution was stirred at room temperature for 90 mins. The solvent was evaporated and the residue purified using a short silica plug ($SiO_2$: DCM to 100:5 DCM:MeOH) before being recrystallized from hexane to yield 439 mg of the white solid product (78%). $^1$H nmr (400 MHz, $CDCl_3$) δ: 4.25 (s, 2H, $CH_2O$), 3.37 (m, 1H, CHO), 1.99-0.58 (m, 31H), 0.89 (d, 3H, J=6.6, $CH_3$), 0.85 (d, 3H, J=2.0, $CH_3$), 0.84 (d, 3H, J=1.4, $CH_3$), 0.80 (s, 3H, $CH_3$), 0.64 (s, 3H, $CH_3$).

2,3,4,6-Tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranosyl isothiocyanate (131)

Bromide 84 (1.8 g, 1.12 mmol), KSCN (3 equiv., 326 mg), molecular sieves and $Bu_4NI$ (cat.) were taken up in dry acetonitrile and stirred at 75° C. overnight. The solvent was evaporated and the residue taken up in DCM and washed with $NaHCO_3$(sat.), before being dried ($Na_2SO_4$) and the solvent was evaporated. The crude product was purified using column chromatography ($SiO_2$:Hexane to 35% EtOAc/Hexane, loaded with toluene) to yield 1.15 g of the white solid product (65%). $^1$H NMR (400 MHz, $CDCl_3$) δ: 8.23-7.12 (m, 50H, Ar), 6.16 (dd, 1H, $J_{3,2}$=9.6, $J_{3,4}$=9.6, H-3$^{III}$), 5.96 (dd, 1H, $J_{3,2}$=9.6, $J_{3,4}$=8.2, H-3$^{II}$), 5.81 (d, 1H, $J_{1,2}$=4.1, H-1$^{III}$), 5.75-5.68 (m, 2H, H-3$^{I}$, H-4$^{III}$), 5.65 (d, 1H, $J_{1,2}$=4.1, H-1$^{II}$), 5.40 (dd, 1H, $J_{2,1}$=8.2, $J_{2,3}$=8.2, H-2$^{I}$), 5.32 (dd, 1H, $J_{2,1}$=4.1, $J_{2,3}$=10.2, H-2$^{III}$), 5.28 (d, 1H, $J_{1,2}$=8.2, H-1$^{I}$), 5.13 (dd, 1H, $J_{2,1}$=4.1, $J_{2,3}$=10.2, H-2$^{II}$), 5.00 (dd, 1H, H-6$^{I}$), 4.77 (dd, 1H, H-6$^{II}$), 4.72-4.65 (m, 2H, H-6$^{I}$, H-6$^{II}$), 4.53-4.41 (m, 5H, H-5$^{II}$, H-5$^{III}$, H-4$^{I}$, H-1$^{II}$, H-6$^{III}$), 4.30 (dd, 1H, H-6$^{III}$), 4.13 (ddd, 1H, H-5$^{I}$).

2-(Cholestan-3-yloxy)acetamido 2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranoside (132)

Isothiocyanate 131 (0.5 g, 315 μmol) and 2-(cholestan-3-yloxy)acetic acid 130 (141 mg, 315 μmol) were dissolved in toluene (6.3 mL). Triethylamine (20 μL) was added and the solution was stirred at room temperature for 4 days. The solvent was evaporated and the residue purified by column chromatography ($SiO_2$: Toluene to 10% EtOAc/toluene) to yield 358 mg of the white solid product (58%). $^1$H NMR (400 MHz, $CDCl_3$) δ: 8.23-7.09 (m, 50H, Ar), 7.50 (d, 1H, NH), 6.09 (dd, 1H, $J_{3,2}$=10.2, $J_{3,4}$=9.9, H-3$^{III}$), 5.91 (dd, 1H, $J_{3,2}$=9.9, $J_{3,4}$=7.8, H-3$^{II}$), 5.82 (dd, 1H, $J_{3,2}$=9.5, $J_{3,4}$=9.2, H-3$^{I}$), 5.74 (d, 1H, $J_{1,2}$=4.1, H-1$^{III}$), 5.67 (dd, 1H, $J_{4,3}$=9.9, $J_{4,5}$=9.9, H-4$^{III}$), 5.60 (d, 1H, $J_{1,2}$=4.1, H-1$^{II}$), 5.51 (dd, 1H, $J_{1,2}$=9.5, $J_{1,NH}$=8.5, H-1$^{I}$), 5.27 (dd, 1H, $J_{2,1}$=4.1, $J_{2,3}$=10.6, H-2$^{III}$), 5.24 (dd, 1H, $J_{2,1}$=9.5, $J_{2,3}$=9.5, H-2$^{I}$), 5.08 (dd, 1H, $J_{2,1}$=4.1, $J_{2,3}$=10.2, H-2$^{II}$), 4.92 (dd, 1H, H-6), 4.70-4.64 (m, 2H, H2×H-6), 4.56 (dd, 1H, H-6), 4.46-4.31 (m, 5H, H-5$^{III}$, H-4$^{I}$, H-4$^{II}$, 2×H-6), 4.22 (ddd, 1H, H-5$^{II}$), 4.15 (ddd, 1H, H-5$^{I}$), 3.95 (dd, 1H, $CH_2O$), 3.73 (dd, 1H, $CH_2O$), 3.11 (m, 1H, CHO), 1.47-0.50 (31H), 0.90 (d, 3H, J=6.8, $CH_3$), 0.86 (d, 3H, J=6.8, $CH_3$), 0.86 (d, 3H, J=6.8, $CH_3$), 0.77 (s, 3H, $CH_3$), 0.64 (s, 3H, $CH_3$).

2-(Cholestan-3-yloxy)acetamido α-D-glucopyranosyl-(1→4)-α-D-glucopyranosyl-(1→4)-β-D-glucopyranoside (133)

Amide 132 (345 mg, 175 μmol) was dissolved in MeOH/THF 1:1 (16 mL). NaOMe (500 μL of a 6M solution) was added and the solution was stirred at room temperature for 24 hrs. The mixture was neutralized with acidic resin and the solution filtered before the solvent was evaporated to yield the white solid product which was triturated with EtOAc and the solvent decanted (×3). The solid was dried under vacuum to yield 124 mg of the white solid product (76%) which was reacted on without further purification or characterisation.

2-(Cholestan-3-yloxy)acetamido 2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, decasodium salt (134)

Polyol 133 (118 mg, 127 μmol) was dissolved in DMF (0.04 M, 4.4 mL). $SO_3$.pyridine (3 equiv./OH, 5.3 mmol, 838 mg) was added and the solution stirred at 60° C. overnight. The solution was cooled to 0° C. and neutralized with 5M NaOH (3 equiv./$SO_3$.pyridine). The mixture was cooled at −20° C. for one hour. The supernatant was decanted and discarded. The precipitate was transferred to a large round-bottomed flask with water, evaporated and dialysed (2000 MWCO cartridge, Pierce) against purified water (5 L, containing 1 mL 1.7 M $NH_4HCO_3$) for 72 hours. The solution was lyophilized to give the product as a yellow solid (195 mg, 79%). $^1$H NMR ($D_2O$, 400 MHz) δ: 5.67 (d, 1H, $J_{1,2}$=2.9, H-1), 5.57 (d, 1H, $J_{1,2}$=1.2, H-1), 5.35 (d, 1H, $J_{1,2}$=7.3, H-1$^{I}$), 5.06-4.06 (m, 20H), 3.48 (m, 1H, CHO), 2.07-0.68 (m, 46H).

Example 29

3-(Cholestan-3-yloxy)propanenitrile (135)

Cholestanol (1.554 g, 3.998 mmol) was dissolved in DCM (6 mL). To this solution was added KOH (40% w/w in water, 1.2 mL) and acrylonitrile (0.8 mL), followed by 18-crown-6 (104 mg). The mixture was stirred at room temperature overnight. The organic layer was washed with brine and dried ($Na_2SO_4$) before the solvent was evaporated. The residue was recrystallized from hot MeOH to yield the pure product as a colourless crystalline solid (1.42 g, 80% yield). $^1$H NMR (400 MHz, $CDCl_3$) δ: 3.68 (t, 2H, $CH_2O$), 3.29 (m, 1H, CHO), 2.57 (t, 2H, $CH_2CN$), 1.98-0.58 (m, 31H), 0.89 (d, 3H, J=6.6, $CH_3$), 0.87 (d, 3H, J=1.8, $CH_3$), 0.85 (d, 3H, J=2.0, $CH_3$), 0.79 (s, 3H, $CH_3$), 0.64 (s, 3H, $CH_3$).

1-Amino-3-(cholestan-3-yloxy)-propane (136)

3-(Cholestan-3-yloxy)propanenitrile 135 (442 mg, 1 mmol) was taken up in a mixture of toluene (1 mL), chloroform (1.5 mL), EtOH (1 mL) and conc. HCl (200 μL). Platinum oxide hydrate (46 mg) was added. The mixture was stirred under hydrogen (80 psi) at room temperature for 48 hours. The solvent was evaporated and the residue taken up with DCM (40 mL) and $NaHCO_3$ (sat.) (40 mL). The organic phase was separated and washed with $NaHCO_3$ (sat.) (30 mL), followed by brine (20 mL), before being dried ($Na_2SO_4$) and the solvent evaporated to yield the white foam product which was reacted on without further purification or characterization.

1-[(Cholestan-3-yloxy)propyl]-3-[2,3,4,6-tetra-O-benzoyl-α-D-glucopyranosyl-(1→4)-2,3,6-tri-O-benzoyl-α-D-glucopyranosyl-(1→4)-2,3,6-tri-O-benzoyl-β-D-glucopyranoside]thiourea (137)

3-(Cholestan-3-yloxy)propan-1-amine 136 (0.5 mmol) was taken up in toluene (3 mL). Isothiocyanate 131 (403 mg, 0.254 mmol) was added. The solution was stirred at room temperature for 3 days. The solvent was evaporated and the crude product purified using column chromatography ($SiO_2$; toluene to 180:30 toluene:EtOAc) to yield the pure product as a white solid (355 mg, 35%). $^1$H nmr (400 MHz, $CDCl_3$) δ: 8.23-7.09 (m, 50H, Ar), 6.90 (dd, 1H, J=4.9, J=4.9, NH), 6.09 (dd, 1H, $J_{3,2}$=10.2, $J_{3,4}$=9.8, H-3$^{III}$), 5.89 (m, 2H, H-3$^{II}$, H-3$^{I}$), 5.74 (d, 1H, $J_{1,2}$=3.9, H-1$^{III}$), 5.67 (dd, 1H, $J_{4,3}$=9.8, $J_{4,5}$=9.8, H-4$^{III}$), 5.58 (d, 1H, $J_{1,2}$=3.9, H-1$^{II}$), 5.28 (dd, 1H, $J_{2,1}$=3.9, $J_{2,3}$=10.7, H-2$^{III}$), 5.19 (dd, 1H, $J_{2,1}$=9.3, $J_{2,3}$=9.3, H-2$^{I}$), 5.09 (dd, 1H, $J_{2,1}$=3.9, $J_{2,3}$=10.2, H-2$^{II}$), 4.92 (dd, 1H, H-6), 4.70 (dd, 1H, H-6), 4.67 (dd, 1H, H-6), 4.58 (dd, 1H, H-6), 4.46-4.34 (m, 5H), 4.27-4.18 (m, 2H), 3.50 (dd, 2H, $CH_2$), 3.18 (m, 1H, CHO), 1.98-0.56 (35H), 0.90 (d, 3H, J=6.8, $CH_3$), 0.87 (d, 3H, J=6.8, $CH_3$), 0.86 (d, 3H, J=6.8, $CH_3$), 0.80 (s, 3H, $CH_3$), 0.64 (s, 3H, $CH_3$).

1-[(Cholestan-3-yloxy)propyl]-3-[α-D-glucopyranosyl-(1→4)-α-D-glucopyranosyl-(1→4)-β-D-glucopyranoside]thiourea (138)

Thiourea 137 (345 mg, 171 μmol) was dissolved in MeOH/THF 1:1 (16 mL). NaOMe (500 μL of a 6M solution) was added and the solution was stirred at room temperature for 24 hrs. The mixture was neutralized with acidic resin and the solution filtered before the solvent was evaporated to yield the white solid product which was triturated with EtOAc and the solvent decanted (×3). The solid was dried under vacuum to yield 169 mg of the white solid product (quantitative) which was reacted on without further purification or characterisation.

1-[(Cholestan-3-yloxy)propyl]-3-[2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside]thiourea, decasodium salt (139)

Polyol 138 (169 mg, 171 μmol) was dissolved in DMF (0.04 M, 4.4 mL). $SO_3$.pyridine (3 equiv./OH, 5.13 mmol, 816 mg) was added and the solution stirred at 60° C. overnight. The solution was cooled to 0° C. and neutralized with 5M NaOH (3 equiv./$SO_3$.pyridine). The mixture was cooled at −20° C. for one hour. The supernatant was decanted and discarded. The precipitate was transferred to a large round-bottomed flask with water, evaporated and dialysed (2000 MWCO cartridge, Pierce) against purified water (5 L, containing 1 mL 1.7 M $NH_4HCO_3$) for 72 hours. The solution was lyophilized and taken up in water before being purified on a prep C18 RP-HPLC system (5% to 95% acetonitrile in water over 20 minutes). CE was used to determine the purity of each fraction collected after HPLC purification. Greater than 90% purity fractions were combined and lyophilized to give the product as a white solid (7 mg, 2%). $^1$H NMR (400 MHz, $D_2O$) δ: 6.00-5.56 (m, 3H, 3×H-1), 4.98-3.14 (m, 21H), 2.04-0.72 (m, 50H).

Example 30

3'-Cholestanyl 2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-D-glucopyranosyl-(1→4)-((1-pyridinium-1-yl)-2,3,5,6-tetra-O-sulfo-D-glucoside, tridecasodium salt (140)

The polyol 64 (3.552) was dissolved in dry DMF (46 mL) and freshly washed and dried $SO_3$.pyridine complex (21.24 g) added and the mixture was stirred for 16 h at 60° C. The reaction mixture was cooled to 0° C. for 10 min, then neutralized by adding ice-cold aqueous NaOH solution (5 M, 54 mL) at 0° C. in one portion (to pH 12). The suspension was stirred for 15 min 0° C., diluted with water (10 mL) and concentrated in vacuo at 40° C. A pale yellow powder was afforded, which was dissolved in water (10 mL) obtaining a solution with pH 11.5. The solution was set to pH 12.5 by adding a aqueous solution of NaOH (5 M, 5 drops) and dialyzed against water (4 L) using 4×Slide-A-Lyzer® cassettes (2000 MWCO, 4-12 mL) for 16 h at r.t. The dialysis against water (4 L) was continued at 0° C. for 3 d, whereby the water was changed after each 24 h, as well as an aqueous solution $NH_4HCO_3$ (3 M, 0.6 mL) was added to the water to set pH ~6.0-6.5. The desalted solution was then lyophilized to afford a mixture of mainly 65 and 140 which was purified on a prep C18 RP-HPLC system (5% to 30% acetonitrile in water over 20 minutes). CE was used to determine the purity of each fraction collected after HPLC purification. Greater than 90% purity fractions were combined and lyophilized to give the product as a white solid (30 mg, purified from approx 1 g of crude material). $^1$H NMR (400 MHz, $D_2O$) δ: 9.09 (m, 2H, Ar), 8.39 (m, 1H, Ar), 7.93 (m, 2H, Ar), 6.40 (d, 1H, H-1$^I$), 5.56 (d, 1H, $J_{1,2}$=3.4, H-1$^{II}$), 5.54 (d, 1H, $J_{1,2}$=2.3, H-1$^{III}$), 5.45 (d, 1H, $J_{1,2}$=3.3, H-1$^{IV}$), 5.00 (ddd, 1H, H-5$^I$), 4.86 (dd, 1H, H-3$^{II}$), 4.79 (dd, 1H, H-3$^{III}$), 4.77 (dd, 1H, H-2$^I$), 4.77 (dd, 1H, H-4$^I$), 4.64 (dd, 1H, H-2$^{III}$), 4.58 (dd, 1H, H-3$^{IV}$), 4.49 (dd, 1H, H-3$^I$), 4.40 (m, 1H, H-6$^I$), 4.32 (m, 1H, H-6$^I$), 4.31 (dd, 1H, H-4$^{IV}$), 4.29 (dd, 1H, H-2$^{II}$), 4.29 (dd, 1H, H-2$^{IV}$), 4.20-4.10 (m, 6H, H6×H-6), 4.13 (ddd, 1H, H-5$^{II}$), 4.12 (dd, 1H, H-4$^{II}$), 4.10 (dd, 1H, H-4$^{III}$), 4.07 (ddd, 1H, H-5$^{III}$), 3.81 (ddd, 1H, H-5$^{IV}$), 2.00-0.67 (m, 31H), 0.93 (d, 3H, $CH_3$), 0.87 (d, 3H, $CH_3$), 0.86 (d, 3H, $CH_3$), 0.83 (s, 3H, $CH_3$), 0.68 (s, 3H, $CH_3$).

Example 31

8-Pentadecanyl 2,3,4,6-tetra-O-acetyl-D-glucopyranoside (141)

To a solution of D-glucose peracetate (250 mg, 640 μmol) in DCE (1 mL) was added 8-pentadecanol (220 mg, 960 μmol). $BF_3.O(Et)_2$ (134 μL, 1.1 mmol) was added and the mixture stirred at room temperature overnight before pouring onto short plug of silica and eluting with EtOAc. The solvent was evaporated before the crude material was purified by column chromatography ($SiO_2$, loaded with DCM, elution with DCM (100 mL), then 20% EtOAc/Hexane to 35% EtOAc/Hexane) to give the glycoside 141 as a white solid (179 mg, 50%). $^1$H NMR ($CDCl_3$, 400 MHz) δ: 5.19 (dd, 1H, $J_{2,3}$=9.5, $J_{3,4}$=0.0, H-3), 5.06 (dd, 1H, $J_{4,5}$=9.7, H-4), 4.96 (dd, 1H, $J_{1,2}$=8.0, $J_{2,3}$=9.6, H-2), 4.52 (d, 1H, H-1), 4.21 (dd, 1H, $J_{5,6b}$=5.2, $J_{6a,6b}$=12.1, H-6b), 4.12 (dd, 1H, $J_{5,6a}$=2.6, H-6a), 3.66 (ddd, 1H, $J_{4,5}$=10.0, H-5), 3.53 (m, 1H, $CH_2CHOCH_2$), 2.07 (s, 3H, $OCOCH_3$), 2.02 (s, 6H, $OCOCH_3$), 2.00 (s, 3H, $OCOCH_3$), 1.60-1.20 (m, ~24H, $CH_2$), 0.88 (t, 3H, J=7.0, $CH_3$), 0.87 (t, 31-1, J=7.0, $CH_3$).

8-Pentadecanyl D-glucopyranoside (142)

The glycoside 141 (70 mg) was deacetylated according to the general procedure to give the polyol 142 (50 mg, quantitative) as a white solid that was reacted on without further purification or characterisation.

8-Pentadecanyl 2,3,4,6-tetra-O-sulfo-D-glucopyranoside, tetrasodium salt (143)

Polyol 142 (50 mg) was dissolved in DMF (5 mL). $SO_3$.pyridine (250 mg) was added and the solution stirred at room temperature overnight. The solution was cooled to 0° C. and neutralized with 2M NaOH to pH 10. The solution was evaporated to dryness. The residue was dissolved in 4 mL of water and purified by Bio-Gel P-2 column chromatography (eluted with 0.1 M $NH_4HCO_3$ at 196 mL/h, 6 min per collection). The product fractions were identified by MBT and CE. Lyophilisation gave the product 143 as pale-yellow powder (33 mg, 32%). $^1$H NMR (400 MHz, $D_2O$) δ: 4.79 (d, 1H, $J_{1,2}$=5.3, H-1), 4.67 (br, 1H), 4.45 (br, 1H, H-2), 4.28 (m, 2H), 4.28 (m, 2H), 3.68 (s, 1H), 1.52-1.38 (m, 4H), 1.32-1.10 (m, ~24H), 0.76-0.71 (m, 6H).

Biological Testing of Compounds

Growth Factor Binding Assay

Binding affinities of compounds for the growth factors FGF-1, FGF-2 and VEGF were measured using a surface plasmon resonance (SPR) based solution affinity assay.[9] Heparin-coated sensorchips used for this assay were prepared via immobilisation of biotinylated BSA-heparin on a streptavidin-coated sensorchip, or via aldehyde coupling using either adipic acid dihydrazide or 1,4-diaminobutane.[9] For each $K_d$ measurement, solutions were prepared containing a fixed concentration of protein and varying concentrations of the ligand in buffer. Ligands binding to FGF-1 and VEGF were measured in HBS-EP buffer (10 mM HEPES, pH 7.4, 150 mM NaCl, 3.0 mM EDTA and 0.005% (v/v) polysorbate 20), while binding to FGF-2 was measured in HBS-EP buffer containing 0.3 M NaCl. Prior to injection, samples were maintained at 4° C. to maximise protein stability. For each assay mixture, 50-200 μL of solution was injected at 5-40 μL/min and the relative binding response measured. All surface binding experiments were performed at 25° C. The surface was regenerated by injection of 40 μL of 4M NaCl at 40 μL/min, followed by injection of 40 μL of buffer at 40 μL/min.

Sensorgram data were analysed using the BIAevaluation software (BIAcore) and $K_d$ values determined as previously described.[9] Where $K_d$ values were measured in duplicate, the values represent the average of the duplicate measurements. The results are presented in Table 1.

Heparanase Inhibition Assay

The enzymatic activity of heparanase can be detected by measuring the cleavage of the substrate fondaparinux.[39,40] The newly formed reducing disaccharide can be detected by reacting with the mono-tetrazolium salt WST-1 (Auspep Pty Ltd, Melbourne, Australia) a to produce a blue colour which can be measured with a microplate reader at 584 nm. In the presence of an inhibitor the catalytic activity of heparanase is reduced, and the amount of disaccharide produced and the optical density of the solution are both decreased. The percent inhibition and $IC_{50}$ of the inhibitor are determined from measurement of the optical density (OD) over a range of inhibitor concentrations.

Assays were carried out in 40 mM sodium acetate buffer, pH 5.0, as follows. Fondaparinux (100 μM) and varying concentrations of inhibitor and buffer to give a final volume of 100 μL were mixed in 96 well plates (Costar EIZ/RIA, Corning) pre-coated with BSA. Purified recombinant human heparanase (2.55 nM) was then added to start the assay. The plate was incubated at 37° C. for 24 h and the assay stopped by addition of WST-1 solution (100 μL). A blue colour was developed by incubation of the plates at 60° C. for 60 min. The OD was determined at 584 nm with a microplate reader (Fluostar) and quantitated using a standard curve constructed with D-galactose as the reducing sugar standard. The $IC_{50}$ value for each compound was evaluated and converted into a $K_i$ (inhibition constant) using the expression $$K_i = \frac{IC_{50}}{1 + \frac{[\text{substrate}]}{K_m}}$$

The $K_m$ (concentration of substrate that leads to half-maximal velocity) for fondaparinux was determined to be 33±6 μM. The results are presented in Table 1.

Growth Factor Induced Endothelial Cell Proliferation Assay

Endothelial Cell Culture

HUVEC cells were maintained and subcultured according to standard cell culture protocols essentially as described by Lonza. Briefly, cells were maintained in Lonza endothelial growth media (EGM) with recommended supplements and growth factors (VEGF, FGF2, EFG, IGF, hydrocortisone, fetal bovine serum (FBS), ascorbic acid, heparin and gentamicin). Cells were subcultured when they reached 70-80% confluence by trypsinisation and reseeding in fresh growth medium in new culture vessels at 2500 to 5000 cells/$cm^2$ of vessel surface area. Cell counts were performed using a haemocytometer and viable cells were visualized with trypan blue.

Medium for the proliferation studies was prepared using EGM with 2% FBS and gentamicin only. In a later study, complete EGM was used for the VEGF groups in an attempt to enhance the proliferative index of VEGF-stimulated groups. For the tube formation assay, complete medium was used with only heparin omitted. Compounds under investigation were weighed out from powder stocks and diluted in PBS to 10 mM stock solutions and stored at −80° C. For experiments, compounds were subsequently diluted in EBM-2 medium (supplemented with 2% FBS and gentamicin) to various working concentration as required.

Proliferation Assay

Proliferation was induced in HUVECs using various concentrations of the growth factors VEGF, FGF-1 or FGF-2 over a period of 72 h. In the first of a series of experiments, the assay was further optimized by examining the cell density and growth factor concentration required to induce maximal proliferation by growth factors. Briefly, 100 μL of cells was added to each well at concentrations between $1\text{-}3\times10^3$ per well. Growth factors and test compounds were then added in 50 μL volumes at specified concentrations to obtain a final volume of 200 μL. Following incubation for 70 h, 20 μL of the CellTitre 96® Aqueous One Solution Cell Proliferation Assay (Promega) was added for 2 h prior to reading the absorbance at 490 nm to obtain OD values. The data are presented in Table 2.

Matrigel™ Microtubule Formation Assay

The tube formation assay was performed essentially as described by Malinda et al., with modifications.[41] HUVECs in the fourth or fifth passage at 70-80% confluence were harvested and resuspended in Lonza endothelial growth medium (EGM2) containing all supplements as directed by manufacturer, except heparin, at a cell density of $4\times10^5$ cells per mL. For each set of triplicate wells, 200 μL of cells ($4\times10^5$/mL) were treated with an equal volume of compound to obtain final concentrations of 10, 50 or 100 μM (thus ensuring 1×300 μL are available for each condition). A 100 μL aliquot of cells was then plated onto 96-well plates pre-coated with growth factor reduced Matrigel™ (50 μL., for 30 min followed by a further 30 μL for 1 h) and incubated for 18-22 h. Tube formation was examined by phase-contrast microscopy and images were collected using an Olympus C5050 digital camera. Tube formation inhibition was quantitated manually from images by recording the total number of nodes connecting 3 or more tubules. Results are expressed as percentage inhibition compared to control and are presented in Table 2. Untreated HUVECs were used as a control for normal cell growth and tube formation in Matrigel.

Endothelial Cell Migration Assay

The BD BioCoat™ Angiogenesis System was used as an in vitro, quantitative endothelial cell migration assay platform. It is composed of a BD Falcon™ 24-Multiwell Insert Plate (and a non-TC treated 24-well receiver plate and lid) containing a fluorescence blocking microporous (3.0 μm pore size) PET membrane (BD FluoroBlok™) evenly coated with human fibronectin. The concentration of fibronectin and the coating procedure is optimized so the pores of the membrane are not occluded. This allows endothelial cells to attach to the membrane and freely migrate towards an angiogenic stimulus in the lower chamber of the plate. A fluorescence plate reader is used to quantify the migrating cells without further manipulation. In this instance, the cells were labeled with a fluorescent dye post-migration.

Briefly, 200 μL of HUVECs at a concentration of $2.5\times10^5$/mL were plated into the upper chambers of each well of the 24-well plate supplied in the kit. Compounds were then added at various concentrations (typically 10 and/or 50 μg/mL) with medium alone (EBM-2) used as the untreated control group. Due to the poor migratory performance of HUVEC stimulated with FGF-2 or VEGF in our laboratory, 10% foetal calf serum (FCS) was used as this led to over a 6-fold increase in HUVEC migration in comparison to HUVEC cultured in media without FCS. Therefore, 750 μL of media containing 10% FCS was added to the lower chambers to act as the migratory stimulus and plates were incubated overnight at 37° C./5% $CO_2$ for 18 h. Following the incubation time, the upper plate was transferred to a fresh 24-well bottom plate and 500 μL, of Calcein AM was added to stain the migrated cells underneath the porous membrane for 90 min at 37° C. Fluorescence was measured using a FLUOstar Optima (BMG laboratories) with an excitation and emission filter of 485 nm and 520 nm respectively. Data is shown as percentage inhibition of migration in comparison to FCS-induced HUVEC (Table 3).

Ex Vivo Angiogenic Sprout Assay

Explants from rat aortas were prepared by a modification of protocols previously described[42-45]. In this model, the rat aortic endothelium exposed to a three dimensional matrix of ECM-derived proteins (Matrigel™), switches to a microvascular phenotype, generating branching networks of microvessels. Angiogenesis is triggered by the injury caused by the dissection procedure and does not require stimulation by exogenous growth factors.

Briefly, thoracic aortas were excised from 2- to 4-month old Sprague Dawley rats and trimmed of remaining fat and connective tissue. Great care was taken at every stage to reduce physical damage of the aorta. Tissue was transferred to complete EBM-2 media (Cambrex) containing 2% FCS and all Singlequots™ (Cambrex) reagents except for heparin. Meanwhile, Matrigel™ (BD Biosciences) was allowed to cool on ice and once in a liquid form, 180 μL was pipetted into 48-well tissue culture plates (Nunc). The plates were incubated at 37° C. for 30 min to allow Matrigel™ to solidify.

Aortas were prepared by cutting 1 mm ring sections and then being bisected. Aortic segments were then carefully placed on top on the Matrigel™ in the centre of each well and once orientated as required, 60 μL, of extra Matrigel™ was placed on top and the plate was returned to the incubator for a further 20 min. Each well was then supplemented with 1.0 mL media in the absence (control) or presence of test compounds usually at two concentrations within the range of 1-50 μM, depending on the particular compound/experiment. Cultures were replenished as appropriate every 48 h and scoring of microvessels was carried out at various timepoints up to 8-10 days. The extent of microvessel sprouting was determined by employing a scoring system from 0-5, where 0=no microvessels to 5=diffuse angiogenesis as previously described[45]. Sprouting vessels were photographed using the 4× objective with an Olympus C-7070 camera and an adaptor for the eyepiece.

In some instances, to determine the potential toxicity of compounds in this assay, the viability of the tissue was assessed by withdrawing the compound/media from the culture on day 6 or 7 and adding complete media with VEGF (typically 10 ng/mL) for up to an additional 7 days. In the absence of toxicity, the viable tissue should sprout microvessels in response to the exogenous growth factor.

The inhibitory effect of compounds of the present invention on angiogenesis was assayed using the angiogenic sprout/microvessel formation (rat aortic) assay described above. Embedding of the rat aortic tissue in Matrigel™ in the absence of any inhibitor (control) yielded extensive angiogenic sprouting (as a score of 5 indicates diffuse angiogenesis) as illustrated by FIG. 1.

Addition of PI-88 and PG524 (a less lipophilic analogue) led to a strong inhibitory response at 10 and 50 μM. However, compounds of the present invention demonstrated further potency by inhibiting angiogenesis up to 100% at 10 μM. The results are presented in Table 4 below.

To examine the viability of the aortic tissue following treatment with the aforementioned compounds, withdrawal of these compounds on day 6 or 7 (depending on the individual experiment) was followed by treatment with VEGF up to an additional 7 days. Appearance of microvessel sprouts demonstrated that the compounds of the invention exert their inhibitory effects via an anti-angiogenic mechanism as opposed to the induction of a toxic effect on the tissue (FIG. 2 below).

Anticoagulant Activity

The anticoagulant activity of the test compounds was determined by measuring the effect of various concentrations of compound (0-100 μg/mL in PBS) on the elevation of the activated partial thromboplastin time (APTT) of pooled normal human plasma. APTT measurements were performed on a STAGO STA-Compact Coagulation Analyser using standard protocols according to the manufacturer's instructions. Unfractionated heparin (UFH) was used as a control. The normal range of APTT for pooled normal human plasma is 26-36 s. The results are presented in Table 5 which shows that the new compounds possess only mild anticoagulant activity and are significantly less potent than PI-88.

In Vivo Mouse Melanoma Model

B16 melanoma is a commonly used cell line for the induction of tumours in syngeneic C57/BL6 mice. It is a non-metastatic, fast-growing tumour unresponsive to most anti-cancer agents.

B16F1 cells were cultured in complete DMEM medium containing 10% FCS, penicillin/streptomycin, L-glutamine, sodium pyruvate, 2-mercapoethanol. Cells were harvested for tumour inoculation, B16F1 cells by disruption with Trypsin/EDTA, washed with HBSS and centrifuged for 5 minutes at 1500 rpm. Cells were then resuspended in PBS to ensure $5\times10^5$ cells were injected in a volume of 50 μL. The tumour was implanted just behind the neck. Three days following tumour inoculation each treatment group was injected subcutaneously at different sites each day and at different concentrations in a volume of injection of 50 or 100 μL. Injections continued until day 15 providing a 12-day treatment period. Mice were monitored daily from the start of injections and palpable tumours were measured daily. Tumour size was determined from the measurement in two dimensions, ×w, where 1=longest dimension and w=shortest dimension. To estimate tumour volume, the formula $0.5\times1\times(w^2)$ was employed. Data is presented as both median tumour growth and the percentage of tumour growth inhibition (% TGI). The % TGI calculation was performed to correct for inter-experimental differences.

Since the compounds of the present invention were shown herein to inhibit angiogenic sprout formation, and since tumour progression is angiogenesis-dependent, the effect of these compounds on primary tumour growth and overall survival was assayed as described above. FIG. 3 provides an illustration of the typical median tumour volumes observed from various studies testing compounds of the invention in the B16 melanoma model.

For directly comparative data, the results shown in FIG. 4 indicate the decreased relative tumour size of tumour bearing mice in comparison to the relevant control and displayed as a parameter known as the percentage of tumour growth inhibition (% TGI). TGI values were calculated using the formula $TGI=[1-(\Delta T/\Delta C)]\times100$, where $\Delta T$ and $\Delta C$ represent the change in mean tumor mass between the last day of therapy and the first day of therapy in the sample compound-treated (T) and vehicle control (C) groups, respectively.

In Vivo Mouse Lung Metastases Model

When B16F1 cells, cultured as described above for the B16 solid tumour mouse melanoma model, are injected via the tail vein into mice, the formation of metastatic nodules in the lungs results. As the tumour cells are black the observation of metastatic nodules are easily identifiable. FIG. 5 shows control and compound-treated mice lungs, with obvious observable differences in the formation of lung colonies (dark spots).

In the metastases model, B16 cells ($2\times10^5$) were injected via the tail vein of C57/BL6 mice in a volume of 50 mL on day 0. Treatment with the test compounds commenced on day 0 and continued daily for 12 days. The number of lung metastases was enumerated on day 12 of the experiment. The results shown in FIG. 6 indicate the selected compounds maintain the potent inhibition of lung metastases exhibited by PI-88. The data is shown as the percentage of lung metastatic nodules observed compared with the saline control.

In Vivo HT29 Colorectal Cancer Xenograft Model

HT-29 human colorectal adenocarcinoma cells (Passage 4 from working stock VP-Stock 325) were cultured in RPMI1640 cell culture medium, which was supplemented with 10% FBS and penicillin-streptomycin (50 IU/mL final concentration). The cells were harvested by trypsinisation, washed twice in HBSS and counted. The cells were then resuspended in HBSS and adjusted to a final volume containing $2\times10^7$ cells/mL. Prior to inoculation the injection site, on the dorsal right flank was liberally swabbed with alcohol and the needle introduced through the skin into the subcutaneous space just below the animal's right shoulder, where 100 μL of cells ($2\times10^6$ cells) were discharged. The treatment of mice commenced with an average tumour volume of approximately 155 $mm^3$. Tumours were measured in two dimensions (length and diameter) and the tumour volume calculated using the equation:

$$V(mm^3)=length\times diameter^2\times\pi/6.$$

The Vehicle Control, sterile PBS, was administered s.c., at a dosing volume of 10 mL/kg, once daily for 21 days. Each animal's body weight was measured immediately prior to dosing each day. The actual volume administered to each mouse was calculated and adjusted based on the body weight. The results presented in FIG. 7 demonstrate the selected compounds possess anti-cancer activity using the murine tumour model of colorectal cancer. All compounds showed improved activity in comparison to PI-88, which was not particularly effective in this model.

Antiviral Activity

The results of the antiviral assays are presented in Tables 6-10.

Cells and Viruses

African green monkey kidney (GMK AH1) cells[46] were cultured in Eagle's minimum essential medium (EMEM) supplemented with 2% calf serum, 0.05% Primaton RL substance (Kraft Inc., Norwich, USA) and antibiotics. Human epidermoid carcinoma (HEp-2) cells were cultured in Dulbecco' s modified EMEM (DMEM) supplemented with 10% fetal calf serum and antibiotics. The HSV strains used were HSV-1 KOS321, a plaque-purified isolate of wild-type strain KOS[47], HSV-1 KOS gC-null variant $gC^-39$[48], and HSV-2 strain 333[49]. The RSV strain A-2[50] was used. The RSV stock was prepared as described by Hallak et al.[51] and stored at −70° C. in the presence of 40% sucrose[52].

Virus Purification and Assay of Virus Binding to Cells

The extracellular, methyl-[$^3$H]thymidine labeled HSV virions were purified by centrifugation through a three-step discontinuous sucrose gradient as previously described[53,54]. The effect of test compound on the binding of purified methyl-[$^3$H]thymidine labeled virus to GMK AH1 cells at 4° C. was assayed as described previously[17]. Briefly, the cells were washed with PBS-A (PBS supplemented with 1 mM $CaCl_2$ and 0.5 mM $MgCl_2$) and then blocked with PBS-A containing 1% BSA for 1 h at room temperature. Serial five-fold dilutions of test compound in PBS-A were mixed with purified virions and incubated for 15 min at 4° C. The cells were washed once with PBS-A, and the virus-compound mixture added and incubated with the cells under moderate agitation for 2 h at 4° C. Subsequently the cells were washed three times with PBS-A, lysed with 0.2 mL of PBS-A containing 5% SDS, and finally transferred to scintillation vials for quantification of radioactivity.

Virus Inactivation Assay

Approximately $10^5$ plaque-forming units of HSV-1 KOS321 or HSV-2 333 stain and specific concentrations of the test compound in 200 μL of serum-free EMEM were mixed and incubated at 37° C. for 15 min. The mixtures were diluted to the non-inhibitory concentrations of the test compound, and then subjected to the infectious titer determination as described under the viral plaque number-reduction assay. In case of RSV, the assay was carried out in similar manner using DMEM supplemented with 2% heat-inactivated fetal calf serum instead of EMEM. To evaluate the effect of a low pH value or the presence of cervical secretions; the virus (HSV-2 333) and compounds were diluted in a low pH buffer (4.5) or cervical secretions were added to the compound dilutions before mixing with the virus (HSV-2 333). The cervical secretions were prepared from cervical swabs generated from 3 different individuals. The swabs were rinsed with distilled water and centrifuged at 5000×g for 10 min. The supernatant was kept at −20° C. In the case of RSV, the assay was carried out in a similar manner using DMEM supplemented with 2% heat-inactivated fetal calf serum instead of EMEM.

Viral Plaque Assays

The viral infectivity (the plaque number-reduction) assay and the plaque size-reduction assay were carried out as described previously[17]. Briefly, for the plaque number-reduction assay, the virus-compound mixtures incubated for 15 min at room temperature prior to the addition to cells and during 1 h period of virus infection of cells at 37° C. Subsequently, the cells were washed with 2 mL of EMEM and overlaid with 1% methylcellulose solution in EMEM. The plaques were visualized by staining with crystal violet solution after 2 (HSV-2) or 3 (HSV-1) days of incubation at 37° C. The concentration of the test compound that inhibited the number of viral plaques by 50% ($IC_{50}$) was interpolated from the dose-response curves. When the compounds were screened for anti-HSV or anti-RSV activity, mixtures of 200 PFU of the virus and the test compound (100 μg/mL) in serum-free EMEM were incubated for 10 min at room temperature before addition to cells and during the entire period of viral infection of cells and the development of viral plaques. In the plaque size-reduction assay, the compounds were added to cells (in methylcellulose overlay medium) after 2 h period of virus infection of cells in the absence of the inhibitor. After 2-3 days of incubation at 37° C., the viral plaques were visualized by staining the cells with 1% solution of crystal violet. For each compound tested, the images of twenty neighboring plaques were captured using a Leica DC300 digital camera attached to a Leitz-Wetzlar Diavert microscope. The area of each plaque was determined using IM500 image software (Leica). Similar protocols were used for RSV, except that the assays were performed in HEp-2 cells and DMEM supplemented with 2% heat-inactivated fetal calf serum was used instead of EMEM.

Cytotoxicity Assay

The assay was performed in GMK AH1 cells that had been seeded in 96 well cluster plates and reached approximately 80-90% confluence at day 2 of culture. The cells were washed with EMEM and incubated for 24 h at 37° C. with 100 μL of serial two-fold dilutions of the test compound in serum-free EMEM. The effect of the test compound on cell viability was measured by using the tetrazolium-based CellTiter96 assay according to the manufacturer's protocol (Promega, Madison, Wis., USA).

Pharmacokinetics

Adult male Sprague-Dawley (SD) rats (approx 300 g) were used for the experiment. Femoral artery cannulae was implanted and exteriorised following isoflurane anaesthesia. Jugular vein artery cannulae was implanted and exteriorized. Animals were allowed to recover from cannula insertion prior to dosing, and housed in metabolism cages for the duration of experimentation with free access to water and food. $^{3}H$ (aglycon labelled) or $^{35}S$ (sulfate labelled) labelled compounds were dissolved in phosphate-buffered saline to give a total drug concentration of between 1.25-5.00 mg/mL. All doses were administered as a bolus of between 2.5-10 mg/kg in a dose volume of approximately 2.0 mL/kg. The total amount of radioactivity administered to each rat was between 0.5-10 μCi. Blood samples (~325 μL) were collected into sample tubes containing the anticoagulant sodium citrate from femoral artery catheter pre-dose and at 5, 20 minutes and 2, 5, 8, 12, 24, and 48 hours post-dose, and kept at reduced temperature (approx 4° C.) until centrifuged. Blood samples were centrifuged, plasma separated and 50 μL aliquot of the plasma transferred to a scintillation vial for counting. At the end of the experimental period animals were euthanased via a lethal overdose of pentobarbital. The level of radioactivity in the plasma was measured following mixing of samples with Packard Ultima Gold liquid scintillation counting cocktail. Counting was conducted on a Beckman liquid scintillation counter (L56500) or Packard TriCarb liquid scintillation counter for 10 minutes per sample. Results (DPM, calculated from an in-built quench curve in the counter) were corrected for background prior to any calculations. The pharmacokinetic parameters were calculated using PK Solutions 2.0 software (Summit Research Services, Ohio, U.S.A.) and are summarised in Table 11 below.

The foregoing embodiments are illustrative only of the principles of the invention, and various modifications and changes will readily occur to those skilled in the art. The invention is capable of being practiced and carried out in various ways and in other embodiments. It is also to be understood that the terminology employed herein is for the purpose of description and should not be regarded as limiting.

The term "comprise" and variants of the term such as "comprises" or "comprising" are used herein to denote the inclusion of a stated integer or stated integers but not to exclude any other integer or any other integers, unless in the context or usage an exclusive interpretation of the term is required.

Any reference to publications cited in this specification is not an admission that the disclosures constitute common general knowledge in Australia.

TABLE 1

The results of the growth factor binding and heparanase inhibition assays as described in the preceding sections.

| Compound | $K_d$ VEGF (nM) | $K_d$ FGF-1 (nM) | $K_d$ FGF-2 (nM) | $K_i$ Heparanase (nM) |
|---|---|---|---|---|
| 4 | 12 ± 3 | 6 ± 3 | 480 ± 70 | 4.2 ± 0.5 |
| 8 | 5.1 ± 1.8 | 2.3 ± 1.3 | 253 ± 25 | 3.5 ± 0.4 |
| 11 | 0.79 ± 0.24 | 0.19 ± 0.10 | 73 ± 23 | 4.8 ± 1.8 |
| 17 | 24 ± 6 | 3.2 ± 0.5 | ND | ND |

TABLE 1-continued

The results of the growth factor binding and heparanase inhibition assays as described in the preceding sections.

| Compound | $K_d$ VEGF (nM) | $K_d$ FGF-1 (nM) | $K_d$ FGF-2 (nM) | $K_i$ Heparanase (nM) |
|---|---|---|---|---|
| 20 | 22 ± 6 | 0.60 ± 0.50 | 160 ± 40 | 5.8 ± 1.5 |
| 24 | 40 ± 17 | 0.44 ± 0.04 | 108 ± 11 | 6.0 ± 2.1 |
| 27 | 1.04 ± 0.19 | 0.24 ± 0.10 | 39 ± 6 | 5.5 ± 2.6 |
| 33 | 1300 ± 300 | 270 ± 30 | 1570 ± 150 | 22.3 ± 1.6 |
| 39 | 319 ± 19 | 18.5 ± 1.8 | 631 ± 4 | 6.4 ± 2.5 |
| 44 | 2.7 ± 0.5 | 0.17 ± 0.07 | 80 ± 40 | 4.4 ± 1.4 |
| 48 | 460 ± 30 | 22.6 ± 1.0 | 480 ± 40 | 8.50 ± 0.14 |
| 56 | 90 ± 30 | 16 ± 7 | 490 ± 40 | 10.5 ± 1.7 |
| 60 | 260 ± 130 | 14.3 ± 3.0 | 474.0 ± 1.4 | 8.4 ± 2.6 |
| 65 | 28.9 ± 2.3 | 8 ± 4 | 390 ± 80 | 6.1 ± 2.5 |
| 70 | 95 ± 8 | 9.7 ± 0.8 | 390 ± 90 | 3.7 ± 0.8 |
| 76 | 790 ± 230 | 50 ± 8 | 610 ± 60 | 16 ± 4 |
| 79 | 3000 ± 400 | 3600 ± 600 | >3000 | 111 ± 28 |
| 83 | 7.95 ± 0.07 | 1.25 ± 0.07 | 50 ± 4 | 20 ± 5 |
| 87 | 190 ± 60 | 24.8 ± 2.3 | 547 ± 50 | 9.1 ± 2.5 |
| 93 | 1600 ± 300 | 610 ± 210 | 1800 ± 300 | 30 ± 7 |
| 97 | 1930 ± 230 | 840 ± 130 | 3400 ± 300 | ND |
| 102 | 1200 ± 400 | 560 ± 30 | 2200 ± 400 | ND |
| 107 | 1350 ± 70 | 870 ± 60 | 2000 ± 400 | ND |
| 112 | 430 ± 140 | 900 ± 150 | 2100 ± 300 | ND |
| 119 | 7.9 ± 0.7 | 5.9 ± 1.6 | 286 ± 25 | ND |
| 123 | 380 ± 110 | 32.2 ± 2.3 | 530 ± 50 | 11.3 ± 0.4 |
| 128 | 14 ± 4 | 4.94 ± 0.08 | 311 ± 25 | 9.1 ± 0.3 |
| 134 | 1080 ± 200 | 13 ± 3 | 630 ± 30 | ND |
| 139 | 379 ± 13 | 72 ± 12 | 880 ± 110 | ND |
| 140 | 12 ± 2 | 1.3 ± 0.6 | 380 ± 40 | ND |

TABLE 2

Data for selected compounds in the Growth Factor Induced Endothelial Cell Proliferation Assay and Matrigel ™ Microtubule Formation Assay.

| Compound | FGF-1 ($IC_{50}$, μM) | FGF-2 ($IC_{50}$, μm) | VEGF ($IC_{50}$, μm) | Microtubule Formation % inhibition at 10 μM |
|---|---|---|---|---|
| PI-88 | 42 | 10 | 20 | 29% |
| 4 | 25 | 10 | 6.54 | ND |
| 8 | 10.1 | 8.1 | 5.4 | 27% |
| 11 | 33 | 17.0 | 19.5 | ND |
| 17 | 4.29 | 3.44 | 5.75 | 71% |
| 20 | 1.29 | 0.847 | 1.18 | 73% |
| 24 | 1.54 | 0.665 | 0.580 | 90% |
| 27 | 0.990 | 0.390 | 0.220 | 74% |
| 33 | >10 | 2.22 | 1.85 | 14% |
| 39 | 4.44 | 2.27 | 0.951 | 74% |
| 44 | 3.79 | 0.349 | 1.18 | 95% |
| 48 | 3.81 | 1.74 | 2.08 | 64% |
| 56 | 2.52 | 1.80 | 1.72 | 67% |
| 60 | 2.61 | 1.22 | 1.44 | 49% |
| 65 | 1.2 | 0.65 | 0.50 | 53% |
| 70 | 2.3 | 0.64 | 2.2 | 52% |
| 76 | 2.1 | 1.2 | 1.8 | 22% |
| 79 | 2.20 | 2.90 | 2.24 | 3% enhancement |
| 83 | >50.0 | >50.0 | >50.0 | ND |
| 87 | 2.5 | 2.3 | 1.6 | 20% |
| 93 | 2.69 | 2.43 | 2.62 | ND |
| 97 | 4.09 | 4.17 | 1.13 | ND |
| 102 | 3.95 | >10 | 5.17 | ND |
| 107 | 5.75 | 5.59 | 5.56 | ND |
| 119 | 4.04 | 2.69 | 2.01 | 32% |
| 123 | 1.69 | 1.7 | 1.1 | 33% |
| 128 | 0.47 | 0.77 | 0.24 | ND |
| 134 | 1.47 | 1.28 | 2.14 | 63% |
| 139 | 2.16 | 1.5 | 2.31 | 36% |
| 140 | 0.56 | 0.005 | 1.1 | 37% |

a) $IC_{50}$ values (μM) for inhibition of HUVEC proliferation induced by FGF-1, FGF-2 and VEGF;
b) % Inhibition of microtubule formation at 10 μM relative to controls.

TABLE 3

Inhibition of HUVEC migration as expressed by percentage inhibition of control by PI-88, a less lipophilic analogue (PG524) and selected compounds at concentrations of 10 and 50 μM.

| Compound | % Inhibition of Migration | |
|---|---|---|
| | 10 μM | 50 μM |
| PI-88 | 10 | 11 |
| PG524 | 3 | 7 |
| 20 | 48 | 99 |
| 24 | 17 | 61 |
| 27 | 48 | 96 |

TABLE 4

Effect of PI-88, a less lipophilic analogue (PG524) and selected test compounds on angiogenic sprout formation in the rat aortic angiogenesis assay.

| Compound | % Inhibition of Angiogenesis (10 μM) |
|---|---|
| PI-88 | 61 |
| PG524 | 65 |
| 20 | 100 |
| 24 | 69 |
| 27 | 100 |
| 65 | 90 |
| 70 | 97 |
| 76 | 80 |
| 87 | 47 |
| 123 | 23 |
| 128 | 65 |
| 134 | 100 |
| 139 | 92 |
| 140 | 88 |

TABLE 5

Anticoagulant activity of selected compounds. Time for normal pooled human plasma to clot in APTT and Heptest assays following addition of test compounds at 0.1 mg/mL.

| Compound. | APTT (s) | Heptest (s) |
|---|---|---|
| PI-88 | >500.0 | >500.0 |
| 4 | 125.9 | 64.2 |
| 20 | 94.0 | 28.0 |
| 24 | 68.1 | 24.5 |
| 27 | 63.3 | 29.6 |
| 33 | 40.6 | 25.5 |
| 39 | 50.7 | 27.3 |
| 44 | 217.0 | 58.5 |
| 48 | 73.3 | 33.1 |
| 56 | 58.5 | 24.2 |
| 60 | 71.4 | 26.4 |
| 65 | 71.9 | 28.6 |
| 70 | 104.0 | 45.5 |
| 76 | 61.2 | 30.2 |
| 79 | 36.1 | 23.9 |
| 83 | 41.0 | 26.8 |
| 87 | 51.6 | 29.2 |
| 93 | 39.6 | 25.3 |
| 97 | 40.3 | 26.7 |
| 102 | 38.6 | 23.9 |
| 107 | 38.8 | 25.3 |
| 112 | 38.9 | 25.4 |
| 119 | 57.1 | 28.6 |
| 123 | 51.1 | 24.9 |
| 128 | 65.8 | 32.2 |
| Plasma control | 35.0 | 24.4 |

TABLE 6

Anti-HSV and anti-RSV activity of compounds found in a screening assay.

| Compound | Residual infectivity (%)[a] | | |
|---|---|---|---|
| | HSV-1 | HSV-2 | RSV |
| PI-88 | 5 | 3 | 19 |
| 4 | 2 | 0.7 | 0 |
| 8 | 7 | 0.2 | 3 |
| 11 | 0 | 0 | 0 |
| 20 | 0 | 0 | 0 |

[a]Percentage of a number of viral plaques found with drug treated virus (100 μg/mL) relative to mock treated controls.

TABLE 7

Antiviral activity and cytotoxicity of test compounds.

| Compound | Cytotoxicity $CC_{50}$[a] | | $IC_{50}$ (Selective index $CC_{50}/IC_{50}$)[b] | | |
|---|---|---|---|---|---|
| | GMK AH1 | HEp-2 | HSV-1 | HSV-2 | RSV |
| PI-88 | >1000 | >400 | 7 (>143) | 1.1 (>909) | 9.9 (>40) |
| 4 | >400 | >400 | 2.1 (>190) | 0.9 (>444) | 4.6 (>87) |
| 11 | >400 | NT | 1.8 (>222) | 0.9 (>444) | 5.7 |
| 20 | 110 | 113 | 2.1 (52) | 1.1 (100) | 1.7 (66) |

[a]Concentration of compound (μg/mL) that reduced GMK AH1 or HEp-2 cell viability by 50%

[b]Concentration of a test compound that reduced the number of HSV plaques in GMK AH1 cells or RSV plaques in HEp-2 cells by 50%. In parentheses are the values of the selectivity index

TABLE 8

Virus-inactivating activities of test compounds[a]

| Virus | Compound Concentration (μg/ml) | Compound | | |
|---|---|---|---|---|
| | | PI-88 | 4 | 20 |
| HSV-1 | 100 | 100.3 | 83.8 | 0 |
| | 10 | 108.0 | 79.4 | 0 |
| | 1 | 99.8 | 83.9 | 88.6 |
| HSV-2 | 100 | 107.7 | 68.1 | 0 |
| | 10 | 102.9 | 97.5 | 0.3 |
| | 1 | 95.1 | 98.6 | 120.3 |
| RSV | 100 | 94.0 | 47.3 | 13.3 |
| | 20 | 95.0 | 82.2 | 79.0 |
| | 4 | 105.8 | 85.2 | 102.2 |

[a]Approximately $2 \times 10^5$ PFU of respective virus were co-incubated with PI-88 (μg/mL), the test compound or the diluent medium (control) for 15 min at 37° C. prior to dilution of the mixtures 1:500 or 1:1000 and viral plaque titration. The results are expressed as a percentage of the number of viral plaques detected with the compound-treated virus relative to mock-treated controls.

TABLE 9

Anti-HSV activity of test compounds

| Compound | HSV-2 $IC_{50}$ (μg/ml)[a] | RSV $IC_{50}$ (μg/ml)[a] |
|---|---|---|
| 24 | 1.8 | 0.45 |
| 27 | 0.52 | 0.28 |
| 33 | 0.7 | 1.8 |
| 39 | 1.1 | 0.61 |
| 44 | 0.41 | 0.33 |
| 48 | 0.18 | 0.25 |
| 56 | 0.3 | 0.45 |
| 60 | 0.24 | 0.39 |
| 65 | 0.45 | 0.35 |
| 70 | 0.15 0.25[b] | 0.23 |
| 76 | 0.07 0.20[b] | 0.37 |
| 79 | 0.28 | 2.9 |
| 83 | 6.0 | 3.0 |

TABLE 9-continued

Anti-HSV activity of test compounds

| Compound | HSV-2 $IC_{50}$ (μg/ml)[a] | RSV $IC_{50}$ (μg/ml)[a] |
|---|---|---|
| 87 | 0.53 | 0.77 |
| 93 | 0.27 | 0.4 |
| 97 | 0.26 | 0.58 |
| 102 | 0.43 | 1.8 |
| 107 | 0.43 | 1.9 |
| 112 | 0.45 | 2.4 |
| 119 | 2.1 | 0.62 |
| 128 | 1.0 | 1.4 |

[a]Concentration of the test compound that reduced the number of viral plaques in GMK AH1 cells by 50%.
[b]Concentration of the test compound that reduced the number of HSV-1 KOS321 strain plaques in GMK AH1 cells by 50%.

TABLE 10

Modulation of the virus-inactivating activities of PI-88 and compound 20 at low pH and in the presence of human cervical secretions[a]

| Virus | Compound concentration (μg/ml) | Compound PI-88 Low pH[b] | PI-88 CS[c] | 20 Low pH[b] | 20 CS[c] |
|---|---|---|---|---|---|
| HSV-2 | 100 | 111.5 | 90.3 | 0.0 | 0.3 |
| | 10 | 110.8 | 98.3 | 6.8 | 78.5 |
| | 1 | 101.1 | 88.4 | 93.7 | 82.6 |

[a]Approximately $2 \times 10^5$ PFU of respective virus were co-incubated with PI-88 (μg/ml), test compound or the diluent medium (control) for 15 min at 37° C. (water bath) prior to dilution of the mixtures 1:500 or 1:1000 and viral plaque titration. The results are expressed as a percentage of the number of viral plaques detected with the compound-treated virus relative to mock-treated controls.
[b]The pH value during the virus-compound incubation was 4.5.
[c]Cervical secretions diluted 1:2.2 was present during the 15 min of the virus-compound

TABLE 11

Pharmacokinetic parameters of test compounds following either intra venous (iv) or subcutaneous (sc) administration in Sprague-Dawley rats.

| Compound | Half-life (iv) | Half-life (sc) |
|---|---|---|
| PI-88 | 1.1 h | 1.2 h |
| 65 | 17.3 h | 21.3 h |
| 70 | 10.3 h | ND |

REFERENCES

1. Parish, C. R.; Freeman, C.; Brown, K. J.; Francis, D. J.; Cowden, W. B. Cancer Res. 1999, 59, 3433.
2. Parish, C. R.; Cowden, W. B. U.S. Pat. No. 6,143,730, 2000.
3. Iversen, P. O.; Sorenson, D. R.; Benestad, H. B. Leukemia 2002, 16, 376.
4. Joyce, J. A.; Freeman, C.; Meyer-Morse, N.; Parish, C. R.; Hanahan, D. Oncogene 2005, 24, 4037.
5. Basche, M.; Gustafson, D. L.; Holden, S, N.; O'Bryant, C. L.; Gore, L.; Witta, S.; Schultz, M. K.; Morrow, M.; Levin, A.; Creese, B. R.; Kangas, M.; Roberts, K.; Nguyen, T.; Davis, K.; Addison, R. S.; Moore, J. C.; Eckhardt, S. G. Clin. Cancer Res. 2006, 12, 5471.
6. Ferro, V.; Dredge, K.; Liu, L.; Hammond, E.; Bytheway, I.; Li, C.; Johnstone, K.; Karoli, T.; Davis, K.; Copeman, E.; Gautam, A. Semin. Thromb. Hemost. 2007, 33, 557.
7. Ferro, V.; Li, C.; Fewings, K.; Palermo, M. C.; Linhardt, R. J.; Toida, T. Carbohydr. Res. 2002, 337, 139.
8. Yu, G.; Gunay, N. S.; Linhardt, R. J.; Toida, T.; Fareed, J.; Hoppensteadt, D. A.; Shadid, H.; Ferro, V.; Li, C.; Fewings, K.; Palermo, M. C.; Podger, D. Eur. J. Med. Chem. 2002, 37, 783.
9. Cochran, S.; Li, C.; Fairweather, J. K.; Kett, W. C.; Coombe, D. R.; Ferro, V. J. Med. Chem. 2003, 46, 4601.
10. Vlodaysky, I.; Friedmann, Y. J. Clin. Invest. 2001, 108, 341.
11. Parish, C. R.; Freeman, C.; Hulett, M. D. Biochim. Biophys. Acta 2001, 1471, M99.
12. Demir, M.; Iqbal, O.; Hoppensteadt, D. A.; Piccolo, P.; Ahmad, S.; Schultz, C. L.; Linhardt, R. J.; Fareed, J. Clin. Appl. Thromb. Hemost. 2001, 7, 131.
13. Wall, D.; Douglas, S.; Ferro, V.; Cowden, W.; Parish, C. Thromb. Res. 2001, 103, 325.
14. Hembrough, T. A.; Ruiz, J. F.; Papathanassiu, A. E.; Green, S. J.; Strickland, D. K. J. Biol. Chem. 2001, 276, 12241.
15. Amirkhosravi, A.; Meyer, T.; Chang, J. Y.; Amaya, M.; Siddiqui, F.; Desai, H.; Francis, J. L. Thromb. Haemost. 2002, 87, 930.
16. Francis, D. J.; Parish, C. R.; McGarry, M.; Santiago, F. S.; Lowe, H. C.; Brown, K. J.; Bingley, J. A.; Hayward, I. P.; Cowden, W. B.; Campbell, J. H.; Campbell, G. R.; Chesterman, C. N.; Khachigian, L. M. Circ. Res. 2003, 92, e70.
17. Nyberg, K.; Ekblad, M.; Bergström, T.; Freeman, C.; Parish, C. R.; Ferro, V.; Trybala, E. Antiviral Res. 2004, 63, 15.
18. Lee, E.; Pavy, M.; Young, N.; Freeman, C.; Lobigs, M. Antiviral Res. 2006, 69, 31.
19. Levidiotis, V.; Freeman, C.; Punier, M.; Martinello, P.; Creese, B.; Ferro, V.; van der Vlag, J.; Berden, J. H. M.; Parish, C. R.; Power, D. A. J. Am. Soc. Nephrol. 2004, 15, 2882.
20. Adams, Y.; Freeman, C.; Schwartz-Albiez, R.; Ferro, V.; Parish, C. R.; Andrews, K. T. Antimicrob. Agents Chemother. 2006, 50, 2850.
21. Ferro, V.; Hammond, E.; Fairweather, J. K. Mini-Rev. Med. Chem. 2004, 4, 159.
22. Foxall, C.; Wei, Z.; Schaefer, M. E.; Casabonne, M.; Fugedi, P.; Peto, C.; Castellot, J. J., Jr; Brandley, B. K. J. Cell. Physiol. 1996, 168, 657.
23. Fugedi, P.; Tyrrell, D. J.; Tressler, R. J.; Stack, R. J.; Ishihara, M. U.S. Pat. No. 5,739,115, 1998.
24. Gunay, N. S.; Linhardt, R. J. Planta Med. 1999, 65, 301.
25. Katsuraya, K.; Nakashima, H.; Yamamoto, N.; Uryu, T. Carbohydr. Res. 1999, 315, 234.
26. Wessel, H. P. Topics Curr. Chem. 1997, 187, 215.
27. Ferro, V.; Fairweather, J. K.; Karoli, T.; Liu, L. PCT Int. Appl. WO 2005/085264 A1, 2005.
28. Karoli, T.; Liu, L.; Fairweather, J. K.; Hammond, E.; Li, C. P.; Cochran, S.; Bergefall, K.; Trybala, E.; Addison, R. S.; Ferro, V. J. Med. Chem. 2005, 48, 8229.
29. Farndale, R. W.; Buttle, D. J.; Barrett, A. J. Biochim. Biophys. Acta 1986, 883, 173.
30. Ferro, V.; Fewings, K.; Palermo, M. C.; Li, C. Carbohydr. Res. 2001, 332, 183.
31. Aucagne, V.; Hanni, K. D.; Leigh, D. A.; Lusby, P. J.; Walker, D. B. J. Am. Chem. Soc. 2006, 128, 2186.
32. Dubber, M.; Lindhorst, T. K. J. Org. Chem. 2000, 65, 5275.
33. Fairweather, J. K.; Karoli, T.; Ferro, V. Bioorg. Med. Chem. 2004, 12, 6063.
34. Chen, L.; Kong, F. J. Carbohydr. Chem. 2002, 21, 341.

35. Narumi, A.; Miura, Y.; Otsuka, I.; Yamane, S.; Kitajyo, Y.; Satoh, T.; Hirao, A.; Kaneko, N.; Kaga, H.; Kakuchi, T. J. Polym. Sci., Part A: Polym. Chem. 2006, 44, 4864.
36. Pazur, J. H. Methods Carbohydr. Chem. 1962, 1, 337.
37. Ahmed, S.; Alauddin, M.; Caddy, B.; Martin-Smith, M.; Sidwell, W. T. L.; Watson, T. R. Aust. J. Chem. 1971, 24, 521.
38. Ferro, V.; Meldal, M.; Bock, K. J. Chem. Soc., Perkin Trans. 1 1994, 2169.
39. Driguez, P. A.; Petitou, M. PCT Int. Appl. WO 2006/021653 A2, 2006.
40. Bisio, A.; Mantegazza, A.; Urso, E.; Naggi, A.; Torri, G.; Viskov, C.; Casu, B. Semin. Thromb. Hemost. 2007, 33, 488.
41. Malinda, K. M.; Nomizu, M.; Chung, M.; Delgado, M.; Kuratomi, Y.; Yamada, Y.; Kleinman, H. K.; Ponce, M. L. Faseb J. 1999, 13, 53.
42. Nicosia, R. F.; Ottinetti, A. Lab. Invest. 1990, 63, 115.
43. Dredge, K.; Marriott, J. B.; Macdonald, C. D.; Man, H. W.; Chen, R.; Muller, G. W.; Stirling, D.; Dalgleish, A. G. Br. J. Cancer 2002, 87, 1166.
44. Ng, S. S. W.; MacPherson, G. R.; Gutschow, M.; Eger, K.; Figg, W. D. Clin. Cancer Res. 2004, 10, 4192.
45. Min, J.-K.; Han, K.-Y.; Kim, E.-C.; Kim, Y.-M.; Lee, S.-W.; Kim, O.-H.; Kim, K.-W.; Gho, Y. S.; Kwon, Y.-G. Cancer Res. 2004, 64, 644.
46. Gunalp, A. Proc. Soc. Exp. Biol. Med. 1965, 118, 185.
47. Holland, T. C.; Homa, F. L.; Marlin, S. D.; Levine, M.; Glorioso, J. J. Virol. 1984, 52, 566.
48. Holland, T. C.; Marlin, S. D.; Levine, M.; Glorioso, J. J. Virol. 1983, 45, 672.
49. Duff, R.; Rapp, F. Nat. New Biol. 1971, 233, 48.
50. Lewis, F. A.; Rae, M. L.; Lehmann, N. I.; Ferris, A. A. Med. J. Aust. 1961, 2, 932.
51. Hallak, L. K.; Collins, P. L.; Knudson, W.; Peeples, M. E. Virology 2000, 271, 264.
52. Gupta, C. K.; Leszczynski, J.; Gupta, R. K.; Siber, G. R. Vaccine 1996, 14, 1417.
53. Karger, A.; Mettenleiter, T. C. Virology 1993, 194, 654.
54. Trybala, E.; Liljeqvist, J. A.; Svennerholm, B.; Bergstrom, T. J. Virol. 2000, 74, 9106.

The invention claimed is:

1. A compound of the general formula:

$$[X]_n—Y—ZR^1R^2 \quad \text{I}$$

wherein:

X and Y are each a monosaccharide unit wherein each hydroxyl group not involved in a glycosidic linkage is substituted independently by a group $SO_3M$ or H, where M is any pharmaceutically acceptable cation;

X and Y are any D- or L-hexose or pentose;

Y is in a cyclic or ring opened form;

Z is O, N, S or C or their higher oxidation states, or a bond, and is linked to the anomeric carbon when Y is a reducing monosaccharide;

$R^1$ is a linker selected from the group consisting of: alkyl, alkenyl, alkynyl, aryl, heteroalkyl, heteroaryl, acyl, aroyl, alkylamido, alkylthioamido, triazolyl, substituted triazolyl, and oxymethyl[1,2,3]-triazole-1-yl linker, or is a bond, wherein if $R^1$ is substituted triazolyl, the triazolyl is substituted by one or more of: halo, hydroxy, C1-6alkyl, C1-6alkoxy, nitro, amino, C1-6alkylamino, C1-6dialkylamino, halomethyl, halomethoxy or acetyl;

$R^2$ is a lipophilic moiety selected from the group consisting of: cholestanyl, and propylstearamide, wherein n is an integer from 0-6; and the level of sulfation of each compound is between 70 and 100% of the total hydroxyl groups.

2. The compound according to claim 1 wherein $R^2$ is cholestanyl.

3. The compound according to claim 1 wherein $R^2$ is propylstearamide.

4. A compound selected from the group consisting of:

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 65);

4-(cholestan-3-yl-oxymethyl)[1,2,3]triazol-1-yl-2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (compound 70);

4-(cholestan-3β-yl-oxymethyl)[1,2,3]triazol-1-yl-2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (compound 76);

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 87);

3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, decasodium salt (compound 123); and 3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, tridecasodium salt (compound 128).

5. A pharmaceutical or veterinary composition for the treatment in a mammalian subject of *cancer or of* a disorder resulting from angiogenesis, metastasis, inflammation, coagulation/thrombosis, raised blood triglyceride levels, microbial infection and/or cardiovascular disease, which composition comprises at least one compound according to claim 1 together with a pharmaceutically or veterinarially acceptable carrier or diluent for at least one said compound.

6. A method for the treatment in a mammalian subject of *cancer or of* a disorder resulting from angiogenesis, metastasis, inflammation, coagulation/thrombosis, raised blood triglyceride levels, microbial infection and/or cardiovascular disease, which method comprises administering to the subject an effective amount of at least one compound according to claim 1, or a composition comprising said at least one compound.

7. The method of claim 6 wherein the compound is selected from the group consisting of:

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 65);

4-(cholestan-3-yl-oxymethyl)[1,2,3]triazol-1-yl-2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (compound 70);

4-(cholestan-3β-yl-oxymethyl)[1,2,3]triazol-1-yl-2,3,4,6-tetra-O-sodium sulfonato-α-D-glucopyranosyl-(1→4)-2,3,6-tri-O-sodium sulfonato-α-D-glucopyranosyl- (1→4)-1-deoxy-2,3,6-tri-O-sodium sulfonato-β-D-glucopyranoside (compound 76);

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 87);

3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, decasodium salt (compound 123); and 3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, tridecasodium salt (compound 128).

8. The compound according to claim 2 wherein $R^1$ is an oxymethyl[1,2,3]-triazole-1-yl linker.

9. The compound according to claim 3 wherein $R^1$ is an oxymethyl[1,2,3]-triazole-1-yl linker.

10. A pharmaceutical or veterinary composition according to claim 5, *wherein the compound is* selected from the group consisting of:

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 65);

4-(cholestan-3-yl-oxymethyl)[1,2,3]triazol-1-yl-2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (compound 70);

4-(cholestan-3β-yl-oxymethyl)[1,2,3]triazol-1-yl-2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (compound 76);

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 87);

3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, decasodium salt (compound 123); and 3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, tridecasodium salt (compound 128), together with a pharmaceutically or veterinarially acceptable carrier or diluent for at least one said compound.

11. A compound selected from the group consisting of:

3β-cholestanyl-2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (compound 20);

3-stearamidopropyl-2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (compound 24);

3β-cholestanyl-2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (compound 27);

3β-cholestanyl-2,3,4,6-tetra-O-sodium sulfonato-α-D-mannopyranosyl-(1→2)-3,4,6-tri-O-sodium sulfonato-α-D-mannopyranoside (compound 33);

3β-cholestanyl-2,3,4,6-tetra-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (compound 39);

3-stearamidopropyl-2,3,4,6-tetra-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (compound 44);

3-{4-(cholestan-3β-yl-oxymethyl)-[1,2,3]triazol-1-yl}propyl-2,3,4,6-tetra-O-sodium sulfonato-α-D-mannopyranosyl-(1→3)-2,4,6-tri-O-sodium sulfonato-α-D-mannopyranosyl-(1→2)-3,4,6-tri-O-sodium sulfonato-α-D-mannopyranoside (compound 48);

3'-cholestanyl-2,3,4,6-tetra-O-sodium sulfonato-α-D-mannopyranosyl-(1→3)-2,4,6-tri-O-sodium sulfonato-α-D-mannopyranosyl-(1→3)-3,4,6-tri-O-sodium sulfonato-α-D-mannopyranoside (compound 56);

3-{4-(cholestan-3β-yl-oxymethyl)-[1,2,3]triazol-1-yl}propyl-2,3,4,6-tetra-O-sodium sulfonato-α-D-mannopyranosyl-(1→3)-2,4,6-tri-O-sodium sulfonato-α-D-mannopyranosyl-(1→3)-3,4,6-tri-O-sodium sulfonato-α-D-mannopyranoside (compound 60);

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 65);

4-(cholestan-3-yl-oxymethyl)[1 ,2,3]triazol-1-yl-2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (compound 70);

4-(cholestan-3β-yl-oxymethyl)[1,2,3]triazol-1-yl-2,3,4,6-tetra-O-sodium sulfonato-α-D-glucopyranosyl-(1→4)-2,3,6-tri-O-sodium sulfonato-α-D-glucopyranosyl-(1→4)-1-deoxy-2,3,6-tri-O-sodium sulfonato-β-D-glucopyranoside (compound 76);

3β-cholestanyl-2,3,4,6-tetra-O-sulfonato-α-D-mannopyranoside tetrasodium salt (compound 79);

3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 87);

4-(cholestan-3β-yl-oxymethyl)[1,2,3]triazol-1-yl-2,3,4,6-tetra-O-sulfo-β-D-galactopyranosyl-(1→4)-2,3,6-tri-O-sulfo-β-D-glucopyranoside, heptasodium salt (compound 93);

4-(cholestan-3β-yl-oxymethyl)[1,2,3]triazol-1-yl 2,3,4,6-tetra-O-sulfo-α-D-glucopyranosyl-(1→4)-2,3,6-tri-O-sulfo-β-D-glucopyranoside, heptasodium salt (compound 97);

3'-cholestanyl-2,3,4,6-tetra-O-sulfo-α-D-glucopyranosyl-(1→4)-2,3,6-tri-O-sulfo-β-D-glucopyranoside, heptasodium salt (compound 102);

3'-cholestanyl-2,3,4,6-tetra-O-sulfo-β-D-glucopyranosyl-(1→4)-2,3,6-tri-O-sulfo-β-D-glucopyranoside, heptasodium salt (compound 107);

3'-cholestanyl-2,3,4,6-tetra-O-sulfo-β-D-galactopyranosyl-(1→4)-2,3,6-tri-O-sulfo-β-D-glucopyranoside, heptasodium salt (compound 112);

3'-cholestanyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranosyl-(1→6)-2,3,4-tri-O-sulfo-α-D-mannopyranoside, tridecasodium salt (compound 119);

3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, decasodium salt (compound 123);

3-stearamidopropyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, tridecasodium salt (compound 128);

2-(cholestan-3-yloxy)acetamido-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside, decasodium salt (compound 134);

1-[(cholestan-3-yloxy)propyl]-3-[2,3,4,6-tetra-O-sulfo-α-D-glucopyranosyl-(1→4)-2,3,6-tri-O-sulfo-α-D-glucopyranosyl-(1→4)-2,3,6-tri-O-sulfo-β-D-glucopyranoside]thiourea, decasodium salt (compound 139); and 3'-cholestanyl-2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-D-glucopyranosyl-(1→4)-((1-pyridinium-1-yl)-2,3,5,6-tetra-O-sulfo-D-glucoside, tridecasodium salt (compound 140).

12. The compound according to claim 2, wherein $R^1$ is a bond.

13. The compound according to claim 12, wherein each X is a D-hexose, and Y is a D-hexose.

14. The compound according to claim 13, wherein n is 3.

15. A pharmaceutical or veterinary composition for the treatment in a mammalian subject of *cancer or of* a disorder resulting from angiogenesis, metastasis, inflammation, coagulation/thrombosis, raised blood triglyceride levels, microbial infection and/or cardiovascular disease, which composition comprises at least one compound according to claim 11 together with a pharmaceutically or veterinarially acceptable carrier or diluent for at least one said compound.

16. A method for the treatment in a mammalian subject of *cancer or of* a disorder resulting from angiogenesis, metastasis, inflammation, coagulation/thrombosis, raised blood triglyceride levels, microbial infection and/or cardiovascular disease, which method comprises administering to the subject an effective amount of at least one compound according to claim 11, or a composition comprising said at least one compound.

17. A compound of the general formula:

$$[X]_n—Y—ZR^1R^2 \quad \text{I}$$

wherein:

X and Y are each a monosaccharide unit wherein each hydroxyl group not involved in a glycosidic linkage is substituted independently by a group $SO_3M$ or H, where M is any pharmaceutically acceptable cation;

X and Y are any D- or L-hexose or pentose;

Y is in a cyclic or ring opened form;

Z is O, N, S or C or their higher oxidation states, or a bond, and is linked to the anomeric carbon when Y is a reducing monosaccharide;

$R^1$ is an oxymethyl[1,2,3]-triazole-1-yl linker;

$R^2$ is a lipophilic moiety selected from the group consisting of: cholesteryl, cholestanyl, cholate, deoxycholate, glycyrrhetinyl, C9 to C18 straight chain alkyl, C9 to C18 substituted alkyl, alkylamido, substituted alkylamido, and propylstearamide, straight chain acyl, branched acyl, and —C(O)-alkyl or —C(O)-aryl, in which the alkyl or aryl groups are optionally substituted by one or more of halo, hydroxy, $C_{1-6}$alkyl, $C_{1-6}$alkoxy, nitro, amino, $C_{1-6}$a1kylamino, $C_{1-6}$dialkylamino, halomethyl, halomethoxy or acetyl, wherein if $R^2$ is substituted alkyl or substituted alkylamido, the group is substituted by one or more of: halo, hydroxy, $C_{1-6}$alkoxy, nitro, amino, $C_{1-6}$alkylamino, $C_{1-6}$dialkylamino, halomethyl, halomethoxy or acetyl;

n is an integer from 0-6; and the level of sulfation of each compound is between 70 and 100% of the total hydroxyl groups.

18. A pharmaceutical or veterinary composition for the treatment in a mammalian subject of *cancer or of* a disorder resulting from angiogenesis, metastasis, inflammation, coagulation/thrombosis, raised blood triglyceride levels, microbial infection and/or cardiovascular disease, which composition comprises at least one compound according to claim 17 together with a pharmaceutically or veterinarially acceptable carrier or diluent for at least one said compound.

19. A method for the treatment in a mammalian subject of *cancer or of* a disorder resulting from angiogenesis, metastasis, inflammation, coagulation/thrombosis, raised blood triglyceride levels, microbial infection and/or cardiovascular disease, which method comprises administering to the subject an effective amount of at least one compound according to claim 17, or a composition comprising said at least one compound.

*20. A method for the treatment of cancer in a mammalian subject, which method comprises administering to the subject an effective amount of:*

*3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 65).*

*21. A compound having the formula:*

*3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 65).*

*22. A pharmaceutical or veterinary composition according to claim 5, wherein the compound is:*

*3β-cholestanyl-2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside (compound 65).*

* * * * *